United States Patent
LeFebvre et al.

(10) Patent No.: US 9,757,446 B2
(45) Date of Patent: Sep. 12, 2017

(54) INFLUENZA VIRUS VECTORS AND USES THEREFOR

(71) Applicant: FluGen, Inc., Madison, WI (US)

(72) Inventors: Matthew Frederick LeFebvre, Roseville, MN (US); Yasuko Hatta, Madison, WI (US); Pamuk Bilsel, Madison, WI (US); Michael J. Moser, Madison, WI (US)

(73) Assignee: FLUGEN, INC., Madison, WI (US)

( * ) Notice: Subject to any disclaimer, the term of this patent is extended or adjusted under 35 U.S.C. 154(b) by 0 days.

(21) Appl. No.: 15/125,763

(22) PCT Filed: Mar. 13, 2015

(86) PCT No.: PCT/US2015/020580
§ 371 (c)(1),
(2) Date: Sep. 13, 2016

(87) PCT Pub. No.: WO2015/142671
PCT Pub. Date: Sep. 24, 2015

(65) Prior Publication Data
US 2017/0106077 A1    Apr. 20, 2017

Related U.S. Application Data

(60) Provisional application No. 61/954,346, filed on Mar. 17, 2014.

(51) Int. Cl.
*C12N 7/00* (2006.01)
*A61K 39/145* (2006.01)
*C12N 15/86* (2006.01)
*C07K 14/005* (2006.01)
*A61K 39/00* (2006.01)

(52) U.S. Cl.
CPC ........ *A61K 39/145* (2013.01); *A61K 39/0011* (2013.01); *C12N 7/00* (2013.01); *A61K 2039/5254* (2013.01); *A61K 2039/5256* (2013.01); *A61K 2039/54* (2013.01); *A61K 2039/543* (2013.01); *A61K 2039/545* (2013.01); *A61K 2039/575* (2013.01); *C12N 2760/16134* (2013.01); *C12N 2760/16143* (2013.01); *C12N 2760/16152* (2013.01)

(58) Field of Classification Search
CPC .. C12N 7/00; C12N 2760/1134; A61K 39/12; A61K 39/145; C07K 14/005
See application file for complete search history.

(56) References Cited

U.S. PATENT DOCUMENTS

| 7,176,021 B2 | 2/2007 | Kawaoka | |
| 8,475,806 B2 * | 7/2013 | Kawaoka | C12N 15/86 424/199.1 |
| 2010/0021499 A1 | 1/2010 | Bilsel et al. | |
| 2011/0172609 A1 | 7/2011 | Moga et al. | |
| 2011/0172637 A1 | 7/2011 | Moga et al. | |
| 2011/0172638 A1 | 7/2011 | Moga et al. | |
| 2011/0172639 A1 | 7/2011 | Moga et al. | |
| 2011/0172645 A1 | 7/2011 | Moga et al. | |
| 2012/0109066 A1 | 5/2012 | Chase et al. | |

FOREIGN PATENT DOCUMENTS

WO    WO2012177924    * 12/2012

OTHER PUBLICATIONS

Enami et al., "High-Efficiency Formation of Influenza Virus Transfectants", Journal of Virology, vol. 65, No. 5, 1991, pp. 2711-2713.
International Search Report and Written Opinion received in PCT/US2015/20580 dated Sep. 8, 2015 (11 pages).
Iwatsuki-Horimoto et al., "The Cytoplasmic Tail of the Influenza A Virus M2 Protein Plays a Role in Viral Assembly", Journal of Virology. vol. 80, No. 11, 2006, pp. 5233-5240.
Kilbourne, Bull, M2 World Health Org., 41, 643, 1969.
Luytjes et al., "Amplification, Expression, and Packaging of a Foreign Gene by Influenza Virus", Cell, vol. 59, 1989, pp. 1107-1113.
McCown et al., "Distinct Domains of the Influenza A Virus M2 Protein Cytoplasmic Tail Mediate Binding to the M1 Protein and Facilitate Infection Virus Production", Journal of Virology, vol. 80, No. 16, 2006, pp. 8178-8189.
McCown et al., "The Influenza A Virus M2 Cytoplasmic Tail is Required for Infections Virus Production and Efficient Genome Packaging", Journal of Virology, vol. 79, No. 6, 2005, pp. 3595-3605.
Neumann et al., "Generation of influenza A viruses entirely from cloned cDNAs", Proc. Natl. Acad. Sci. vol. 96, 1999, pp. 9345-9350.
Reed et al., "A Simple Method of Estimating Fifty Per Cent Endpoints", The American Journal of Hygiene, vol. 27, No. 3, 1938, pp. 493-497.
Reuman et al., "Assessment of signs of influenza illness in the ferret model", Journal of Virological Methods, vol. 24, 1989, pp. 27-34.
Robertson et al., Biologicals, 20, 2013, 1992.
Treanor et al., "Passively Transferred Monoclonal Antibody to the M2 Protein Inhibits Influenza A Virus Replication in Mice", Journal of Virology, vol. 64, No. 3, 1990, pp. 1375-1377.
Watanabe et al., "Influenza A Virus Lacking M2 Protein as a Live Attenuated Vaccine", Journal of Virology, vol. 83, No. 11, 2009, pp. 5947-5950.

(Continued)

*Primary Examiner* — Janet L Andres
*Assistant Examiner* — Barry A Chestnut
(74) *Attorney, Agent, or Firm* — Foley & Lardner LLP

(57) ABSTRACT

Disclosed herein are compositions and methods related to mutant viruses, and in particular, mutant influenza viruses. The mutant viruses disclosed herein include a mutant M2 sequence, and are useful in immunogenic compositions, e.g., as vaccines. The mutant viruses disclosed herein including a mutant M2 sequence are also useful to deliver antigens to a subject, e.g., to induce an immune response to the antigen. Also disclosed herein are methods, compositions and cells for propagating the viral mutants, and methods, devices and compositions related to vaccination.

19 Claims, 66 Drawing Sheets

(56) References Cited

OTHER PUBLICATIONS

Watanabe et al., "Novel Approach to the Development of Effective H5N1 Influenza A Virus Vaccines: Use of M2 Cytoplasmic Tail Mutants”, Journal of Virology, vol. 82, No. 5, 2008, pp. 2486-2492.
Zebedee et al., “Influenza A Virus M2 Protein: Monoclonal Antibody Restriction of Virus Growth and Detection of M2 in Virions”, Journal of Virology, vol. 62, No. 8, 1988, pp. 2762-2772.

* cited by examiner

FIGURE 3

"wild-type" M1/M2 nucleic acid sequence (5' to 3')

AGCAAAAGCAGGTAGATATTGAAAGatgagtcttctaaccgaggtcgaaacGTACGTACTCTCTATC
ATCCCGTCAGGCCCCCTCAAAGCCGAGATCGCACAGAGACTTGAAGATGTCTTTGCA
GGGAAGAACACCGATCTTGAGGTTCTCATGGAATGGCTAAAGACAAGACCAATCCT
GTCACCTCTGACTAAGGGGATTTTAGGATTTGTGTTCACGCTCACCGTGCCCAGTGA
GCGAGGACTGCAGCGTAGACGCTTTGTCCAAAATGCCCTTAATGGGAACGGGGATC
CAAATAACATGGACAAAGCAGTTAAACTGTATAGGAAGCTCAAGAGGGAGATAACA
TTCCATGGGGCCAAAGAAATCTCACTCAGTTATTCTGCTGGTGCACTTGCCAGTTGT
ATGGGCCTCATATACAACAGGATGGGGGCTGTGACCACTGAAGTGGCATTTGGCCT
GGTATGTGCAACCTGTGAACAGATTGCTGACTCCCAGCATCGGTCTCATAGGCAAAT
GGTGACAACAACCAATCCACTAATCAGACATGAGAACAGAATGGTTTTAGCCAGCA
CTACAGCTAAGGCTATGGAGCAAATGGCTGGATCGAGTGAGCAAGCAGCAGAGGCC
ATGGAGGTTGCTAGTCAGGCTAGACAAATGGTGCAAGCGATGAGAACCATTGGGAC
TCATCCTAGCTCCAGTGCTGGTCTGAAAAATGATCTTCTTGAAAATTTGCAGgcctatcag
aaacgaatgggggtgcagatgcaacggttcaagtgatcctctcactattgccgcaaatatcattgggatcttgcacttgacattgtggattcttg
atcgtctttttttcaaatgcatttaccgtcgctttaaatacggactgaaaggagggccttctacggaaggagtgccaaagtctatgagggaaga
atatcgaaaggaacagcagagtgctgtggatgctgacgatggtcattttgtcagcatagagctggagtaaAAAACTACCTTGTT
TCTACT FIGURE 5
A. Anti-PR8 polyclonal sera
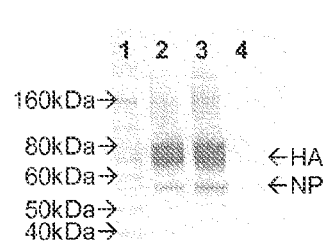
B. Anti-M2 monoclonal antibody
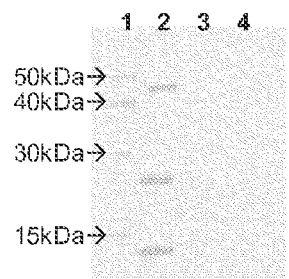

PR8 H1N1 challenge

Aichi (H3N2) challenge

FIGURE 20
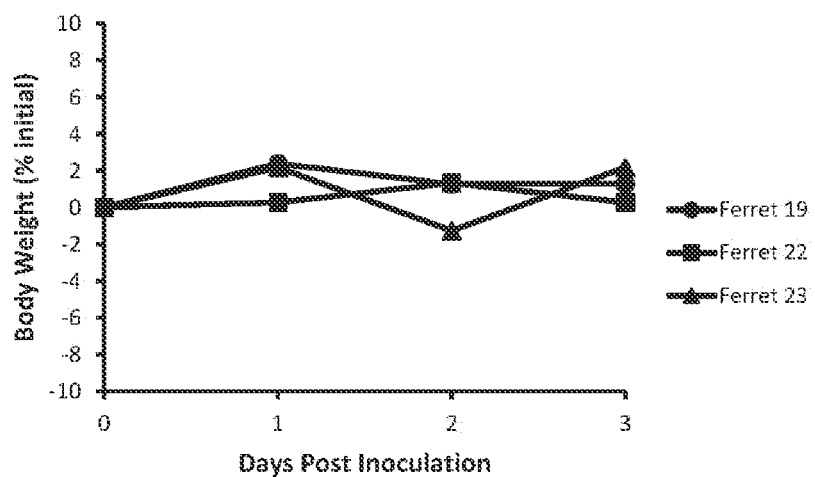
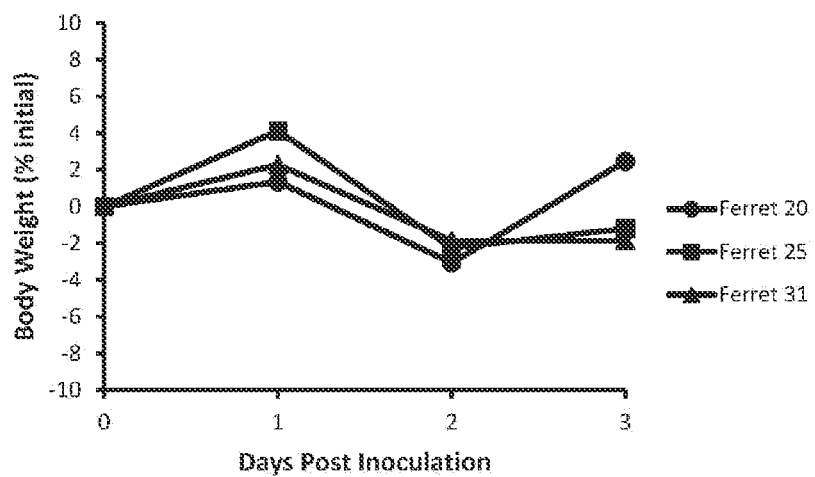

FIGURE 21
A.
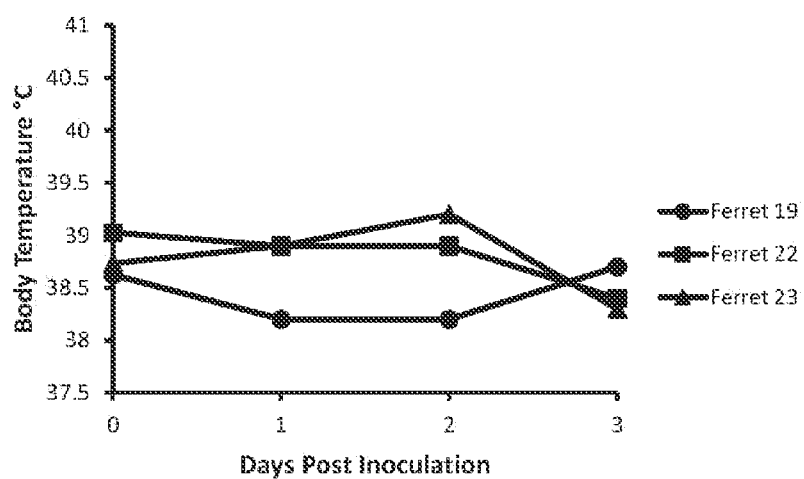
B.
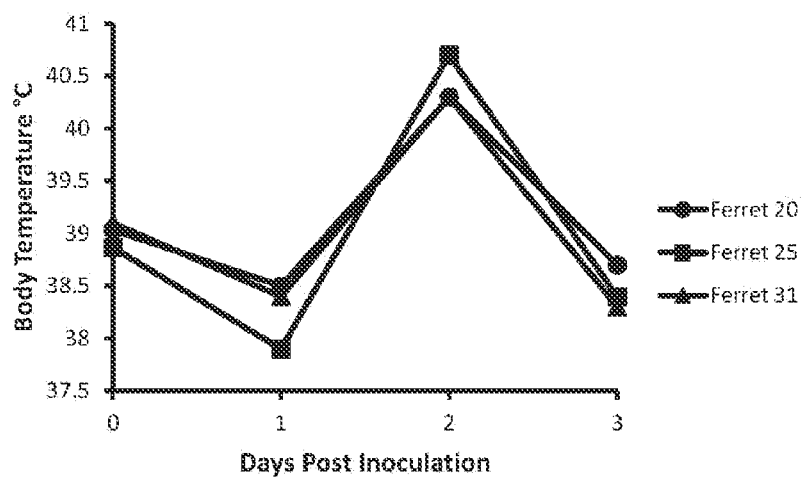

FIGURE 22
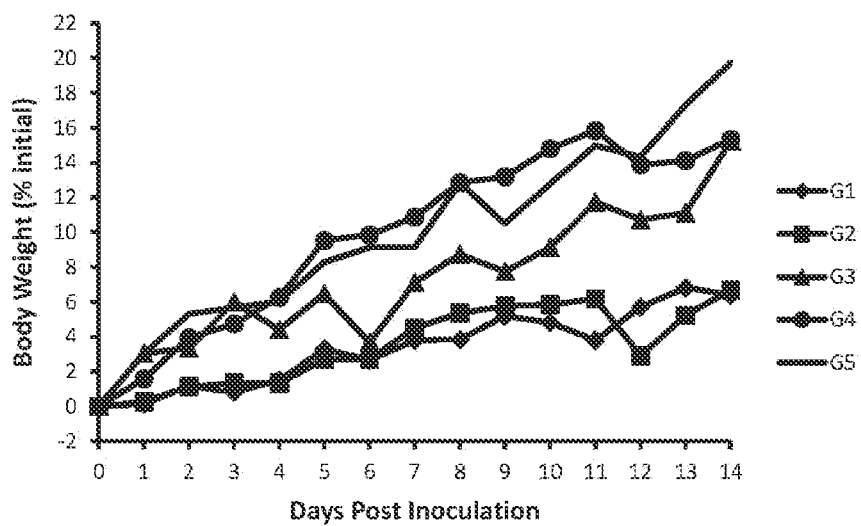
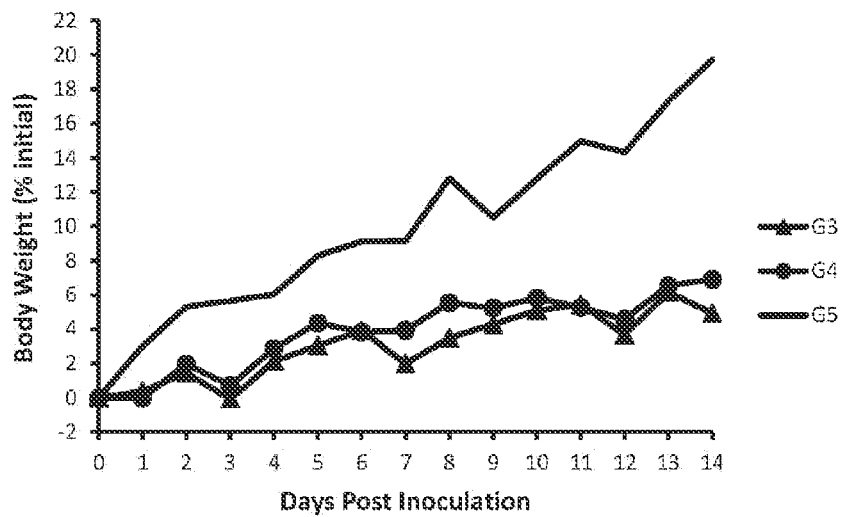

FIGURE 24
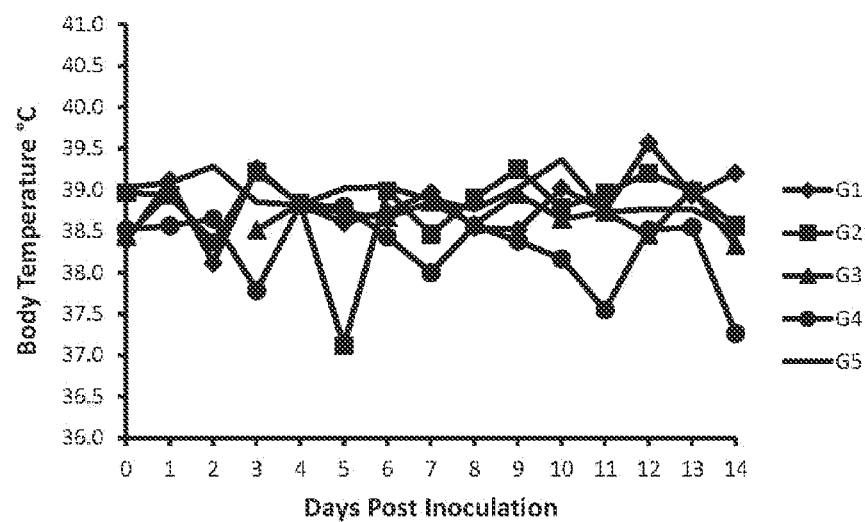
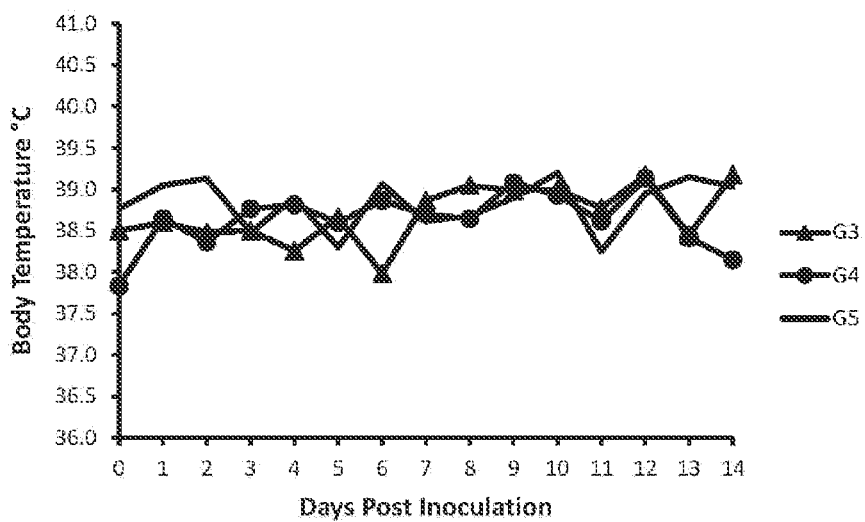

FIGURE 26
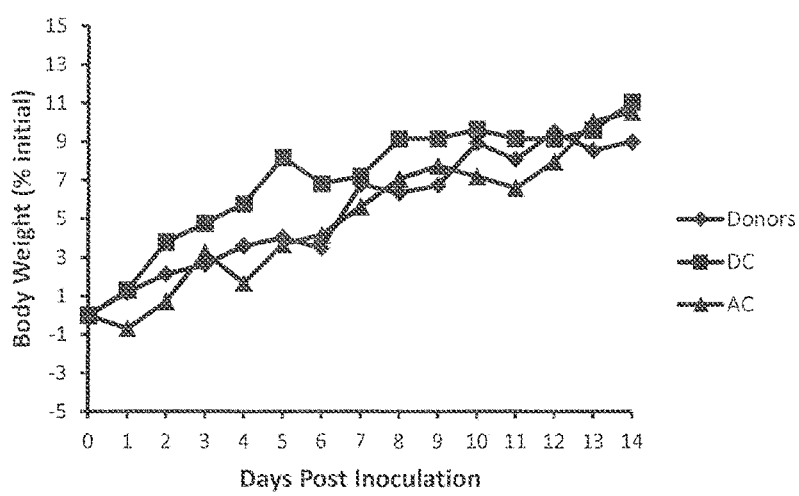
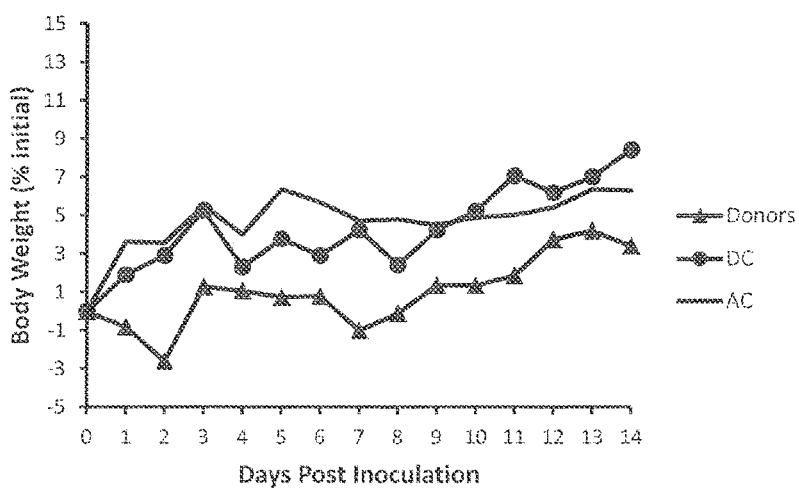

FIGURE 27
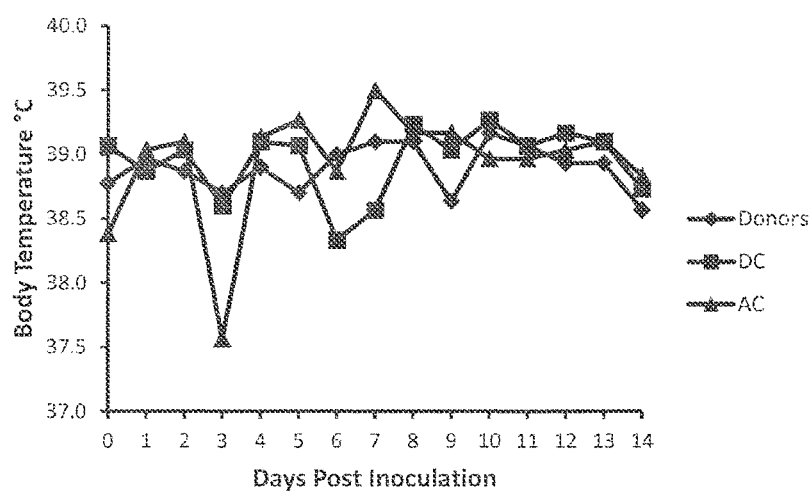
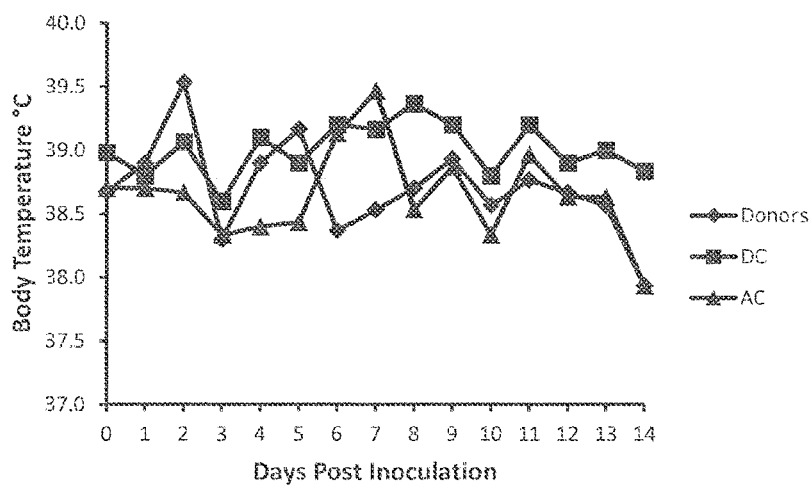

FIGURE 28
A. Sera
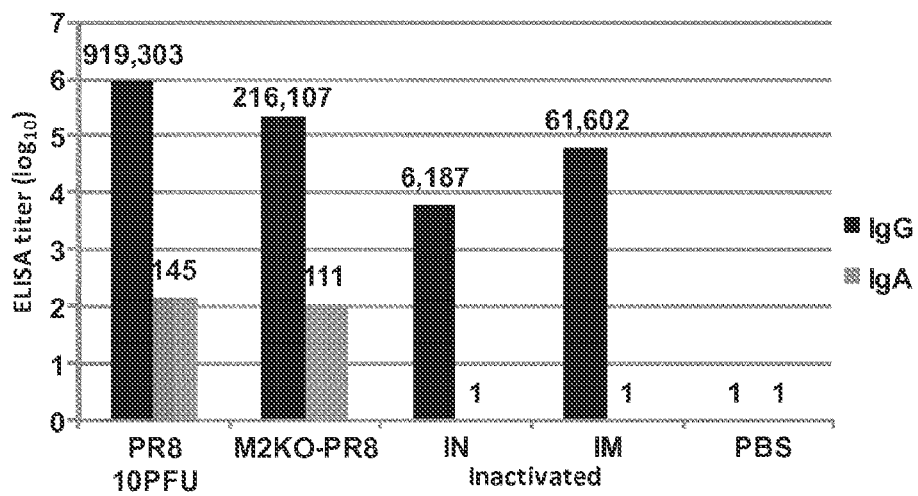
B. Lung Wash
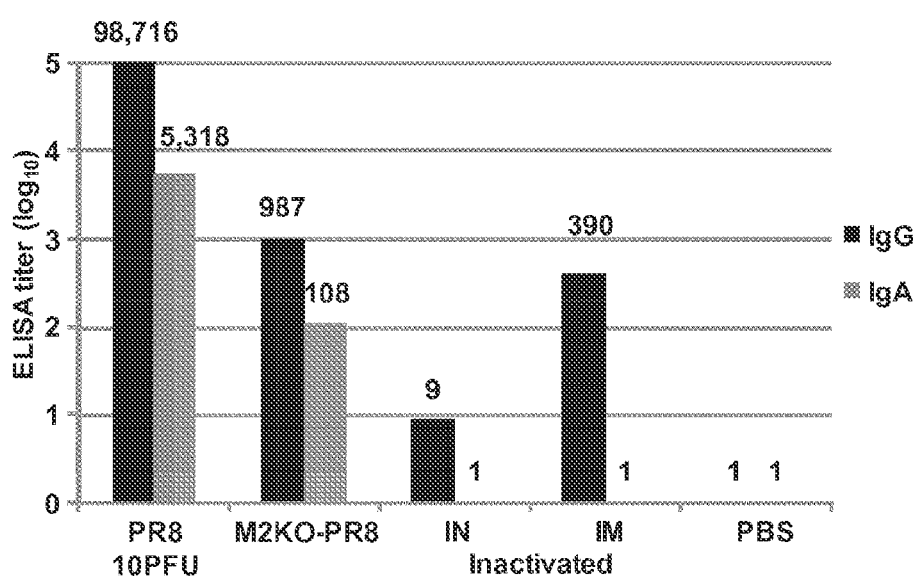

FIGURE 29
A. Mouse body weight change after homologous PR8 (H1N1) challenge.
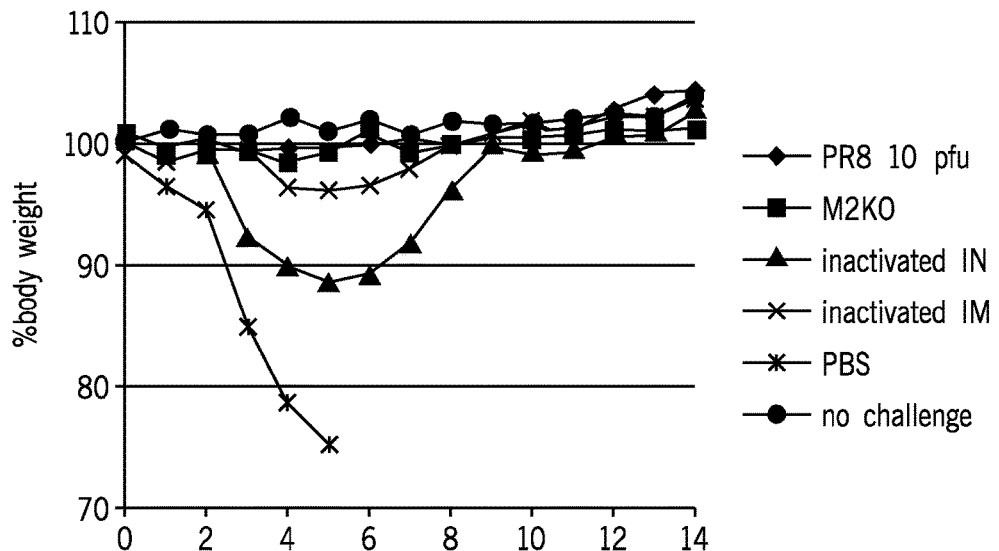
B. Mouse survival after heterologous Aichi (H3N2) challenge.
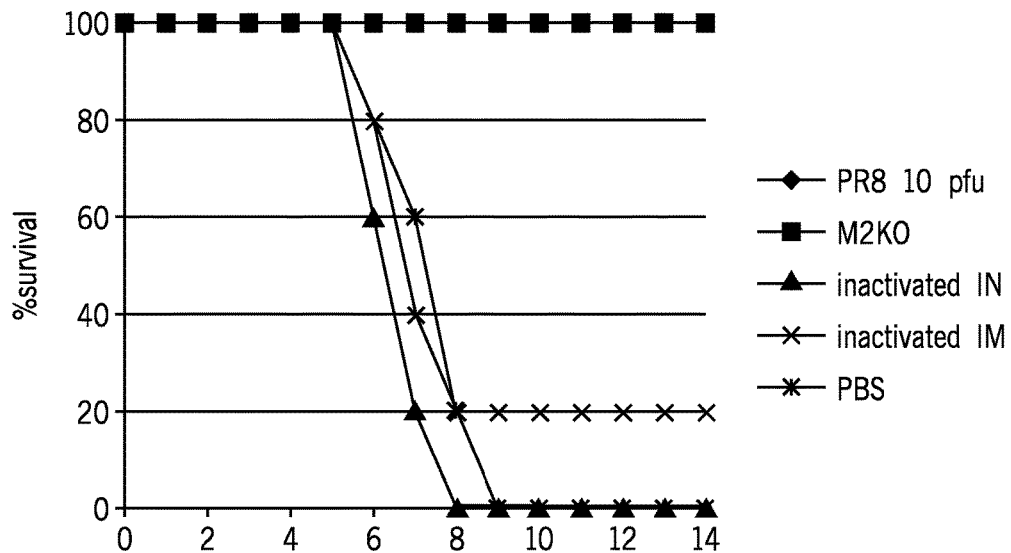

FIGURE 30
A. Virus titers after PR8 (H1N1) challenge
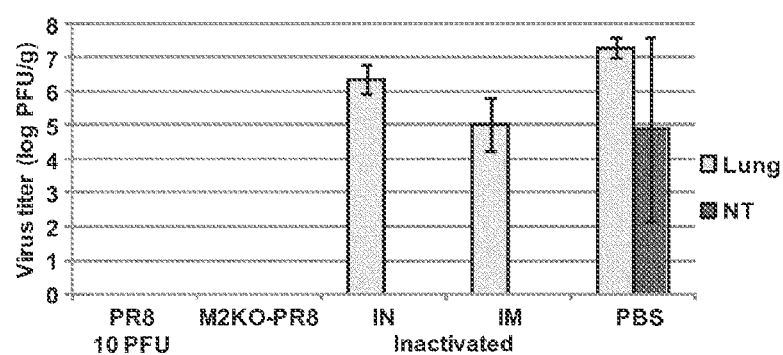
B. Virus titers after Aichi (H3N2) challenge
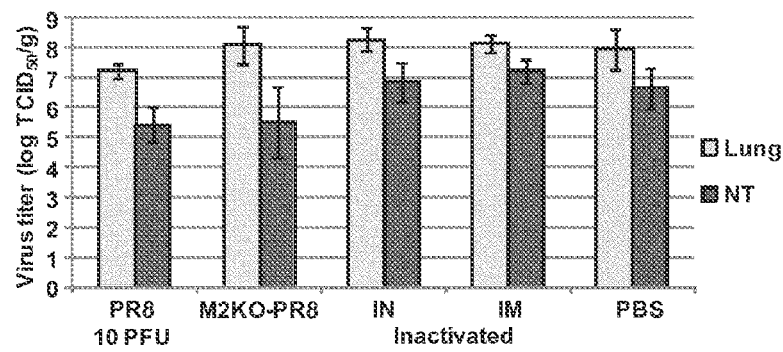

Brisbane 10

Legend: Donor A, Donor B, Donor C, Contact A, Contact B, Contact C, Aerosol A, Aerosol B, Aerosol C X-axis: Days post inoculation or introduced (1, 3, 5, 7, 9, 14)
Y-axis: Virus titer (1, 10, 100, 1000, 10000, 100000, 1000000)

FIGURE 53

| | Guinea Pig | day 0 | day 30 | day 60 | |
|---|---|---|---|---|---|
| Saline | 1 | 1 | 1 | 263 | |
| | 2 | 1 | 1 | 1 | |
| | 3 | 1 | 100 | 259 | Av. 211 ± 59 |
| | 4 | 1 | 1 | 1 | |
| | 5 | 1 | 1 | 150 | |
| | 6 | 1 | 1 | 170 | |
| IM (prime boost) | 13 | 1 | 2,238 | 8,272 | |
| | 14 | 1 | 3,217 | 8,794 | |
| | 15 | 1 | 770 | 25,799 | Av. 15,877 ± 12,333 |
| | 16 | 318 | 3,952 | 7,408 | |
| | 17 | 1 | 9,276 | 36,543 | |
| | 18 | 1 | 1,109 | 8,446 | |
| ID FGN (prime boost) | 19 | 1 | 2,072 | 7,220 | |
| | 20 | 1 | 4,254 | 5,545 | |
| | 21 | 188 | 6,765 | 9,589 | Av. 6,391 ± 3,109 |
| | 22 | 124 | 792 | 941 | |
| | 23 | 1 | 7,402 | 9,015 | |
| | 24 | 1 | 3,397 | 6,034 | |
| IM (prime only) | 31 | 1 | 1,696 | 3,778 | |
| | 32 | 1 | 1,720 | 1,181 | |
| | 33 | 273 | 897 | 2,533 | Av. 3,463 ± 2,704 |
| | 34 | 1 | 5,530 | 2,425 | |
| | 35 | 1 | 6,929 | 8,714 | |
| | 36 | 1 | 1,070 | 2,147 | |
| ID FGN (prime only) | 37 | 119 | 5,217 | 6,875 | |
| | 38 | 1 | 7,785 | 8,812 | |
| | 39 | 1 | 5,404 | 7,041 | Av. 6,312 ± 1,966 |
| | 40 | 1 | 2,426 | 2,894 | |
| | 41 | 1 | 5,707 | 6,616 | |
| | 42 | 1 | 2,063 | 5,634 | |

FIGURE 57 (cont.)

```
                        490       500       510       520       530       540       550       560
                  ----------+---------+---------+---------+---------+---------+---------+---------+
PR8 M             ACAGATTGCTGACTCCCAGCATCGGTCTCATAGGCAAATGGTGACAACCAATCCACTAATCAGACATGAGAACAGAA 560
M2SR-TMdel        ACAGATTGCTGACTCCCAGCATCGGTCTCATAGGCAAATGGTGACAACCAATCCACTAATCAGACATGAGAACAGAA 560
M2SR-TMdel-His    ACAGATTGCTGACTCCCAGCATCGGTCTCATAGGCAAATGGTGACAACCAATCCACTAATCAGACATGAGAACAGAA 560

570       580       590       600       610       620       630       640
                  ----------+---------+---------+---------+---------+---------+---------+---------+
PR8 M             TGGTTTTAGCCAGCACTACAGCTAAGGCTATGGAGCAAATGGCTGAGTGAGCAAGCAGCAGAGAGGCCATGGAGGTT 640
M2SR-TMdel        TGGTTTTAGCCAGCACTACAGCTAAGGCTATGGAGCAAATGGCTGAGTGAGCAAGCAGCAGAGAGGCCATGGAGGTT 640
M2SR-TMdel-His    TGGTTTTAGCCAGCACTACAGCTAAGGCTATGGAGCAAATGGCTGAGTGAGCAAGCAGCAGAGAGGCCATGGAGGTT 640

650       660       670       680       690       700       710       720
                  ----------+---------+---------+---------+---------+---------+---------+---------+
PR8 M             GCTAGTCAGGCTAGACAAATGGTGCAAGCGATGAGAACGATGAGAACCATTGGGACTCATCCTAGCTCCAGTGCTGGTCTGAAAAATGA 720
M2SR-TMdel        GCTAGTCAGGCTAGACAAATGGTGCAAGCGATGAGAACGATGAGAACCATTGGGACTCATCCTAGCTCCAGTGCTGGTCTGAAAAATGA 720
M2SR-TMdel-His    GCTAGTCAGGCTAGACAAATGGTGCAAGCGATGAGAACGATGAGAACCATTGGGACTCATCCTAGCTCCAGTGCTGGTCTGAAAAATGA 720

730       740       750       760       770       780       790       800
                  ----------+---------+---------+---------+---------+---------+---------+---------+
PR8 M             TCTTCTTGAAAATTTGCAGGCCTATCAGAAACGAATGGGGTGCAGATGCAACGTTCAAGTGATCCTCTCACTATTGCC 800
M2SR-TMdel        TCTTCTTGAAAATTTGCAGGCCTATCAGAAACGAATGGGGTGCAGATGCAACGTTCAAGTGAT------------- 785
M2SR-TMdel-His    TCTTCTTGAAAATTTGCAGGCCTATCAGAAACGAATGGGGTGCAGATGCAACGTTCAAGTGATGCGACCACCACCAC 800

810       820       830       840       850       860       870       880
                  ----------+---------+---------+---------+---------+---------+---------+---------+
PR8 M             GCAAATATCATTGGGATCTTGCACTTGACATTGTGACATTCTTGATCGTCTTTTTTCAAATGCATTTACCGTCGCTTTAA 880
M2SR-TMdel        ---------------------------------------TAATAGGATCGTCTTTTTTCAAATGCATTTACCGTCGCTTTAA 829
M2SR-TMdel-His    CACCATCATCACCACCACCACCAC---------------TAATAG----------------TGCATTTACCGTCGCTTTAA 850
```

FIGURE 57 (cont.)

```
                     890       900       910       920       930       940       950       960
                       +---------+---------+---------+---------+---------+---------+---------+
PR8 M             ATACGGACTGAAAGGAGGGCCCTTCTACGGAAGGAGTGCCAAAGTCTATGAGGAAGAATATCGAAAGGAACAGCAGAGTG   960
M2SR-TMdel        ATACGGACTGAAAGGAGGGCCCTTCTACGGAAGGAGTGCCAAAGTCTATGAGGAAGAATATCGAAAGGAACAGCAGAGTG   909
M2SR-TMdel-His    ATACGGACTGAAAGGAGGGCCCTTCTACGGAAGGAGTGCCAAAGTCTATGAGGAAGAATATCGAAAGGAACAGCAGAGTG   930

970       980       990

INFLUENZA VIRUS VECTORS AND USES THEREFOR

CROSS-REFERENCE TO RELATED APPLICATIONS

This application is a 371(c) National Stage entry of PCT/US2015/020580, filed Mar. 13, 2015, which claims priority to U.S. Provisional Application No. 61/954,346, filed Mar. 17, 2014, the contents of which are incorporated by reference in their entireties.

SEQUENCE LISTING

The instant application contains a Sequence Listing which has been submitted electronically in ASCII format and is hereby incorporated by reference in its entirety. Said ASCII copy, created on May 1, 2015, is named 090248-0139_SL.Txt and is 55,935 bytes in size.

BACKGROUND

Vaccination is an important method for preventing infectious disease, using live, attenuated, or inactivated (killed) pathogens. Administration of live and attenuated pathogens carries a risk of the recipients developing active infections. By contrast, delivery of isolated epitopes derived from infectious agents presents considerably less risk to the recipient.

SUMMARY

In one aspect, the present disclosure provides a nucleic acid sequence comprising SEQ ID NO:35, wherein SEQ ID NO:35 further comprises a nucleic acid sequence encoding one or more foreign antigens. In some embodiments, the nucleic acid sequence further comprises part or all of SEQ ID NO:36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In one aspect, the present disclosure provides a composition comprising a nucleic acid sequence comprising SEQ ID NO:35, wherein SEQ ID NO:35 further comprises a nucleic acid sequence encoding one or more foreign antigens, operably linked to (i) a promoter, and (ii) a transcription termination sequence. In some embodiments, the nucleic acid further comprises part or all of SEQ ID NO:36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the wherein the one or more foreign antigens elicits an immune response in a host subject.

In one aspect, the present disclosure provides a recombinant influenza virus, comprising a nucleic acid sequence comprising SEQ ID NO:35, wherein SEQ ID NO:35 further comprises a nucleic acid sequence encoding one or more foreign antigens. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In one aspect, the present disclosure provides a vaccine comprising a recombinant influenza virus comprising a nucleic acid sequence comprising SEQ ID NO:35, wherein SEQ ID NO:35 further comprises a nucleic acid sequence encoding one or more foreign antigens. In some embodiments, the nucleic acid further comprises part or all of SEQ ID NO:36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In one aspect, the present disclosure provides a method for propagating a recombinant influenza virus, comprising: contacting a host cell with a recombinant influenza virus comprising a nucleic acid sequence comprising SEQ ID NO:35, wherein SEQ ID NO:35 further comprises a nucleic acid sequence encoding one or more foreign antigens, incubating the host cell for a sufficient time and under conditions suitable for viral replication, and isolating progeny virus particles. In some embodiments, the recombinant influenza virus further comprises part or all of SEQ ID NO:36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In one aspect, the present disclosure provides a method of preparing a vaccine, comprising: placing a host cell in a bioreactor; contacting the host cell with a recombinant virus comprising a nucleic acid sequence comprising SEQ ID NO:35, wherein SEQ ID NO:35 further comprises a nucleic acid sequence encoding one or more foreign antigens, incubating the host cell for a sufficient time and under conditions suitable for viral propagation; isolating the progeny virus particles; and formulating the progeny virus particles for administration as a vaccine. In some embodiments, the nucleic acid sequence further comprises part or all of SEQ ID NO: 36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In one aspect, the present disclosure provides a method for immunizing a subject, comprising: administering a composition comprising a recombinant influenza virus comprising a nucleic acid sequence comprising SEQ ID NO:35, wherein SEQ ID NO:35 further comprises a nucleic acid sequence encoding one or more foreign antigens. In some embodiments, the nucleic acid sequence further comprises part or all of SEQ ID NO:36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In one aspect, the present disclosure provides a method for reducing the likelihood or severity of infection by a pathogen in a subject comprising: administering a composition comprising a nucleic acid sequence comprising SEQ ID NO:35, wherein SEQ ID NO:35 further comprises a nucleic acid sequence encoding one or more foreign antigens, wherein the one or more foreign antigens comprises an antigen derived from a pathogen. In some embodiments, the nucleic acid sequence further comprises part or all of SEQ ID NO:36. In some embodiments, the pathogen comprises a virus, bacteria, fungus, protozoan, multi-cellular parasite, or prion. In some embodiments, the one or more foreign antigens elicits an immune response in a host subject. In some embodiments, the method comprises providing at least one booster dose of the composition, wherein the at least one booster dose is provided at three weeks after a first administration. In some embodiments, the method comprises administering the composition intranasally, intramuscularly or intracutaneously. In some embodiments, the administering is performed intracutaneously. In some embodiments, the administering is performed using a microneedle delivery device.

In one aspect, the present disclosure provides a kit comprising a nucleic acid sequence comprising SEQ ID NO:35, wherein SEQ ID NO:35 further comprises a nucleic acid sequence encoding one or more foreign antigens, or a kit comprising the nucleic acid of SEQ ID NO:35 in an expression vector. In some embodiments, the nucleic acid sequence further comprises part or all of SEQ ID NO:36. In some embodiments, the one or more foreign antigens comprises an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject. In some embodiments, the further comprises one or more expression vectors comprising influenza viral genes.

In one aspect, the present disclosure provides a composition for eliciting an immune response in a subject, comprising an influenza viral vector, wherein the influenza viral vector comprises nucleic acid encoding one or more foreign antigens. In some embodiments, the influenza viral vector nucleic acid bears a mutation in the M gene. In some embodiments, the mutation is in the M2 gene. In some embodiments, the mutation causes the loss of M2 expression. In some embodiments, the mutation causes the expression of a truncated M2 protein. In some embodiments, the virus comprises SEQ ID NO:1 or a variant thereof. In some embodiments, the virus comprises SEQ ID NO:34 or a variant thereof. In some embodiments, the virus comprises SEQ ID NO:35 or a variant thereof.

In one aspect, the present disclosure provides a method for eliciting an immune response in a subject, comprising administering to the subject an influenza viral vector, wherein the influenza viral vector comprises nucleic acid encoding one or more foreign antigens. In some embodiments, the influenza viral vector nucleic acid bears a mutation in the M gene. In some embodiments, the mutation is in the M2 gene. In some embodiments, the mutation causes the loss of M2 expression. In some embodiments, the mutation causes the expression of a truncated M2 protein. In some embodiments, the virus comprises SEQ ID NO:1 or a variant thereof. In some embodiments, the virus comprises SEQ ID NO:34 or a variant thereof. In some embodiments, the virus comprises SEQ ID NO:35 or a variant thereof. In some embodiments, the composition comprises a recombinant influenza virus comprising the nucleic acid of SEQ ID NO:1. In some embodiments, the one or more foreign antigens are expressed from within a viral gene selected from the group consisting of the M2 gene, the M1 gene, the NA gene, the HA gene, the NS gene, the NP gene, the PA gene, the PB1 gene, and the PB2 gene. In some embodiments, part or all of the viral gene is deleted and replaced with the one or more foreign antigens.

In one aspect, the present disclosure provides a kit comprising the nucleic acid of SEQ ID NO: 35 in an expression vector. In some embodiments, the kit further comprises one or more expression vectors comprising influenza viral genes.

BRIEF DESCRIPTION OF THE DRAWINGS

FIG. 3 shows the nucleotide sequence (SEQ ID NO:28) of unprocessed M1 and M2.

FIG. 5 is a western blot showing that M2KO(ΔTM) virus produces viral antigens, but not M2, in normal cells. Cellular lysates were probed with PR8-infected mouse sera (panel A) or anti-M2 monoclonal antibody (panel B). Lane 1, Molecular weight marker; Lane 2, MDCK cells infected with PR8; Lane 3 MDCK cells infected with M2KO(ΔTM); Lane 4, Uninfected MDCK cells.

FIG. 20 is a chart showing changes in body weight of inoculated ferrets. Ferrets were inoculated with $10^7$ TCID$_{50}$ of M2KO(ΔTM) virus (panel A) or with $10^7$ TCID$_{50}$ of A/Brisbane/10/2007 (H3N2) influenza A virus (panel B). Body weight was monitored for 3 days post inoculation.

FIG. 21 is a chart showing changes in body temperature of inoculated ferrets. Ferrets were inoculated with $10^7$ TCID$_{50}$ of M2KO(ΔTM) virus (panel A) or with $10^7$ TCID$_{50}$ of A/Brisbane/10/2007 (H3N2) influenza A virus (panel B). Body temperature was monitored for 3 days post inoculation.

FIG. 22 is a chart showing changes in body weight of ferrets after vaccination. Ferrets were inoculated with $10^7$ TCID$_{50}$ of M2KO(ΔTM) virus [G1 and G3], with $10^7$ TCID$_{50}$ of FM#6 virus [G2 and G4] or OPTI-MEM™ [G5]. Changes in body weight were monitored for 14 days following prime vaccination (panel A) and after receiving a booster vaccine (panel B).

FIG. 24 is a chart showing changes in body temperature of ferrets after vaccination. Ferrets were inoculated with $10^7$ TCID$_{50}$ of M2KO(ΔTM) virus [G1 and G3], with $10^7$ TCID$_{50}$ of FM#6 virus [G2 and G4] or OPTI-MEM™ [G5]. Changes in body temperature were monitored for 14 days following prime vaccination (panel A) and after receiving a booster vaccine (panel B).

FIG. 26 is a chart showing changes in weight of ferrets after virus inoculation. Donor ferrets were inoculated on day 0 with either $10^7$ TCID$_{50}$ of M2KO(ΔTM) virus (panel A) or with $10^7$ TCIDso of A/Brisbane/10/2007 (H3N2) virus (panel B). 24 hours (Day 1) after inoculation donors were placed in a cage with direct contacts (DC) adjacent to a cage housing an aerosol contact (AC). Changes in body weight were monitored for 14 days following donor inoculation.

FIG. 27 is a chart showing changes in body temperature of ferrets after virus inoculation. Donor ferrets were inoculated on day 0 with either $10^7$ TCID$_{50}$ of M2KO(ΔTM) virus (panel A) or with $10^7$ TCID$_{50}$ of A/Brisbane/10/2007 (H3N2) virus (panel B). 24 hours (Day 1) after inoculation donors were placed in a cage with direct contacts (DC) adjacent to a cage housing an aerosol contact (AC). Changes in body temperature were monitored for 14 days following donor inoculation.

FIG. 28 is a chart showing that M2KO(ΔTM) vaccine elicits humoral and mucosal responses. Panel A shows serum IgG and IgA titers following administration of PR8, M2KO(ΔTM), inactivated PR8 (IN, IM), or PBS. Panel B shows lung wash IgG and IgA titers following administration of PR8, M2KO(ΔTM), inactivated PR8 (IN, IM), or PBS.

FIG. 29 is a chart showing that M2KO(ΔTM) vaccine protects mice from lethal homosubtypic and heterosubtypic viral challenge. Panel A shows mouse body weight change following homologous PR8 (H1N1) challenge. Panel B shows mouse survival following heterologous Aichi (H3N2) challenge.

FIG. 30 is a chart showing that M2KO(ΔTM) vaccine controls challenge virus replication in respiratory tract. Panel A shows viral titers following PR8 (H1N1) challenge. Panel B shows viral titers following Aichi (H3N2) challenge.

FIG. 44A-D is a chart showing a sequence alignment of pCMV-PR8-M2 to the open reading frame of the influenza M2 gene. FIG. 44 discloses SEQ ID NOS 29-33, respectively, in order of appearance.

FIG. 50 is a chart showing viral titers in nasal washes from ferrets in transmission study. M2KO(ΔTM) virus did not transmit (no virus detected), whereas the control Brisb/10 virus did transmit.

FIG. 53 is a chart showing viral titers in guinea pigs inoculated with FluLaval: A/California/7/2009 NYMC X-181, A/Victoria/210/2009 NYMC X-187 (an A/Perth/16/2009-like virus), and B/Brisbane/60/2008 by intramuscular (IM) and intradermal (ID) delivery at 0, 30, and 60 days post-inoculation.

DETAILED DESCRIPTION

I. Definitions

Figure 1:
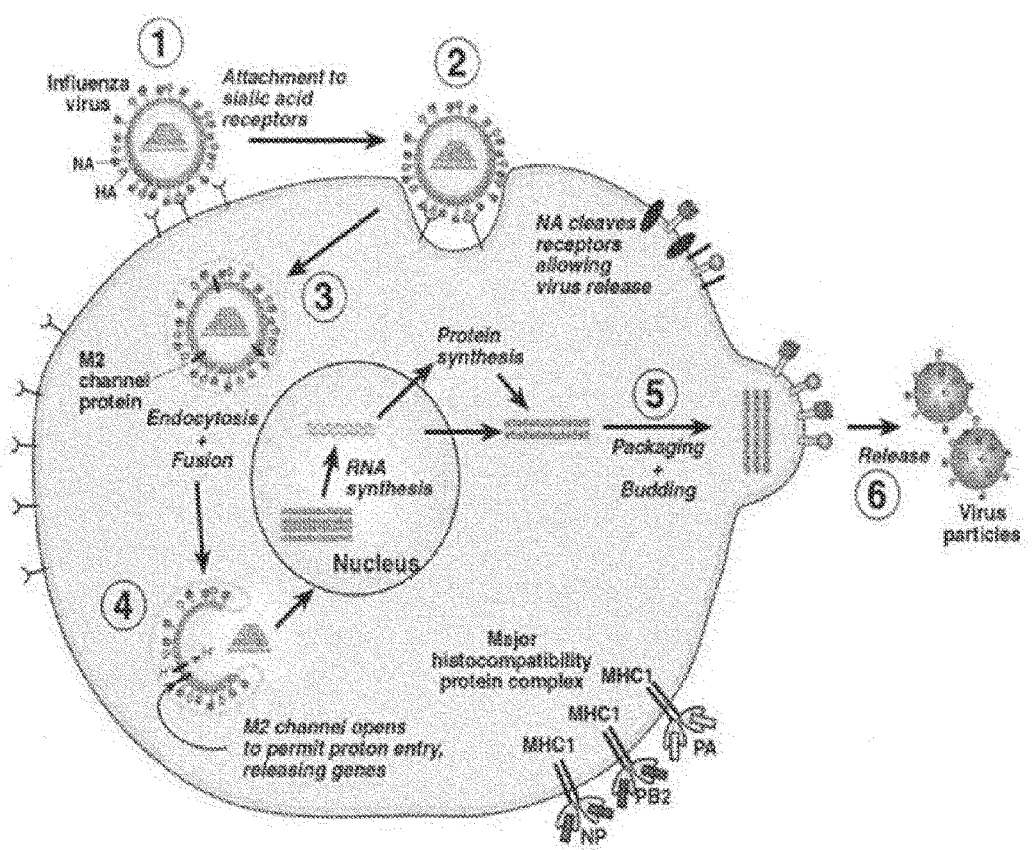
FIG. 1 is a graphic depicting the role of M2 ion channel in an influenza virus life cycle, wherein (1) the influenza virus attaches to sialic acid receptors on a cell surface; (2) the virus is internalized into the cell; (3) the M2 ion channel is expressed on the viral surface; (4) the M2 ion channel opens to permit proton entry, leading to a release of viral RNA that enters the nucleus, is replicated and results in viral protein synthesis; and (5) the viral components are packaged into virions and released.

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" and "patient" are used interchangeably and refer to an animal, for example, a member of any vertebrate species. The methods and compositions of the presently disclosed subject matter are particularly useful for warm-blooded vertebrates including mammals and birds. Exemplary subjects may include mammals such as humans, as well as mammals and birds of importance due to being endangered, of economic importance (animals raised on farms for consumption by humans) and/or of social importance (animals kept as pets or in zoos) to humans. In some embodiments, the subject is a human. In some embodiments, the subject is not human.

As used herein, the terms "effective amount" or "therapeutically effective amount" or "pharmaceutically effective amount" refer to a quantity sufficient to achieve a desired therapeutic and/or prophylactic effect, e.g., an amount which results in the prevention of, disease, condition and/or symptom(s) thereof. In the context of therapeutic or prophylactic applications, the amount of a composition administered to the subject will depend on the type and severity of the disease and on the characteristics of the individual, such as general health, age, sex, body weight and tolerance to the composition drugs. It will also depend on the degree, severity and type of disease or condition. The skilled artisan will be able to determine appropriate dosages depending on these and other factors. In some embodiments, multiple doses are administered. Additionally or alternatively, in some embodiments, multiple therapeutic compositions or compounds (e.g., immunogenic compositions, such as vaccines) are administered.

As used herein, the terms "isolated" and/or "purified" refer to in vitro preparation, isolation and/or purification of a nucleic acid (e.g., a vector or plasmid), polypeptide, virus or cell such that it is not associated with unwanted in vivo substances, or is substantially purified from unwanted in vivo substances with which it normally occurs. For example, in some embodiments, an isolated virus preparation is obtained by in vitro culture and propagation, and is substantially free from other infectious agents. As used herein, "substantially free" means below the level of detection for a particular compound, such as unwanted nucleic acids, proteins, cells, viruses, infectious agents, etc. using standard detection methods for that compound or agent.

As used herein the term "recombinant virus" refers to a virus that has been manipulated in vitro, e.g., using recombinant nucleic acid techniques, to introduce changes to the viral genome and/or to introduce changes to the viral proteins. For example, in some embodiments, recombinant viruses may include both wild-type, endogenous, nucleic acid sequences and mutant and/or exogenous nucleic acid sequences. Additionally or alternatively, in some embodiments, recombinant viruses may include modified protein components, such as mutant or variant matrix, hemagglutinin, neuraminidase, nucleoprotein, non-structural and/or polymerase proteins.

As used herein the term "recombinant cell" or "modified cell" refer to a cell that has been manipulated in vitro, e.g., using recombinant nucleic acid techniques, to introduce nucleic acid into the cell and/or to modify cellular nucleic acids. Examples of recombinant cells includes prokaryotic or eukaryotic cells carrying exogenous plasmids, expression vectors and the like, and/or cells which include modifications to their cellular nucleic acid (e.g., substitutions, mutations, insertions, deletions, etc., into the cellular genome). An exemplary recombinant cell is one which has been manipulated in vitro to express an exogenous protein, such as a viral M2 protein.

As used herein the terms "mutant," "mutation," and "variant" are used interchangeably and refer to a nucleic acid or polypeptide sequence which differs from a wild-type sequences. In some embodiments, mutant or variant sequences are naturally occurring. In other embodiments, mutant or variant sequences are recombinantly and/or chemically introduced. In some embodiments, nucleic acid mutations include modifications (e.g., additions, deletions, substitutions) to RNA and/or DNA sequences. In some embodiments, modifications include chemical modification (e.g., methylation) and may also include the substitution or addition of natural and/or non-natural nucleotides. Nucleic acid mutations may be silent mutations (e.g., one or more nucleic acid changes which code for the same amino acid as the wild-type sequence) or may result in a change in the encoded amino acid, result in a stop codon, or may introduce splicing defects or splicing alterations. Nucleic acid mutations to coding sequences may also result in conservative or non-conservative amino acid changes.

As used herein, the term "vRNA" refers to the RNA comprising a viral genome, including segmented or non-segmented viral genomes, as well as positive and negative strand viral genomes. vRNA may be wholly endogenous and "wild-type" and/or may include recombinant and/or mutant sequences.

As used herein, the term "host cell" refers to a cell in which a pathogen, such as a virus, can replicate. In some embodiments, host cells are in vitro, cultured cells (e.g., CHO cells, Vero cells, MDCK cells, etc.) Additionally or alternatively, in some embodiments, host cells are in vivo (e.g., cells of an infected vertebrate, such as an avian or mammal). In some embodiments, the host cells may be modified, e.g., to enhance viral production such as by enhancing viral infection of the host cell and/or by enhancing viral growth rate. By way of example, but not by way of limitation, exemplary host cell modifications include recombinant expression of 2-6-linked sialic acid receptors on the cell surface of the host cell, and/or recombinant expression of a protein in the host cells that has been rendered absent or ineffective in the pathogen or virus.

As used herein, the term "infected" refers to harboring a disease or pathogen, such as a virus. An infection can be intentional, such as by administration of a virus or pathogen (e.g., by vaccination), or unintentional, such as by natural transfer of the pathogen from one organism to another, or from a contaminated surface to the organism.

As used herein, the term "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus. This is in contrast to killed or completely inactivated virus.

As used herein, the term "type" and "strain" as used in conjunction with a virus are used interchangeably, and are used to generally refer to viruses having different characteristics. For example, influenza A virus is a different type of virus than influenza B virus. Likewise, influenza A H1N1 is a different type of virus than influenza A H2N1, H2N2 and H3N2. Additionally or alternatively, in some embodiments, different types of virus such as influenza A H2N1, H2N2 and H3N2 may be termed "subtypes."

As used herein, "M2KO" or "M2KO(ΔTM)" refers to SEQ ID NO:1, a virus comprising SEQ ID NO:1, or a vaccine comprising a virus comprising SEQ ID NO:1, depending on the context in which it is used. For example, in describing mutations of the M2 gene demonstrated herein, "M2KO" or "M2KO(ΔTM)" refers to SEQ ID NO:1. When describing the viral component of a vaccine, "M2KO" or "M2KO(ΔTM)" refers to a recombinant influenza virus which possesses internal 6 genes of PR8 (nucleoprotein (NP), polymerase genes (PA, PB1, PB2), non-structural (NS), matrix (M)), but which does not express functional M2 protein. When describing a vaccine, "M2KO" or "M2KO(ΔTM)" refers to a vaccine comprising the M2KO (ΔTM) recombinant virus.

As used herein, "M2KO(ΔTM) virus" encompasses a recombinant influenza virus which possesses internal 6 genes of PR8 (nucleoprotein (NP), polymerase genes (PA, PB1, PB2), non-structural (NS), matrix (M)), but which does not express functional M2 protein, alone or in combination with other viral components and/or genes encoding other viral components. In some embodiments, the M2KO(ΔTM) virus comprises genes of other influenza viruses. In some embodiments, the virus comprises the HA and NA genes of Influenza A/Brisbane/10/2007-like A/Uruguay/716/2007 (H3N2). In some embodiments, the M2KO(ΔTM) virus comprises the HA and NA genes of the A/Vietnam/1203/2004 (H5N1) virus. In some embodiments, the M2KO (ΔTM) virus comprises the HA and NA genes of the A/California/07/2009 (CA07) (H1N1pdm) virus.

As used herein, "infectious disease" refers to transmissible communicable diseases comprising clinically evident illness (i.e., characteristic medical signs and/or symptoms of disease) resulting from the infection, presence, and/or growth of pathogenic agents in an individual host organism. In certain cases, infectious diseases may be asymptomatic for much or even all of their course in a given host. In the latter case, the disease may only be defined as a "disease" (which by definition means an illness) in hosts who secondarily become ill after contact with an asymptomatic carrier. The term "infection" is not synonymous with "infectious disease," as some infections do not cause illness in a host. Exemplary infectious pathogens include, but are not limited to, viruses, bacteria, fungi, protozoa, multi-cellular parasites, and prions. As used herein, "infectivity" refers to the capacity of a pathogenic organism to enter, survive, and multiply in a host organism, while "infectiousness" refers to the relative/comparative ease with which the disease is transmitted among host organisms. Transmission of pathogen can occur in various ways including, but not limited to, direct physical contact with an infected host or a contaminated object, contact with or ingestion of contaminated food or bodily fluid, airborne inhalation of pathogenic particles, or transmission through vector organisms.

As used herein, "pathogen" refers generally to a microorganism or protein (e.g. a prion) that can cause an infectious disease. Exemplary non-limiting examples of pathogens include a virus, bacterium, prion, multi-cellular parasite, or fungus that causes disease in a host organism. The host may be an animal (e.g., mammals, humans), a plant, or another microorganism. As used herein, the term refers to both primary and secondary (e.g. opportunistic) pathogens. As used herein, the term "infectious agent" is synonymous with "pathogen." In some embodiments, foreign epitopes are derived from one or more pathogens.

Non-limiting examples of pathogenic viruses include viruses of the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

Non-limiting examples of pathogenic bacteria include those of the genera *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, and *Yersinia*.

Non-limiting examples of pathogenic fungi include those of the genera *Candida, Aspergillus, Cryptococcus, Histoplasma, Pneumocystis*, and *Stachybotrys*.

Non-limiting examples of pathogenic parasites include protazoa, coccidia, Nematodes, Trematodes, and Cestodes.

Non-limiting examples of pathogenic prions include the causative agents of scrapie, bovine spongiform encephalopathy, and Creutzfeldt-Jakob disease.

As used herein, "antigen" refers to a molecule which can elicit an immune response. In some embodiments, compositions and methods are provided to deliver one or more antigens to a subject, to elicit and immune response in that subject against the antigen (e.g., to confer heightened immunity to the antigen). In some embodiments, an antigen comprises one or more discreet epitopes. In some embodiments, the antigen includes a nucleic acid and/or polypeptide. In some embodiments, "antigen" is used to refer to a nucleic acid which encodes a peptide antigen. The antigen may comprise a whole or partial peptide, polypeptide, or protein, or the nucleic acid encoding such. As used herein, the term also refers to "chimeric" or "fusion" nucleic acid or amino acid sequences, comprising sequences derived from multiple genes or proteins, wherein the multiple genes or proteins are derived from the same or different sources.

In some embodiments, antigens are derived from a pathogen. Non-limiting examples of pathogens include viruses, bacteria, fungi, protozoa, multi-cellular parasites, and prions. In some embodiments, antigens are derived from a molecule present in the host. For example, in some embodiments, antigens are derived from a tumor. Cancer-related antigens include, by way of example but not by way of limitation, proteins or other molecules expressed by tumor or non-tumor cancers, such as molecules that are present in cancer cells but absent in non-cancer cells, and molecules that are up-regulated in cancer cells as compared to non-cancer cells. Non-limiting examples of cancer-related antigens include, but are not limited to antigens derived from Her2/neu, the cancer-testis antigen (NY-ESO-1), and tumor-specific calcitonin. Non-limiting examples of host molecules include cytokines, antibodies, or any host molecule against which an immune response is desired, such as, for example, to neutralize the activity of the molecule.

As used herein, the term "foreign antigen" refers to an antigen not normally identified with, or native to a particular organism. For example, a bacterial antigen or epitope sequence that is cloned into an influenza vector as disclosed herein would be a "foreign antigen" as to the virus/viral vector. The same bacterial antigen or epitope would also be considered a foreign antigen to the subject (e.g., a human). If the antigen is derived from the subject (e.g., a tumor cell molecule), then the antigen would be foreign as to the virus.

As used herein, "viral vector" or "influenza virus vector" or "M2 viral vector" or "M2 vector" refers to an influenza virus comprising a mutation in the M2 gene such that M2 is not expressed, or is expressed but is non-functional (e.g., a truncated, non-functional M2 polypeptide is expressed). As used herein, an "empty" vector refers to a viral vector that does not include nucleic acid sequences of a foreign antigen or epitope of interest. As used herein, a "loaded" vector refers to a viral vector which includes foreign antigen nucleic acid sequences of interest. The M2 mutation may include any of the influenza M2 viral mutants disclosed herein, or variants thereof. In some embodiments, the M2 vectors are used to provide an antigen (e.g., a foreign antigen) to a subject. In some embodiments, the antigen nucleic acid sequence is cloned into the M2 gene, thereby rendering the M2 gene mutant (e.g., not expressed or non-functional). A non-limiting example is shown in SEQ ID NO:34. In SEQ ID NO: 34, an Ala linker and two hexa-his sequences are cloned into a portion of the M2 gene of influenza A.

The viral vectors disclosed herein may be derived from influenza virus A, B or C. While influenza A is exemplified herein, this exemplification is not intended to be limiting, and a corresponding mutation in the M2 functional equivalent of A virus (e.g., the BM2 or NB protein of influenza B, or the CM1 protein of influenza C) is also suitable. The viral vectors disclosed herein typically do not have M2 ion channel activity, exhibit attenuated growth properties in vivo, cannot produce infectious progeny and are non-pathogenic or show reduced pathogenesis in infected subjects. Additionally, the influenza virus vectors disclosed herein are stable, and do not mutate to express a functional M2 polypeptide, regardless of the host cell used. Additionally or alternatively, in some embodiments, the M1 protein of these vectors is produced without detectable alteration to its function. In some embodiments, viruses vectors harboring the mutant M2 nucleic acid sequences cannot replicate in a host cell in which a corresponding wild-type virus could be propagated. By way of example but not by way of limitation, in some embodiments, the wild-type virus can be grown, propagated and replicate in culturing MDCK cells, CHO cells and/or Vero cells, while a corresponding virus vector harboring a mutant M2 sequence cannot grow, replicate or be propagated in the same type of cells. In some embodiments, the M2 virus vector is stable, and does not mutate or revert to wild-type or to a non-wild-type sequence encoding a functional M2 protein in a host cell. For example, in some embodiments, the M2 virus vectors are stable for 2 passages, 3 passages, 5 passages, 10 passages, 12 passages, 15 passages, 20 passages, 25 passages or more than 25 passages in a host cell. In some embodiments, the host cell is an unmodified host cell. In other embodiments, the host cell is a modified host cell, such as a MDCK cell which expresses the M2 protein. In some embodiments, the M2 virus vectors include one or more nucleic acid substitutions and/or deletions. In some embodiments, the mutations are localized in nucleic acids which code for one or more of the extracellular domain of the M2 protein, the transmembrane domain of the M2 proteins and/or the cytoplasmic tail of the M2 protein. Additionally or alternatively, in some embodiments, one or more nucleic acid mutations results in a splice variant, one or more stop codons and/or one or more amino acid deletions of the M2 peptide.

In some embodiments, virus vectors carrying the mutant M2 nucleic acid produce a non-functional M2 polypeptide. In some embodiments, virus vectors carrying the mutant M2 nucleic acid do not produce an M2 polypeptide. In some embodiments, virus vectors carrying the mutant M2 nucleic acid produce a truncated M2 polypeptide. In some embodiments, truncated M2 polypeptide has the amino acid sequence MSLLTEVETPIRNEWGCRCNGSSD (SEQ ID NO:4).

In some embodiments, the viral vector includes SEQ ID NO: 1 or variant thereof. In some embodiments, the viral vector includes SEQ ID NO: 2 or variant thereof. In some embodiments, the viral vector includes SEQ ID NO: 3 or variant thereof. In some embodiments, the variant includes one or more of a linker (e.g., an Ala linker), an epitope sequence, his-tag sequence, stop codon sequence, and nucleic acid deletions. In some embodiments, the viral vector includes SEQ ID NO: 34 or a variant thereof. In some embodiments, the viral vector comprises an influenza virus comprising a corresponding mutation in the M2 functional equivalent of A virus (e.g., the BM2 or NB protein of influenza B, or the CM1 protein of influenza C).

In some embodiments, the viral vector is engineered for cloning and delivery of foreign epitopes to a subject. In some embodiments, the M2 nucleic acid region is engineered to receive one or more epitope sequences. In some embodiments, one or more restriction enzyme sites is provided in the M2 nucleic acid region. In some embodiments, one or more antigens are cloned into an M2 nucleic acid sequence. By way of example, but not by way of limitation, in a viral vector comprising SEQ ID NO: 34, the hexa-his tag sequences are replaced with the antigen sequence(s). In some embodiments, the ala linker and the hexa-his tag sequences are replaced with the antigen sequence(s). In some embodiments, the empty vector comprises SEQ ID NO: 1 and the sequence gcctatcagaaacgaatggggtgcagatgcaacggttcaagtgatTAATAGgatcgtctttttttcaaatgcatttaccgtcgcttt aaatacggactgaaaggagggccttctacggaaggagtgccaaagtctatgagggaagaatatcgaaaggaacagcagagtgctgt ggatgctgacgatggtcattttgtcagcatagagctggagtaa of SEQ ID NO: 1 is fully or partially replaced by an antigen sequence, and is thus absent or truncated in the loaded vector.

In some embodiments, the one or more foreign antigens are expressed from within a viral gene selected from the group consisting of the M2 gene, the M1 gene, the NA gene, the HA gene, the NS gene, the NP gene, the PA gene, the PB1 gene, and the PB2 gene. In some embodiments, part or all of the viral gene is deleted and replaced with the one or more foreign antigens.

The technology of the present disclosure is suitable for inducing immune responses against infectious disease agents. A list of non-limiting, illustrative disease indications suitable for use with the present technology is shown in Table A. One of skill in the art will understand that any infectious disease agent would be suitable for use with the present technology, such as those known in the art and described in public databases such as the Immune Epitope Database available at http://www.iedb.org/.

According to the present disclosure, epitopes from one or more infectious disease agents (foreign epitopes) is cloned into the M2SR virus and delivered to a host. The foreign epitopes are then expressed, and elicit a host immune response against the foreign epitopes. A list of non-limiting, illustrative, infectious disease-related epitopes suitable for use with the present technology is shown in Table B. One of skill in the art will understand that any epitope from any infectious disease agent would be suitable for use with the present technology, such as, without limitation, those known in the art and available in public databases such as the Immune Epitope Database available at http://www.iedb.org/.

TABLE A

Disease Indications

| Fungal Diseases and Agents (Mycotic diseases) | Bacterial, Parasite Diseases and Agents |
|---|---|
| *Cryptococcus gattii* cryptococcosis | *Listeria*, |
| *Cryptococcus neoformans* cryptococcosis | Meningitis - *Haemophilus influenzae* (most often |
| *Candida* Infection [Candidiasis] The most common species is *Candida albicans*. | caused by type b, Hib), *Streptococcus pneumoniae*, group B *Streptococcus, Listeria* |
| *Histoplasma capsulatum* Infection [Histoplasmosis] | *monocytogenes*, and *Neisseria meningitidis*. Methicillin-resistant *Staphylococcus aureus* |
| *Aspergillus* Infection [Aspergillosis] | (MRSA), |
| Blastomycosis [*Blastomyces dermatitidis* infection] | Malaria - *Plasmodium* *Mycoplasma pneumoniae* |
| Fungal Keratitis | Trichomoniasis - *Trichomonas vaginalis* |
| Histoplasmosis [*Histoplasma capsulatum* Infection] | *Chlamydia*, Trachoma - *Chlamydia trachomatis* |
| Mucormycosis - *Mucoromycotina* | Bacterial Vaginosis *Gardnerella* |
| Pneumocystis pneumonia (PCP) [*Pneumocystis jirovecii* pneumonia (previously *Pneumocystis carinii*)] | *Legionella pneumophila, Legionella* sp. *Streptococcus pneumoniae* *Haemophilus influenzae* type b (Hib) |
| Ringworm [Dermatophyte Infection] | *Pertussis* |
| Sporotrichosis [*Sporothrix schenckii* infection] | *Mycobacterium tuberculosis* - Tuberculosis |
| Valley Fever [Coccidioidomycosis] | |
| *Exserohilum, Cladosporium*, | |
| Bioweapons | Select Agents and Toxins |
| Anthrax (*Bacillus anthracis*) | Abrin |
| Botulism (*Clostridium botulinum* toxin) | *Botulinum* neurotoxins* |
| Plague (*Yersinia pestis*) | *Botulinum* neurotoxin producing species of |
| Smallpox (variola major) | *Clostridium*\* |
| Tularemia (*Francisella tularensis*) | Conotoxins (Short, paralytic alpha conotoxins |
| Viral hemorrhagic fevers (filoviruses [e.g., Ebola, Marburg] and arenaviruses [e.g., Lassa, Machupo]) | containing the following amino acid sequence X1CCX2PACGX3X4X5X6CX7)1 *Coxiella burnetii* |
| Brucellosis (*Brucella* species) | Crimean-Congo haemorrhagic fever virus |

TABLE A-continued

Disease Indications

| | |
|---|---|
| Epsilon toxin of *Clostridium perfringens* | Eastern Equine Encephalitis virus |
| Food safety threats (e.g., *Salmonella* species, *Escherichia coli* O157:H7, *Shigella*) | Ebola virus |
| | *Francisella tularensis* |
| Glanders (*Burkholderia mallei*) | Lassa fever virus |
| Melioidosis (*Burkholderia pseudomallei*) | Lujo virus |
| Psittacosis (*Chlamydia psittaci*) | Marburg virus |
| Q fever (*Coxiella burnetii*) | Monkeypox virus |
| Ricin toxin from *Ricinus communis* (castor beans) | Ricin |
| | *Rickettsia prowazekii* |
| Staphylococcal enterotoxin B | SARS-associated coronavirus (SARS-CoV) |
| Typhus fever (*Rickettsia prowazekii*) | Saxitoxin |
| Viral encephalitis (alphaviruses [e.g., Venezuelan equine encephalitis, eastern equine encephalitis, western equine encephalitis]) | South American Haemorrhagic Fever viruses: Chapare |
| | Guanarito |
| Water safety threats (e.g., *Vibrio cholerae*, *Cryptosporidium parvum*) | Junin |
| | Machupo |
| | Sabia |
| | Tick-borne encephalitis complex (flavi) viruses: Far Eastern subtype |
| | Siberian subtype |
| | Kyasanur Forest disease virus |
| | Omsk hemorrhagic fever virus |
| | Variola major virus (Smallpox virus)* |
| | Variola minor virus (Alastrim)* |
| | *Yersinia pestis* |
| Respiratory Virus Disease | Tick Borne Diseases |
| Measles? | Lyme Disease, Babesiosis, *Borellia*, Rocky Mountain spotted fever (RMSF), *Rickettsia*, Chikungunya |
| RSV: RSV F, RSV G, RSV M2 | |
| Rhinovirus? | |
| hMPV | |
| PIV1-4 | |
| Coronavirus | |
| Bocavirus | |
| Adenovirus | |
| Hemorrhagic Fevers | GI |
| Ebola, Marburg, Rift Valley Fever, Lassa Fever, WNV, Dengue Fever, Yellow fever, SARS, MERS | Noroviruses, Rotaviruses, Enteroviruses |
| | *Campylobacter* |
| | *Clostridium difficile*, Toxin A/B |
| | *Escherichia coli* O157 |
| | Enterotoxigenic *E. coli* (ETEC) LT/ST |
| | Shiga-like Toxin producing *E. coli* (STEC) stx1/stx2 |
| | *Salmonella* |
| | *Shigella* |
| | *Vibrio cholerae* |
| | *Yersinia enterocolitica* |
| | *Cryptosporidium* |
| | *Entamoeba histolytica* |
| Others, STDs | HIV |
| Varicella | Cancer |
| HPV | |
| Syphillis - *Treponema pallidum* | |
| Gonorrhea - *Neisseria gonorrhoeae* | |
| HSV | |
| All herpes viruses EBV, HHV6 | |
| CMV and other polyoma viruses like BK | |
| Hepatitis A, B, C, E | |

TABLE B

Illustrative Foreign Epitopes

| Description | Starting Position | Ending Position | Antigen Name |
|---|---|---|---|
| *Bordetella Pertussis* | | | |
| KPDQGEVVAVGPGKKTED | 34 | 51 | 10 kDa chaperonin |
| GVAPTAQQL | 1647 | 1655 | adhesin |
| GVATKGLGVHAKSSDWG | 54 | 70 | Bifunctional hemolysin/adenylate cyclase precursor |

TABLE B-continued

Illustrative Foreign Epitopes

| Description | Starting Position | Ending Position | Antigen Name |
|---|---|---|---|
| QVDLHDLSAARGADISG | 579 | 595 | filamentous hemagglutinin |
| LAAIASAAH | 17 | 25 | fimbrial protein |
| LSAPHGNVIETGGA | 326 | 339 | pertactin |
| STPGIVIPPQEQITQHGSPYGRC | 28 | 50 | pertussis toxin subunit 2 |

Cytomegalovirus: Human herpesvirus 5 strain AD169

| Description | Starting Position | Ending Position | Antigen Name |
|---|---|---|---|
| ALSTPFLMEHTMPVT | 438 | 452 | 45 kDa immediate-early protein 2 |
| KKDELRRKMMYMCYR | 196 | 210 | 55 kDa immediate-early protein 1 |
| MSIYVYALPLKMLNI | 109 | 123 | 65 kDa lower matrix phosphoprotein |
| IMREFNSYK | 683 | 691 | glycoprotein B |
| PSAMLSAI | 498 | 505 | Glycoprotein B precursor |

Ebola virus sp.

| Description | Starting Position | Ending Position | Antigen Name |
|---|---|---|---|
| KQIPIWLPL | 60 | 68 | Chain A, Crystal Structure Of The Matrix Protein Of Ebola Virus |
| TELRTFSI | 577 | 584 | Envelope glycoprotein precursor |
| YQVNNLEEI | 44 | 52 | major nucleoprotein |
| VYQVNNLEEIC | 43 | 53 | Nucleoprotein |
| GRIPVSDIF | 36 | 44 | ORF |

Enteroviruses

| Description | Starting Position | Ending Position | Antigen Name |
|---|---|---|---|
| EAIPALTAVETGHTSQV | 597 | 613 | capsid protein |
| ATCRFYTLDSIK | 128 | 139 | polyprotein VP0 |
| GDVEEAIERAVV | 17 | 28 | VP1 |
| EIPALTAVE | 40 | 48 | coat protein VP1 |
| AHETSLNAAGNSVIHYTNIN | 12 | 31 | polyprotein capsid protein precursor |

Hepatitis C

| Description | Starting Position | Ending Position | Antigen Name |
|---|---|---|---|
| DSTVTENDIRVEESIYQCCDLAPEARQAIKSLTERLY | 231 | 267 | Chain A, Hepatitis C Virus Ns5b Rna-Dependent Rna Polymerase |
| MAPITAYSQQTRGLL | 3 | 17 | Chain A, Ns3/ns4a Protease With Inhibitor |
| QLINTNGSWHVN | 412 | 423 | core envelope protein |
| MSTNPKPQRKTKRN | 1 | 14 | core protein |
| NTYASGGAVGHQTASFVRLLAPGPQQN | 384 | 410 | core, env and part of E2/NS1 |

HIV

| Description | Starting Position | Ending Position | Antigen Name |
|---|---|---|---|
| EIYKRWII | 260 | 267 | gag polyprotein |
| ELDKWA | 662 | 667 | Envelope glycoprotein gp160 precursor |
| GPGHKARVLA | 355 | 364 | Gag polyprotein |
| IVLPEKDSW | 831 | 839 | Gag-Pol polyprotein (Pr160Gag-Pol) |

TABLE B-continued

Illustrative Foreign Epitopes

| Description | Starting Position | Ending Position | Antigen Name |
|---|---|---|---|
| LELDKWAGLWSW | 660 | 671 | Envelope glycoprotein gp160 precursor |

Human parvovirus B19

| Description | Starting Position | Ending Position | Antigen Name |
|---|---|---|---|
| GIMTVTMTFKLGPRKATGRW | 484 | 503 | major capsid protein VP2 |
| GLFNNVLYH | 102 | 110 | Non-capsid protein NS-1 |
| HHRHGYEKPEELWTAKSRVH | 760 | 779 | Probable coat protein VP1 |
| LASEESAFYVLEHSSFQLLG | 204 | 223 | viral protein 2 |
| HGYEKPEELWTAKSRVHPL | 536 | 554 | VP2 protein |

Measles Virus

| Description | Starting Position | Ending Position | Antigen Name |
|---|---|---|---|
| SLWGSGLLML | 166 | 175 | C protein |
| MTRSSHQSLVIKLMP | 46 | 60 | Fusion glycoprotein F0 |
| MGLKVNVSAIFMAVL | 1 | 15 | Fusion glycoprotein F0 precursor |
| ILLERLDVGT | 455 | 464 | fusion protein |
| KFLNPDREYDFRDLT | 123 | 137 | haemagglutinin protein |

Mumps virus

| Description | Starting Position | Ending Position | Antigen Name |
|---|---|---|---|
| GEQARYLALLEA | 307 | 318 | Nucleoprotein |
| NSTLGVKSAREF | 329 | 340 | hemagglutinin-neuraminidase protein |
| G352, P353, D358, R360 | | | hemagglutinin-neuraminidase protein |
| A269 | | | hemagglutinin-neuraminidase |
| DIFIVSPR | 735 | 742 | L protein |

Mycobacterium tuberculosis H37Rv

| Description | Starting Position | Ending Position | Antigen Name |
|---|---|---|---|
| AAAGFASKTPANQAISMIDG | 284 | 303 | Phosphate-binding protein pstS 1 precursor |
| AAASAIQG | 13 | 20 | 6 kDa early secretory antigenic target |
| EGGTWRIG | 552 | 559 | DnaK |
| EGKQSLTKL | 31 | 39 | early secreted antigenic target 6 kDa |
| FAYGSFVRTVSLPVGA | 93 | 108 | HEAT SHOCK PROTEIN HSPX (ALPHA-CRSTALLIN HOMOLOG) (14 kDa ANTIGEN) (HSP16.3) |

Norovirus

| Description | Starting Position | Ending Position | Antigen Name |
|---|---|---|---|
| SWVPRLYQL | 519 | 527 | capsid protein |
| DVALLRFVNPDTGRV | 471 | 485 | capsid protein |
| PFLLHLSQMYNGWVG | 91 | 105 | Capsid protein VP1 |
| AKLHKLGFITIAKNGDSPITVPPNGYFRFE | 497 | 526 | major capsid protein |
| CKLTANPSLAAVV | 20 | 32 | RNA-dependent RNA polymerase |

TABLE B-continued

Illustrative Foreign Epitopes

| Description | Starting Position | Ending Position | Antigen Name |
|---|---|---|---|
| *Parainfluenza* | | | |
| IPKSAKLFF | 285 | 293 | matrix protein |
| IPNPLLGLD | 98 | 106 | phosphoprotein |
| GKPIPNPLLGLDST | 95 | 108 | V protein |
| *Plasmodium falciparum* | | | |
| ADELIKYL | 66 | 73 | RAP-2 |
| ADIKKLTE | 609 | 616 | Merozoite surface protein 1 precursor |
| GPAVVEES | 959 | 966 | Merozoite surface protein 1 precursor |
| GPFMKAVCV | 228 | 236 | Thrombospondin-related anonymous protein precursor |
| GPLDNTSEETTERISNNEYK | 1048 | 1067 | erythrocyte binding protein |
| *Respiratory Syncytial Virus* | | | |
| AKTLERTWDTLNHL | 10 | 23 | Major surface glycoprotein G |
| AVIRRANNVLKNEMKRYKGL | 181 | 200 | Nucleoprotein |
| CEYNVFHNKTFELPRA | 45 | 60 | small hydrophobic protein SH |
| CSICSNNPTCWAICK | 173 | 187 | Major surface glycoprotein G |
| CSISNIETVIE | 212 | 222 | Fusion glycoprotein F0 precursor |
| *Rhinovirus* | | | |
| AETRLNPDLQ | 158 | 167 | Chain 2, Human *Rhinovirus* Serotype 2 (Hrv2) |
| FCLRMARDTNLHLQSGAIAQ | 548 | 567 | Genome polyprotein |
| KLILAYTPPGARGPQD | 126 | 141 | Chain 3, Three-Dimensional Structures Of Drug-Resistant Mutants Of Human *Rhinovirus* 14 |
| LNPDLQ | 162 | 167 | Chain 2, Human *Rhinovirus* Serotype 2 (Hrv2) |
| GAQVSRQNVGTHSTQNMVSNGSSL | 1 | 24 | Chain 4, Human *Rhinovirus* 16 Coat Protein |
| *SARS Coronavirus* | | | |
| AANTVIWDY | 6509 | 6517 | Replicase polyprotein 1ab |
| AATKMSECVLGQSKRVD | 1007 | 1023 | E2 glycoprotein precursor |
| AATVLQLPQGTTLPK | 156 | 170 | N protein |
| VLNDILSRL | 958 | 966 | Spike glycoprotein precursor |
| VLPFHRWHTMVQTCT | 27 | 41 | Non-structural protein 8b |
| *Strepto pneumococcus* | | | |
| PKPEQ | 426 | 430 | pneumococcal surface protein A |

TABLE B-continued

Illustrative Foreign Epitopes

| Description | Starting Position | Ending Position | Antigen Name |
| --- | --- | --- | --- |
| VRGAVNDLLAKWHQDYGQ | 123 | 140 | Pneumolysin (Thiol-activated cytolysin) |
| WEWWR | 433 | 437 | Pneumolysin (Thiol-activated cytolysin) |
| YFSKAYGVPSAYIWE | 210 | 224 | Manganese ABC transporter substrate-binding lipoprotein |
| QISNYVGRK | 417 | 425 | serine-threonine protein kinase |

In some embodiments, viral vectors disclosed herein may also include components well known in the art of molecular biology and which are useful in the typical processes of cloning, purification, nucleic acid expression and the like. Such components include, without limitation, promoters, terminators, enhancers, selectable markers, antigen/insert sequences, restriction enzyme sites (e.g., multi-cloning sites), purification tags, primer sites, and the like.

II. Influenza A Virus

A. General

The influenza A virus is an enveloped, negative-strand RNA virus. The genome of influenza A virus is contained on eight single (non-paired) RNA strands the complements of which code for eleven proteins (HA, NA, NP, M1, M2, NS1, NEP, PA, PB1, PB1-F2, PB2). The total genome size is about 14,000 bases. The segmented nature of the genome allows for the exchange of entire genes between different viral strains during cellular cohabitation. The eight RNA segments are as follows: 1) HA encodes hemagglutinin (about 500 molecules of hemagglutinin are needed to make one virion); 2) NA encodes neuraminidase (about 100 molecules of neuraminidase are needed to make one virion); 3) NP encodes nucleoprotein; 4) M encodes two proteins (the M1 and the M2) by using different reading frames from the same RNA segment (about 3000 M1 molecules are needed to make one virion); 5) NS encodes two proteins (NS1 and NEP) by using different reading frames from the same RNA segment; 6) PA encodes an RNA polymerase; 7) PB1 encodes an RNA polymerase and PB1-F2 protein (induces apoptosis) by using different reading frames from the same RNA segment; 8) PB2 encodes an RNA polymerase.

There are several subtypes of influenza A, named according to an H number (for the type of hemagglutinin) and an N number (for the type of neuraminidase). Currently, there are 16 different H antigens known (H1 to H16) and nine different N antigens known (N1 to N9). Each virus subtype has mutated into a variety of strains with differing pathogenic profiles; some pathogenic to one species but not others, some pathogenic to multiple species. Exemplary Influenza A virus subtypes that have been confirmed in humans, include, but are not limited to H1N1 which caused the "Spanish Flu" and the 2009 swine flu outbreak; H2N2 which caused the "Asian Flu" in the late 1950s; H3N2 which caused the Hong Kong Flu in the late 1960s; H5N1, considered a global influenza pandemic threat through its spread in the mid-2000s; H7N7; H1N2 which is currently endemic in humans and pigs; and H9N2, H7N2, H7N3, H5N2, H10N7.

Some influenza A variants are identified and named according to the known isolate to which they are most similar, and thus are presumed to share lineage (e.g., Fujian flu virus-like); according to their typical host (example Human flu virus); according to their subtype (example H3N2); and according to their pathogenicity (example LP, Low Pathogenic). Thus, a flu from a virus similar to the isolate A/Fujian/411/2002 (H3N2) can be called Fujian flu, human flu, and H3N2 flu.

In addition, influenza variants are sometimes named according to the species (host) the strain is endemic in or adapted to. The main variants named using this convention are: bird flu, human flu, swine influenza, equine influenza and canine influenza. Variants have also been named according to their pathogenicity in poultry, especially chickens, e.g., Low Pathogenic Avian Influenza (LPAI) and Highly Pathogenic Avian Influenza (HPAI).

B. Life Cycle and Structure

The life cycle of influenza viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell. Different viral proteins play a role in each of these steps.

The influenza A particle is made up of a lipid envelope which encapsulates the viral core. The inner side of the envelope is lined by the matrix protein (M1), while the outer surface is characterized by two types of glycoprotein spikes: hemagglutinin (HA) and neuraminidase (NA). M2, a transmembrane ion channel protein, is also part of the lipid envelope. See e.g., FIG. 1.

The HA protein, a trimeric type I membrane protein, is responsible for binding to sialyloligosaccharides (oligosaccharides containing terminal sialic acid linked to galactose) on host cell surface glycoproteins or glycolipids. This protein is also responsible for fusion between viral and host cell membranes, following virion internalization by endocytosis.

Neuraminidase (NA), a tetrameric type II membrane protein, is a sialidase that cleaves terminal sialic acid residues from the glycoconjugates of host cells and the HA and NA, and thus is recognized as receptor-destroying enzyme. This sialidase activity is necessary for efficient release of progeny virions from the host cell surface, as well as prevention of progeny aggregation due to the binding activity of viral HAs with other glycoproteins. Thus, the receptor-binding activity of the HA and the receptor-destroying activity of the NA likely act as counterbalances, allowing efficient replication of influenza.

The genome segments are packaged into the core of the viral particle. The RNP (RNA plus nucleoprotein, NP) is in helical form with three viral polymerase polypeptides associated with each segment.

The influenza virus life cycle begins with binding of the HA to sialic acid-containing receptors on the surface of the host cell, followed by receptor-mediated endocytosis. FIG. 1. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: (1) synthesis of an mRNA with a 5' cap and 3' polyA structure, (2) a full-length complementary RNA (cRNA), and (3) genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuramimidase (NA) protein plays a role late in infection by removing sialic acid from sialyloligosaccharides, thus releasing newly assembled virions from the cell surface and preventing the self-aggregation of virus particles. Although virus assembly involves protein-protein and protein-vRNA interactions, the nature of these interactions remains largely unknown.

C. Role of the M2 protein

Figure 2:
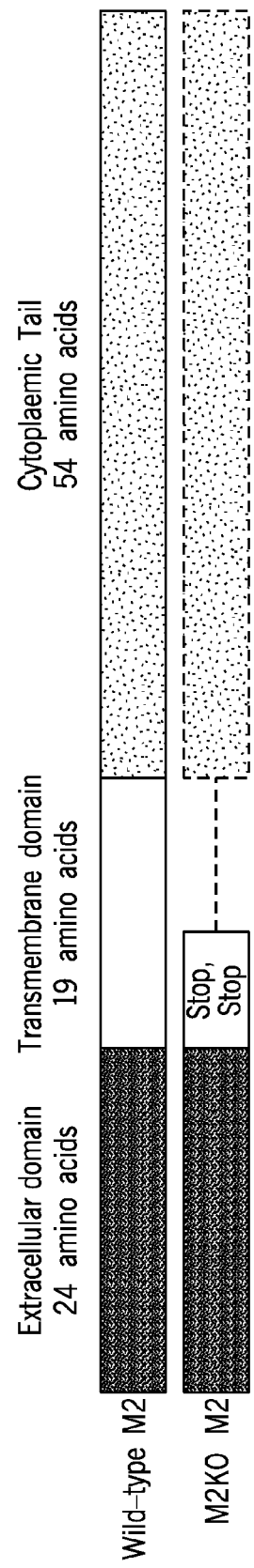
FIG. 2 is a schematic diagram of wild-type and mutant M2 genes. The M2 gene of A/Puerto Rico/8/1934 (PR8) M segment was deleted by insertion of two stop codons downstream of the open reading frame of the M1 protein followed by deletion of 51 nucleotides in the transmembrane domain to inhibit expression of full-length M2 protein.

As described above, spanning the viral membrane are three proteins: hemagglutinin (HA), neuramimidase (NA), and M2. The extracellular domains (ectodomains) of HA and NA are quite variable, while the ectodomain domain of M2 is essentially invariant among influenza A viruses. Without wishing to be bound by theory, in influenza A viruses, the M2 protein which possesses ion channel activity, is thought to function at an early state in the viral life cycle between host cell penetration and uncoating of viral RNA. Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm. In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment. It was also shown that the M2 transmembrane domain itself can function as an ion channel. M2 protein ion channel activity is thought to be essential in the life cycle of influenza viruses, because amantadine hydrochloride, which blocks M2 ion channel activity, has been shown to inhibit viral replication. However, a requirement for this activity in the replication of influenza A viruses has not been directly demonstrated. The structure of the M2 protein is shown in FIG. 2. The nucleic acid sequence of the M2 protein, along with the M1 sequence, is shown in FIG. 3.

Although influenza B and C viruses are structurally and functionally similar to influenza A virus, there are some differences. For example, influenza B virus does have an M2 protein with ion channel activity, however it is not encoded in an overlapping reading frame with the M1 protein. Thus a similar function to the influenza A virus M2 protein does exist in influenza B virus. Similarly, influenza C virus does not have an M2 protein with ion channel activity. However, the CM1 protein of the influenza C virus is likely to have this activity.

III. M2 Viral Mutants

In one aspect, influenza A viruses harboring a mutant M2 vRNA sequence are disclosed. Typically, such mutants do not have M2 ion channel activity, exhibit attenuated growth properties in vivo, cannot produce infectious progeny and are non-pathogenic or show reduced pathogenesis in infected subjects. The mutant viruses are immunogenic, and when used as a vaccine, provide protection against infection with a counterpart wild-type and/or other pathogenic virus. Additionally, the M2 mutants disclosed herein are stable, and do not mutate to express a functional M2 polypeptide, regardless of the host cell used. Additionally or alternatively, in some embodiments, the M1 protein of these mutants is produced without detectable alteration to its function. In some embodiments, viruses harboring the mutant M2 nucleic acid sequences cannot replicate in a host cell in which a corresponding wild-type virus could be propagated. By way of example, but not by way of limitation, in some embodiments, the wild-type virus can be grown, propagated and replicate in culturing MDCK cells, CHO cells and/or Vero cells, while the corresponding virus harboring a mutant M2 sequence cannot grow, replicate or be propagated in the same type of cells.

As noted above, in some embodiments, the M2 mutant virus is stable, and does not mutate or revert to wild-type or to a non-wild-type sequence encoding a functional M2 protein in a host cell. For example, in some embodiments, the M2 mutant virus is stable for 2 passages, 3 passages, 5 passages, 10 passages, 12 passages, 15 passages, 20 passages, 25 passages or more than 25 passages in a host cell. In some embodiments, the host cell is an unmodified host cell. In other embodiments, the host cell is a modified host cell, such as a MDCK cell which expresses the M2 protein.

In some embodiments, the M2 mutants include one or more nucleic acid substitutions and/or deletions. In some embodiments, the mutations are localized in nucleic acids which code for one or more of the extracellular domain of the M2 protein, the transmembrane domain of the M2 proteins and/or the cytoplasmic tail of the M2 protein. Additionally or alternatively, in some embodiments, one or more nucleic acid mutations results in a splice variant, one or more stop codons and/or one or more amino acid deletions of the M2 peptide. In some embodiments, viruses carrying the mutant M2 nucleic acid produce a non-functional M2 polypeptide. In some embodiments, viruses carrying the mutant M2 nucleic acid do not produce an M2 polypeptide. In some embodiments, viruses carrying the mutant M2 nucleic acid produce a truncated M2 polypeptide. In some embodiments, truncated M2 polypeptide has the amino acid sequence (SEQ ID NO: 4)
MSLLTEVETPIRNEWGCRCNGSSD.

Three exemplary, non-limiting M2 viral mutants (M2-1, M2-2 and M2-3) are provided below in Tables 1-3. In the tables, lower case letters correspond to the M2 sequence; upper case letters correspond to the M1 sequence; mutant sequence (e.g., stop codons, splice defect) are in bold, underlined. Underlined lower case bases in the M2-2 mutant indicate the region deleted in the M2-1 and M2-3 mutants.

TABLE 1

M gene sequence of the M2-1 *influenza virus* a mutant M2 gene including an exemplary antigenic insert.

M2-1-(SEQ ID NO: 1) M2 ectodomain + 2 stop codons + TM deletion (PR8 M segment + 2 stops (786-791) without 792-842 (TM)); also known as "M2KOTMdel," "M2KOΔTM," or "M2KO(ΔTM)"
5'AGCAAAAGCAGGTAGATATTGAAAGatgagtcttctaaccgaggtcga
aacGTACGTACTCTCTATCATCCCGTCAGGCCCCCTCAAAGCCGAGATCG
CACAGAGACTTGAAGATGTCTTTGCAGGGAAGAACACCGATCTTGAGGTT
CTCATGGAATGGCTAAAGACAAGACCAATCCTGTCACCTCTGACTAAGGG
GATTTTAGGATTTGTGTTCACGCTCACCGTGCCCAGTGAGCGAGGACTGC
AGCGTAGACGCTTTGTCCAAAATGCCCTTAATGGGAACGGGGATCCAAAT
AACATGGACAAAGCAGTTAAACTGTATAGGAAGCTCAAGAGGGAGATAAC
ATTCCATGGGGCCAAAGAAATCTCACTCAGTTATTCTGCTGGTGCACTTG
CCAGTTGTATGGGCCTCATATACAACAGGATGGGGCTGTGACCACTGAA
GTGGCATTTGGCCTGGTATGTGCAACCTGTGAACAGATTGCTGACTCCCA
GCATCGGTCTCATAGGCAAATGGTGACAACAACCAATCCACTAATCAGAC
ATGAGAACAGAATGGTTTTAGCCAGCACTACAGCTAAGGCTATGGAGCAA
ATGGCTGGATCGAGTGAGCAAGCAGCAGAGGCCATGGAGGTTGCTAGTCA
GGCTAGACAAATGGTGCAAGCGATGAGAACCATTGGGACTCATCCTAGCT
CCAGTGCTGGTCTGAAAAATGATCTTCTTGAAAATTTGCAGgcctatcag
aaacgaatgggggtgcagatgcaacggttcaagtgatTAATAGagtcgtc
tttttttcaaatgcatttaccgtcgctttaaatacggactgaaaggaggg
ccttctacggaaggagtgccaaagtctatgagggaagaatatcgaaagga
acagcagagtgctgtggatgctgacgatggtcattttgtcagcatagagc
tggagtaAAAACTACCTTGTTTCTACT

M2SRTMDEL_HIS (SEQ ID NO: 34) (sense)
5'AGCAAAAGCAGGTAGATATTGAAAGatgagtcttctaaccgaggtcga
aacGTACGTACTCTCTATCATCCCGTCAGGCCCCCTCAAAGCCGAGATCG
CACAGAGACTTGAAGATGTCTTTGCAGGGAAGAACACCGATCTTGAGGTT
CTCATGGAATGGCTAAAGACAAGACCAATCCTGTCACCTCTGACTAAGGG
GATTTTAGGATTTGTGTTCACGCTCACCGTGCCCAGTGAGCGAGGACTGC
AGCGTAGACGCTTTGTCCAAAATGCCCTTAATGGGAACGGGGATCCAAAT
AACATGGACAAAGCAGTTAAACTGTATAGGAAGCTCAAGAGGGAGATAAC
ATTCCATGGGGCCAAAGAAATCTCACTCAGTTATTCTGCTGGTGCACTTG
CCAGTTGTATGGGCCTCATATACAACAGGATGGGGCTGTGACCACTGAA
GTGGCATTTGGCCTGGTATGTGCAACCTGTGAACAGATTGCTGACTCCCA
GCATCGGTCTCATAGGCAAATGGTGACAACAACCAATCCACTAATCAGAC
ATGAGAACAGAATGGTTTTAGCCAGCACTACAGCTAAGGCTATGGAGCAA
ATGGCTGGATCGAGTGAGCAAGCAGCAGAGGCCATGGAGGTTGCTAGTCA
GGCTAGACAAATGGTGCAAGCGATGAGAACCATTGGGACTCATCCTAGCT
CCAGTGCTGGTCTGAAAAATGATCTTCTTGAAAATTTGCAGgcctatcag
aaacgaatgggggtgcagatgcaacggttcaagtgatgcg<u>CACCACCACC
ACCACCATCATCACCACCACCACCAC</u>TAATAG------------------
tgcatttaccgtcgctttaaatacggactgaaaggagggccttctacgga
aggagtgccaaagtctatgagggaagaatatcgaaaggaacagcagagtg
ctgtggatgctgacgatggtcattttgtcagcatagagctggagta**AAA
ACTACCTTGTTTCTACT**3'
bold lower case = Ala linker
<u>Underline</u> = Two 6-His Tag inserted; option for cloning site for antigen sequence
Bold Upper Case = Stop Codons
Highlight = designates deleted nucleotides, or nucleotides which may be deleted to facilitate cloning of antigen sequence M2SRTMDEL (SEQ ID NO: 35) (sense)
5'AGCAAAAGCAGGTAGATATTGAAAGatgagtcttctaaccgaggtcga
aacGTACGTACTCTCTATCATCCCGTCAGGCCCCCTCAAAGCCGAGATCG
CACAGAGACTTGAAGATGTCTTTGCAGGGAAGAACACCGATCTTGAGGTT
CTCATGGAATGGCTAAAGACAAGACCAATCCTGTCACCTCTGACTAAGGG
GATTTTAGGATTTGTGTTCACGCTCACCGTGCCCAGTGAGCGAGGACTGC
AGCGTAGACGCTTTGTCCAAAATGCCCTTAATGGGAACGGGGATCCAAAT
AACATGGACAAAGCAGTTAAACTGTATAGGAAGCTCAAGAGGGAGATAAC
ATTCCATGGGGCCAAAGAAATCTCACTCAGTTATTCTGCTGGTGCACTTG
CCAGTTGTATGGGCCTCATATACAACAGGATGGGGCTGTGACCACTGAA
GTGGCATTTGGCCTGGTATGTGCAACCTGTGAACAGATTGCTGACTCCCA
GCATCGGTCTCATAGGCAAATGGTGACAACAACCAATCCACTAATCAGAC
ATGAGAACAGAATGGTTTTAGCCAGCACTACAGCTAAGGCTATGGAGCAA
ATGGCTGGATCGAGTGAGCAAGCAGCAGAGGCCATGGAGGTTGCTAGTCA
GGCTAGACAAATGGTGCAAGCGATGAGAACCATTGGGACTCATCCTAGCT
CCAGTGCTGGTCTGAAAAATGATCTTCTTGAAAATTTGCAG-------AA
AACTACCTTGTTTCTACT TABLE 1-continued M gene sequence of the M2-1 *influenza virus* a mutant M2 gene including an exemplary antigenic insert.

(SEQ ID NO: 36) (sense)
5'gcctatcagaaacgaatgggggtgcagatgcaacggttcaagtgat**TA
ATAG**gatcgtctttttttcaaatgcatttaccgtcgctttaaatacggac
tgaaaggagggccttctacggaaggagtgccaaagtctatgagggaagaa
tatcgaaaggaacagcagagtgctgtggatgctgacgatggtcattttgt
cagcatagagctggagtaa (SEQ ID NO: 37) (sense)
5'gcctatcagaaacgaatgggggtgcagatgcaacggttcaagtgatga
tcgtctttttttcaaatgcatttaccgtcgctttaaatacggactgaaag
gagggccttctacggaaggagtgccaaagtctatgagggaagaatatcga
aaggaacagcagagtgctgtggatgctgacgatggtcattttgtcagcat
agagctggagtaa The M2 polypeptide sequence produced from the M2-1 mutant is as follows:

(SEQ ID NO: 4)
MSLLTEVETPIRNEWGCRCNGSSD..

TABLE 2

M gene sequence of the M2-2 influenza virus mutant

M2-2-SEQ ID NO: 2 M2 ectodomain + 2 stops + splice defect (PR8 M segment + 2 stops (786-791) + splice defect nt 52) (also known as "Splice def M2KO" or "Splice def")
5'AGCAAAAGCAGGTAGATATTGAAAGatgagtcttctaaccgaggtcgaa
ac<u>C</u>ACGTACTCTCTATCATCCCGTCAGGCCCCCTCAAAGCCGAGATCGCAC
AGAGACTTGAAGATGTCTTTGCAGGGAAGAACACCGATCTTGAGGTTCTCA
TGGAATGGCTAAAGACAAGACCAATCCTGTCACCTCTGACTAAGGGGATTT
TAGGATTTGTGTTCACGCTCACCGTGCCCAGTGAGCGAGGACTGCAGCGTA
GACGCTTTGTCCAAAATGCCCTTAATGGGAACGGGGATCCAAATAACATGG
ACAAAGCAGTTAAACTGTATAGGAAGCTCAAGAGGGAGATAACATTCCATG
GGGCCAAAGAAATCTCACTCAGTTATTCTGCTGGTGCACTTGCCAGTTGTA
TGGGCCTCATATACAACAGGATGGGGCTGTGACCACTGAAGTGGCATTTG
GCCTGGTATGTGCAACCTGTGAACAGATTGCTGACTCCCAGCATCGGTCTC
ATAGGCAAATGGTGACAACAACCAATCCACTAATCAGACATGAGAACAGAA
TGGTTTTAGCCAGCACTACAGCTAAGGCTATGGAGCAAATGGCTGGATCGA
GTGAGCAAGCAGCAGAGGCCATGGAGGTTGCTAGTCAGGCTAGACAAATGG
TGCAAGCGATGAGAACCATTGGGACTCATCCTAGCTCCAGTGCTGGTCTGA
AAAATGATCTTCTTGAAAATTTGCAGgcctatcagaaacgaatgggggtgc
agatgcaacggttcaagtgatTAATAGactattgccgcaaatatcattggg
atcttgcacttgacattgtggattcttgatcgtctttttttcaaatgcatt
taccgtcgctttaaatacggactgaaaggagggccttctacggaaggagtg
ccaaagtctatgagggaagaatatcgaaaggaacagcagagtgctgtggat
gctgacgatggtcattttgtcagcatagagctggagta**AAAACTACCTTG
TTTCTACT**

No M2 polypeptide sequence is produced from the M2-2 mutant.

TABLE 3

M gene sequence of the M2-3 influenza virus mutant

M2-3-SEQ ID NO: 3 M2 ectodomain + 2 stops + splice defect + TM deletion (PR8 M segment + 2 stops (786-791) without 792-842 (TM) + splice defect nt 52) (also known as TMdel + Splice def M2KO)
3'AGCAAAAGCAGGTAGATATTGAAAGatgagtcttctaaccgaggtcga
aac<u>C</u>TACGTACTCTCTATCATCCCGTCAGGCCCCCTCAAAGCCGAGATCG
CACAGAGACTTGAAGATGTCTTTGCAGGGAAGAACACCGATCTTGAGGTT
CTCATGGAATGGCTAAAGACAAGACCAATCCTGTCACCTCTGACTAAGGG
GATTTTAGGATTTGTGTTCACGCTCACCGTGCCCAGTGAGCGAGGACTGC
AGCGTAGACGCTTTGTCCAAAATGCCCTTAATGGGAACGGGGATCCAAAT
AACATGGACAAAGCAGTTAAACTGTATAGGAAGCTCAAGAGGGAGATAAC
ATTCCATGGGGCCAAAGAAATCTCACTCAGTTATTCTGCTGGTGCACTTG TABLE 3 -continued M gene sequence of the M2-3 influenza virus mutant

```
CCAGTTGTATGGGCCTCATATACAACAGGATGGGGGCTGTGACCACTGAA
GTGGCATTTGGCCTGGTATGTGCAACCTGTGAACAGATTGCTGACTCCCA
GCATCGGTCTCATAGGCAAATGGTGACAACAACCAATCCACTAATCAGAC
ATGAGAACAGAATGGTTTTAGCCAGCACTACAGCTAAGGCTATGGAGCAA
ATGGCTGGATCGAGTGAGCAAGCAGCAGAGGCCATGGAGGTTGCTAGTCA
GGCTAGACAAATGGTGCAAGCGATGAGAACCATTGGGACTCATCCTAGCT
CCAGTGCTGGTCTGAAAAATGATCTTCTTGAAAATTTGCAGgcctatcag
aaacgaatgggggtgcagatgcaacggttcaagtgatTAATAGgatcgtc
ttttttcaaatgcatttaccgtcgctttaaatacggactgaaaggaggg
ccttctacggaaggagtgccaaagtctatgagggaagaatatcgaaagga
acagcagagtgctgtggatgctgacgatggtcattttgtcagcatagagc
tggagtaaAAAACTACCTTGTTTCTACT
```

No M2 polypeptide sequence is produced from the M2-3 mutant or the M2-C vector.

Additionally or alternatively, in some embodiments, M2 mutations are introduced into the cytoplasmic tail. FIG. 2. The M2 protein cytoplasmic tail is a mediator of infectious virus production. In some embodiments, truncations of the M2 cytoplasmic tail result in a decrease in infectious virus titers, a reduction in the amount of packaged viral RNA, a decrease in budding events, and a reduction in budding efficiency. It has been shown that the 5' sequence is more important than 3' sequence for genome packaging, and that a longer 5' sequence is better for genome packaging. In addition, studies have shown that nucleotide length is important, but the actual sequence is less so (random sequences are sufficient to generate viruses). Stable M2 cytoplasmic tail mutants have been challenging to develop, and the literature includes numerous examples of mutant reversion.

For example, Pekosz et at JVI, 2005; 79(6): 3595-3605, replaced two codons with stop codons at amino acid position 70, but the virus soon reverted. Another exemplary M2 cytoplasmic tail mutation is termed M2del 11. In the M2del 11 mutant, 11 amino acid residues are deleted from carboxyl end of cytoplasmic tail. This truncation is due to the introduction of two stop codons, and a full length M2 polypeptide is not made. While this mutant is stable when passaged in M2 expressing MDCK cells (M2CK), it reverts to full length M2 during passaging in normal MDCK cells (J Virol. 2008 82(5):2486-92). Without wishing to be bound by theory, it is likely that reversion occurs with selective pressure in the MDCK cells.

Another M2 cytoplasmic tail mutant, M2Stop90ala78-81 did not reduce virus titer but ala70-77 did (JVI 2006; 80 (16) p 8178-8189). Alanine-scanning experiments further indicated that amino acids at positions 74 to 79 of the M2 tail play a role in virion morphogenesis and affect viral infectivity. (J Virol. 2006 80(11):5233-40.)

Accordingly, presented herein are novel cytoplasmic mutants, with characteristics different than those described above. For example, in some embodiments, the cytoplasmic mutants are stable (do not revert to express a full-length M2 polypeptide) in MDCK cells. In some embodiments, the cytoplasmic mutants are stable for 2 passages, 3 passages, 5 passages, 10 passages, 15 passages, 20 passages, 25 passages or more than 25 passages in a host cell.

The wild-type M2 polypeptide is shown below in Table 4. For each of the sequences, the bold text indicates the transmembrane domain. The extracellular domain is first (left), followed by the transmembrane domain (center, bold) and the cytoplasmic tail sequence (right).

TABLE 4

Wild-type M2 polypeptide and cytoplasmic tail mutants

Wild-type M2 polypeptide
MSLLTEVETPIRNEWGCRCNGSSDPLTIAANIIGILHLTLWILDRLFFKC
IYRRFKYGLKGGPSTEGVPKSMREEYRKEQQSAVDADDGHFVSIELE
(SEQ ID NO: 5)

M2-4: M2del FG#1; delete M2's 44-54 aa
(delete nucleotides 843-875; 11 aa)
MSLLTEVETPIRNEWGCRCNGSSDPLTIAANIIGILHLTLWILFKYGLKG
GPSTEGVPKSMREEYRKEQQSAVDADDGHFVSIELE
(SEQ ID NO: 6)

M2-5: M2del FG#2; delete M2's 44-48 aa
(delete nucleotides 843-857; 5 aa)
MSLLTEVETPIRNEWGCRCNGSSDPLTIAANIIGILHLTLWILKCIYRRF
KYGLKGGPSTEGVPKSMREEYRKEQQSAVDADDGHFVSIELE
(SEQ ID NO: 7)

M2-6: M2del FG#3; delete M2's 44 and 45 aa
(delete nucleotides 843-848; 2 aa)
MSLLTEVETPIRNEWGCRCNGSSDPLTIAANIIGILHLTLWILLFFKCIY
RRFKYGLKGGPSTEGVPKSMREEYRKEQQSAVDADDGHFVSIELE
(SEQ ID NO: 8)

M2-4 (M2del FG#1) was generated but was not passagable in normal MDCK cells, but may be passagable in a modified host cell (e.g., a cell expressing a wild-type M2 polypeptide). M2-5 (M2del FG#2) and M2-6 (FG#3) were generated and passaged in normal MDCK cells. The nucleotide sequence of the M gene of these viruses are stable at least to passage 10 in MDCK cells. These mutants could be propagated and passaged in other cells as well (e.g., cells that support influenza replication). It was also found that these mutants are not attenuated and are pathogenic.

As described in the Examples below, the M2 mutant viruses described herein do not replicate in the respiratory tract or disseminate to other organs in the ferret model and are not transmitted in the ferret model. Vaccines comprising M2 mutant elicit robust immune responses in mammals and protect mammals against influenza virus challenge. M2KO virus elicits both humoral and mucosal immune responses in mice, and protects mice from lethal homosubtypic and heterosubtypic challenge. Vaccines comprising M2 mutant virus as described herein provide effective protection against influenza challenge and have the advantage of being attenuated in mammalian hosts. These findings demonstrate that the M2 mutant viruses described herein are useful for vaccines against influenza.

IV. Cell-Based Virus Production System

A. Producing "First Generation" Mutant Viruses

Mutant virus, such as those carrying mutant M2 nucleic acid, can be generated by plasmid-based reverse genetics as described by Neumann et al., *Generation of influenza A viruses entirely from clone cDNAs*, Proc. Natl. Acad. Sci. USA 96:9345-9350 (1999), herein incorporated by reference in its entirety. Briefly, eukaryotic host cells are transfected with one or more plasmids encoding the eight viral RNAs. Each viral RNA sequence is flanked by an RNA polymerase I promoter and an RNA polymerase I terminator. Notably, the viral RNA encoding the M2 protein includes the mutant M2 nucleic acid sequence. The host cell is additionally transfected with one or more expression plasmids encoding the viral proteins (e.g., polymerases, nucleoproteins and structural proteins), including a wild-type M2 protein. Transfection of the host cell with the viral RNA plasmids results in the synthesis of all eight influenza viral RNAs, one of which harbors the mutant M2 sequence. The co-transfected viral polymerases and nucleoproteins assemble the viral RNAs into functional vRNPs that are replicated and transcribed, ultimately forming infectious influenza virus having a mutant M2 nucleic acid sequence, yet having a functional M2 polypeptide incorporated into the viral lipid envelope.

Alternative methods of producing a "first generation" mutant virus include a ribonucleoprotein (RNP) transfection system that allows the replacement of influenza virus genes with in vitro generated recombinant RNA molecules, as described by Enami and Palese, *High-efficiency formation of influenza virus transfectants*, J. Virol. 65(5):2711-2713, which is incorporated herein by reference.

The viral RNA is synthesized in vitro and the RNA transcripts are coated with viral nucleoprotein (NP) and polymerase proteins that act as biologically active RNPs in the transfected cell as demonstrated by Luytjes et al., *Amplification, expression, and packaging of a foreign gene by influenza virus*, Cell 59:1107-1113, which is incorporated herein by reference.

The RNP transfection method can be divided into four steps: 1) Preparation of RNA: plasmid DNA coding for an influenza virus segment is transcribed into negative-sense RNA in an in vitro transcription reaction; 2) Encapsidation of the RNA: the transcribed RNA is then mixed with gradient purified NP and polymerase proteins isolated from disrupted influenza virus to form a biologically active RNP complex; 3) Transfection and rescue of the encapsidated RNA: the artificial ribonucleocapsid is transfected to the cells previously infected with a helper influenza virus that contains a different gene from the one being rescued; the helper virus will amplify the transfected RNA; 4) Selection of transfected gene: because both the helper virus and the transfectant containing the rescued gene are in the culture supernatant, an appropriate selection system using antibodies is necessary to isolate the virus bearing the transfected gene.

The selection system allows for the generation of novel transfectant influenza viruses with specific biological and molecular characteristics. Antibody selection against a target surface protein can then be used for positive or negative selection.

For example, a transfectant or mutant virus that contains an M2 gene that does not express an M2 protein can be grown in a suitable mammalian cell line that has been modified to stably express the wild-type functional M2 protein. To prevent or inhibit replication of the helper virus expressing the wild-type M2 gene, and therefore the M2e protein at the membrane surface, antibodies against M2e can be used. Such antibodies are commercially available and would inhibit the replication of the helper virus and allow for the transfectant/mutant virus containing the mutant M2 to grow and be enriched in the supernatant Inhibition of influenza virus replication by M2e antibodies has been described previously in *Influenza A virus M2 protein: monoclonal antibody restriction of virus growth and detection of M2 in virions*, J Virol 62:2762-2772 (1988) and Treanor et al, *Passively transferred monoclonal antibody to the M2 protein inhibits influenza A virus replication in mice*, J. Virol. 64:1375-1377 (1990).

Additionally or alternatively, the same antibodies can be used to 'capture' the helper virus and allow for the enrichment of the transfectant. For example, the antibodies can be used to coat the bottom of a tissue culture dish or can be used in a column matrix to allow for enrichment for the transfectant in the supernatant or eluate.

The transfectant virus can be grown in M2 expressing cells in multi-well plates by limit dilution and then be identified and cloned, for example, by creating replica plates. For example, one-half of an aliquot of a given well of the multi-well plate containing the grown virus can be used to infect MDCK cells and the other half to infect MDCK cells that express M2 protein. Both the transfectant virus and helper virus will grow in MDCK cells that express M2 protein. However, only helper virus will grow in standard MDCK cells allowing for identifying the well in the multi-well plate that contains the transfectant. The transfectant virus can be further plaque purified in the cells that express M2 protein.

B. Propagating Viral Mutants

In some embodiments, viral mutants described herein are maintained and passaged in host cells. By way of example, but not by way of limitation, exemplary host cells appropriate for growth of influenza viral mutants, such as influenza A viral mutants include any number of eukaryotic cells, including, but not limited to Madin-Darby canine kidney cells (MDCK cells), simian cells such as African green monkey cells (e.g., Vero cells), CV-1 cells and rhesus monkey kidney cells (e.g., LLcomk.2 cells), bovine cells (e.g., MDBK cells), swine cells, ferret cells (e.g., mink lung cells) BK-1 cells, rodent cells (e.g., Chinese Hamster Ovary cells), human cells, e.g., embryonic human retinal cells (e.g., PER-C6®), 293T human embryonic kidney cells and avian cells including embryonic fibroblasts.

Additionally or alternatively, in some embodiments, the eukaryotic host cell is modified to enhance viral production, e.g., by enhancing viral infection of the host cell and/or by enhancing viral growth rate. For example, in some embodiments, the host cell is modified to express, or to have increased expression, of 2,6-linked sialic acid on the cell surface, allowing for more efficient and effective infection of these cells by mutant or wild-type influenza A viruses. See e.g., U.S. Patent Publication No. 2010-0021499, and U.S. Pat. No. 7,176,021, herein incorporated by reference in their entirety. Thus, in some illustrative embodiments, Chinese Hamster Ovary Cells (CHO cells) and/or Vero cells modified to express at least one copy of a 2,6-sialyltransferase gene (ST6GAL 1) are used. By way of example, but not by way of limitation, the *Homo sapiens* ST6 beta-galatosamide alpha-2,6-sialyltransferase gene sequence denoted by the accession number BC040009.1, is one example of a ST6Gal gene that can be integrated into and expressed by a CHO cell. One or more copies of a polynucleotide that encodes a functional ST6Gal I gene product can be engineered into a cell. That is, cells which have been stably transformed to express 1, 2, 3, 4, 5, 6, 7, 8, 9, 10, 11, 12, or more than 12 copies of a ST6Gal I gene may be used. A single expression cassette may include one or more copies of the ST6Gal I gene to be expressed, which is operably linked to regulatory elements, such as promoters, enhancers, and terminator and polyadenylation signal sequences, to facilitate the expression of the ST6Gal I gene or its copies. Alternatively, a single expression cassette may be engineered to express one copy of an ST6Gal I gene, and multiple expression cassettes integrated into a host cell genome. Accordingly, in some embodiments, at least one ST6Gal I gene is incorporated into the genome of a host cell, such that the cell expresses the ST6Gal I gene and its enzymatic protein product. Depending on the copy number, a single host cell may express many functional ST6Gal I gene proteins.

Suitable vectors for cloning, transfecting and producing stable, modified cell lines are well known in the art. One non-limiting example includes the pcDNA3.1 vectors (Invitrogen).

Additionally or alternatively, in some embodiments, the eukaryotic host cell is modified to produce a wild-type version of a mutant viral gene, thereby providing the gene to the virus in trans. For example, a viral strain harboring a mutant M2 protein may exhibit an enhanced growth rate (e.g., greater viral production) when passaged in host cells producing the wild-type M2 protein. In some embodiments, the a viral strain harboring a mutant M2 protein may not grow or replicate in a cell which does not express a wild-type M2 gene. In addition, such host cells may slow or prevent viral reversion to a functional M2 sequence, because, for example, there is no selective pressure for reversion in such a host.

Method for producing both expression vectors and modified host cells are well known in the art. For example, an M2 expression vector can be made by positioning the M2 nucleic acid sequence (M2 ORF sequence; this is "wild-type" M2's start codon to stop codon (Table 5)) below in a eukaryotic expression vector.

TABLE 5

Wild-type M2 nucleic acid sequence

Atgagtcttctaaccgaggtcgaaacgcctatcagaaacgaatggggtg
cagatgcaacggttcaagtgatcctctcactattgccgcaaatatcattg
ggatcttgcacttgacattgtggattcttgatcgtcttttttcaaatgc
atttaccgtcgctttaaatacggactgaaaggagggccttctacggaagg
agtgccaaagtctatgagggaagaatatcgaaaggaacagcagagtgctg
tggatgctgacgatggtcattttgtcagcatagagctggagtaa
(SEQ ID NO: 9)

Host cells (e.g., MDCK cells) can then be transfected by methods known in the art, e.g., using commercially available reagents and kits, such as TransIT® LT1 (Mirus Bio, Madison, Wis.). By way of example, but not by way of limitation, cells can be selected and tested for M2 expression by cotransfection with a detectable marker or a selectable marker (e.g., hygromycin-resistance) and/or by screening, for example, with indirect immunostaining using an M2 antibody. M2 expression can be determined by indirect immunostaining, flow cytometry or ELISA.

By way of example, but not by way of limitation, 293T human embryonic kidney cells and Madin-Darby canine kidney (MDCK) cells were maintained in Dulbecco's modified Eagle's medium supplemented with 10% fetal calf serum and in minimal essential medium (MEM) containing 5% newborn calf serum, respectively. All cells were maintained at 37° C. in 5% $CO_2$. Hygromycin-resistant MDCK cells stably expressing M2 protein from A/Puerto Rico/8/34 (H1N1) were established by cotransfection with plasmid pRHyg, containing the hygromycin resistance gene, and plasmid pCAGGS/M2, expressing the full-length M2 protein, at a ratio of 1:1. The stable MDCK cell clone (M2CK) expressing M2 was selected in medium containing 0.15 mg/mL of hygromycin (Roche, Mannheim, Germany) by screening with indirect immunostaining using an anti-M2 (14C2) monoclonal antibody (Iwatsuki e al., JVI, 2006, Vol. 80, No. 1, p. 5233-5240). The M2CK cells were cultured in MEM supplemented with 10% fetal calf serum and 0.15 mg/mL of hygromycin. In M2CK cells, the expression levels and localization of M2 were similar to those in virus-infected cells (data not shown). M2 expressing Vero cells can be made in a similar fashion.

In some embodiments, cells and viral mutants are cultured and propagated by methods well known in the art. By way of example, but not by way of limitation, in some embodiments, host cells are grown in the presence of MEM supplemented with 10% fetal calf serum. Cells expressing M2 are infected at an MOI of 0.001 by washing with PBS followed by adsorbing virus at 37° C. In some embodiments, viral growth media containing trypsin/TPCK is added and the cells are incubated for 2-3 days until cytopathic effect is observed.

Along these lines, disposable bioreactor systems have been developed for mammalian cells, with or without virus, whose benefits include faster facility setup and reduced risk of cross-contamination. The cells described herein, for instance, can be cultured in disposable bags such as those from Stedim, Bioeaze bags from SAFC Biosciences, HybridBag™ from Cellexus Biosytems, or single use bioreactors from HyClone or Celltainer from Lonza. Bioreactors can be 1 L, 10 L, 50 L, 250 L, 1000 L size formats. In some embodiments, the cells are maintained in suspension in optimized serum free medium, free of animal products. The system can be a fed-batch system where a culture can be expanded in a single bag from 1 L to 10 L for example, or a perfusion system that allows for the constant supply of nutrients while simultaneously avoiding the accumulation of potentially toxic by-products in the culture medium.

For long term storage, mutant virus can be stored as frozen stocks.

V. Delivery of Antigens to a Subject to Elicit an Immune Response

A. Compositions

In one aspect, the present disclosure provides methods and compositions for the delivery of antigens to a subject using M2 influenza viral vectors in order to elicit an immune response against the antigens. In some embodiments, the antigen is one or more discreet epitopes.

The use of an influenza viral vector for the delivery of foreign antigens is useful for several reasons. Use of the virus permits administration of the foreign antigens to a subject by any means or route by which an influenza vaccine may be administered. For example, nasal administration. Use of the viral vector also permits the foreign antigens to be produced naturally within the host, and eliminates the need for an adjuvant to elicit a robust immune response to the antigens. As known in the art, purified antigens are often not highly immunogenic when administered to a subject. However, because the influenza viral vector elicits an immune response itself, subjects may mount a robust immune response to a foreign antigen that is otherwise only poorly immunogenic.

Vectors

As discussed herein, in some embodiments, mutations in the M2 gene cause the influenza virus vector to be replication defective, and to replicate only when the M2 gene product is provided in trans, such as by expression from a host cell genome. As discussed herein, in some embodiments, without wishing to be bound by theory, it is thought that replication defective viruses have the advantage that there is no selective pressure for the virus to revert to wild-type or to delete any aspect of the virus, including any foreign sequences cloned into the virus.

According to the compositions and methods described herein, one or more antigens may be cloned into nucleic acids carried by a viral vector for delivery to a subject, wherein the vector comprises an influenza virus bearing a mutation in the M2 gene that causes the gene product to not be expressed, or causes the expression of a truncated form of the gene product.

In some embodiments, the vector comprises the M2-1 (SEQ ID NO:1) sequence or a variant thereof. In some embodiments, the vector comprises the M2-2 (SEQ ID NO:2) sequence or a variant thereof. In some embodiments, the vector comprises the M2-3 (SEQ ID NO:3) sequence or a variant thereof. In some embodiments, the vector includes SEQ ID NO: 34 or a variant thereof. In some embodiments, the vector is empty. In some embodiments, the vector is loaded. In some embodiments, the "variant" comprises the antigen sequence.

In some embodiments, viral vectors disclosed herein may also include components well known in the art of molecular biology and which are useful in the typical processes of cloning, purification, vector production and the like. Such components include, without limitation, promoters, terminators, enhancers, selectable markers, epitope sequences, restriction enzyme sites (e.g., multi-cloning sites), purification tags, reporter genes, primer sites and the like.

Antigens

The compositions and methods disclosed herein are not intended to be limited by the choice of antigen. While numerous examples of antigens are provided, the skilled artisan can easily utilize the influenza vectors disclosed herein with an antigen of choice. Exemplary antigens suitable for use in the methods include any immunogenic antigens associated with, for example, an infectious agent, a cancer, or a host molecule against which an immune response is desired. Infectious agents include any pathogenic microorganism, including but not limited to viruses, bacteria, fungi, protozoa, multi-cellular parasites, and prions. Cancer-related antigens include proteins or other molecules expressed by tumor or non-tumor cancers, such as molecules that are present in cancer cells but absent in non-cancer cells, and molecules that are up-regulated in cancer cells as compared to non-cancer cells. Non-limiting examples of cancer-related antigens include antigens derived from Her2/neu, the cancer-testis antigen (NY-ESO-1), and tumor-specific calcitonin. Non-limiting examples of host molecules include cytokines, antibodies, or any host molecule against which an immune response is desired, such as, for example, to neutralize the activity of the molecule.

In some embodiments the antigen sequence is about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 950, or about 1000, nucleotides in length or more.

In some embodiments, the antigen sequence is inserted into an M2 vector, for example, in the M2 gene region. By way of example, but not by way of limitation, in some embodiments, the antigen sequence of interest is cloned into the position of the two hexa-his tag sequences, e.g., the insert antigen sequence replaces the hexa-his sequence, e.g., of SEQ ID NO: 34. In some embodiments, the antigen sequence replaces the hexa-his sequence and some or all of the M2 sequence, e.g., of SEQ ID NO: 34. In some embodiments, the antigen sequence replaces some or all of the M2 sequence. By way of example, but not by way of limitation, some or all of the highlighted nucleic acids shown in SEQ ID NO: 34 in Table 1 could be replaced with an antigen sequence. By way of example, but not by way of limitation, some or all of the following sequence could be replaced by an antigen sequence in an M2 vector comprising SEQ ID NO: 1:

gcctatcagaaacgaatgggggtgcagatgcaacggttcaagtgatTAAT
AGgatcgtcttttttttcaaatgcatttaccgtcgctttaaatacggactg
aaaggagggccttctacggaaggagtgccaaagtctatgagggaagaata
tcgaaaggaacagcagagtgctgtggatgctgacgatggtcattttgtca
gcatagagctggagtaa.

In some embodiments, foreign antigens are cloned into an M2 vector in-frame with the ectodomain of the M2 protein, such that the antigens are produced as a fusion with the ectodomain of the M2 protein when administered to a host. In some embodiments, foreign antigens are cloned into an M2 vector out of frame with the ectodomain of the M2 protein, and are expressed using an internal ribosome entry site (IRES) sequence.

Vaccines

In some embodiments, compositions comprising an M2 mutant influenza viral vector containing one or more foreign antigen sequences are formulated into vaccines. In some embodiments, the vaccines are administered to a subject in order to elicit an immune response against the antigens. In some embodiments, the vaccines are administered to a subject in order to confer active immunity against the pathogen from which the antigens is derived. In some embodiments, the vaccines are administered to a subject in order to elicit an immune response against the antigen(s) such that antibodies against the antigens can be recovered from the subject. In some embodiments, antibodies recovered from a subject are used to confer on another subject passive immunity against the pathogen from which the foreign antigen is derived.

B. Methods

In one aspect, the present disclosure provides methods for eliciting an immune response in a subject, the method comprising administering to the subject an M2 mutant influenza virus vector comprising one or more antigen sequences, wherein the one or more antigen sequences are derived from, for example, a pathogenic agent or a tumor, and wherein the subject mounts an immune response against the antigens.

The use of M2 mutant influenza virus vectors for the delivery of antigens confers certain advantages. Without wishing to be bound by theory, the presence of a pre-existing, influenza-neutralizing antibody in a subject can be circumvented through use of a viral vector of a subtype not recognized by the subject's immune system. This allows for multiple vaccinations of the subject using the same vector without neutralization by subject. In addition, because the influenza genome is a negative-strand RNA, it is not a typical substrate for host subject polymerases. Because there is no DNA intermediate derived from the viral vector, there is limited risk of the viral sequences integrating into the host genome. Moreover, because M2 mutant influenza viral vectors are non-replicating, there is limited risk of influenza to recipients of vaccines comprising the vectors. As discussed above, because the viral vector undergoes multi-cycle replications only in the presence of M2 protein provided in trans, there is no selective pressure for the virus to revert to wild-type or to delete any of the vector or foreign epitope sequences during the production of the viral vector.

In some embodiments, the methods are used to induce systemic immunity in a host subject. In some embodiments, the methods are used to induce local immunity in a host. In some embodiments, the methods are used to induce local mucosal immunity, such as, for example, against respiratory diseases.

In some embodiments, the methods comprise the use of M2 mutant influenza viral vectors containing T-cell epitopes. In some embodiments, the T-cell epitopes comprise epitopes related to HIV, HCV, malaria, tuberculosis, cytomegalovirus, respiratory syncytial virus, norovirus, paramyxoviruses, bacterial infections, fungal infections, or cancer. Non-limiting examples of foreign epitopes suitable with the present methods include the Lymphocytic choriomeningitis virus (LCV) SERPQASGVYMG (nucleoprotein), Respiratory syncytial virus (RSV) RARRELPRF and IAVGLLLYC (fusion protein), VITIELSNI (RSV glycoprotein), Parainfluenza virus 3 GEPQSSIIQY and EMAIDEEP-EQFEHRADQEQDGEPQSSIIQYAWAEGNRSDD (nucleocapsid protein), foot and mouth disease virus (FMDV) epitopes [VP1 (133-156)-3A (11-40)-VP4 (20-34)]; class I and class II epitopes from *Bordetella pertussis* toxin subunit 1 precursor: GNNDNVLDHLTGR (61-73), QQTRANPNPYTSRRSVAS (203-220), DDPPATVYRYD-SRPPED (35-51), SARS coronovirus spike glycoprotein FIAGLIAIV; Norwalk virus (Norovirus) capsid protein MMMASKDATSSVDGASGAGQLVPEVNTSDPLAMD-PVAGSSTAV, and immunomodulatory cytokines, the human cytokine (e.g. IL-2) QASGVYMG epitope.

In some embodiments, the disclosure provides methods comprising administering a vaccine comprising an M2 mutant influenza viral vector comprising one or more antigen sequences to a subject in order to elicit an immune response against the antigens. In some embodiments, the vaccines are administered to a subject in order to confer active immunity against the pathogen from which the antigen is derived. In some embodiments, the vaccines are administered to a subject in order to elicit an immune response against the antigens such that antibodies against the antigens can be recovered from the subject. In some embodiments, antibodies recovered from a subject are used to confer on another subject passive immunity against the pathogen from which the antigens is derived.

VI. Vaccines and Method of Administration

A. Immunogenic Compositions/Vaccines

There are various different types of vaccines which can be made from the cell-based virus production system disclosed herein and the viral vectors, harboring an antigen sequence of interest, disclosed herein. The present disclosure includes, but is not limited to, the manufacture and production of live attenuated virus vaccines, inactivated virus vaccines, whole virus vaccines, split virus vaccines, virosomal virus vaccines, viral surface antigen vaccines and combinations thereof. Thus, there are numerous vaccines capable of producing a protective immune response specific for different influenza viruses where appropriate formulations of any of these vaccine types are capable of producing an immune response, e.g., a systemic immune response. Live attenuated virus vaccines have the advantage of being also able to stimulate local mucosal immunity in the respiratory tract. As discussed above, the viral vectors also provide advantages for vaccination against an antigen or epitope(s) of interest.

In some embodiments, vaccine antigens used in the compositions described herein are "direct" antigens, i.e. they are not administered as DNA, but are the antigens themselves. Such vaccines may include a whole virus or only part of the virus, such as, but not limited to viral polysaccharides, whether they are alone or conjugated to carrier elements, such as carrier proteins, live attenuated whole microorganisms, inactivated microorganisms, recombinant peptides and proteins, glycoproteins, glycolipids, lipopeptides, synthetic peptides, or ruptured microorganisms in the case of vaccines referred to as "split" vaccines.

In some embodiments a complete virion vaccine is provided. A complete virion vaccine can be concentrated by ultrafiltration and then purified by zonal centrifugation or by chromatography. Typically, the virion is inactivated before or after purification using formalin or beta-propiolactone, for instance.

In some embodiments, a subunit vaccine is provided, which comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as that commercialized under the name TRITON X100. The hemagglutinin may also be isolated after treatment of the virions with a protease such as bromelin, then purified by standard methods.

In some embodiments, a split vaccine is provided, which comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

In some embodiments, inactivated influenza virus vaccines are provided. In some embodiments, the inactivated vaccines are made by inactivating the virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

Additionally or alternatively, in some embodiments, live attenuated influenza virus vaccines are provided. Such vaccines can be used for preventing or treating influenza virus infection, according to known method steps.

In some embodiments, attenuation is achieved in a single step by transfer of attenuated genes from an attenuated donor virus to an isolate or reassorted virus according to known methods (see, e.g., Murphy, Infect. Dis. Clin. Pract. 2, 174 (1993)). In some embodiments, a virus is attenuated by mutation of one or more viral nucleic acid sequences, resulting in a mutant virus. For example, in some embodiments, the mutant viral nucleic acid sequence codes for a defective protein product. In some embodiments, the protein product has diminished function or no function. In other embodiments, no protein product is produced from the mutant viral nucleic acid.

The virus can thus be attenuated or inactivated, formulated and administered, according to known methods, as an immunogenic composition (e.g., as a vaccine) to induce an immune response in an animal, e.g., an avian and/or a mammal. Methods are well-known in the art for determining whether such attenuated or inactivated vaccines have maintained similar antigenicity to that of the clinical isolate or a high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) or other mutant sequences (e.g., M2) are not present in the attenuated viruses. See, e.g., Robertson et al., Giornale di Igiene e Medicina Preventiva, 29, 4 (1988); Kilbourne, Bull. M2 World Health Org., 41, 643 (1969); and Robertson et al., Biologicals, 20, 213 (1992).

In some embodiments, the vaccine includes an attenuated influenza virus that lacks expression of a functional M2 protein. In some embodiments, the mutant virus replicates well in cells expressing M2 proteins, but in the corresponding wild-type cells, expresses viral proteins without generating infectious progeny virions.

In some embodiments, the vaccine includes a viral vector as disclosed herein, comprising one or more antigen sequences of interest.

Pharmaceutical compositions of the present invention, suitable for intradermal administration, inoculation or for parenteral or oral administration, comprise attenuated or inactivated influenza viruses, and may optionally further comprising sterile aqueous or non-aqueous solutions, suspensions, and emulsions. The compositions can further comprise auxiliary agents or excipients, as known in the art. See, e.g., Berkow et al., The Merck Manual, 15th edition, Merck and Co., Rahway, N.J. (1987); Goodman et al., eds., Goodman and Gilman's The Pharmacological Basis of Therapeutics, Eighth Edition, Pergamon Press, Inc., Elmsford, N.Y. (1990); Avery's Drug Treatment: Principles and Practice of Clinical Pharmacology and Therapeutics, Third Edition, ADIS Press, LTD., Williams and Wilkins, Baltimore, Md. (1987); and Katzung, ed., Basic and Clinical Pharmacology, Fifth Edition, Appleton and Lange, Norwalk, Conn. (1992).

In some embodiments, preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances that augment a specific immune response, can be used. Normally, the adjuvant and the composition are mixed prior to presentation to the immune system, or presented separately, but into the same site of the organism being immunized.

In some embodiments, the immunogenic compositions (e.g., vaccines) disclosed herein include multiple, different types of antigen sequences cloned into viral vectors, virus or viral antigens. In some embodiments, at least one viral antigen or viral vector for delivery of an antigen includes a mutant M2 gene (e.g., a virus comprising the M2KO($\Delta$TM) (SEQ ID NO:1) mutation), and/or a corresponding mutation in the M2 functional equivalent of that virus (e.g., the NB protein of influenza B, or the CM1 protein of influenza C). In other embodiments, the immunogenic compositions include a single type of virus or viral antigen which includes a mutant M2 gene (e.g., a virus comprising the M2KO ($\Delta$TM) (SEQ ID NO:1) mutation) and/or a corresponding mutation in the M2 functional equivalent of that virus (e.g., the NB protein of influenza B, or the CM1 protein of influenza C). For example, in some embodiments, the main constituent of an immunogenic compositions such as a vaccine composition includes one or more influenza viruses of type A, B or C, or any combination thereof or any combination of antigens from these viruses, wherein at least one virus includes a mutant M2 gene (e.g., a virus comprising the M2KO($\Delta$TM) (SEQ ID NO:1) mutation) and/or a corresponding mutation in the M2 functional equivalent of that virus (e.g., the NB protein of influenza B, or the CM1 protein of influenza C). For example, in some embodiments, at least two of the three types, at least two of different subtypes, at least two of the same type, at least two of the same subtype, or a different isolate(s) or reassortant(s) are provided in an immunogenic composition (e.g., a vaccine). By way of example, but not by way of limitation, human influenza virus type A includes H1N1, H2N2 and H3N2 subtypes. In some embodiments, the immunogenic compositions (e.g., vaccines) include a virus comprising a mutant M2 gene (e.g., a virus comprising the M2KO($\Delta$TM) (SEQ ID NO:1) mutation) and/or a corresponding mutation in the M2 functional equivalent of that virus (e.g., the NB protein of influenza B, or the CM1 protein of influenza C) and about 0.1 to 200 µg, e.g., 10 to 15 µg of hemagglutinin from each of the strains entering into the composition. Heterogeneity in a vaccine may be provided by mixing replicated influenza viruses for at least two influenza virus strains, such as from 2-50 strains, or any range or value therein. In some embodiments, influenza A or B virus strains having a modern antigenic composition are used. In addition, immunogenic compositions (e.g., vaccines) can be provided for variations in a single strain of an influenza virus, using techniques known in the art.

In some embodiments, the vaccine comprises a virus comprising the M2KO($\Delta$TM) (SEQ ID NO:1) mutation together with other viral components and/or genes expressing other viral components. In some embodiments, the vaccine (e.g., a virus comprising the M2KO($\Delta$TM) (SEQ ID NO:1) mutation) comprises genes from other viral strains, including but not limited to, for example, HA and NA genes from other viral strains. In some embodiments, the vaccine comprises HA and NA genes from human influenza virus type A subtypes H5N1, H1N1, H2N2 or H3N2. In some embodiments, the vaccine comprises HA and NA genes from, for example, PR8×Brisbane/10/2007, A/Vietnam/1203/2004, or A/California/07/2009 (CA07) viruses.

A pharmaceutical composition according to the present invention (e.g., a viral vector as disclosed herein harboring one or more antigen sequences of interest) may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-α, interferon-β, interferon-γ, tumor necrosis factor-α, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition of the invention is administered.

B. Administration

An immunogenic composition (e.g., vaccine) as disclosed herein may be administered via any of the routes conventionally used or recommended for vaccines: parenteral route, mucosal route, and may be in various forms: injectable or sprayable liquid, formulation which has been freeze-dried or dried by atomization or air-dried, etc. Vaccines may be administered by means of a syringe or by means of a needle-free injector for intramuscular, subcutaneous or intradermal injection. Vaccines may also be administered by means of a nebulizer capable of delivering a dry powder or a liquid spray to the mucous membranes, whether they are nasal, pulmonary, vaginal or rectal.

A vaccine as disclosed herein may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

The present invention thus includes methods for preventing or attenuating a disease or disorder, e.g., infection by a pathogen expressing the antigen of interest, or at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, or viral vector harboring one or more antigen sequences of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. In some embodiments, an immunogenic composition as disclosed herein is by intramuscular or subcutaneous application.

In some embodiments, a regimen for preventing, suppressing, or treating an infectious disease or an influenza virus related pathology comprises administration of an effective amount of a vaccine composition as described herein, administered as a single treatment, or repeated as enhancing or booster dosages, over a period up to and including between one week and about 24 months, or any range or value therein. In some embodiments, an influenza vaccine as disclosed herein is administered annually.

According to the present invention, an "effective amount" of a vaccine composition is one that is sufficient to achieve a desired biological effect. It is understood that, in some embodiments, the effective dosage will be dependent upon the age, sex, health, and weight of the recipient, kind of concurrent treatment, if any, frequency of treatment, and the nature of the effect wanted. The ranges of effective doses provided below are not intended to be limiting and represent exemplary dose ranges. Thus, in some embodiments, the dosage will be tailored to the individual subject, as is understood and determinable by one of skill in the art. The dosage of an attenuated virus vaccine for a mammalian (e.g., human) adult can be from about $10^3$-$10^7$ plaque forming units (PFU), or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

C. Intracutaneous Delivery

Live flu vaccines are traditionally delivered intranasally to mimic the natural route of infection and promote a similar immune response to that of natural virus infection. As an alternative, disclosed herein are intradermal delivery methods which involve the use of a novel microneedle device to capitalize on the immunological benefits of intradermal delivery. In some embodiments, an attenuated virus (e.g., an M2 viral mutant) is used in a vaccine composition for intradermal administration. In some embodiments, an M2 viral mutant, which does not produce infectious progeny virus, is provided in a vaccine (e.g., as a vaccine itself or as a vector harboring one or more antigen sequences of interest). Thus, any potential of reassortment with wild-type circulating influenza viruses is virtually eliminated.

In embodiments disclosed herein, intradermal delivery (intracutaneous) administers vaccine to the skin. In some embodiments, intradermal delivery is performed using a microneedle delivery device. As disclosed herein, intracutaneous delivery has numerous advantages. For example, the immunogenicity of the vaccine is enhanced by triggering the immunological potential of the skin immune system. The vaccine has direct access to the potent antigen-presenting dendritic cells of the skin, i.e., epidermal Langerhans Cells and dermal dendritic cells. Skin cells produce proinflammatory signals which enhance the immune response to antigens introduced through the skin. Further, the skin immune system produces antigen-specific antibody and cellular immune responses. Intradermal delivery allows for vaccine dose sparing, i.e., lower doses of antigen may be effective, in light of the above factors, when delivered intracutaneously.

And, because the vaccine is delivered to the skin through the device's microneedle array, the risk of unintended needle-sticks is reduced, and intracutaneous vaccine delivery via microneedle array is relatively painless compared to intramuscular injections with conventional needle and syringe.

Microneedle devices are known in the art, are known in the art, including, for example, those described in published U.S. patent applications 2012/0109066, 2011/0172645, 2011/0172639, 2011/0172638, 2011/0172637, and 2011/0172609. Microneedle devices may be made, for example, by fabrication from stainless steel sheets (e.g., Trinity Brand Industries, Georgia; SS 304; 50 µm thick) by wet etching. In some embodiments, individual microneedles have a length of between about 500 µm and 1000 µm, e.g., about 750 µm, and a width of between about 100 µm to 500 µm, e.g., about 200 µm. Vaccine can then be applied to the microneedles as a coating. By way of example, but not by way of limitation, a coating solution may include 1% (w/v) carboxymethyl cellulose sodium salt (low viscosity, USP grad; Carbo-Mer, San Diego Calif.), 0.5% (w/v) Lutrol F-68 NF (BASF, Mt. Olive, N.J.) and the antigen (e.g., soluble HA protein at 5 ng/ml; live, attenuated virus such as the M2 mutant virus described herein, etc.). To reach a higher vaccine concentration, the coating solution may be evaporated for 5 to 10 minutes at room temperature (~23° C.). Coating may be performed by a dip coating process. The amount of vaccine per row of microneedles can be determined by submerging the microneedles into 200 µl of phosphate-buffered saline (PBS) for 5 minutes and assaying for the antigen by methods known in the art.

In some embodiments, a microneedle device is used that is made mainly of polypropylene and stainless steel first-cut pieces that fit together with simple snap fits and heat seals. In some embodiments, the device is completely self-contained and includes the vaccine, a pump mechanism, an activation mechanism, and a microneedle unit. These components are hidden within a plastic cover. With the device, vaccine infusion is initiated by pressing an actuation button. Pressing the button simultaneously inserts the microneedles into the skin and initiates the pumping mechanism that exerts pressure on the primary drug container. When a spring mechanism exerts sufficient pressure on the vaccine reservoir, vaccine begins to flow through the microneedle array, and into the skin. In some embodiments, the delivery of the vaccine dose is completed within about 2 minutes after actuation of the device. After infusion is complete, the device is gently removed from the skin.

In some embodiments, a method for intracutaneous administration of an immunogenic composition (e.g., a vaccine) is provided using a microneedle device. In some embodiments, the microneedle device comprises a puncture mechanism and an immunogenic composition layer comprising a plurality of microneedles capable of puncturing skin and allowing an immunogenic composition to be administered intracutaneously. In some embodiments, the method comprises depressing the puncture mechanism. In some embodiments, the immunogenic composition (e.g. vaccine) comprises a virus comprising a nucleic acid sequence encoding a mutant M2 protein that is expressed or a mutant M2 protein that is not expressed; wherein the expressed mutant M2 protein comprises, or consists of, the amino acid sequence of SEQ ID NO:4. In some embodiments, the immunogenic composition comprises a viral vector as disclosed herein, harboring one or more antigen sequences of interest. In some embodiments, the microneedle array is initially positioned inside of a device housing, and upon actuation of a lever allows the microneedles to extend through the device bottom and insert into the skin thereby allowing infusion of the vaccine fluid into the skin.

The delivery device described herein may be utilized to deliver any substance that may be desired. In one embodiment, the substance to be delivered is a drug, and the delivery device is a drug delivery device configured to deliver the drug to a subject. As used herein the term "drug" is intended to include any substance delivered to a subject for any therapeutic, preventative or medicinal purpose (e.g., vaccines, pharmaceuticals, nutrients, nutraceuticals, etc.). In one such embodiment, the drug delivery device is a vaccine delivery device configured to deliver a dose of vaccine to a subject. In one embodiment, the delivery device is configured to deliver a flu vaccine. The embodiments discussed herein relate primarily to a device configured to deliver a substance transcutaneously. In some embodiments, the device may be configured to deliver a substance directly to an organ other than the skin.

Kits

In some embodiments, kits are provided. In some embodiments, the kit includes a cloning intermediate, and one or more expression vectors comprising influenza viral genes. In some embodiments, the cloning intermediate includes a vector backbone, and an M gene region of an influenza virus, comprising a mutant M2 sequence. In some embodiments, the mutation in the M2 coding sequence causes the failure of M gene expression by an influenza virus, or the expression of a truncated M2 protein having the amino acid sequence of SEQ ID NO:4.

In some embodiments, the vector backbone comprises SEQ ID NO:35, wherein SEQ ID NO:35 further comprises a nucleic acid sequence encoding one or more foreign antigens, and wherein the nucleic acid sequence encoding one or more foreign antigens is positioned within the region of SEQ ID NO:35 encoding the influenza M2 gene. In some embodiments, the nucleic acid sequence further comprises part or all of SEQ ID NO:36. In some embodiments, the one or more foreign antigens comprise an amino acid sequence derived from a pathogen or a tumor. In some embodiments, the pathogen comprises a virus, bacteria, fungus, protozoan, multi-cellular parasite, or prion. In some embodiments, the one or more foreign antigens elicits an immune response in a host subject.

In some embodiments, the vector backbone comprises SEQ ID NO:35. In some embodiments, the vector backbone comprises SEQ ID NO:1. In some embodiments, the vector backbone further comprises part or all of SEQ ID NO:36.

EXAMPLES

While the following examples are demonstrated with influenza A, it is understood that the mutations and methods described herein are equally applicable to other viruses which express an M2, an M2-like protein or a protein with the same or similar function as the influenza A M2 protein.

Example 1

Generation of M2 Viral Mutants

M2 mutants were constructed as follows:
a) M2-1: M2 ectodomain+2 stop codons+TM deletion (PR8 M segment+2 stops (786-791) without 792-842 (TM))
Partial wild-type M genes from PR8 were amplified by PCR using oligo set 1 and oligo set 2 as shown below.

TABLE 6

```
Oligo Set 1
acacacCGTCTCTAGgatcgtcttttttcaaatgcatttacc
(SEQ ID NO: 10)
CACACACGTCTCCTATTAGTAGAAACAAGGTAGTTTTT
(SEQ ID NO: 11)

Oligo Set 2
acacacCGTCTCatcCTATTAatcacttgaaccgttgc
(SEQ ID NO: 12)
CACACACGTCTCCGGGAGCAAAAGCAGGTAG
(SEQ ID NO: 13)
```

The PCR products were then digested with BsmBI. An expression vector (pHH21) was also digested with BsmBI, and the digested PCR products were ligated into the vector using T4 DNA ligase. *E. coli* cells were transformed with the vector, and after appropriate incubation, vectors were isolated and purified by methods known in the art. The mutant M2 portion of the vector was characterized by nucleic acid sequencing.

b) M2-2: M2 ectodomain+2 stops+splice defect (PR8 M segment+2 stops (786-791)+splice defect nt 51)

Partial wild-type M genes from PR8 were amplified by PCR using the primer set shown below.

TABLE 7

PCR primers

5'acacacCGTCTCcCTACGTACTCTCTATCATCCCG (SEQ ID NO: 14)

5'CACACACGTCTCCTATTAGTAGAAACAAGGTAGTTTTT (SEQ ID NO: 15)

The PCR products were then digested with BsmBI. An expression vector (pHH21) was also digested with BsmBI. A double-stranded DNA fragment was then made by annealing the two nucleotides shown below.

TABLE 8

Annealing nucleotides

5'GGGAGCAAAAGCAGGTAGATATTGAAAGatgagtcttctaaccgaggt cgaaac (SEQ ID NO: 16)

5'GTAGgtttcgacctcggttagaagactcatCTTTCAATATCTACCTGC TTTTGC (SEQ ID NO: 17)

The digested vector, PCR product and double-stranded fragment were then ligated using T4 DNA ligase. *E. coli* cells were transformed with the vector, and after appropriate incubation, the vectors were isolated and purified by methods known in the art. The mutant M2 portion of the vector was characterized by nucleic acid sequencing.

c) M2-3: M2 ectodomain+2 stops+splice defect+TM deletion (PR8 M segment+2 stops (786-791) without 792-842 (TM)+splice defect nt 51)

The partial M2-1 mutant (M2 ectodomain+2 stop codons+ TM deletion (PR8 M segment+2 stops (786-791) without 792-842 (TM)) was amplified from PR8 by PCR using the following primers:

TABLE 9

PCR primers

5'acacacCGTCTCcCTACGTACTCTCTATCATCCCG (SEQ ID NO: 18)

5'CACACACGTCTCCTATTAGTAGAAACAAGGTAGTTTTT (SEQ ID NO: 19)

The PCR products were then digested with BsmBI. An expression vector (pHH21) was also digested with BsmBI. A double-stranded DNA fragment was then made by annealing the two nucleotides shown below.

TABLE 10

Annealing nucleotides

5'GGGAGCAAAAGCAGGTAGATATTGAAAGatgagtcttctaaccgaggt cgaaac (SEQ ID NO: 20)

TABLE 10 -continued

Annealing nucleotides

5'GTAGgtttcgacctcggttagaagactcatCTTTCAATATCTACCTGC TTTTGC (SEQ ID NO: 21)

The digested vector, PCR product and double-stranded fragment were then ligated using T4 DNA ligase. *E. coli* cells were transformed with the vector, and after appropriate incubation, the vectors were isolated and purified by methods known in the art. The mutant M2 portion of the vector was characterized by nucleic acid sequencing.

The sequence of each of the three M2 mutant constructs is provided in Tables 1-3.

Example 2

Generation and Culturing of M2 Mutant Virus

This example demonstrates the culturing of the PR8 virus comprising the M2KO(ΔTM) (SEQ ID NO:1) mutation. Mutant viruses were generated as reported in Neumann et al., *Generation of influenza A viruses entirely from clone cDNAs*, Proc. Natl. Acad. Sci. USA 96:9345-9350 (1999), with some modifications. Briefly, 293T cells were transfected with 17 plasmids: 8 PolI constructs for 8 RNA segments, one of which harbors the mutant M2 sequence, and 9 protein-expression constructs for 5 structural proteins as follows: NP (pCAGGS-WSN-NP0/14); M2 (pEP24c); PB1 (pcDNA774); PB2 (pcDNA762); and PA (pcDNA787) of A/Puerto Rico/8/34 (H1N1) virus.

The plasmids were mixed with transfection reagent (2 µL of Trans IT® LT-1 (Mirus, Madison, Wis.) per µg of DNA), incubated at room temperature for 15-30 minutes, and added to 1×10$^6$ 293 T cells. Forty-eight hours later, viruses in the supernatant were serially diluted and inoculated into M2CK cells. Two to four days after inoculation, viruses in supernatant of the last dilution well in which cells showing clear cytopathic effect (CPE) were inoculated into M2CK cells for the production of stock virus. The M genes of generated viruses were sequenced to confirm the gene and the presence of the intended mutations and to ensure that no unwanted mutations were present.

Mutant M2 viruses were grown and passaged as follows. M2CK host cells were grown in the presence of MEM supplemented with 10% fetal calf serum. Cells were infected at an MOI of 0.001 by washing with PBS followed by adsorbing virus at 37° C. Virus growth media containing trypsin/TPCK was added and the cells were incubated for 2-3 days until cytopathic effect was observed.

Example 3

M2KO Replication is Restricted in Normal Cells

Figure 4:
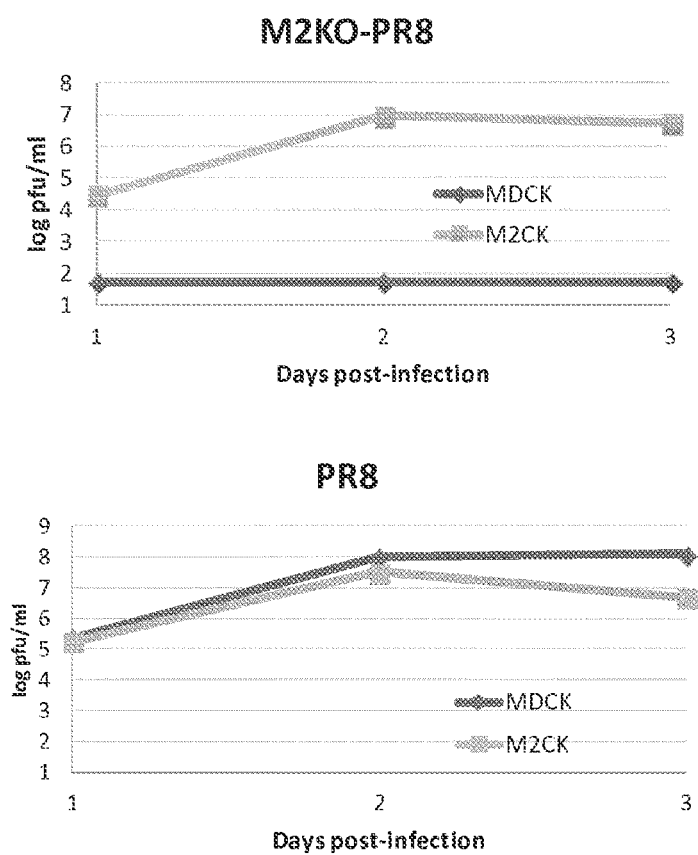
FIG. 4 is a chart showing the growth kinetics of M2KO (ΔTM) (upper panel) and wild-type PR8 (lower panel) viruses in normal MDCK cells and MDCK cells stably expressing M2 protein (M2CK). Cells were infected with viruses at multiplicity of infection of $10^{-5}$. Virus titers in cell supernatants were determined. Wild-type PR8 grew to high titers in both cell types whereas M2KO(ΔTM) grew well only in M2CK cells and not at all in MDCK cells.

Growth kinetics of the PR8 virus with the M2KO(ΔTM) (SEQ ID NO:1) mutation and wild-type PR8 were analyzed in both normal MDCK cells and MDCK cells stably expressing M2 protein (M2CK). Cells were infected with viruses at multiplicity of infection of 10$^{-5}$. Virus titers in cell supernatant were determined in MDCK or M2CK cells. Wild-type PR8 grew to high titers in both cell types whereas M2KO grew well only in M2CK cells and not at all in MDCK cells (FIG. 4).

Example 4

M2KO Virus Produces Viral Antigens, but not M2, in Normal Cells

This example demonstrates that the PR8 virus with the M2KO(ΔTM) (SEQ ID NO:1) mutation produces viral antigens, but not M2 protein, in normal cells. Viral protein expression was evaluated by infecting wild-type MDCK cells with wild-type PR8 or M2KO at a multiplicity of infection (MOI) of 0.5 in medium without trypsin to ensure that viruses complete only one life cycle. Viral proteins in the cell lysates were separated on a 4-12% SDS-PAGE gel and detected by Western blot using PR8 infected mouse sera (Panel A) or anti-M2 monoclonal antibody (14C2, Santa Cruz Biotechnology) (Panel B). FIG. 3A shows that antisera against PR8 detects similar levels of protein expression for both PR8 and M2KO. When the lysates are probed with an anti-M2 monoclonal antibody (Panel B), M2 expression is detected only in PR8 infected cells, not M2KO. These results indicate that M2KO virus expresses all viral proteins, except M2 protein, to similar levels as PR8 virus (FIG. 5).

Example 5

M2 Mutants are Attenuated In Vivo

An experiment was performed to demonstrate that M2 mutant viruses are attenuated in vivo. Six weeks old BALB/c, female mice (23 per group) were inoculated intranasally with one of the following mutants: M2KO(yk) as described in J. Virol (2009) 83:5947-5950; M2-1 (TM del M2KO aka M2KO(ΔTM)) and M2-2 (Splice def M2KO) (collectively termed "M2KO variants"). The mutant was administered at a dose of $1.2\times10^4$ pfu per mouse. A control group of mice was given PBS. The mice were observed for 14 days after inoculation for any change in body weight and symptoms of infection. Additionally, after 3 days post-inoculation, virus titers were taken from the lungs and nasal turbinates (NT) from 3 mice in each group.

Figure 6:
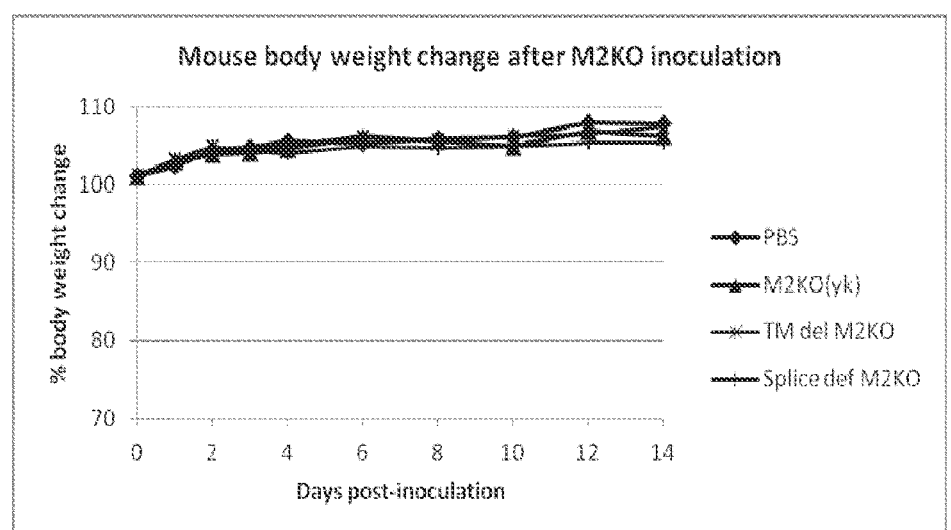
FIG. 6 is a chart showing the change in mouse body weight after inoculation with M2KO variants.

As shown in FIG. 6, mice inoculated with the M2KO variants and PBS did not show any clinical symptoms of infection nor lose any body weight over the 14 day period. The change in body weight between the groups were comparable over the 14 day period. Additionally, no virus was detected in the titers that were gathered from the lungs and NT. Together, the lack of clinical symptoms, lack of loss of body weight and absence of virus indicate that the M2 mutant viruses are attenuated and not pathogenic in mice.

Example 6

Figure 7A:
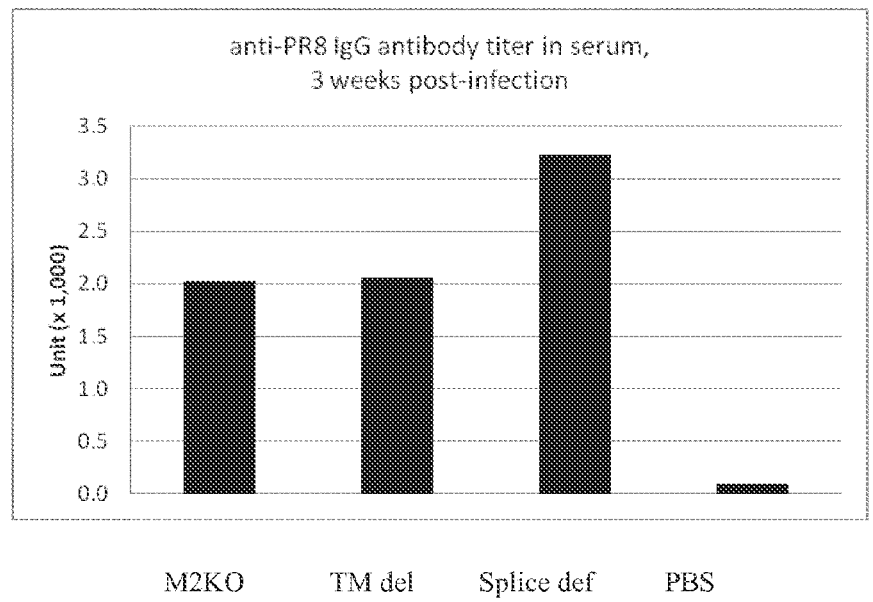
FIG. 7A is a chart showing antibody response in mice inoculated with M2KO variants.

M2 Mutants Induce Antibodies Against Influenza Virus and Protect Mice from Lethal Virus Challenge Testing was also performed to determine antibody titers from the mice described in Example 5 above and their survival after being challenged with a lethal viral dose. Serum samples were taken 3 weeks after inoculation and anti-virus IgG antibody titers from the serum samples were determined by enzyme-linked immunosorbent assay (ELISA). The humoral response is shown in FIG. 7, which shows that all three M2 mutants elevated anti-influenza virus antibodies higher than the control PBS group.

Figure 7B:
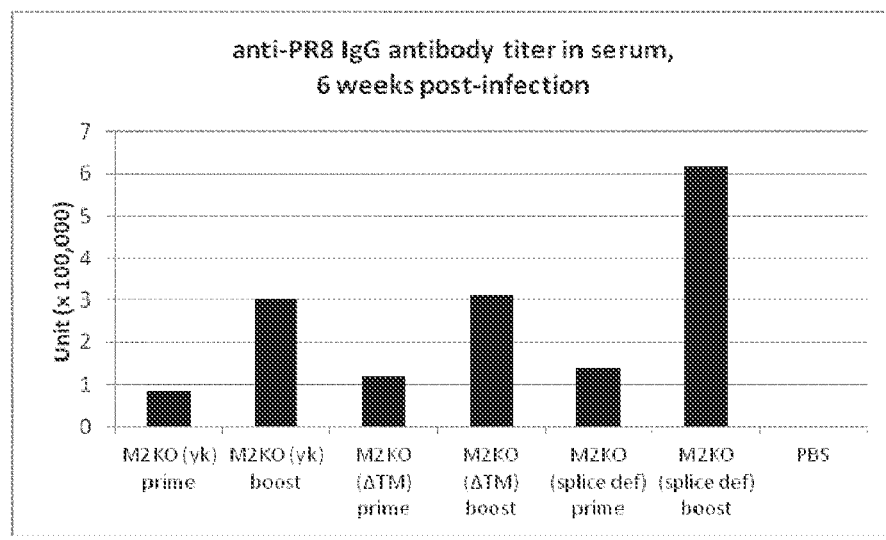
FIG. 7B is a chart showing anti-PR8 IgG antibody titer in the serum of boosted mice 6 weeks post infection.

In addition, half of the mice within each of the groups were boosted 28 days after inoculation with same amount of M2 mutant virus. Serum was then collected 6 weeks after the first inoculation and IgG titers against the virus were determined. As shown in FIG. 7B, mice boosted by M2 mutant viruses had a higher level of anti-influenza virus antibodies than ones were not boosted.

Figure 8:
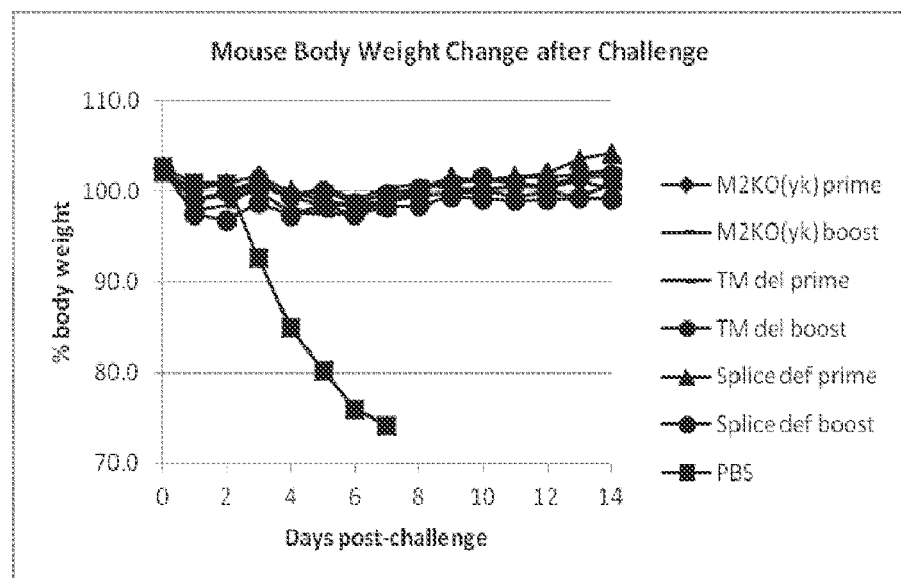
FIG. 8 is a chart showing change in mouse body weight after influenza challenge, post-inoculation with M2KO variants.
Figure 9:
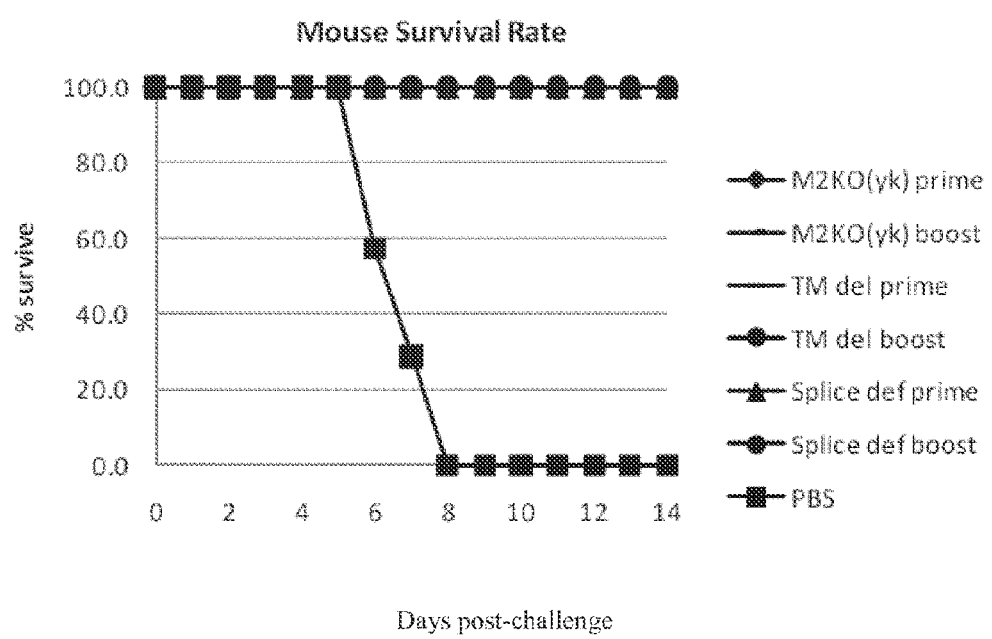
FIG. 9 is a chart showing mouse survival after influenza challenge, post-inoculation with M2KO variants.

49 days after the first inoculation (3 weeks after the boost), the mice were challenged with a lethal dose of PR8 virus (40 mouse 50% lethal dose ($MLD_{50}$)). As shown in FIG. 8 and FIG. 9, all mice vaccinated with the M2KO variants survived the challenge and lost no weight. The control mice that were given only PBS, however, lost body weight and did not survive 8 days past the challenge date. On day 3 after the challenge, lungs and NT were obtained and virus titers determined in MDCK cells by plaque assay. As depicted in Table 11, lung virus titers in M2KO variants were at least one log lower than titers in naïve control PBS. And almost no viruses were detected in nasal turbinates in M2KO variants groups but more than 100,000 PFU/g were detected in the naïve control PBS group, indicating that the M2 mutant vaccines confer protection and limits the replication of the challenge virus.

TABLE 11

| Virus Titer (log10 PFU/g) in Mouse Tissue After Challenge | | |
|---|---|---|
| | Lung | Nasal Turbinates |
| M2KO (yk) | 6.1, 5.9, ND | 1.7, ND, ND |
| M2KO (ΔTM) | 5.8 ± 0.25 | 2.5, ND, ND |
| M2KO (splice def) | ND, ND, ND | ND, ND, ND |
| PBS | 7.9 ± 0.27 | 5.3 ± 0.55 |

In another experiment, six weeks after immunization, the M2KO(ΔTM) groups were challenged with homosubtypic or heterosubtypic influenza viruses. Mice were challenged with Aichi (H3N2) virus and scored for survival for 14 days. Results for the heterotypic challenge are shown in FIG. 16.

Example 7

Intradermal Vaccine Delivery

An experiment was performed to show that intradermal vaccine delivery/immunizing will protect a subject from influenza. BALB/c female, 6-7 weeks old mice (5 per group) (Harland Laboratories) were inoculated either intranasally (IN), intramuscularly (IM) or intradmermally (ID) with PR8 virus ($3.5\times10^7$pfu) at a concentration of $1.8\times10^1$, $1.8\times10^2$, $1.8\times10^3$ or $1.8\times10^4$ pfu (50 μl) per mouse. Control mice were also given PBS through the three different routes of administration. Body weight and survival were monitored for 14 days after inoculation. For the mouse experiments, allergy syringes with intradermal bevel needles were used.

Most vaccines are administered by intramuscular or subcutaneous injection using conventional needles and syringes. However, recent studies demonstrate that intradermal vaccine delivery achieves better immunogenicity than intramuscular or subcutaneous administration. Intradermal vaccination delivers antigen directly to the enriched skin immune system and has been shown to be effective for a range of vaccines, including rabies, hepatitis B and influenza. Intradermal delivery may also provide dose sparing, achieving the same immune response using less vaccine than required with intramuscular injection. The current state-of-the-art for intradermal delivery (using conventional needles and syringes) is the Mantoux technique, which requires extensive training, is difficult to perform, and often results in misdirected (subcutaneous) or incomplete administration. The lack of suitable delivery devices has hampered intradermal vaccination research and product development even though superior immune responses with this administration route have been documented.

Figure 10:
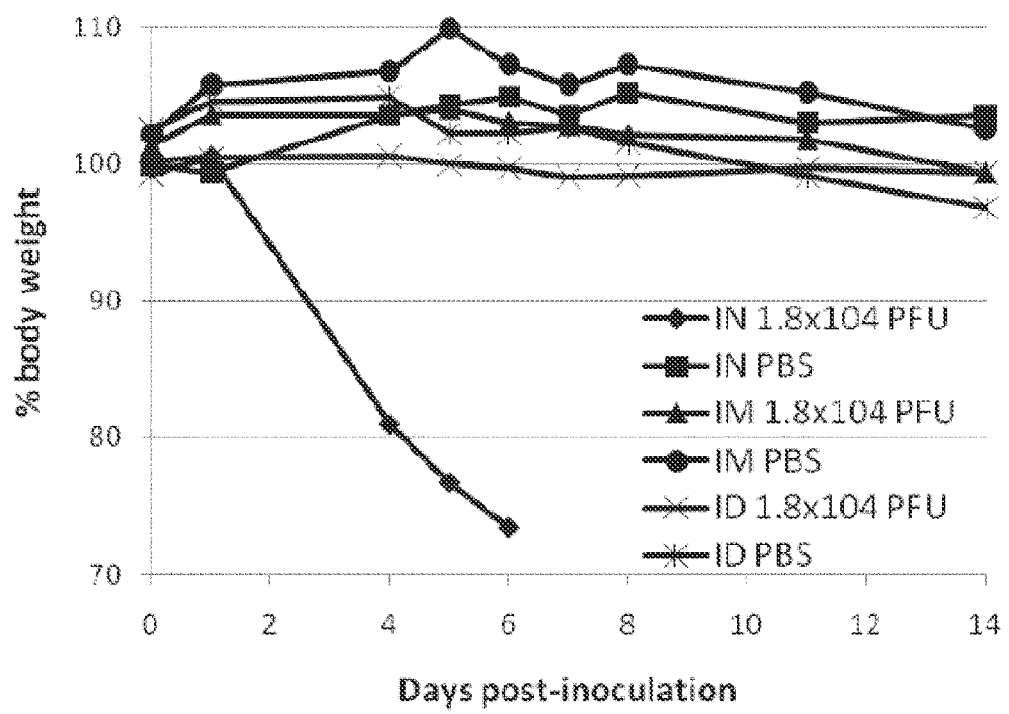
FIG. 10 is a chart showing the change in mouse body weight after inoculation with PR8 intranasally (IN), intradermally (ID) or intramuscularly (IM).

As shown in Table 12, IN-inoculated mice succumbed to influenza infection at the higher doses of $1.8 \times 10^3$ and $1.8 \times 10^4$ pfu per mouse, with complete survival only at the lowest dose of $1.8 \times 10^1$. However, IM- and ID-inoculated mice at all dosages survived. Table 13 shows the median lethal dose for mice in the IN-inoculated group ($MLD_{50}$). FIG. 10 shows that IM- and ID-inoculated mice inoculated with $1.8 \times 10^4$ pfu of the virus displayed no change in body weight, and shows the lack of survival for IN-inoculated mice inoculated with $1.8 \times 10^4$ pfu of virus.

TABLE 12

Mice survival after PR8 inoculation

| Virus Dose | Route of Administration | | |
|---|---|---|---|
| (pfu) | IM | ID | IN |
| $1.8 \times 10^1$ | 5/5 | 5/5 | 5/5 |
| $1.8 \times 10^2$ | 5/5 | 5/5 | 1/5 |
| $1.8 \times 10^3$ | 5/5 | 5/5 | 0/5 |
| $1.8 \times 10^4$ | 5/5 | 5/5 | 0/5 |
| PBS | 5/5 | 5/5 | 5/5 |

TABLE 13

Median lethal dose for mice ($MLD_{50}$).

| Route | $MLD_{50}$ (pfu$^a$/mouse) |
|---|---|
| IN | 76 |
| IM | $>1.8 \times 10^4$ |
| ID | $>1.8 \times 10^4$ |

$^a$pfu: plaque forming unit.

Figure 11A:
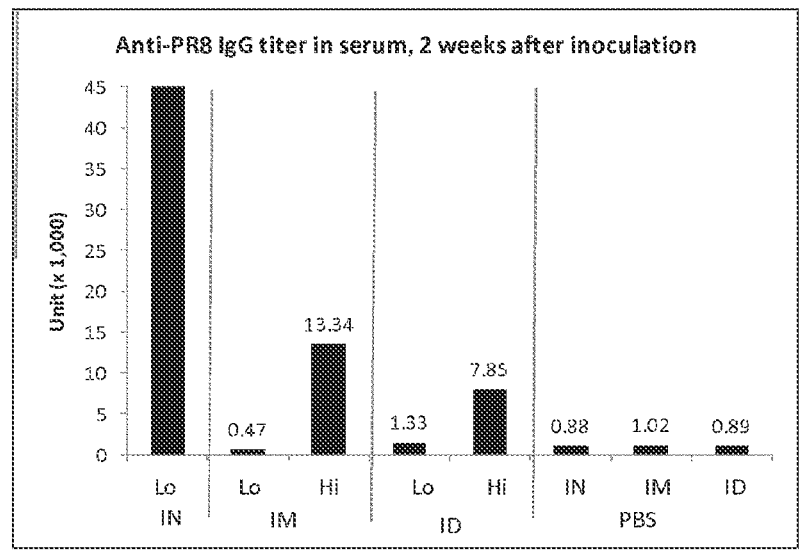
FIG. 11A is a chart showing antibody titer in serum, collected at 2 weeks post-inoculation with PR8, from mouse with $1.8 \times 10^1$ pfu (Lo) or $1.8 \times 10^4$ pfu (Hi) concentration of virus.
Figure 11B:
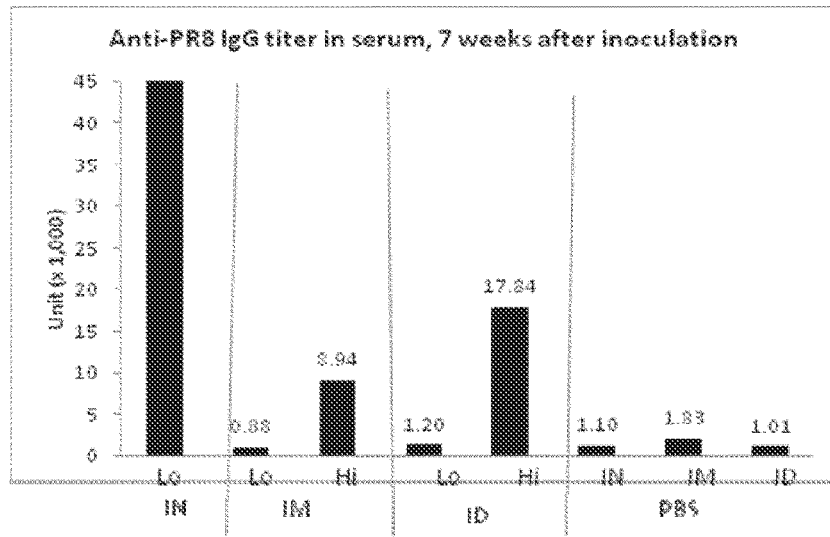
FIG. 11B is a chart showing antibody titer in serum, collected at 7 weeks post-inoculation with PR8, from mouse with $1.8 \times 10^1$ pfu (Lo) or $1.8 \times 10^4$ pfu (Hi) concentration of vaccine.

Serum was collected at 2 weeks (FIG. 11A) and 7 weeks (FIG. 11B) after inoculation and evaluated for anti-PR8 IgG antibody as determined by an ELISA. "Hi" represents $1.8 \times 10^4$ pfu inoculations, and "Lo" represents $1.8 \times 10^1$ pfu. The responses of the IN-, IM- and ID-inoculated mice at both time periods are similar. At each time period, IN-inoculated mice presented the highest number of antibodies. Only IN-inoculated mice inoculated with $1.8 \times 10^1$ pfu were identified (i.e., "Lo"), because by this time, the IN-inoculated mice inoculated with higher doses had expired. IM- and ID-inoculated mice presented lower levels of antibodies than the IN-inoculated mice, although mice inoculated at the higher doses exhibited greater amounts of antibodies when compared with the control mice given only PBS. Additionally, over time, the intradermal administration route produced more antibodies than the intramuscular route, as demonstrated by the higher titer levels shown in FIG. 11B.

In another experiment, groups of IN-, IM- and ID-inoculated mice (5 mice per group, except for 4 mice in $1.8 \times 10^3$ group) were challenged 8 week after vaccination. Specifically, $1.8 \times 10^1$ IN-inoculated mice, $1.8 \times 10^3$ IM-inoculated mice, $1.8 \times 10^4$ IM-inoculated mice, $1.8 \times 10^3$ ID-inoculated mice and $1.8 \times 10^4$ ID-inoculated mice were challenged. Mice that lost more than 25% of their body weight were euthanized.

Figure 12:
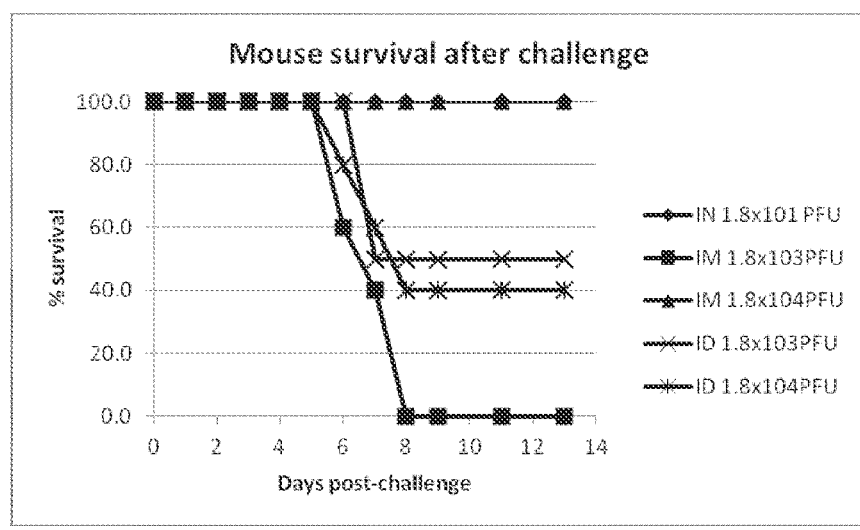
FIG. 12 is a chart showing mouse survival after influenza challenge, post-inoculation with PR8.
Figure 13:
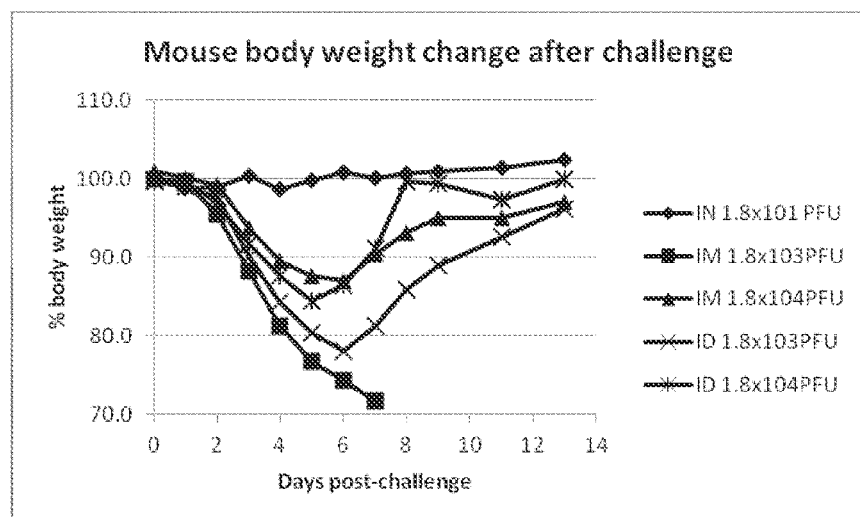
FIG. 13 is a chart showing change in mouse body weight after influenza challenge, post-inoculation with PR8.

As shown in FIG. 12, 100% of IM-inoculated mice at a dose of $1.8 \times 10^3$ did not survive 8 days after the challenge. The survival rate of all ID-inoculated mice was between 40% and 60%. The survival rate of IM-inoculated mice at $1.8 \times 10^4$, however, was 100%. FIG. 13 shows that the ID-inoculated and IM-inoculated ($1.8 \times 10^4$) groups of mice had an initial average weight loss, but ended up with a relative low weight loss from the challenge date.

Figure 14:
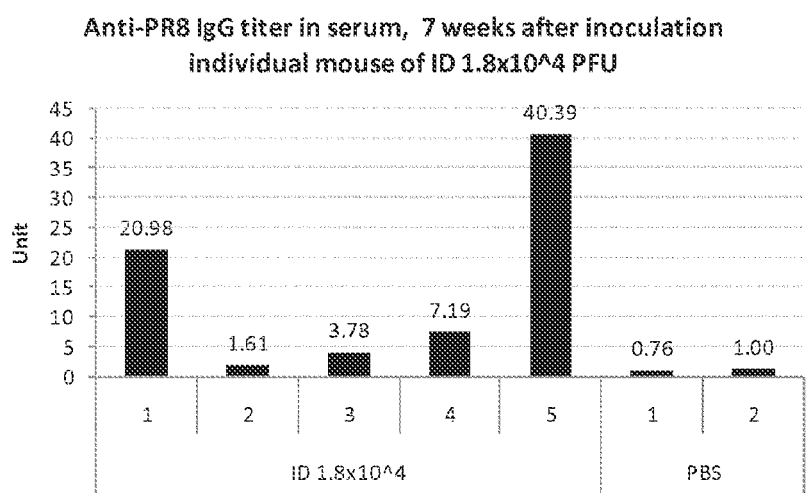
FIG. 14 is a chart showing antibody titer in serum, collected from a mouse inoculated with $1.8 \times 10^4$ pfu PR8 intradermally at 7 weeks post-inoculation.
Figure 15:
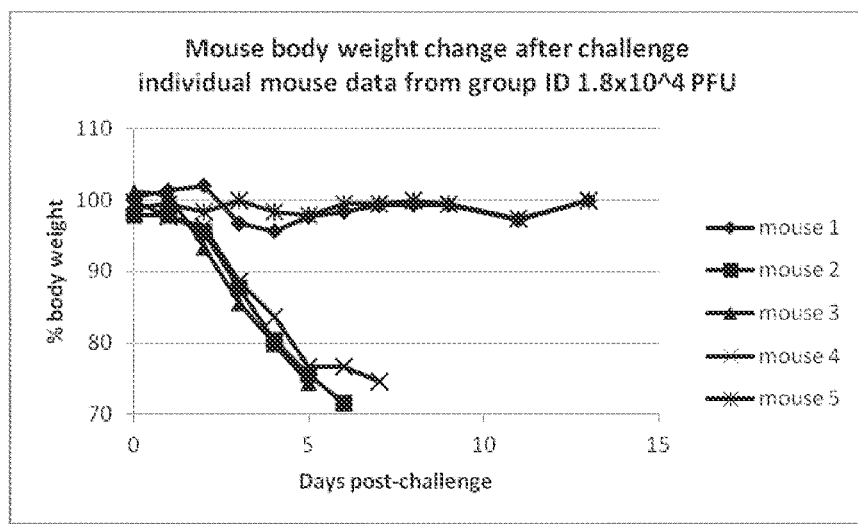
FIG. 15 is a chart showing the change in body weight of mice inoculated with $1.8 \times 10^4$ pfu PR8 intradermally.
Figure 16:
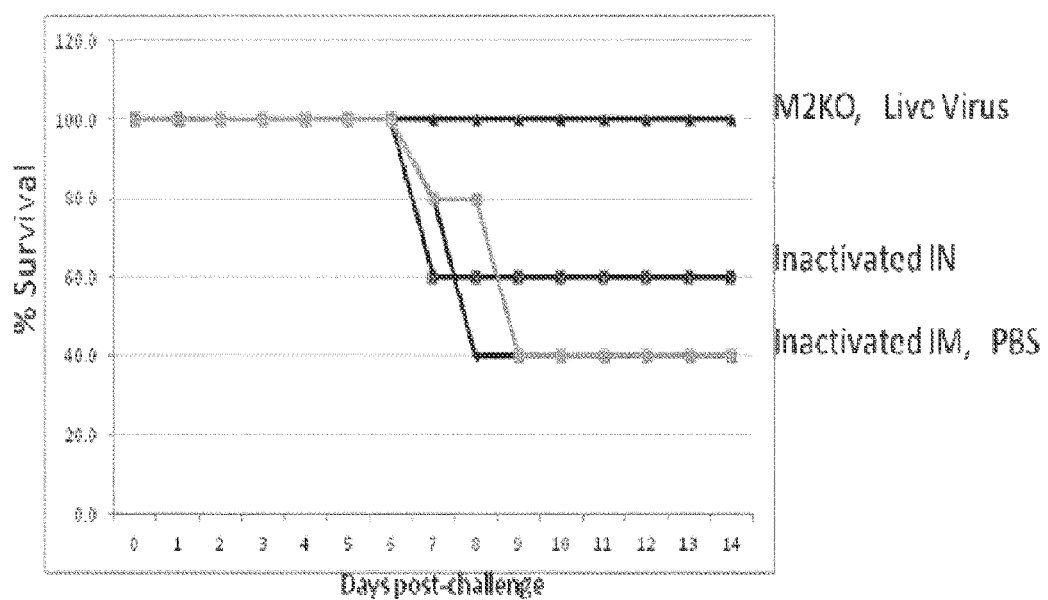
FIG. 16 is a chart showing % survival post challenge for mice infected with a heterosubtypic virus.
Figure 17:
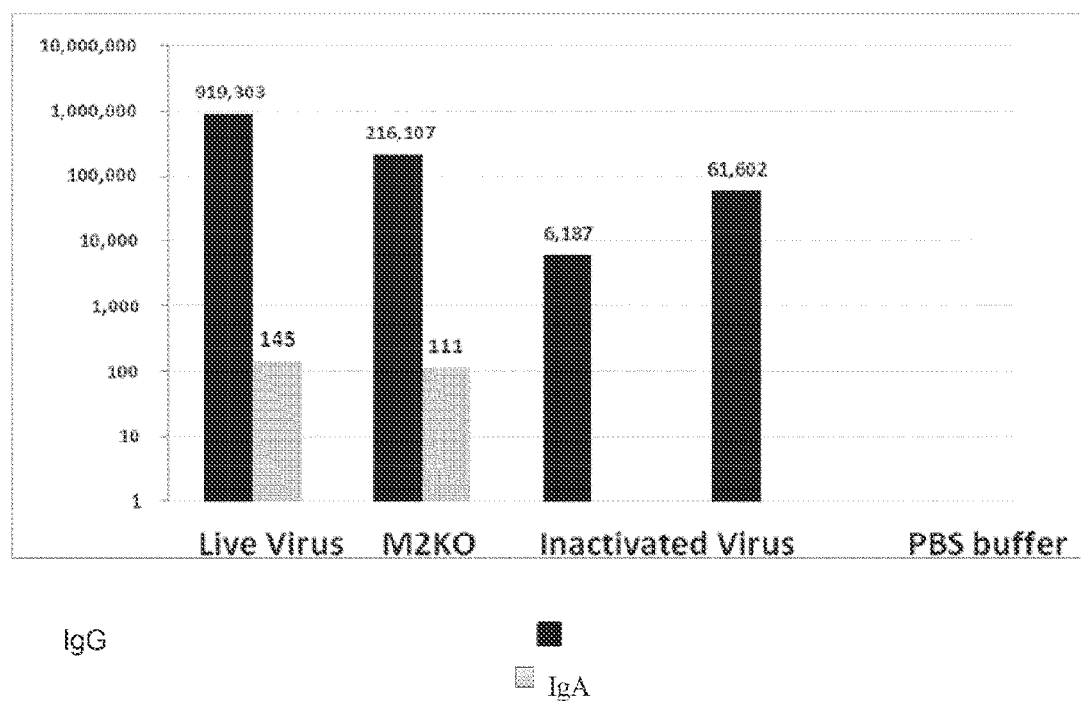
FIG. 17 is a chart showing ELISA titers of mice from different vaccination groups.
Figure 18:
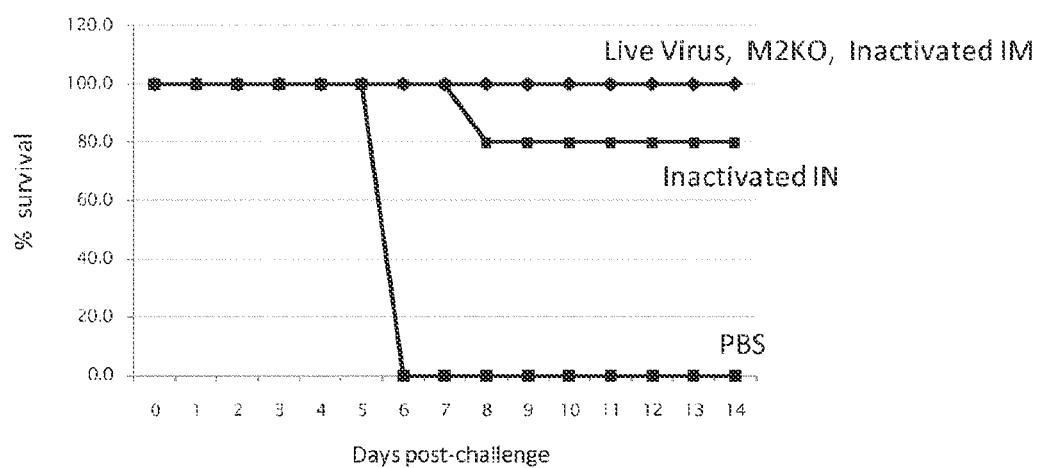
FIG. 18 is a chart showing % survival of mice after homosubtypic virus infection.
Figure 19:
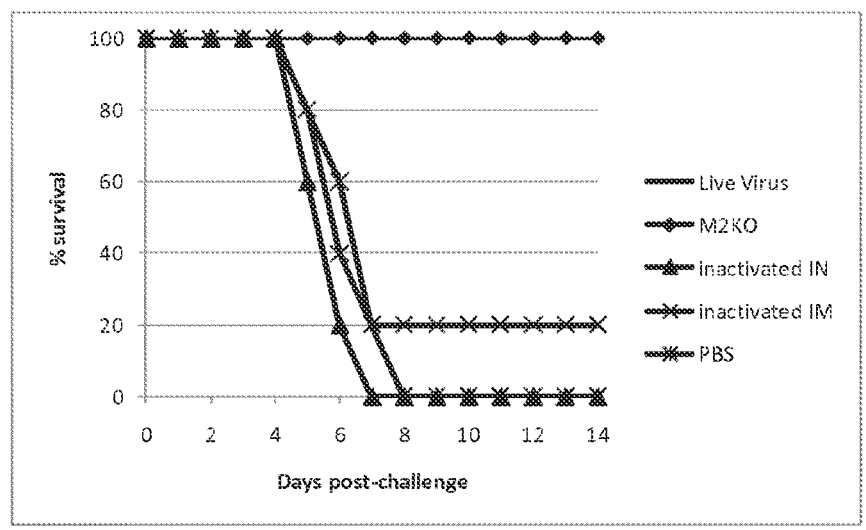
FIG. 19 is a chart showing % survival of mice after hetersubtypic virus challenge.

An evaluation of the ID-incoulated mice ($1.8 \times 10^4$) showed that two mice (1 and 5 in FIG. 14 and FIG. 15), elicited a better immune response than the other mice, and further did not develop symptoms of influenza infection (e.g., body weight loss, rough fur, quietness, etc.). However, all mice in the IM-inoculated group ($1.8 \times 10^4$) showed some symptoms and lost at least 10% in body weight.

Example 8

Stability of M2KO Variants

To test the stability of M2 gene of M2KO variants in wild-type cells, the M2KO variants were passaged in wild-type MDCK cells, which lacks M2 protein expression, along with M2CK cells which are M2 protein expressing MDCK cells. All M2KO variants were passageable in M2CK cells without any mutations until at least passage 10. Although, M2-1 (TM del M2KO), M2-2 (Splice def M2KO), and M2-3 (TM del+Splice def M2KO) were not able to be passaged in wild-type MDCK cells (no cytopathic effect (CPE) is seen in wild-type MDCK cells), M2KO(yk) showed CPE even after $4^{th}$ passage in MDCK cells. M segment RNAs were extracted from M2KO(yk) passage 4 in wild-type MDCK and the cDNA were sequenced. As shown in Table 14, two inserted stop codons of M2KO(yk) were edited and M2KO (yk) passage 4 in wild-type MDCK possessed full length M2 protein gene.

TABLE 14

Sequence around inserted 2 stop codons (nt 700-800 of M segment, stop codons at nt 786-791.)

| Virus | Sequence |
|---|---|
| Original M2KO(yk) | 3'CAACGGTTCAAGTGATTAATAAACTATTGCC (SEQ ID NO: 22) |
| M2KO(yk) passage 2 in M2CK | 3'CAACGGTTCAAGTGATTAATAAACTATTGCC (SEQ ID NO: 22) |
| M2KO(yk) passage 4 in MDCK | 3'CAACGGTTCAAGTGATTGGTGGACTGTTGCC (SEQ ID NO: 23) |

Example 9

M2KO Vaccinations

To demonstrate that the M2KO vaccine can stimulate an immune response similar to a natural influenza infection, a vaccine experiment was conducted. Natural influenza infection was represented by a low inoculum of PR8 virus and the standard inactivated flu vaccine was represented by inactivated PR8 virus (Charles River) delivered the standard intramuscular route and intranasally.

Six to seven week old BALB/c mice were immunized intranasally with live virus (10 pfu PR8), PR8 virus comprising M2KO(ΔTM) ($10^4$ pfu), or 1 μg inactivated PR8 virus, delivered both intranasally and intramuscularly. Mice given $10^4$ infectious particles of M2KO(ΔTM) intranasally lost no weight and showed no signs of infection. Further-more, the lungs of mice treated with M2KO(ΔTM) contained no detectable infectious particles three days post-inoculation. Sera was obtained from the immunized mice on day 21 and antibody titers against the hemagglutinin were determined by a standard ELISA assay. FIG. 17 shows that anti-HA IgG titers were highest in the live virus and M2KO (ΔTM) groups relative to the inactivated vaccine groups. Mucosal IgA antibody against influenza was detected in sera only in the live PR8 or M2KO vaccinated mice.

Six weeks after immunization, all groups were challenged with homosubtypic (PR8, H1N1) or heterosubtypic (Aichi, H3N2) influenza viruses. Both M2KO and inactivated vaccinations protected mice from homosubtypic virus infection (FIG. 18). However, only M2KO vaccinated mice were protected from heterosubtypic virus challenge (FIG. 19). The mice immunized with inactivated vaccine succumbed to infection similar to naïve mice.

Example 10

The M2KO(ΔTM) Virus does not Replicate in the Respiratory Tract or Other Organs

Summary—This example demonstrates that the M2KO (ΔTM) virus does not replicate in the respiratory tract or disseminate to other organs in the ferret model. The M2KO (ΔTM) virus was administered intranasally to 3 male ferrets at a dose level of $1\times10^7$ $TCID_{50}$. As a control, second group of 3 male ferrets was administered A/Brisbane/10/2007 (H3N2) influenza A virus intranasally at a dose of $1\times10^7$ $TCID_{50}$. Following virus inoculation, ferrets were observed until Day 3 post inoculation for mortality, with body weights, body temperatures and clinical signs measured daily. Necropsy was performed on all animals 3 days post inoculation. Organs were collected for histopathology and viral titers.

The control group receiving A/Brisbane/10/2007 (H3N2) exhibited a transient reduction in weight and an increase in body temperature 2 days after inoculation which was not observed in the M2KO(ΔTM) group. Activity levels were also reduced in the A/Brisbane/10/2007 group with sneezing observed on days 2-3 post infection. No changes in activity level or clinical signs associated with virus exposure were observed in the M2KO(ΔTM) group. Histopathological analysis revealed changes in the nasal turbinates in animals exposed to influenza A/Brisbane/10/2007 (H3N2) that were not seen in ferrets exposed to the M2KO(ΔTM) virus. Exposure to A/Brisbane/10/2007 resulted in atrophy of respiratory epithelium, infiltrates of neutrophils and edema in the nasal turbinates. No other organ was affected by the virus inoculation. Under the conditions of the experiment, the M2KO(ΔTM) virus did not induce clinical signs of infection or result in histological changes in the organs analyzed.

Materials and Methods

A. Vaccine Material and Control Virus: The M2KO(ΔTM) virus is a recombinant virus which possesses internal 6 genes of PR8 (nucleoprotein (NP), polymerase genes (PA, PB1, PB2), non-structural (NS), matrix (M)), but which does not express functional M2 protein, as well as HA and NA genes of Influenza A/Brisbane/10/2007-like A/Uruguay/716/2007 (H3N2). The A/Brisbane/10/2007 (H3N2) wild type virus served as the control virus and was supplied by IITRI. The viruses were kept frozen at −65° C. until used.

B. Test Article and Positive Control Dose Formulation: The M2KO(ΔTM) virus dosing solution of $1\times10^7$ $TCID_{50}$/mL per 316 μL was prepared by diluting 8 μL of 1×1010 $TCID_{50}$/mL into 2.528 mL PBS. The A/Brisbane/10/2007 (H3N2) at a titer of $1\times10^7$ $TCID_{50}$/mL per 316 μL was used undiluted.

C. Animals and Animal Care: Eight male ferrets were purchased from Triple F Farms and six of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison Wis.) and city of Chicago tap water were provided ad libitum and were refreshed at least once daily. Fluorescent lighting in the animal rooms was maintained on a 12-hr light/dark cycle. Animal room temperature and relative humidity were within respective protocol limits and ranged from 22.0 to 25.0° C. and 33 to 56%, respectively, during the study.

D. Animal Quarantine and Randomization: The ferrets were held in quarantine for five days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

E. Experimental Design: All animal procedures were performed in an animal biosafety level-2 facility in accordance with the protocols approved by the animal care and use committee at IIT Research Institute. 6 male ferrets (Triple F Farms, Sayre Pa.), 4 months of age at the time of study initiation were utilized for the study. Prior to infection, ferrets were monitored for 3 days to measure body weight and establish baseline body temperatures. Temperature readings were recorded daily through a transponder (BioMedic data systems, Seaford, Del.) implanted subcutaneously in each ferret. Blood was collected prior to study initiation via the jugular vein, and serum tested for influenza antibodies. Study animals free of influenza antibodies were randomized and divided into two groups (3 ferrets/group) as shown in Table 15. A group of 3 ferrets was anesthetized and inoculated intranasally with a single dose of 316 μL at $1\times10^7$ $TCID_{50}$ of M2KO(ΔTM) virus. A control group (3 ferrets) was inoculated with 316 μL at $1\times10^7$ $TCID_{50}$ of A/Brisbane/10/2007 (H3N2). Ferrets were observed daily to monitor body weight, body temperature and clinical symptoms. On Day 3 post-inoculation, ferrets (3 ferrets per group) were euthanized and necropsied. The following tissue samples were collected: nasal turbinates, trachea, lungs, kidneys, pancreas, olfactory bulbs, brains, livers, spleens, small and large intestines. One part of the collected samples was fixed with buffered neutral formalin for histological evaluation and the other part of the samples were stored at −65° C. for virus titration.

TABLE 15

Immunization and sample collection schedule

| Group | Dose | N | Organ collection (days post infection) |
|---|---|---|---|
| M2KO | $1 \times 10^7$ TCID$_{50}$ | 3 | 3 |
| Brisbane/10 | $1 \times 10^7$ TCID$_{50}$ | 3 | 3 |

F. Virus Inoculation: Ferrets were inoculated with either the M2KO(ΔTM) virus or wild type A/Brisbane/10/2007 (H3N2) influenza A virus. A vial of frozen stock was thawed and diluted to the appropriate concentration in phosphate buffered saline solution. Ferrets were anesthetized with ketamine/xylazine and the virus dose administered intranasally in a volume of 316 μL for the M2KO(ΔTM) virus and 316 μL for the A/Brisbane/10/2007 (H3N2) virus. To confirm the inoculation titer of the A/Brisbane/10/2007 (H3N2) virus, a TCID$_{50}$ assay was performed at IITRI on a portion of the prepared viral challenge solution. The viral titer assay was performed according to Illinois Institute of Technology Research Institute (IITRI) Standard Operating Procedures.

G. Moribundity/Mortality Observations: Following challenge, all animals were observed twice daily for mortality or evidence of moribundity. Animals were observed for 3 days post-challenge. Animals were euthanized by overdose with Sodium Pentobarbital 150 mg/kg, administered intravenously.

H. Body Weights and Body Weight Change: Body weights of animals were recorded upon receipt (random 10% sample), at randomization (Day −3 to 0), and daily after virus inoculation.

I. Clinical Observations: The change in temperature (in degrees Celsius) was determined daily for each ferret. Clinical signs of, inappetence, respiratory signs such as dyspnea, sneezing, coughing, and rhinorrhea and level of activity was assessed daily. A scoring system based on that described by Reuman, et al., "Assessment of signs of influenza illness in the ferret model," *J. Virol*, Methods 24:27-34 (1989), was used to assess the activity level as follows: 0, alert and playful; 1, alert but playful only when stimulated; 2, alert but not playful when stimulated; and 3, neither alert nor playful when stimulated. A relative inactivity index (RII) was calculated as the mean score per group of ferrets per observation (day) over the duration of the study.

J. Euthanasia: Study animals were euthanized by an intravenous dose of sodium pentobarbital 150 mg/kg. Death was confirmed by absence of observable heartbeat and respiration. Necropsies were performed on all study animals.

K. Necropsy: Nasal turbinates, trachea, lungs, kidneys, pancreas, olfactory bulbs, brain, liver, spleen, small and large intestines were harvested. One portion of each tissue was fixed in formalin and the other portion given to IITRI staff for freezing and storage. Tissue harvested for titers are: right nasal turbinates, upper ⅓ of trachea, right cranial lung lobe, right kidney, right arm of pancreas (near duodenum), right olfactory bulb, right brain, right lateral lobe of liver, right half of spleen (end of spleen seen on opening the abdominal cavity), small intestine and large intestine.

L. Histopathological analysis: Tissues were processed through to paraffin blocks, sectioned at approximately 5-microns thickness, and stained with hematoxylin and eosin (H & E).

M. Serum Collection: Pre-vaccination (Day −3) serum was collected from all ferrets. Ferrets were anesthetized with a ketamine (25 mg/kg) and xylazine (2 mg/kg) mixture. A sample of blood (approximately 0.5-1.0 mL) was collected via the vena cava from each ferret and processed for serum. Blood was collected into Serum Gel Z/1.1 tubes (Sarstedt Inc. Newton, N.C.) and stored at room temperature for not more than 1 hour before collecting serum. Serum Gel Z/1.1 tubes were centrifuged at 10,000×g for 3 minutes and the serum collected. Individual pre-inoculation serum samples were collected and two aliquots made from each sample. One aliquot was tested prior to the initiation of the study to confirm ferrets are free of antibodies to influenza A viruses and one aliquot of the serum stored at −65° C.

N. Hemagglutination Inhibition (HI) Assay: Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2) influenza A virus. After incubation, 0.5% chicken red blood cells were added to each sample and incubated. Presence or absence of hemagglutination was then scored.

O. Virus Titers: The concentration of infectious virus in the pre- and post-challenge virus inoculum samples was determined by TCID$_{50}$ in Madin-Darby Canine Kidney (MDCK) cells. Briefly, samples kept at −65° C. were thawed and centrifuged to remove cellular debris. The resulting supernatant were diluted 10-fold in triplicate in 96-well microtiter plates in Dulbecco's Modified Eagle Medium (DMEM) (Gibco, Carlsbad, Calif., USA) containing Penicillin/Streptomycin, 0.1% Gentamicin, 3% NaCO$_3$, 0.3% BSA fraction V (Sigma St. Louis, Mo.), 1% MEM vitamin solution (Sigma) and 1% L-glutamine (Mediatech, Manassas, Va., USA). After 10-fold serial dilutions were made, 100 L was transferred into respective wells of a 96-well plate which contained a monolayer of MDCK cells. Plates were incubated at 37° C.±2° C. in 5±2% CO$_2$ 70% humidity. After 48 hours, the wells were observed for cytopathogenic effect (CPE). Supernatant from each well (50 μl) was transferred to a 96 well plate and the hemagglutination (HA) activity determined and recorded. The HA activity of the supernatant was assessed by HA assay with 0.5% packed turkey red blood cells (cRBCs). TCID$_{50}$ titers were calculated using the method of Reed L J and Muench H, "A simple method for estimating 50% endpoints," *Am. J. Hygiene* 27: 493-497 (1938).

P. Data Analysis: Body weights and body weight gains (losses) and changes in body temperature were determined for each individual animal expressed as mean and standard deviations of the mean for each test group.

Results

After inoculation with either the M2KO(ΔTM) virus or A/Brisbane/10/2007 (H3N2) influenza A virus, ferrets were monitored for survival and clinical signs of infection. Results are presented in Table 16A and 16B. All ferrets survived infection with M2KO(ΔTM) virus and A/Brisbane/10/2007 (H3N2). Ferrets inoculated with A/Brisbane/10/2007 presented respiratory signs (sneezing) on Day 2 and 3. The relative inactivity index of ferrets inoculated with A/Brisbane/10/2007 was 0.67; whereas ferrets inoculated with M2KO(ΔTM) showed no reduction activity level with a relative inactivity index of 0.0.

Changes in body weight and temperature after virus inoculation are shown in FIG. 20 and FIG. 21. After inoculation with A/Brisbane/10/2007 (H3N2), a 2-3% loss of body weight was observed on Day 2 post inoculation in all animals. Minimal to zero weight loss was observed in ferrets inoculated with the M2KO(ΔTM) virus. One M2KO(ΔTM) inoculated ferret exhibited weight loss on Day 2 post inoculation of 1%. Elevated body temperatures of 40.3-40.7° C. were observed in ferrets inoculated with A/Brisbane 10/2007 on Day 2 post inoculation. Body temperatures returned to normal range by Day 3. Body temperatures for M2KO (ΔTM) inoculated ferrets remained in normal range throughout the duration of the study. To determine if the M2KO (ΔTM) virus would replicate in the respiratory tract or other organs and induce pathology, tissues of ferrets were histologically examined on day 3 post inoculation and compared to those from ferrets inoculated with A/Brisbane/10/2007. In ferrets inoculated with A/Brisbane/10/2007, pathology was observed only in the nasal turbinates. Atrophy of respiratory epithelium, infiltrates of neutrophils and edema were observed in the nasal turbinates. No histopathological changes associated with viral infection were observed in ferrets inoculated with the M2KO(ΔTM) virus. The concentrations of pre- and post-challenge virus dosing solutions were $10^{7.5}$ TCID$_{50}$/mL and $10^{7.75}$ TCID$_{50}$/mL, respectively, indicating good stability of the challenge material throughout administration.

TABLE 16A

Effect of virus inoculation on survival and clinical signs of infection in ferrets.

| Group | N | Serum HI Titer[a] | Total number dead | Respiratory signs (observed day of onset) | Loss of Appetite | Lethargy (RII)[c] |
|---|---|---|---|---|---|---|
| M2KO | 3 | <10 | 0/3 | 0/3 | 0/3 | 0 |
| Brisbane/10 | 3 | <10 | 0/3 | 2/3 (2) | 0/3 | 0.67 |

Clinical signs[b]

[a]Hemagglutination inhibition (HI) antibody titers to homologous virus in ferret serum prior to virus inoculation.
[b]Clinical signs were observed for 3 days after virus inoculation. Except for lethargy, findings for clinical signs are given as no. of ferrets with sign/total no. Respiratory signs included sneezing.
[c]Determined twice daily for 3 days of observation based on the scoring system and was calculated as the mean score per group of ferrets per observation (day) over the 3-day period. The relative inactivity index before inoculation was 0.

TABLE 16B

M2KO(ΔTM) Does Not Replicate in Ferret Respiratory Organs Harvested On Day 3 Virus Titer (log pfu/g)

|  | Brisbane/10 | M2KO(ΔTM) |
|---|---|---|
| Nasal Turbinates | 5.43 | 0 |
| Lung | 0 | 0 |

Conclusion

This example shows that by Day 3 post inoculation, the M2KO(ΔTM) virus does not induce clinical signs of disease or histopathological changes associated with infection of wild type virus. This shows that the M2KO(ΔTM) virus of the present technology is useful for intranasal influenza vaccines.

Example 11

Immune Response and Protective Effects M2KO(ΔTM) Virus Relative to Other Vaccines Summary—This example demonstrates the immune response elicited by the M2KO(ΔTM) vaccine and the protective effects of the vaccine in the ferret model. The M2KO(ΔTM) virus was administered intransally to 12 male ferrets at a dose level of $1 \times 10^7$ TCID$_{50}$. As a control, a second group of 12 male ferrets was administered the FM#6 virus intranasally at a dose of $1 \times 10^7$ TCID$_{50}$. A third group of ferrets was administered OPTI-MEM™ as a placebo control. A prime only or prime-boost vaccination regimen was utilized for each treatment group. Ferrets receiving the prime-boost vaccination regimen were administered the prime vaccine (Day 0) and the boost vaccination 28 days later (Day 28). Ferrets receiving only the prime vaccines were administered a single vaccination on the same day as the booster vaccine was given to the prime-boost ferrets (Day 28). Following each vaccination, ferrets were observed for 14 days post inoculation for mortality, with body weights, body temperatures and clinical signs measured daily. Nasal washes were collected from ferrets on days 1, 3, 5, 7 and 9 post-prime vaccination to look for viral shedding. Nasal washes and serum were collected weekly from all ferrets post-vaccination to evaluate antibody levels over time.

All animals were challenged intranasally on Day 56 with $1 \times 10^7$ TCID$_{50}$ of A/Brisbane/10/2007 (H3N2). Following challenge, ferrets were monitored for 14 days post inoculation for mortality, with body weights, body temperatures and clinical signs measured daily. Nasal washes were collected on days 1, 3, 5, 7, 9 and 14 post challenge from ferrets in each group for viral titers. Additionally, serum was collected post-challenge (day 70) from surviving ferrets for analysis. Necropsy was performed on 3 ferrets per group 3 days post challenge. Organs were collected for histopathology and viral titers.

No vaccine related adverse events were observed among the 5 groups. After challenge, the placebo control group exhibited an increase in body temperature 2 days after challenge and a reduction in weight. A reduction in weight was also observed in M2KO(ΔTM) and FM#6 vaccinated groups; however, the reduction was to less than that observed in the OPTI-MEM™ group. Activity levels were not reduced in any groups; however sneezing was observed in all groups after challenge. Histopathological analysis revealed an increase in severity of mixed cell infiltrates in the lung of vaccinated ferrets when compared to the lung infiltrates in the OPTI-MEM™ control group. In the nasal turbinates, animals receiving a prime or prime plus boost regimen of either M2KO(ΔTM) or FM#6 had lower severity of atrophy of respiratory epithelium when compared to the OPTI-MEM™ control group. Vaccination with the M2KO (ΔTM) virus appeared to provides similar protection against viral challenge as the FM#6 virus.

Materials and Methods

A. Vaccine Material: The M2KO(ΔTM) virus is a recombinant virus which possesses internal 6 genes of PR8 (nucleoprotein (NP), polymerase genes (PA, PB1, PB2), non-structural (NS), matrix (M)), but which does not express functional M2 protein, as well as HA and NA genes of Influenza A/Brisbane/10/2007-like A/Uruguay/716/2007 (H3N2). The FM#6 virus is clone #6 of the A/Uruguay/716/2007 (H3N2) influenza A virus from FluMist® (2009-2010 formula). The M2KO(ΔTM) virus and FM#6 virus were administered intranasally to the animals in a 316 µL dose of $1 \times 10^7$ TCID$_{50}$ (50% Tissue Culture Infectious Doses).

B. Test Article and Positive Control Dose Formulation: The M2KO(ΔTM) virus dosing solution of $1 \times 10^7$ TCID$_{50}$/mL per 316 µL was prepared by diluting 120 µL of $1 \times 10^9$ TCID$_{50}$/mL into 3.680 mL PBS. The FM#6 virus at a titer of $1 \times 10^7$ TCID$_{50}$/mL per 316 µL was prepared by diluting 120 µL of $1 \times 10^9$ TCID$_{50}$/mL into 3.680 mL PBS.

C. Animals and Animal Care: Thirty-six male ferrets were purchased from Triple F Farms and 30 of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison Wis.) and city of Chicago tap water were provided ad libitum and were refreshed at least three time per week. Fluorescent lighting in the animal rooms was maintained on a 12-hr light/dark cycle. Animal room temperature and relative humidity were within respective protocol limits and ranged from 20.0 to 25.0° C. and 30 to 63%, respectively, during the study.

D. Animal Quarantine and Randomization: The ferrets were held in quarantine for seven days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

E. Experimental Design: To assess the M2KO(ΔTM) vaccine efficacy, ferrets were immunized with M2KO(ΔTM) virus, cold adapted live attenuated virus (FM#6) or mock immunized by medium (OPTI-MEM™). The animals body weight, body temperature and clinical symptoms were monitored and immunological responses evaluated 30 male ferrets (Triple F Farms, Sayre Pa.), 4 months of age at the time of study initiation were utilized for the study. All animal procedures were performed in an animal biosafety level-2 or biosafety level-3 facility in accordance with the protocols approved by the animal care and use committee at IIT Research Institute. Prior to inoculation, ferrets were monitored for 3 days to measure body weight and establish baseline body temperatures. Temperature readings were recorded daily through a transponder (BioMedic data systems, Seaford, Del.) implanted subcutaneously in each ferret. Blood was collected prior to study initiation, and serum tested for influenza antibodies. Only ferrets with HAI (hemagglutination inhibition) titers 40 to A/Brisbane/10/2007 (H3N2) were considered seronegative and used in this study. Study animals were randomized and divided into 5 groups (6 ferrets/group) as shown in Table 17. Two groups (1 & 3) received the M2KO(ΔTM) virus and 2 groups (2 & 4) received the FM#6 virus. One group (5) was mock immunized with OPTI-MEM™. Within each vaccine group, ferrets were divided into two vaccine regimens, six receiving a prime vaccination only (Prime only) and six receiving a prime vaccination followed by a booster vaccine 28 days after prime vaccination (Prime/Boost). Prime/Boost Groups: Ferrets were inoculated intranasally with a single dose of 316 µL of $1 \times 10^7$ TCID$_{50}$ of M2KO(ΔTM) virus on days 0 and 28. Control groups were inoculated intranasally with 316 µL of $1 \times 10^7$ TCID$_{50}$ (same dose as M2KO(ΔTM)) of FM#6 or mock inoculated with 316 µL of OPTI-MEM™ on days 0 and 28. Ferret body temperatures, weights, and clinical symptoms were monitored daily for 14 days post-inoculations. Nasal washes were collected from all ferrets, including OPTI-MEM™ control group, on days 1, 3, 5, 7, 9 and 14 post prime vaccination for virus titration in cells and on days 21 and 49 for antibody titration. Nasal wash samples were kept at −65° C. Blood was collected prior to inoculation (day −3 to −5) and days 7, 14, 21 35, 42, and 49 and serum kept at −65° C. until measurement of antibody titer by ELISA and HI assay.

Prime only Groups: Ferrets were inoculated intranasally with a single dose of 316 µL of $1 \times 10^7$ TCID$_{50}$ of M2KO (ΔTM) virus on day 28. Control groups were inoculated intranasally with 316 µL of $1 \times 10^7$ TCID$_{50}$ (same dose as M2KO(ΔTM)) of FM#6 or mock inoculated with 316 µL of OPTI-MEM™ on day 28. Ferret body temperatures, weights, and clinical symptoms were monitored daily for 14 days post-inoculation. Nasal washes were collected from all ferrets on days 29, 31, 33, 35, 37, and 42 for virus titration in cells and on day 49 for antibody titration. Nasal wash samples were kept at −65° C. Blood was collected prior to inoculation (day 23 to 25) and days 35, 42, and 49 and serum was kept at −65° C. until measurement of antibody titer by ELISA and HAI assay. All ferrets were challenged with a dose of 316 µL of $1 \times 10^7$ TCID$_{50}$ of wild-type A/Brisbane/10/2007 (H3N2) influenza virus on day 56, 4 weeks after the prime/boost vaccine was administered. Ferret body weight, body temperature and clinical symptoms were monitored for 14 days after challenge and nasal washes and organs collected. Nasal washes were collected from challenged ferrets on days 1, 3, 5, 7, 9, and 14 post-challenge (days 57, 59, 61, 63, 65, and 70) and the samples kept at −65° C. for virus titration in cells. On Day 3 post-challenge (day 59), the animals (3 animals per group, total 15 animals) were euthanized and the following tissue samples collected: nasal turbinates, trachea, and lungs. One part of the collected samples was fixed with buffered neutral formalin for histological evaluation and the other part of the samples was stored at −65° C. for virus titration. Blood was collected 14 days post-challenge (day 70) and all surviving animals were euthanized.

TABLE 17

Vaccination and sample collection schedule

| Group | Vaccine Virus[1] | N | Vaccination (days) | Nasal Washes[2] (days) | Challenge (day) | Nasal Washes (days) | Organs[3] N = 3 (day) | Serum Collections |
|---|---|---|---|---|---|---|---|---|
| Prime Only | | | | | | | | |
| 1 | M2KO | 6 | 28 | 29, 31, 33, 35, 37, 42, 49 | 56 | 57, 59, 61, 63, 65, 70 | 59 | 35, 42, 49, 70 |
| 2 | FM#6 | 6 | 28 | 29, 31, 33, 35, 37, 42, 49 | 56 | 57, 59, 61, 63, 65, 70 | 59 | 35, 42, 49, 70 |
| Prime/Boost | | | | | | | | |
| 3 | M2KO | 6 | 0, 28 | 1, 3, 5, 7, 9, 14, 21, 49 | 56 | 57, 59, 61, 63, 65, 70 | 59 | 7, 14, 21, 35, 42, 49, 70 |
| 4 | FM#6 | 6 | 0, 28 | 1, 3, 5, 7, 9, 14, 21, 49 | 56 | 57, 59, 61, 63, 65, 70 | 59 | 7, 14, 21, 35, 42, 49, 70 |
| 5 | Vehicle (Control) | 6 | 0, 28 | 1, 3, 5, 7, 9, 14, 21, 49 | 56 | 57, 59, 61, 63, 65, 70 | 59 | 7, 14, 21, 35, 42, 49, 70 |

[1]Intranasally inoculated with a dose of $1 \times 10^7$ TCID$_{50}$
[2]Nasal Washes only collected from animals after prime vaccination.
[3]Organs (nasal terminated, trachea and lung) collected from 3 ferrets per group for histology and viral titers.

F. Virus Inoculation: Ferrets were inoculated with either the M2KO(ΔTM) virus or FM#6 influenza A virus. A vial of frozen stock was thawed and diluted to the appropriate concentration in phosphate buffered saline solution. Ferrets were anesthetized with ketamine/xylazine and the virus dose administered intranasally in a volume of 316 μL for the M2KO(ΔTM) virus and 316 μL for the FM#6 virus. To confirm the inoculation titer of the M2KO(ΔTM) and FM#6 viruses, aliquots of the dosing solutions were collected prior to dosing (pre-dose) and after dosing (post-dose). The aliquots were stored at −65° C. for virus titration.

G. Challenge Virus: Influenza A virus, strain A/Brisbane/10/2007, serotype H3N2 was used to challenge the ferrets. The virus was stored at approximately −65° C. prior to use. The dose level of challenge virus used was prepared at $1\times10^7$ $TCID_{50}$ in a volume of 316 μL. A quantitative viral infectivity assay, $TCID_{50}$ assay was performed at IITRI on a portion of the prepared viral challenge solution. The viral titer assay was performed according to IITRI Standard Operating Procedures.

H. Moribundity/Mortality Observations: Following challenge, all animals were observed twice daily for mortality or evidence of moribundity. Animals were observed for 14 days after vaccine inoculation and for 14 days after challenge.

I. Body Weights and Body Weight Change: Body weights were recorded within two days of receipt and at randomization. All study animals were weighed prior to inoculation, daily for 14 days following each vaccination and assessed daily for 14 days post challenge. Prior to inoculation, ferrets were monitored for 3-5 days to measure establish baseline body temperatures. Temperature readings were recorded daily for 14 days following each vaccination and recorded daily for 14 days post challenge through a transponder (BioMedic data systems, Seaford, Del.) implanted subcutaneously in each ferret. The change in temperature (in degrees Celsius) was calculated at each time point for each animal.

J. Clinical Observations: The change in temperature (in degrees Celsius) was determined daily for each ferret. Clinical signs of, inappetence, respiratory signs such as dyspnea, sneezing, coughing, and rhinorrhea and level of activity was assessed daily. A scoring system based on that described by Reuman, et al., "Assessment of signs of influenza illness in the ferret model," *J. Virol*, Methods 24:27-34 (1989), was used to assess the activity level as follows: 0, alert and playful; 1, alert but playful only when stimulated; 2, alert but not playful when stimulated; and 3, neither alert nor playful when stimulated. A relative inactivity index (RII) was calculated as the mean score per group of ferrets per observation (day) over the duration of the study.

K. Survival Checks: Two survival checks were performed daily on all study animals throughout the study. Both survival checks occurred simultaneously with the clinical observations. The second check was performed later within the same day.

L. Nasal Washes: Ferrets were anesthetized with a ketamine (25 mg/kg) and xylazine (2 mg/kg) mixture, and 0.5 ml of sterile PBS containing penicillin (100 U/ml), streptomycin (100 μg/ml), and gentamicin (50 μg/ml) was injected into each nostril and collected in a specimen cup when expelled by the ferret. The nasal wash was collected into a cryovial and the recovered volume recorded.

M. Euthanasia: Study animals were euthanized by an intravenous dose of sodium pentobarbital 150 mg/kg. Death was confirmed by absence of observable heartbeat and respiration.

N. Necropsy: Necropsy was performed by Charles River Laboratories, Pathology Associates (PAI). The PAI team was comprised of a supervising pathologist and two prosectors. Nasal turbinates, trachea and lungs were harvested. One portion of each tissue was fixed in formalin and the other portion given to IITRI staff for freezing and storage. Tissue harvested for titers are: right nasal turbinates, upper ⅓ of trachea and right cranial lung lobe.

O. Histopathological analysis: Following each necropsy, tissues were transported to the PAI Chicago facility. Upon receipt, partial tissues from all 15 ferrets were processed through to paraffin blocks, sectioned at approximately 5-microns thickness, and stained with hematoxylin and eosin (H & E). All paraffin H & E slides were evaluated microscopically.

P. Serum Collection: Pre-vaccination serum (days −3 to −5 for groups 3, 4, and 5, and days 23 to 25 for groups 1 and 2) serum was collected from the ferrets. Post inoculation, serum was collected on days 7, 14, 21, 35, 42, 49, and 70 from groups 3, 4, and 5. Serum was collected on days 35, 42, 49, and 70 from groups 1 and 2. Ferrets were anesthetized with a ketamine (25 mg/kg) and xylazine (2 mg/kg) mixture. A sample of blood (approximately 0.5-1.0 mL) was collected via the vena cava from each ferret and processed for serum. Blood was collected into Serum Gel Z/1.1 tubes (Sarstedt Inc. Newton, N.C.) and stored at room temperature for not more than 1 hour before collecting serum. Serum Gel Z/1.1 tubes were centrifuged at 10,000×g for 3 minutes and the serum collected.

Q. Hemagglutination Inhibition (HI) Assay: Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2) influenza A virus. After incubation, 0.5% avian red blood cells were added to each sample and incubated for 30 ±5 minutes. Presence or absence of hemagglutination was then scored.

R. Virus Titers: The concentration of infectious virus in the pre- and post-challenge virus inoculum samples was determined by $TCID_{50}$ assay in Madin-Darby Canine Kidney (MDCK) cells. Briefly, samples kept at −65° C. were thawed and centrifuged to remove cellular debris. The resulting supernatant were diluted 10-fold in triplicate in 96-well microtiter plates in Dulbecco's Modified Eagle Medium (DMEM) (Gibco, Carlsbad, Calif., USA) containing Pencillin/Streptomycin, 0.1% Gentamicin, 3% $NaCO_3$, 0.3% BSA fraction V (Sigma St. Louis, Mo.), 1% MEM vitamin solution (Sigma) and 1% L-glutamine (Mediatech, Manassas, Va., USA). After 10-fold serial dilutions were made, 100 μL was transferred into respective wells of a 96-well plate which contained a monolayer of MDCK cells. Plates were incubated at 37° C.±2° C. in 5±2% CO2 70% humidity. After 48 hours, the wells were observed for cytopathogenic effect (CPE). Supernatant from each well (50 μl) was transferred to a 96 well plate and the hemagglutination (HA) activity determined and recorded. The HA activity of the supernatant was assessed by HA assay with 0.5% packed turkey red blood cells (tRBCs). $TCID_{50}$ titers were calculated using the method of Reed L J and Muench H, "A simple method for estimating 50% endpoints," *Am. J. Hygiene* 27: 493-497 (1938).

S. Data Analysis: Body weights and body weight gains (losses) and changes in body temperature were determined for each individual animal expressed as mean and standard deviations of the mean for each test group.

Results

After intranasal vaccination with either the M2KO(ΔTM) virus or the FM#6 virus, ferrets were monitored daily for clinical signs of infection. Nasal washes were collected after prime vaccination to monitor viral shedding and serum collected to measure serum antibody titers. Results are presented in Tables 18A, 18B, and 18C.

TABLE 18A

Effect of vaccination on survival and clinical signs of infection in ferrets.

| | | | | | Clinical signs[b] | | |
| | | | | | Respiratory signs | | |
| Group | Treatment | N | Serum HI Titer[a] | Total number dead | (observed day of onset) | Loss of Appetite | Lethargy (RII)[c] |
|---|---|---|---|---|---|---|---|
| | | | Prime | | | | |
| 1 | M2KO | 6 | <10 | 0/6 | 2/6 (8) | 0/6 | 0 |
| 2 | FM#6 | 6 | <10 | 0/6 | 0/6 | 0/6 | 0 |
| 3 | M2KO | 6 | <10 | 0/6 | 0/6 | 0/6 | 0.07 |
| 4 | FM#6 | 6 | <10 | 0/6 | 0/6 | 0/6 | 0.29 |
| 5 | Vehicle (Control) | 6 | <10 | 0/6 | 0/6 | 0/6 | 0 |
| | | | Boost | | | | |
| 3 | M2KO | 6 | <10 | 0/6 | 0/6 | 0/6 | 0 |
| 4 | FM#6 | 6 | <10 | 0/6 | 2/6 (7) | 0/6 | 0 |
| 5 | Vehicle (Control) | 6 | <10 | 0/6 | 2/6 (4) | 0/6 | 0 |

[a]Hemagglutination inhibition (HI) antibody titers to homologous virus in ferret serum prior to virus inoculation.
[b]Clinical signs were observed for 3 days after virus inoculation. Except for lethargy, findings for clinical signs are given as no. of ferrets with sign/total no. Respiratory signs included sneezing.
[c]Determined twice daily for 3 days of observation based on the scoring system and was calculated as the mean score per group of ferrets per observation (day) over the 3-day period. The relative inactivity index before inoculation was 0.

TABLE 18B

Virus Titers in Ferret Respiratory Organs After Challenge

| | Nasal Turbinates (N = 3, Log pfu/g) | Trachea (N = 3, Log pfu/g) |
|---|---|---|
| M2KO(ΔTM) prime only | 5.23 ± 0.24 | ** |
| FluMist ® prime only | 5.53 ± 0.82 | 2.52 ± 1.73 |
| M2KO(ΔTM) prime-boost | 6.16 ± 1.17 | 1.37 ± 1.06 |
| FluMist ® prime-boost | 6.24 ± 1.31 | 3.30 ± 1.96 |

** Not Detected

TABLE 18C

Mucosal IgA Responses in Ferret
α-HA ELISA IgA titers 14 days post-challenge:

|  | Nasal Wash | Sera |
|---|---|---|
| M2KO(ΔTM) prime only | 14 | Not Tested |
| FluMist ® prime only | 29 | Not Tested |

Figure 23:
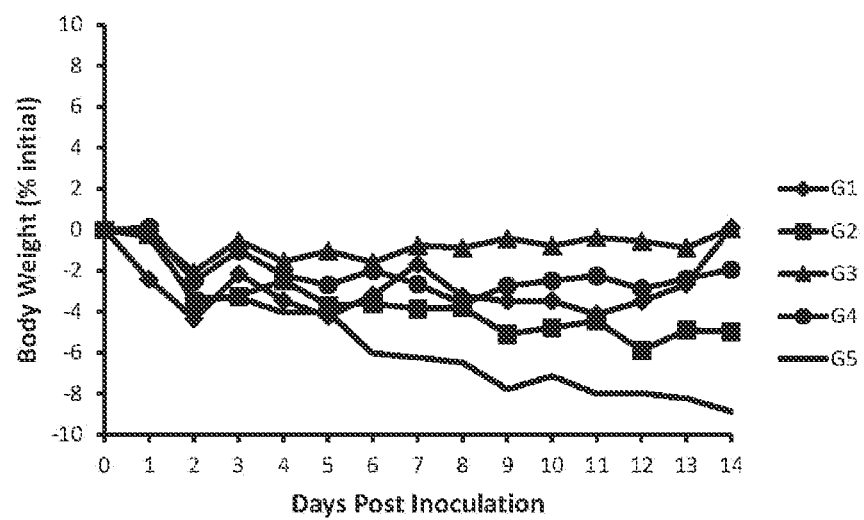
FIG. 23 is a chart showing changes in body weight of ferrets after challenge. Ferrets were challenged with $10^7$ TCID$_{50}$ of A/Brisbane/10/2007 (H3N2) influenza A virus. Body weight was monitored for 14 days post inoculation.
Figure 25:
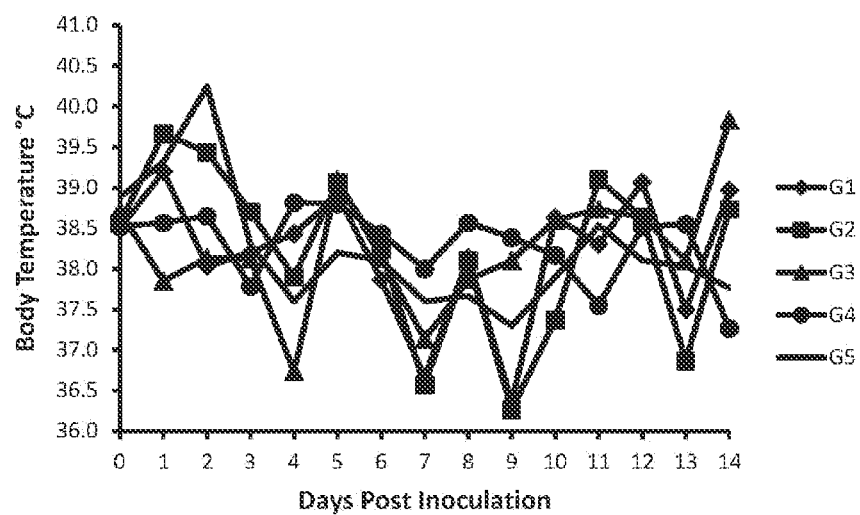
FIG. 25 is a chart showing changes in body temperature of ferrets after challenge. Ferrets were challenged with $10^7$ TCID$_{50}$ of A/Brisbane/10/2007 (H3N2) influenza A virus. Body temperature was monitored for 14 days post inoculation.

All ferrets survived vaccination with M2KO(ΔTM) virus and FM#6 virus. After prime vaccination, two ferrets inoculated with M2KO(ΔTM) virus presented respiratory signs (sneezing) on Day 8. After boost vaccination, ferrets inoculated with the FM#6 virus presented respiratory signs (sneezing) 7 days post vaccination. Sneezing was also observed in the OPTI-MEM™ ferrets on day 4 post boost. After prime vaccination, the relative inactivity index of ferrets inoculated with M2KO(ΔTM) virus and FM#6 virus was 0.07 and 0.27, respectively. This reduction in activity was only observed in one group per virus after prime vaccination. After boost vaccination no reduction in activity level was observed. Changes in body weight and temperature after virus inoculation are shown in FIG. 22 and FIG. 23. No weight loss was observed after vaccination; however, vaccination appeared to have an effect on weight gain. After vaccination, body weights of OPTI-MEM™ control ferrets increased 20% during the 14 day observation whereas body weight gain of the M2KO(ΔTM) or FM#6 vaccinated ferrets ranged from 6-15% after prime and 4-6% after boost. No increase in body temperature was observed in any groups after vaccination. Changes in body weight and temperature after challenge are shown in FIG. 24 and FIG. 25 and clinical signs summarized in Table 19.

TABLE 19

Effect of virus challenge on survival and clinical signs of infection in ferrets.

| Group | Treatment | N | Total number dead | Respiratory signs (observed day of onset) | Loss of Appetite | Lethargy (RII)[b] |
|---|---|---|---|---|---|---|
| 1 | M2KO | 6 | 0/6 | 5/6 (2) | 0/6 | 0 |
| 2 | FM#6 | 6 | 0/6 | 5/6 (1) | 0/6 | 0 |
| 3 | M2KO | 6 | 0/6 | 3/6 (2) | 0/6 | 0 |
| 4 | FM#6 | 6 | 0/6 | 3/6 (2) | 0/6 | 0 |
| 5 | Vehicle (Control) | 6 | 0/6 | 3/6 (3) | 0/6 | 0 |

Clinical signs[a]

[a]Clinical signs were observed for 3 days after virus inoculation. Except for lethargy, findings for clinical signs are given as no. of ferrets with sign/total no. Respiratory signs included sneezing.
[b]Determined twice daily for 3 days of observation based on the scoring system and was calculated as the mean score per group of ferrets per observation (day) over the 3-day period. The relative inactivity index before inoculation was 0.

After challenge with A/Brisbane/10/2007 (H3N2), a 2-4% loss of body weight was observed on Day 2 post challenge in all animals. Throughout the 14 day observation period animal body weights remained below their initial weight. OPTI-MEM™ ferrets lost the most weight (8%). Weight loss among vaccinated ferrets was dependent on the vaccine regimen. Ferrets receiving the prime only regimen of M2KO (ΔTM) or FM#6 lost a maximum of 5% and 4% respectively. Ferrets receiving a booster lost a maximum of 3% for the FM#6 group and 2% for the M2KO(ΔTM) group. Elevated body temperatures post challenge were observed on Day 2 in OPTI-MEM™ ferrets and on Day 1 ferrets receiving the prime only regimens of M2KO(ΔTM) or FM#6 (FIG. 25). Body temperatures for ferrets receiving a booster remained within normal range.

To determine if the vaccination would prevent replication of challenge virus in the respiratory tract and reduce organ pathology tissues of challenged ferrets were histologically examined on day 3 post inoculation. Changes in the lungs of animals receiving the M2KO(ΔTM) prime only or prime/boost regimen were associated with increase in severity of mixed cell infiltrates in the lung when compared to the OPTI-MEM™ group. Minor differences in lung infiltrate incidences were observed between the M2KO(ΔTM) prime group and the M2KO(ΔTM) prime/boost group. An increase in the severity of mixed cell infiltrates in the lung was also seen in the FM#6 prime group and FM#6 prime/boost group when compared to the OPTI-MEM™ group. A slight increase in severity in lung mixed cell infiltrates was observed in the FM#6 prime/boost group over the FM#6 prime only group. In the nasal turbinates, animals receiving the prime or prime/boost of the M2KO(ΔTM) virus had lower severity of atrophy of respiratory epithelium when compared to the OPTI-MEM™ group. There were no differences in atrophy of the nasal turbinates when comparing prime versus prime/boost M2KO(ΔTM) groups. A slight increase in severity of atrophy of respiratory epithelium in animals receiving the FM#6 prime/boost regimen was observed versus animals FM#6 prime only regimen; the severity of atrophy of respiratory epithelium in all FM#6 animals was lower than that seen in the OPTI-MEM™ group. There was a decrease in incidence of neutrophilic infiltrates into the nasal cavity (lumen) in the M2KO(ΔTM) prime and prime/boost groups compared to the OPTI-MEM™ group. Neutrophilic luminal infiltrates in the M2KO(ΔTM) prime only group was interpreted as not different from the OPTI-MEM™ group. There was a slight increase in severity of luminal neutrophilic infiltrates in the FM#6 prime only and prime/boost groups when compared to the OPTI-MEM™ group. The concentrations of pre- and post-challenge virus dosing solutions were $10^7 0.83$ $TCID_{50}$/mL and $10^7 0.25$ $TCID_{50}$/mL, respectively, indicating good stability of the challenge material throughout administration.

Figure 45:
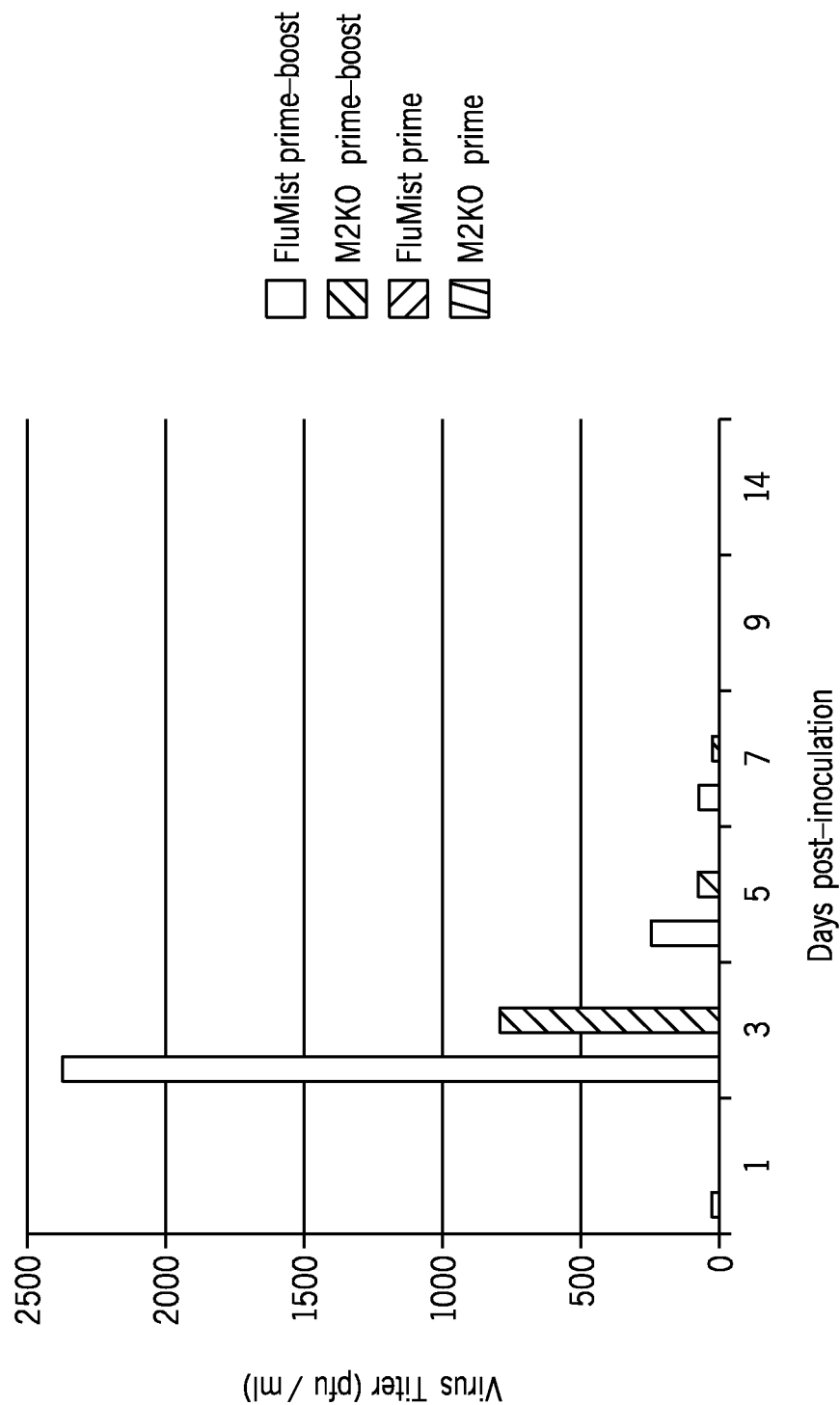
FIG. 45 is a chart showing M2KO(ΔTM) and FluMist® virus replication in the ferret respiratory tract.

FIG. 45 shows M2KO(ΔTM) and FluMist® virus replication in the ferret respiratory tract.

Figure 46:
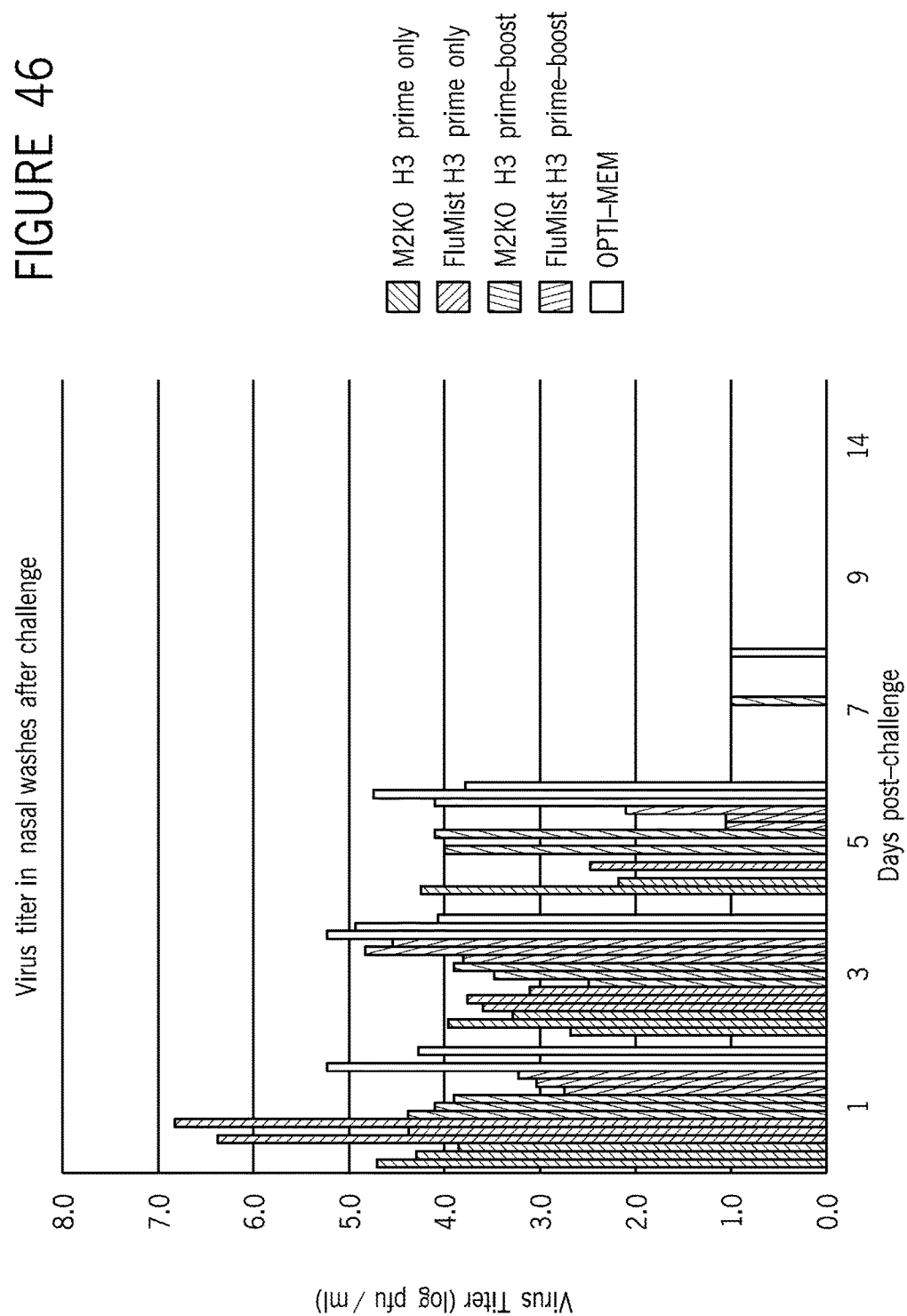
FIG. 46 is a chart showing M2KO(ΔTM) and FluMist® viral titers in nasal washes after intranasal challenge with A/Brisbane/10/2007 (H3N2) virus.

FIG. 46 shows M2KO(ΔTM) and FluMist® viral titers in nasal washes after intranasal challenge with A/Brisbane/10/2007 (H3N2) virus.

Figure 47:
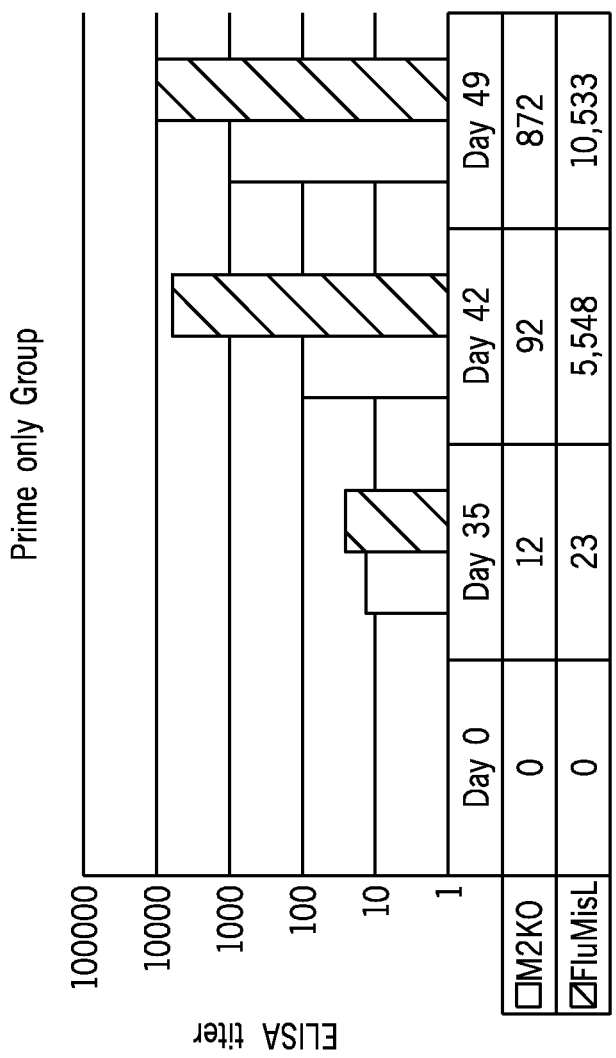
FIG. 47 is a chart showing IgG titers in ferrets following vaccination with M2KO(ΔTM) and FluMist®, prime group only.

FIG. 47 shows IgG titers in ferrets following vaccination with M2KO(ΔTM) and FluMist®, prime group only.

Figure 48:
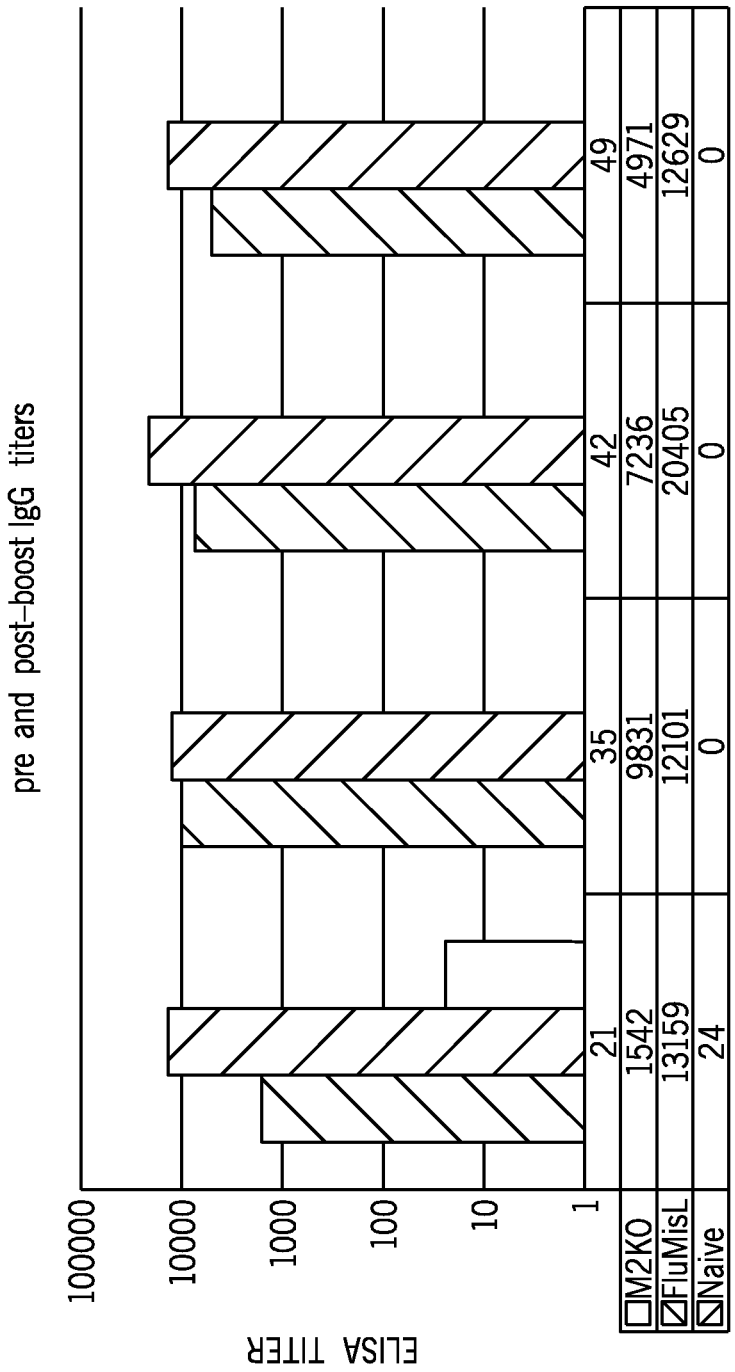
FIG. 48 is a chart showing IgG titers in ferrets following vaccination with M2KO(ΔTM) and FluMist®, prime-boost groups.

FIG. 48 shows IgG titers in ferrets following vaccination with M2KO(ΔTM) and FluMist®, prime-boost groups.

Figure 49:
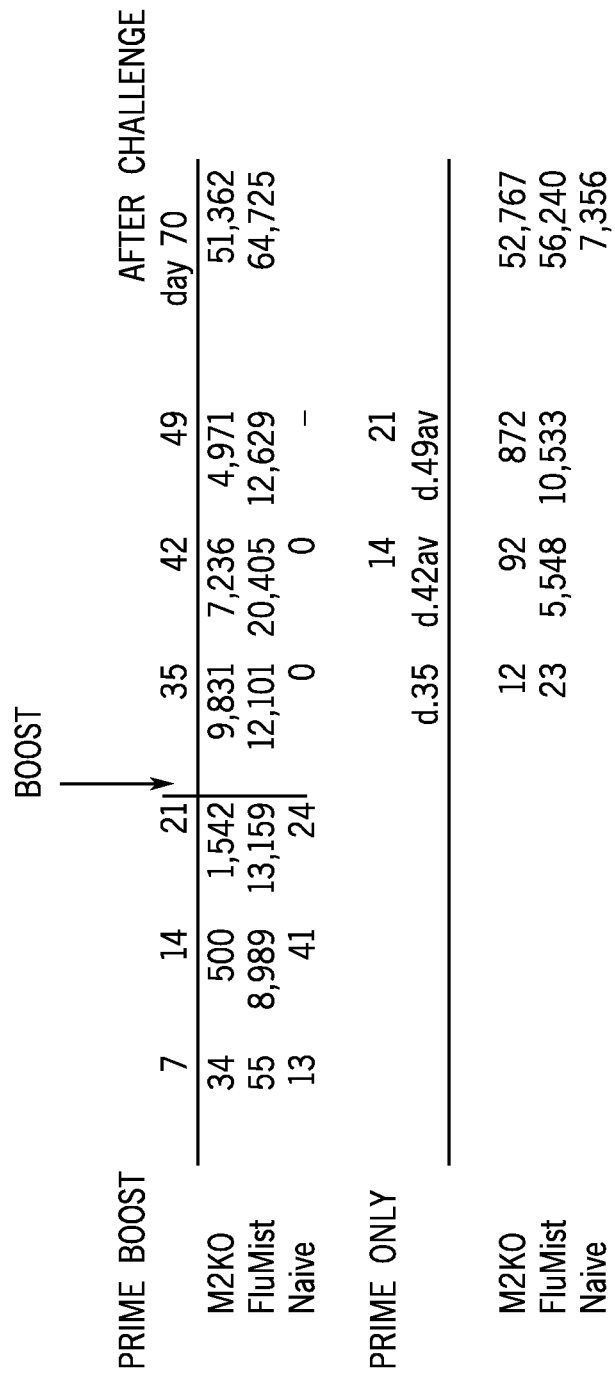
FIG. 49 is a chart showing a summary of ELISA IgG titers in ferret sera from vaccination with M2KO(ΔTM) or FluMist® to post-challenge.

FIG. 49 shows a summary of ELISA IgG titers in ferret sera from vaccination with M2KO(ΔTM) or FluMist® to post-challenge.

Conclusion

This example shows that intranasal administration of the M2KO(ΔTM) virus was not associated with any vaccine related adverse events (elevated body temperature, loss of weight or clinical signs). These results show that the M2KO (ΔTM) virus of the present technology is useful for use in an intranasal influenza vaccine.

Example 12

M2KO(ΔTM) Virus in not Transmitted in the Ferret Model

Summary—This example demonstrates that the M2KO (ΔTM) virus is not transmitted in the ferret model. The M2KO(ΔTM) virus was administered intranasally to 3 female ferrets at a dose level of 1×10$^7$ TCID$_{50}$. As a control, a second group of 3 female ferrets was administered the A/Brisbane/10/2007 (H3N2) virus intranasally at a dose of 1×10$^7$ TCID$_{50}$. Twenty four hours after inoculation, each donor ferret was introduced into a transmission chamber with two naive ferrets (a direct contact and aerosol contact). Following inoculation, ferrets were observed for 14 days post inoculation for mortality, with body weights, body temperatures and clinical signs measured daily. Nasal washes were collected from all inoculated donor ferrets on days 1, 3, 5, 7, 9 and from all contact (direct and aerosol) ferrets on days 2, 4, 6, 8, 10 to look for viral shedding. Nasal washes and serum were collected from all ferrets at the inoculation of the study (Day 14) to evaluate antibody levels. No clinical signs of infection were observed in the M2KO(ΔTM) group; however, ferrets in the A/Brisbane/10/2007 (H3N2) group had weight loss, increased body temperatures and were sneezing. After inoculation with Brisbane/1 0, the donor ferrets exhibited an increase in body temperature 2 days after challenge and a reduction in weight. Activity levels were not reduced in any groups. Ferrets in direct contact with the donor ferrets showed progressive weight gain until day 4 post inoculation. A similar trend was observed in the aerosol contact ferrets beginning on day 6 post inoculation. The loss in body weight in the contact ferrets correlated with an increase in body temperature. Inoculation with the M2KO(ΔTM) virus does not elicit clinical signs of infection in inoculated animals. Spread to contact ferrets is unlikely.

Materials and Methods

A. Vaccine Material: The M2KO(ΔTM) virus is a recombinant virus which possesses internal 6 genes of PR8 (nucleoprotein (NP), polymerase genes (PA, PB1, PB2), non-structural (NS), matrix (M)), but which does not express functional M2 protein, as well as HA and NA genes of Influenza A/Brisbane/10/2007-like A/Uruguay/716/2007 (H3N2). M2KO(ΔTM) virus was administered intranasally to the animals in a 316 µL dose of 1×107 TCID$_{50}$ (50% Tissue Culture Infectious Doses).

B. Test Article Dose Formulation: The M2KO(ΔTM) virus dosing solution of 1×10$^7$ TCID$_{50}$/mL per 316 µL was prepared by diluting 45 of 1×10$^9$ TCID$_{50}$/mL into 1.377 mL PBS.

C. Animals and Animal Care: 22 female ferrets were purchased from Triple F Farms and 18 of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison Wis.) and city of Chicago tap water were provided ad libitum and were refreshed at least once daily. Fluorescent lighting in the animal rooms was maintained on a 12-hr light/dark cycle. Animal room temperature and relative humidity were within respective protocol limits and ranged from 23.0 to 25.0° C. and 36 to 50%, respectively, during the study.

D. Animal Quarantine and Randomization: The ferrets were held in quarantine for seven days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

E. Experimental Design: To assess the transmissibility of the M2KO(ΔTM) virus, ferrets were inoculated with M2KO (ΔTM) virus or A/Brisbane/10/2007 (H3N2) virus. The animals body weight, body temperature, clinical symptoms and viral shedding were monitored and immunological responses evaluated. 18 female ferrets (Triple F Farms, Sayre Pa.), 4 months of age at the time of study initiation were utilized for the study. All animal procedures were performed in an animal biosafety level-2 or level 3 facility. Prior to inoculation, ferrets were monitored for 3 days to measure body weight and establish baseline body temperatures. Temperature readings were recorded daily through a transponder (BioMedic data systems, Seaford, Del.) implanted subcutaneously in each ferret. Blood was collected prior to study initiation, and serum tested for influenza antibodies. Only ferrets with HI titers 40 to A/Brisbane/10/2007 (H3N2) virus were considered seronegative and used in this study. Study animals were randomized and divided into 2 groups (9 ferrets/group, 3/transmission chamber) as shown in Table 20. Ferrets in group 1 (Chambers A-C) were assigned to receive the M2KO(ΔTM) virus. Ferrets in group 2 (Chambers A-C) were assigned to receive the A/Brisbane/1 0/2007 (H3N2) virus. Within each group, ferrets were divided into inoculated donors or naive contacts.

TABLE 20

Study Design

| Group | Chamber | Virus | N[1] | Inoculation (day)[2] | Donor Nasal Washes (day) | Contact Nasal Washes (day) | Serum Collection |
|---|---|---|---|---|---|---|---|
| 1 | A | M2KO | 3 | 0 | 1, 3, 5, 7, 9, 14 | 2, 4, 6, 8, 10, 14 | 14 |
| 1 | B | M2KO | 3 | 0 | 1, 3, 5, 7, 9, 14 | 2, 4, 6, 8, 10, 14 | 14 |
| 1 | C | M2KO | 3 | 0 | 1, 3, 5, 7, 9, 14 | 2, 4, 6, 8, 10, 14 | 14 |
| 2 | A | Brisbane/10 | 3 | 0 | 1, 3, 5, 7, 9, 14 | 2, 4, 6, 8, 10, 14 | |

TABLE 20-continued

Study Design

| Group | Chamber | Virus | N[1] | Inoculation (day)[2] | Donor Nasal Washes (day) | Contact Nasal Washes (day) | Serum Collection |
|---|---|---|---|---|---|---|---|
| 2 | B | Brisbane/10 | 3 | 0 | 1, 3, 5, 7, 9, 14 | 2, 4, 6, 8, 10, 14 | 14 |
| 2 | C | Brisbane/10 | 3 | 0 | 1, 3, 5, 7, 9, 14 | 2, 4, 6, 8, 10, 14 | 14 |

[1]Each chamber consisted of three female ferrets; an infected donor ferret and 2 naïve contact ferrets (1 direct contact and 1 aerosol contact).
[2]Intranasally inoculated with a single dose of 316 µl of 1 × 10$^7$ TCID$_{50}$ of M2KO or 1 × 10$^7$ TCID$_{50}$ of A/Brisbane/10/2007 (H3N2) virus.

Each group was housed in separate rooms, and individuals working with the animals followed a strict work flow pattern to prevent cross contamination between the two groups. In each group, one donor ferret was inoculated intranasally with a single dose of 316 µL of 1×10$^7$ TCID$_{50}$ of M2KO(ΔTM) (Group1) or 1×10$^7$ TCID$_{50}$ of A/Brisbane/10/2007 (H3N2) virus (Group 2). Twenty-four hours post inoculation; each donor was placed in the same cage with 1 naïve ferret (direct contact), dual housed within a wire cage. An additional ferret (aerosol contact) was placed in a separate adjacent wire cage (single housed) within the transmission chamber separated from the donor's cage by a distance of 10-12 cm. Ferret body temperatures, weights, and clinical symptoms were monitored daily for 14 days post-inoculation. Nasal washes were collected from all inoculated donor ferrets on days 1, 3, 5, 7, 9 and from all contact (direct and aerosol) ferrets on days 2, 4, 6, 8, 10 for virus titration in cells. Nasal washes were collected from all ferrets on day 14 for antibody titration. Nasal wash samples were kept at −65° C.

F. Transmission Chambers: Each transmission chamber was 2 cubic meters. A computerized air handling unit was used for HEPA filtration and to monitor and control environmental conditions within the transmission chambers. To provide directional airflow, HEPA-filtered air was supplied through an inlet port located at one end of the chamber, exited through an outlet port at the opposite end the chamber, HEPA filtered and exhausted into the room. Air exchange rate was 20 complete air changes per hour for each chamber, airflow was maintained as <0.1 m/sec. Chambers were maintained at a negative pressure of −0.15 inches of water. Ferrets were housed in wire cages with slat bottoms which were suspended over paper-lined waste pans. Ferrets were either dual housed in 32×24×14 cages or single housed in 24×24×14 wire cages which were placed inside each HEPA-filtered transmission chamber.

G. Virus Inoculation: Ferrets were inoculated with the M2KO(ΔTM) virus. A vial of frozen stock was thawed and diluted to the appropriate concentration in phosphate buffered saline solution. Ferrets were anesthetized with ketamine/xylazine and the virus dose administered intranasally in a volume of 316 µL for the M2KO(ΔTM). To confirm the inoculation titer of the M2KO(ΔTM) virus, aliquots of the dosing solutions were collected prior to dosing (pre-dose) and after dosing (post-dose). The aliquots were stored at 65° C. for virus titration.

H. Challenge Virus: Influenza A virus, strain A/Brisbane/10/2007, serotype H3N2 was used to inoculate the control ferrets. The virus was stored at approximately −65° C. prior to use. The dose level of challenge virus used was prepared at 1×1 07 TCID$_{50}$ in a volume of 316 µL. A quantitative viral infectivity assay, TCID$_{50}$ assay was performed at IITRI on a portion of the prepared viral challenge solution. The viral titer assay was performed according to IITRI Standard Operating Procedures.

I. Moribundity/Mortality Observations: Following challenge, all animals were observed twice daily for mortality or evidence of moribundity. Animals were observed for 14 days after vaccine inoculation and for 14 days after challenge.

J. Body Weights and Body Weight Change: Body weights were recorded within two days of receipt and at randomization. All study animals were weighed prior to inoculation, daily for 14 days following each vaccination and assessed daily for 14 days post challenge. Prior to inoculation, ferrets were monitored for 3-5 days to measure establish baseline body temperatures. Temperature readings were recorded daily for 14 days following each vaccination and recorded daily for 14 days post challenge through a transponder (BioMedic data systems, Seaford, Del.) implanted subcutaneously in each ferret. The change in temperature (in degrees Celsius) was calculated at each time point for each animal.

K. Clinical Observations: The change in temperature (in degrees Celsius) was determined daily for each ferret. Clinical signs of, inappetence, respiratory signs such as dyspnea, sneezing, coughing, and rhinorrhea and level of activity was assessed daily. A scoring system based on that described by Reuman, et al., "Assessment of signs of influenza illness in the ferret model," J. Virol, Methods 24:27-34 (1989), was used to assess the activity level as follows: 0, alert and playful; 1, alert but playful only when stimulated; 2, alert but not playful when stimulated; and 3, neither alert nor playful when stimulated. A relative inactivity index (RII) was calculated as the mean score per group of ferrets per observation (day) over the duration of the study.

L. Survival Checks: Two survival checks were performed daily on all study animals throughout the study. Both survival checks occurred simultaneously with the clinical observations. The second check was performed later within the same day.

M. Nasal Washes: Ferrets were anesthetized with a ketamine (25 mg/kg) and xylazine (2 mg/kg) mixture, and 0.5 ml of sterile PBS containing penicillin (100 U/ml), streptomycin (100) and gentamicin (50) was injected into each nostril and collected in a specimen cup when expelled by the ferret.

N. Euthanasia: Study animals were euthanized by an intravenous dose of sodium pentobarbital 150 mg/kg. Death was confirmed by absence of observable heartbeat and respiration. Necropsies were performed on all study animals.

O. Serum Collection: Pre-vaccination serum (days −3 to −5) and post inoculation serum (day 14) was collected from all ferrets. Ferrets were anesthetized with a ketamine (25 mg/kg) and xylazine (2 mg/kg) mixture. A sample of blood (approximately 0.5-1.0 mL) was collected via the vena cava from each ferret and processed for serum. Blood was collected into Serum Gel Z/1.1 tubes (Sarstedt Inc. Newton, N.C.) and stored at room temperature for not more than 1 hour before collecting serum. Serum Gel Z/1.1 tubes were centrifuged at 10,000×g for 3 minutes and the serum collected. Individual pre-inoculation serum samples were collected and two aliquots made from each sample. One aliquot was tested prior to the initiation of the study to confirm ferrets are free of antibodies to influenza A viruses and one aliquot of the serum stored at −65° C.

P. Hemagglutination Inhibition (HI) Assay: Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2) influenza A virus. After incubation, 0.5% avian red blood cells were added to each sample and incubated for 30±5 minutes. Presence or absence of hemagglutination was then scored.

Q. Virus Titers: The concentration of infectious virus in the pre- and post-challenge virus inoculum samples was determined by $TCID_{50}$ assay in Madin-Darby Canine Kidney (MDCK) cells. Briefly, samples kept at −65° C. were thawed and centrifuged to remove cellular debris. The resulting supernatant were diluted 10-fold in triplicate in 96-well microtiter plates in Dulbecco's Modified Eagle Medium (DMEM) (Gibco, Carlsbad, Calif., USA) containing Pencillin/Streptomycin, 0.1% Gentamicin, 3% $NaCO_3$, 0.3% BSA fraction V (Sigma St. Louis, Mo.), 1% MEM vitamin solution (Sigma) and 1% L-glutamine (Mediatech, Manassas, Va., USA). After 10-fold serial dilutions were made, 1 00flL was transferred into respective wells of a 96-well plate which contained a monolayer of MDCK cells. Plates were incubated at 37° C.±2° C. in 5±2% $CO_2$ 70% humidity. After 48 hours, the wells were observed for cytopathogenic effect (CPE). Supernatant from each well (50 µl) was transferred to a 96 well plate and the hemagglutination (HA) activity determined and recorded. The HA activity of the supernatant was assessed by HA assay with 0.5% packed turkey red blood cells (tRBCs). $TCID_{50}$ titers were calculated using the method of Reed L J and Muench H, "A simple method for estimating 50% endpoints," *Am. J. Hygiene* 27: 493-497 (1938).

R. Data Analysis: Body weights and body weight gains (losses) and changes in body temperature were determined for each individual animal expressed as mean and standard deviations of the mean for each test group.

Results

After inoculation of donor ferrets with either the M2KO (ΔTM) virus or the A/Brisbane/10/2007 (H3N2) influenza A virus donor ferrets were introduced into transmission chambers containing naive contact ferrets. Ferrets were monitored daily for clinical signs of infection, nasal washes were collected to monitor viral shedding and serum collected to measure serum antibody titers. All ferrets survived inoculation with M2KO(ΔTM) virus and A/Brisbane/10/2007 (Table 21). No clinical signs of disease were observed in ferrets in the M2KO(ΔTM) group. Two of the three donor ferrets inoculated with A/Brisbane/10/2007 virus presented respiratory signs (sneezing) on Day 6 and 8. Direct contact ferrets in all chambers presented with sneezing on Day 8. No sneezing was observed in the aerosol contact ferrets. A reduction in activity level was not observed.

TABLE 21

Clinical signs in inoculated donor ferrets and contact ferrts.

| Group | Treatment | N | Serum HI Titer[a] | Total Number Dead | Respiratory signs (observed day of onset) | Loss of Appetite | Lethargy (RII)[c] |
|---|---|---|---|---|---|---|---|
| | | | | Clinical signs[b] | | | |
| | | | | M2KO | | | |
| Donors | M2KO | 3 | <10 | 0/3 | 0/3 | 0/3 | 0 |
| Direct Contracts | M2KO | 3 | <10 | 0/3 | 0/3 | 0/3 | 0 |
| Aerosol Contracts | M2KO | 3 | <10 | 0/3 | 0/3 | 0/3 | 0 |
| | | | | Brisbane | | | |
| Donors | Brisbane/10 | 3 | <10 | 0/3 | 2/3 (6, 8) | 0/3 | 0 |
| Direct Contracts | Brisbane/10 | 3 | <10 | 0/3 | 3/3 (8, 8, 8) | 0/3 | 0 |
| Aerosol Contracts | Brisbane/10 | 3 | <10 | 0/3 | 0/3 | 0/3 | 0 |

[a]Hemagglutination inhibition (HI) antibody titers to homologous virus in ferret serum prior to virus inoculation.
[b]Clinical signs were observed for 14 days after virus inoculation. Except for lethargy, findings for clinical signs are given as no. of ferrets with sign/total no. Respiratory signs were sneezing, day of onset for each ferret in parentheses.
[c]Determined twice daily for 14 days of observation based on the scoring system and was calculated as the mean score per group of ferrets per observation (day) over the 14-day period. The relative inactivity index before inoculation was 0.

Changes in body weight and temperature after virus inoculation are shown in FIG. 26 and FIG. 27. No significant weight loss was observed after inoculation with the M2KO (ΔTM) virus. The aerosol contacts averaged a 1% loss in weight on day; however, it is unlikely this due to exposure to virus. Body weights of ferrets in the M2KO(ΔTM) virus increased was 9% for donor ferrets and 10-11% for contact ferrets during the 14 day observation (FIG. 26A). Body weight gain of the A/Brisbane/10/2007 was only 3% for donor ferrets and 6-8% for contact ferrets indicating a viral infection (FIG. 26B). In the M2KO(ΔTM) group, body temperatures remained with in normal levels with the exception of Day 3 post infection (FIG. 27A). Body temperatures were lower than normal for the aerosol contact ferrets. This was attributed to faulty or failing temperature transponders, temperatures were recorded within normal range throughout the rest of the study. Elevated body temperatures were observed on Day 2 in A/Brisbane/10/2007 donor ferrets and on Day 7 for aerosol contacts (FIG. 27B). The concentrations of pre- and post-challenge virus dosing solution were $10^{7.50}TCID_{50}$/mL and $10^{7.25}TCID_{50}$/mL, respectively, indicating good stability of the challenge material throughout administration.

FIG. 50 shows viral titers in nasal washes from ferrets in a virus transmission study. The data shows that M2KO (ΔTM) virus does not transmit (no virus detected), whereas the control Brisb/10 virus is transmitted.

Conclusion

This example shows that ferrets inoculated with the A/Brisbane/10/2007 virus exhibited clinical signs of infection (sneezing, loss in body weight and a transient elevated body temperature), whereas ferrets inoculated with the M2KO(ΔTM) virus showed no clinical signs of disease. Therefore, inoculation of donor ferrets with the M2KO (ΔTM) did not appear to cause an infection or transmit virus via contact or via aerosol. These findings show that the M2KO(ΔTM) virus of the present technology is useful for intranasal influenza vaccines.

Example 13

M2KO(ΔTM) Virus Elicits Both Humoral and Mucosal Immune Responses in Mice

This examples demonstrates that the M2KO(ΔTM) virus elicits both humoral and mucosal immune responses in mice. The immunogenicity of M2KO(ΔTM) was evaluated in mice and compared to the immune responses generated by other modes of vaccination. An immunogenicity study was performed containing the following groups as outline in Table 22: 1. M2KO(ΔTM) virus, 2. PR8 virus (10 pfu), live vaccine representative, 3. Inactivated PR8 virus (Charles River Laboratories, Wilmington, Mass.), 1 µg, intranasal (IN) 4. Inactivated PR8 virus, 1 µg, intramuscular (IM), or PBS only.

TABLE 22

Vaccine Groups in Immunogenicity Study

| Immunogen | Route of Delivery | Dose | Rationale |
|---|---|---|---|
| M2KO(ΔTM) virus | Intranasal | 1 × 10⁴ pfu | Comprises M2KO(ΔTM) (SEQ ID NO: 1) Mutation |
| PR8 virus | Intranasal | 10 pfu | Represents the immune responses associated with a natural infection |

TABLE 22-continued

Vaccine Groups in Immunogenicity Study

| Immunogen | Route of Delivery | Dose | Rationale |
|---|---|---|---|
| Inactivated PR8, whole virus | Intranasal | 1 µg | Demonstrates baseline response generated by killed flu virus delivered intranasally and/or live flu vaccine |
| Inactivated PR8, whole virus | Intramuscular | 1 µg | Standard delivery route for traditional inactivated flu vaccine |

To test the immunogenicity of M2KO(ΔTM) virus, mice were intranasally inoculated with $1.2 \times 10^4$ pfu of M2KO (ΔTM), 10 pfu of wild-type PR8, 1 µg of inactivated whole PR8 (Charles River Laboratories, Wilmington, Mass.), or PBS as control, along with a group intramuscularly administered 1 µg of inactivated whole PR8. Three weeks after the immunization, serum and trachea-lung washes were collected from mice and anti-PR8 immunoglobulin G (IgG) and IgA levels were measured by enzyme linked immunosorbent assay (ELISA). Briefly, ELISA plates were coated by whole inactivated PR8, blocked by bovine serum albumin (BSA), and samples were applied. Mouse IgG and IgA antibodies were detected by horseradish peroxidase labeled anti-mouse IgG- and IgA-goat antibodies (KPL, Inc., Gaithersburg, Md.) and SureBlue TMB (KPL, Inc.) substrate.

As expected, mice in the immunized groups showed significant elevation of anti-PR8 antibodies in serum and trachea-lung wash compare to the PBS only group (FIG. 28). Anti-PR8 IgG levels in sera for M2KO(ΔTM) virus are higher than the inactivated PR8 groups and similar to live PR8 virus. More importantly anti-PR8 IgA antibodies were present only in the PR8 and M2KO(ΔTM) immunized mice in both sera and trachea-lung washes. These data suggest that M2KO(ΔTM) virus elicits significant humoral and mucosal immune response in mice.

Example 14

M2KO(ΔTM) Virus Protects Mice from Lethal Homosubtypic and Heterosubtypic Challenge This example demonstrates that the M2KO(ΔTM) virus protects mice from lethal homosubtypic and heterosubtypic challenge. The protective efficacy M2KO(ΔTM) virus was evaluated by challenging the immunized mice with lethal doses of the wild-type PR8 (H1N1; homosubtypic challenge) or mouse-adapted influenza A/Aichi/2/68 (Aichi; H3N2; heterosubtypic challenge) six weeks post-immunization. None of the mice immunized with either M2KO(ΔTM) or 10 pfu of PR8 and subsequently challenged by wild-type PR8 showed any clinical symptoms including weight loss (FIG. 29A). In contrast, naive PBS mice died or were euthanized due to greater than 20% weight loss by day 5. Virus replication in the respiratory tracts of challenged mice was determined on day 3 post-challenge by $TCID_{50}$ assay in MDCK cells. As shown in FIG. 30A, no virus was detected (limit of detection $10^{2.75}TCID_{50}$/organ) in the lungs of M2KO(ΔTM) or PR8 immunized mice indicating that M2KO(ΔTM) provided sterile immunity similar to PR8 infection. In contrast, challenge virus was recovered from the inactivated PR8 and PBS groups.

For heterosubtypic challenge, mice were challenged by Aichi (H3N2). M2KO(ΔTM) and wild-type PR8 immunized mice survived challenge whereas mice that received inactivated PR8 or PBS succumbed to infection (FIG. 29). Virus titers in mouse respiratory tracts on day 3 post-challenge did not show significant reduction in M2KO(ΔTM)-vaccinated mice compared to mice in other groups (FIG. 30). These results suggest that the cross-protection observed against Aichi challenge may in part be due to T-cell mediated immune responses induced by the M2KO(ΔTM) vaccine. Hemagglutination inhibition (HI) antibodies to Aichi were not detectable (less than 1:40) in post-challenge sera from challenged mice suggesting that protection was not mediated by neutralizing antibodies.

The M2KO(ΔTM) virus stimulates both humoral and cellular immune responses and confers protective immunity to animals against lethal homo- and hetero-subtypic challenge as summarized in Table 23.

TABLE 23

Protection After Homosubtypic (H1N1) and Heterosubtypic (H3N2) Influenza Challenge Survival (%)

| Vaccine Group | PR8 (H1N1) Challenge | Aichi (H3N2) Chalenge |
|---|---|---|
| M2KO(ΔTM) | 100% | 100% |
| PR8 | 100% | 100% |
| Inactivated PR8, IN | 100% | 0% |
| Inactivated PR8, IM | 100% | 20% |
| PBS | 0% | 0% |

Example 15

M2KO(ΔTM) Vaccine Compared to Fluzone® and FluMist®

This example demonstrates the efficacy of the M2KO (ΔTM) virus compared to ive attenuated virus (FluMist®), Fluzone® inactivated flu vaccine. Mice were immunized with M2KO(ΔTM) virus, cold adapted live attenuated virus (FluMist®), Fluzone® inactivated flu vaccine or mock immunized by PBS. M2KO(ΔTM)-H3 virus was constructed by inserting the HA and NA coding sequences of Influenza A/Brisbane/10/2007-like, A/Uruguay/716/2007 (H3N2) in to the M2KO(ΔTM) backbone (SEQ ID NO:1). FluMist®-H3, internal genes from the cold-adapted A/AA/6/60 backbone, containing the HA and NA genes of Influenza A/Brisbane/10/2007-like, A/Uruguay/716/2007 (H3N2) was plaque purified from the 2009/2010 trivalent vaccine formulation. Fluzone® 2009/2010 formulation was used directly as the trivalent formulation.

Figure 31:
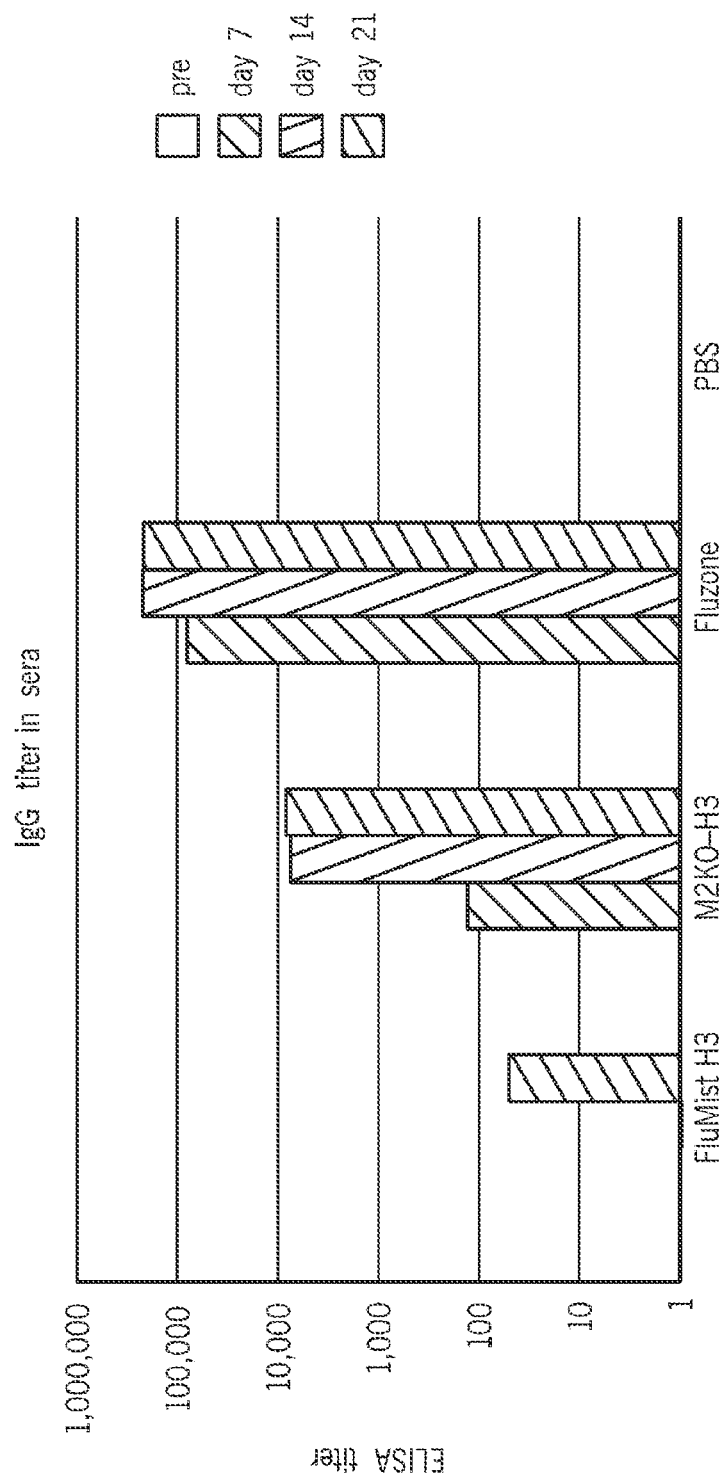
FIG. 31 is a chart showing the kinetics of antibody response to M2KO(ΔTM) vaccine in sera.

Sera was obtained on days 7, 14, 21 post-immunization to compare the kinetics of antibody response by ELISA (FIG. 31). M2KO(ΔTM)-H3 virus, a replication deficient virus, developed antibodies earlier than FluMist®-H3, a live flu virus vaccine that undergoes multi-cycle replication in an attenuated manner. The inactivated vaccine Fluzone® had the highest antibody titers in sera as it is a concentrated presentation of antigen.

Figure 32:
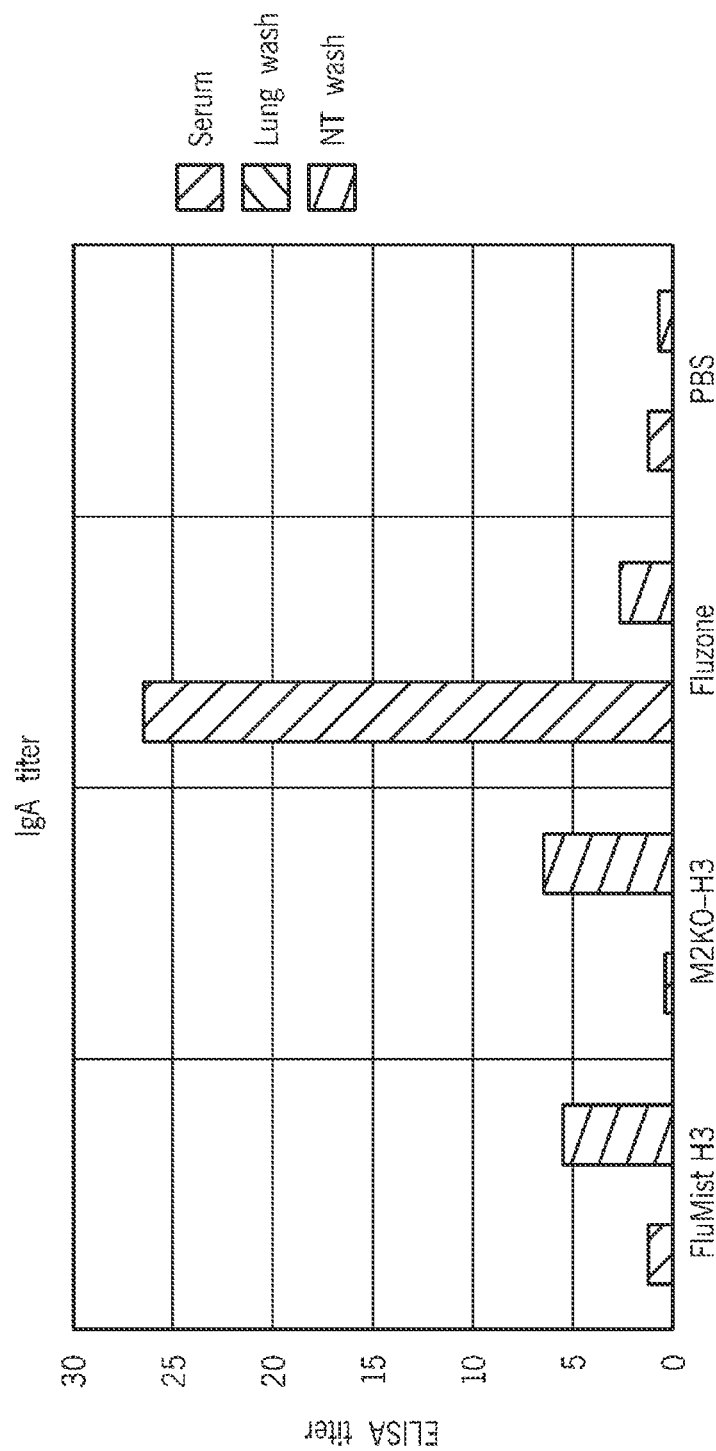
FIG. 32 is a chart showing the mucosal antibody response to M2KO(ΔTM) vaccine in sera and respiratory tract.

The presence of anti-HA mucosal antibody in sera, lung wash, and nasal turbinates was evaluated by ELISA. M2KO (ΔTM)-H3 and FluMist®, the two live flu vaccines, had higher IgA in the respiratory tract than the inactivated vaccine Fluzone®. (FIG. 32)

Example 16

Comparison of Protection and Immunogenicity Elicited by Live Viruses

Figure 33:
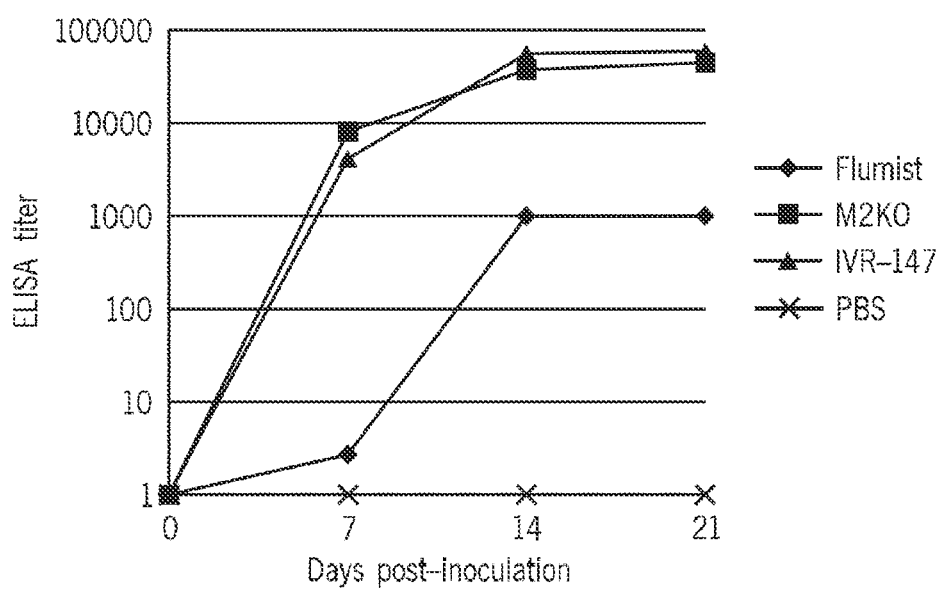
FIG. 33 is a chart showing the kinetics of anti-HA IgG in mice in response to M2KO(ΔTM) vaccine.

Six-week-old female BALB/c mice, anesthetized with isoflurane, were infected intranasally on days 0 and 28 with $10^6$ $TCID_{50}/50$ μl of M2KO(ΔTM)-H3 (described above), FluMist® (2009-2010) (H3N2) IVR-147 (PR8×Brisbane/10/2007). IVR-147 is the wild-type version of the M2KO (ΔTM) virus; i.e. contains a functional M2 protein. Mock-infected control mice received 50 μl PBS instead of virus. Serum was collected weekly from all the mice and analyzed for the presence of anti-HA antibodies by ELISA. As shown in FIG. 33, M2KO(ΔTM) virus and IVR-147 generated higher antibody levels with rapid kinetics compared to FluMist®.

Figure 34A:
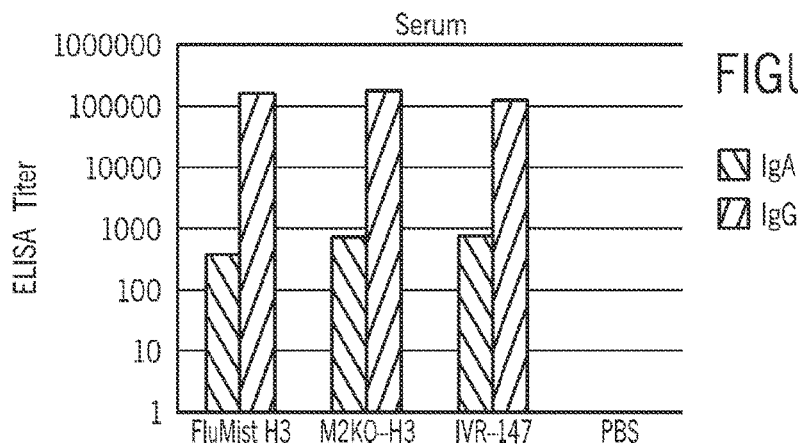
FIG. 34 is a chart showing that M2KO(ΔTM) vaccine induces immune responses similar to FluMist® and IVR-147. Panel A shows serum viral titers in animals administered FluMist® H3, M2KO(ΔTM) H3, IVR-147, and PBS. Panel B shows lung wash viral titers in animals administered FluMist® H3, M2KO(ΔTM) H3, IVR-147, and PBS. Panel C shows nasal turbinate viral titers in animals administered FluMist® H3, M2KO(ΔTM) H3, IVR-147, and PBS.
Figure 34B:
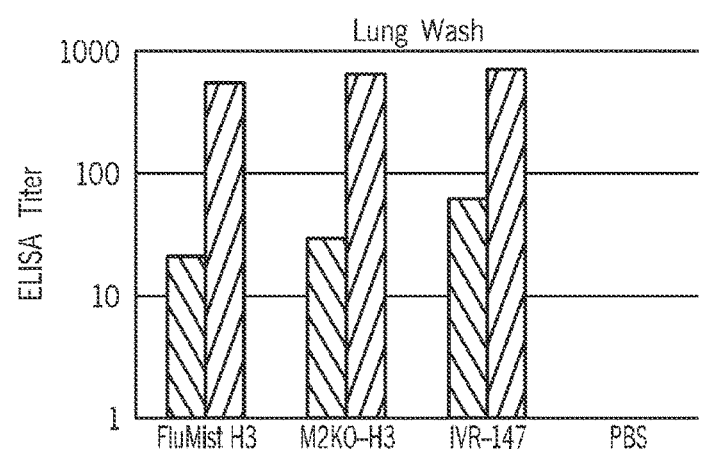
Figure 34C:
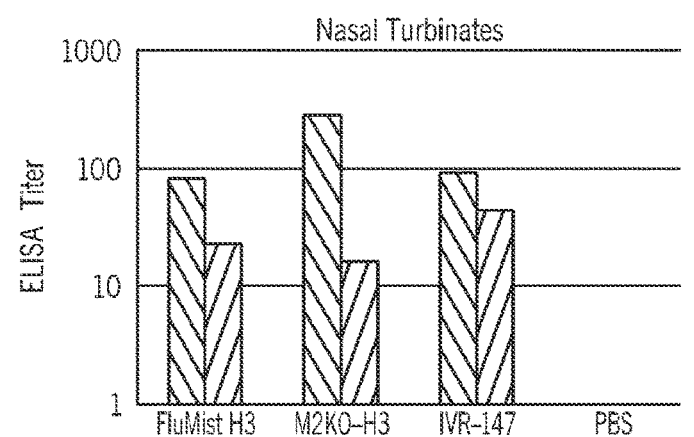

Body weights of animals were monitored for 14 days after infection. Vaccinated mice did not lose any weight. On day 21 post-boost, 3 mice per group were euthanized and their trachea-lung washes, nasal washes, and sera were collected for antibody titer determinations (FIG. 34). M2KO(ΔTM) induced both humoral and mucosal antibodies to similar levels as FluMist® and IVR-147 in sera and respiratory tract.

Figure 35A:
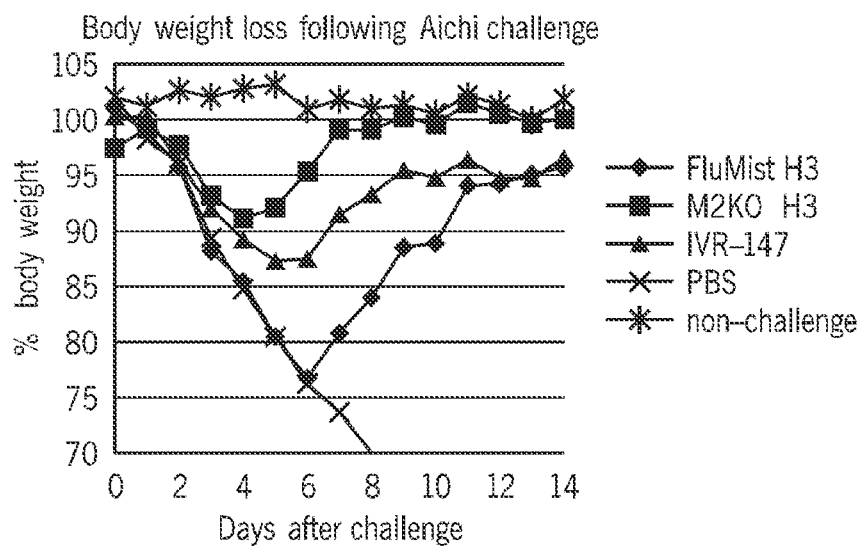
FIG. 35 is a chart showing that M2KO(ΔTM) vaccine protects against Aichi challenge. Panel A shows body weight loss following Aichi challenge in animals administered FluMist® H3, M2KO(ΔTM) H3, IVR-147, and PBS. Panel B shows the percent survival following Aichi challenge of animals administered FluMist® H3, M2KO(ΔTM) H3, IVR-147, and PBS.
Figure 35B:
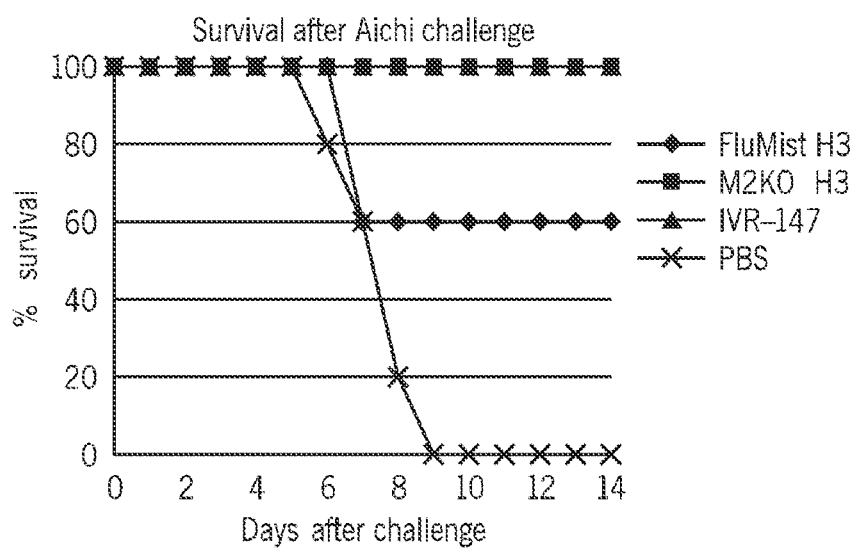

Mice were intranasally challenged with $40MLD_{50}$ of A/Aichi/2/68 virus six weeks post-boost. Mice were observed for loss of body weight and survival for 14 days (FIG. 35). M2KO(ΔTM) protected mice from lethal Aichi challenge as indicated by less body weight loss (Panel A) and 100% survival (Panel B) in contrast to FluMist®. On day 3 post-challenge, 3 mice per group were euthanized and their lungs and nasal turbinates were collected for virus titer determinations (Table 24). M2KO(ΔTM) controlled the challenge virus better than FluMist® as shown in Table 24.

TABLE 24

Challenge virus titers in respiratory tract.

| | Lung (Log $TCID_{50}/g$) Mean ± SD | Nasal Turbinate (Log $TCID_{50}/g$) Mean ± SD |
|---|---|---|
| M2KO H3 | 7.05 ± 0.14 | 4.37 ± 1.01 |
| FluMist H3 | 7.32 ± 0.38 | 6.83 ± 1.50 |
| IVR 147 | 7.08 ± 0.14 | 4.87 ± 0.14 |
| PBS | 7.95 ± 0.63 | 6.25 ± 0.29 |

Example 17

Generation of an M2KO(ΔTM) Vaccine Against Highly Pathogenic Avian H5n1 Influenza Virus Summary: M2KO(ΔTM) is an influenza virus that lacks expression of a functional M2 protein. The M2 protein is crucial for initiation of influenza viral infection and for efficient viral RNA incorporation into progeny virions. M2KO(ΔTM) can enter cells and express viral proteins but cannot make infectious progeny viruses due to deletion of the M2 gene. M2KO(ΔTM) is produced in permissive M2 protein expressing cells but not in non-permissive wild-type cells. M2KO(ΔTM) elicits both mucosal and humoral immunity in mice and protects from both homo- and heterosubtypic lethal challenge.

The H5N1 M2KO(ΔTM) virus contains the HA (avirulent) and NA genes of A/Vietnam/1203/2004 on the M2KO (ΔTM) backbone. By "M2KO(ΔTM) backbone" is meant the sequence of PR8 comprising the M2KO(ΔTM) (SEQ ID NO:1) mutation. The A/Vietnam/1203/2004 HA (avirulent) (SEQ ID NO:24) and NA (SEQ ID NO:25) sequences used are shown below:

```
>Avirulent VN1203 HA ORF + PR8 non-coding
AGCAAAAGCAGGGGAAAATAAAAACAACCAAAATGGAGAAAATAGTGCTTCTTTTTGCAATAGTCAGTCTTGTTAAAAGT
GATCAGATTTGCATTGGTTACCATGCAAACAACTCGACAGAGCAGGTTGACACAATAATGGAAAAGAACGTTACTGTTAC
ACATGCCCAAGACATACTGGAAAAGAAACACAACGGGAAGCTCTGCGATCTAGATGGAGTGAAGCCTCTAATTTTGAGAG
ATTGTAGCGTAGCTGGATGGCTCCTCGGAAACCCAATGTGTGACGAATTCATCAATGTGCCGGAATGGTCTTACATAGTG
GAGAAGGCCAATCCAGTCAATGACCTCTGTTACCCAGGGGATTTCAATGACTATGAAGAATTGAAACACCTATTGAGCAG
AATAAACCATTTTGAGAAAATTCAGATCATCCCCAAAAGTTCTTGGTCCAGTCATGAAGCCTCATTAGGGGTGAGCTCAG
CATGTCCATACCAGGGAAAGTCCTCCTTTTTCAGAAATGTGGTATGGCTTATCAAAAAGAACAGTACATACCCAACAATA
AAGAGGAGCTACAATAATACCAACCAAGAAGATCTTTTGGTACTGTGGGGGATTCACCATCCTAATGATGCGGCAGAGCA
GACAAAGCTCTATCAAAACCCAACCACCTATATTTCCGTTGGGACATCAACACTAAACCAGAGATTGGTACCAAGAATAG
CTACTAGATCCAAAGTAAACGGGCAAAGTGGAAGGATGGAGTTCTTCTGGACAATTTTAAAGCCGAATGATGCAATCAAC
TTCGAGAGTAATGGAAATTTCATTGCTCCAGAATATGCATACAAAATTGTCAAGAAAGGGGACTCAACAATTATGAAAAG
TGAATTGGAATATGGTAACTGCAACACCAAGTGTCAAACTCCAATGGGGGCGATAAACTCTAGCATGCCATTCCACAATA
TACACCCTCTCACCATTGGGGAATGCCCCAAATATGTGAAATCAAACAGATTAGTCCTTGCGACTGGGCTCAGAAATAGC
CCTCAAAGAGAGACTAGAGGATTATTTGGAGCTATAGCAGGTTTTATAGAGGGAGGATGGCAGGGAATGGTAGATGGTTG
GTATGGGTACCACCATAGCAATGAGCAGGGGAGTGGGTACGCTGCAGACAAAGAATCCACTCAAAAGGCAATAGATGGAG
TCACCAATAAGGTCAACTCGATCATTGACAAAATGAACACTCAGTTTGAGGCCGTTGGAAGGGAATTTAACAACTTAGAA
AGGAGAATAGAGAATTTAAACAAGAAGATGGAAGACGGGTTCCTAGATGTCTGGACTTATAATGCTGAACTTCTGGTTCT
CATGGAAAATGAGAGAACTCTAGACTTTCATGACTCAAATGTCAAGAACCTTTACGACAAGGTCCGACTACAGCTTAGGG
ATAATGCAAAGGAGCTGGGTAACGGTTGTTTCGAGTTCTATCATAAATGTGATAATGAATGTATGGAAAGTGTAAGAAAT
GGAACGTATGACTACCCGCAGTATTCAGAAGAAGCGAGACTAAAAAGAGAGGAAATAAGTGGAGTAAAATTGGAATCAAT
AGGAATTTACCAAATACTGTCAATTTATTCTACAGTGGCGAGTTCCCTAGCACTGGCAATCATGGTAGCTGGTCTATCCT
TATGGATGTGCTCCAATGGGTCGTTACAATGCAGAATTTGCATTTAAGATTAGAATTTCAGAGATATGAGGAAAAACACC
CTTGTTTCTACT >VN1203 NA ORF + PR8 non-coding
AGCAAAAGCAGGGGTTTAAAATGAATCCAAATCAGAAGATAATAACCATCGGATCAATCTGTATGGTAACTGGAATAGTT
AGCTTAATGTTACAAATTGGGAACATGATCTCAATATGGGTCAGTCATTCAATTCACACAGGGAATCAACACCAATCTGA
ACCAATCAGCAATACTAATTTTCTTACTGAGAAAGCTGTGGCTTCAGTAAAATTAGCGGGCAATTCATCTCTTTGCCCCA
TTAACGGATGGGCTGTATACAGTAAGGACAACAGTATAAGGATCGGTTCCAAGGGGGATGTGTTTGTTATAAGAGAGCCG
TTCATCTCATGCTCCCACTTGGAATGCAGAACTTTCTTTTTGACTCAGGGAGCCTTGCTGAATGACAAGCACTCCAATGG
GACTGTCAAAGACAGAAGCCCTCACAGAACATTAATGAGTTGTCCTGTGGGTGAGGCTCCCTCCCCATATAACTCAAGGT
TTGAGTCTGTTGCTTGGTCAGCAAGTGCTTGCCATGATGGCACCAGTTGGTTGACGATTGGAATTTCTGGCCCAGACAAT
GGGGCTGTGGCTGTATTGAAATACAATGGCATAATAACAGACACTATCAAGAGTTGGAGGAACAACATACTGAGAACTCA
AGAGTCTGAATGTGCATGTGTAAATGGCTCTTGCTTTACTGTAATGACTGACGGACCAAGTAATGGTCAGGCATCACATA
AGATCTTCAAAATGGAAAAGGGAAAGTGGTTAAATCAGTCGAATTGGATGCTCCTAATTATCACTATGAGGAATGCTCC
TGTTATCCTAATGCCGGAGAAATCACATGTGTGTGCAGGGATAATTGGCATGGCTCAAATCGGCCATGGGTATCTTTCAA
TCAAAATTTGGAGTATCAAATAGGATATATATGCAGTGGAGTTTTCGGAGACAATCCACGCCCCAATGATGGAACAGGTA
GTTGTGGTCCGGTGTCCTCTAACGGGGCATATGGGGTAAAAGGGTTTTCATTTAAATACGGCAATGGTGTCTGGATCGGG
```

```
AGAACCAAAAGCACTAATTCCAGGAGCGGCTTTGAAATGATTTGGGATCCAAATGGGTGGACTGAAACGGACAGTAGCTT

TTCAGTGAAACAAGATATCGTAGCAATAACTGATTGGTCAGGATATAGCGGGAGTTTTGTCCAGCATCCAGAACTGACAG

GACTAGATTGCATAAGACCTTGTTTCTGGGTTGAGTTGATCAGAGGGCGGCCCAAAGAGAGCACAATTTGGACTAGTGGG

AGCAGCATATCTTTTTGTGGTGTAAATAGTGACACTGTGGGTTGGTCTTGGCCAGACGGTGCCGAGTTGCCATTCACCAT

TGACAAGTAGTCTGTTCAAAAAACTCCTTGTTTCTACT
```

Generation of H5N1 M2KO(ΔTM): The avirulent HA and NA of A/Vietnam/1203/2004 (H5N1) were chemically synthesized by GeneArt® Gene Synthesis based on the CDC sequences for each gene (CDC ID: 2004706280, Accession Numbers: EF541467 and EF541403). The sequences of the constructs were confirmed and sub-cloned into appropriate vectors to allow for the generation of seed virus using standard protocols. M2KO(ΔTM) VN1203avHA,NA (H5N1 M2KO(ΔTM)) virus was amplified in M2CK cells (MDCK cells stably expressing the M2 protein), the supernatant clarified of cell debris and concentrated 100-fold by Centricon Plus-70 (Millipore). This virus was used as the immunogen in the mice study.

Mouse Study Design: Mice (7-8 weeks old, female BALB/c) were intranasally inoculated with H5N1 M2KO (ΔTM) ($10^6$ TCID$_{50}$/mouse), M2KO(ΔTM) CA07HA, NA ($10^6$ TCID$_{50}$/mouse) or VN1203 protein (1.5 µg) administered intramuscularly. Body weight and clinical symptoms were observed for 14 days post-inoculation. Sera was collected on days 7, 14, 21 post-inoculation. Mice were boosted on day 28 with a new prime only group initiated at the same time.

Boost immunization and 'prime only' groups: On day 28 the mice previously inoculated with H5N1 M2KO(ΔTM) were boosted with a second immunization of $10^6$ pfu/mouse. At the same time the 'prime only' groups were given their first dose. Weight loss was followed for all groups following the day 28 inoculation. The mice that received a boost dose of M2KO(ΔTM) vaccine lost at most 5% of their body weight. The 'prime only' group lost up to 10% of their body weight.

TABLE 25

Vaccine groups in mice study

| Group[1] | Immunogen | Doses | Route of Administration | Challenge Virus |
|---|---|---|---|---|
| 1 | H5N1 M2KO(ΔTM) | 2 | Intranasal | Challenged 5 months post-immunization with 20 MLD$_{50}$ A/VN/1203/2004 |
| 2 | H5N1 M2KO(ΔTM) | 1 | Intranasal | |
| 3 | H1N1pdm M2KO(ΔTM) | 2 | Intranasal | |
| 4 | H5 HA VN1203 protein | 2 | Intramuscular | |
| 5 | Naïve (OPTI-MEM ™) | 2 | Intranasal | |
| 6 | H5N1 M2KO(ΔTM) | 1 | Intranasal | Challenged 4 |

TABLE 25-continued

Vaccine groups in mice study

| Group[1] | Immunogen | Doses | Route of Administration | Challenge Virus |
|---|---|---|---|---|
| 7 | Naïve (OPTI-MEM ™) | 1 | Intranasal | weeks post-immunization with 20 MLD$_{50}$ A/VN/1203/2004 |

[1] 5 mice/group for survival assessment after challenge

Figure 36:
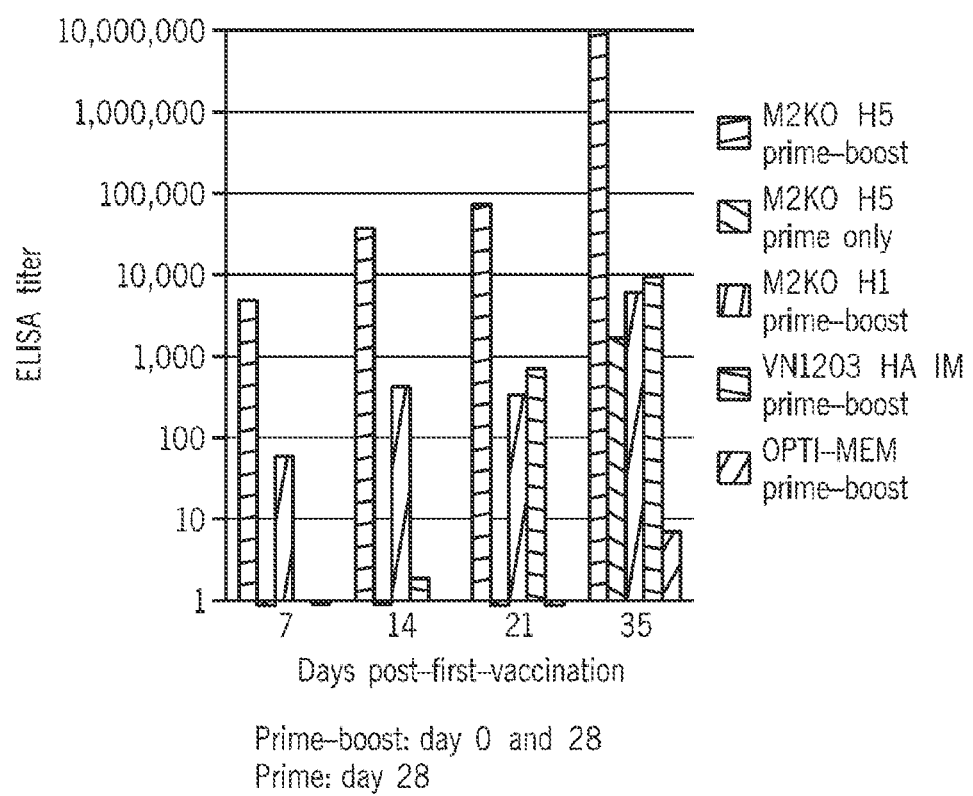
FIG. 36 is a chart showing that H5N1 M2KO(ΔTM) vaccine elicits IgG antibody titers against HA.

H5N1 M2KO(ΔTM) elicits IgG antibody titers against HA: Sera was obtained from mice on day 7, 14, 21 post-inoculation and analyzed by ELISA for antibodies against the hemagglutinin. M2KO(ΔTM) generated at least 100 fold higher titers than H5 HA protein (FIG. 36). Mice were boosted on day 28 and sera was obtained a week later (day 35). The M2KO(ΔTM) titers were boosted 130 fold, whereas the HA protein only boosted 13 fold. The first week bleed at day 35 for the M2KO(ΔTM) prime only groups demonstrated high IgG titers as the first week of the prime-boost groups.

Figure 54:
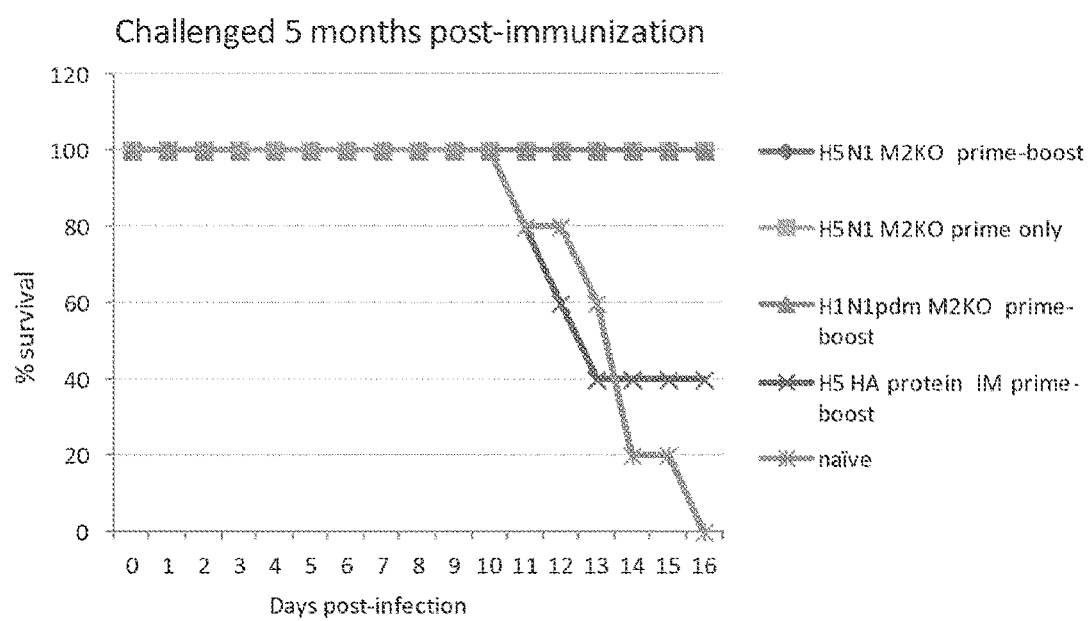
FIG. 54 is a chart showing the percent survival of H5N1 M2KO(ΔTM) vaccinated subjects challenged 5 months post-immunization with Vietnam/1203/2004 virus.
Figure 55:
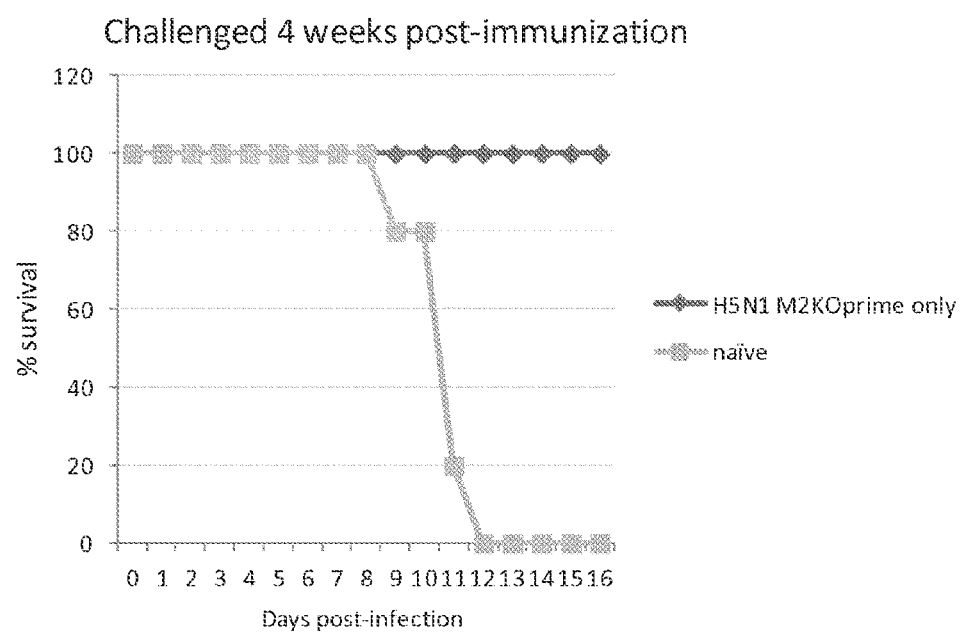
FIG. 55 is a chart showing the percent survival of H5N1 M2KO(ΔTM) vaccinated subjects challenged 4 weeks post-immunization with Vietnam/1203/2004 virus.

Mice were challenged with a lethal dose of Vietnam/1203/2004 virus (20 MLD$_{50}$). All H5N1 M2KO(ΔTM) vaccinated (prime only and prime-boost) mice survived (FIGS. 54 and 55). The high survival rate of mice challenged 5 months post-immunization suggests that the H5N1 M2KO(ΔTM) vaccine primes memory responses. Mice challenged 4 weeks post-immunization had received only one dose of vaccine, indicating that the M2KO(ΔTM) vaccine stimulates a strong immune response. H1N1pdm M2KO(ΔTM) immunized mice also survived H5N1 challenge after 5 months indicating that M2KO(ΔTM) primes cross-reactive immune responses that provide protection against heterologous challenge.

Example 18

H1N1pdm: FluMist® CA07 vs M2KO(ΔTM) CA07

The HA and NA cDNA clones of A/California/07/2009 (CA07) (H1N1pdm) were generated by standard molecular biology protocols. The sequences of the constructs were confirmed and sub-cloned into appropriate vectors to allow for the generation of seed M2KO(ΔTM) virus and M2WTCA07/PR8 virus using standard protocols. FluMist® CA07 (H1N1pdm) was plaque purified in MDCK cells from FluMist® 2011-2012 vaccine Lot# B11K1802. The A/California/07/2009 (CA07) HA (SEQ ID NO:26) and NA (SEQ ID NO:27) sequences used are shown below:

```
A/California/07/2009 (H1N1) HA in M2KOTMdel
AGCAAAAGCAGGGGAAAACAAAAGCAACAAAAATGAAGGCAATACTAGTAGTTCTGCTATATACATTTGCAACCGCAAAT

GCAGACACATTATGTATAGGTTATCATGCGAACAATTCAACAGACACTGTAGACACAGTACTAGAAAAGAATGTAACAGT

AACACACTCTGTTAACCTTCTAGAAGACAAGCATAACGGGAAACTATGCAAACTAAGAGGGGTAGCCCCATTGCATTTGG
```

-continued

```
GTAAATGTAACATTGCTGGCTGGATCCTGGGAAATCCAGAGTGTGAATCACTCTCCACAGCAAGCTCATGGTCCTACATT

GTGGAAACACCTAGTTCAGACAATGGAACGTGTTACCCAGGAGATTTCATCGATTATGAGGAGCTAAGAGAGCAATTGAG

CTCAGTGTCATCATTTGAAAGGTTTGAGATATTCCCCAAGACAAGTTCATGGCCCAATCATGACTCGAACAAAGGTGTAA

CGGCAGCATGTCCTCATGCTGGAGCAAAAAGCTTCTACAAAAATTTAATATGGCTAGTTAAAAAAGGAAATTCATACCCA

AAGCTCAGCAAATCCTACATTAATGATAAAGGGAAAGAAGTCCTCGTGCTATGGGGCATTCACCATCCATCTACTAGTGC

TGACCAACAAAGTCTCTATCAGAATGCAGATGCATATGTTTTTGTGGGGTCATCAAGATACAGCAAGAMGTTCAAGCCGG

AAATAGCAATAAGACCCAAAGTGAGGGATCRAGAAGGGAGAATGAACTATTACTGGACACTAGTAGAGCCGGGAGACAAA

ATAACATTCGAAGCAACTGGAAATCTAGTGGTACCGAGATATGCATTCGCAATGGAAAGAAATGCTGGATCTGGTATTAT

CATTTCAGATACACCAGTCCACGATTGCAATACAACTTGTCAAACACCCAAGGGTGCTATAAACACCAGCCTCCCATTTC

AGAATATACATCCGATCACAATTGGAAAATGTCCAAAATATGTAAAAAGCACAAAATTGAGACTGGCCACAGGATTGAGG

AATATCCCGTCTATTCAATCTAGAGGCCTATTTGGGGCCATTGCCGGTTTCATTGAAGGGGGTGGACAGGGATGGTAGA

TGGATGGTACGGTTATCACCATCAAAATGAGCAGGGGTCAGGATATGCAGCCGACCTGAAGAGCACACAGAATGCCATTG

ACGAGATTACTAACAAAGTAAATTCTGTTATTGAAAAGATGAATACACAGTTCACAGCAGTAGGTAAAGAGTTCAACCAC

CTGGAAAAAAGAATAGAGAATTTAAATAAAAAAGTTGATGATGGTTTCCTGGACATTTGGACTTACAATGCCGAACTGTT

GGTTCTATTGGAAAATGAAAGAACTTTGGACTACCACGATTCAAATGTGAAGAACTTATATGAAAAGGTAAGAAGCCAGC

TAAAAAACAATGCCAAGGAAATTGGAAACGGCTGCTTTGAATTTTACCACAAATGCGATAACACGTGCATGGAAAGTGTC

AAAAATGGGACTTATGACTACCCAAAATACTCAGAGGAAGCAAAATTAAACAGAGAAGAAATAGATGGGGTAAAGCTGGA

ATCAACAAGGATTTACCAGATTTTGGCGATCTATTCAACTGTCGCCAGTTCATTGGTACTGGTAGTCTCCCTGGGGGCAA

TCAGTTTCTGGATGTGCTCTAATGGGTCTCTACAGTGTAGAATATGTATTTAACATTAGGATTTCAGAAGCATGAGAAAA

AAACACCCTTGTTTCTACT

>A/California/07/2009 (H1N1) NA in M2KOTMdel
AGCAAAAGCAGGAGTTTAAAATGAATCCAAACCAAAAGATAATAACCATTGGTTCGGTCTGTATGACAATTGGAATGGCT

AACTTAATATTACAAATTGGAAACATAATCTCAATATGGATTAGCCACTCAATTCAACTTGGGAATCAAAATCAGATTGA

AACATGCAATCAAAGCGTCATTACTTATGAAAACAACACTTGGGTAAATCAGACATATGTTAACATCAGCAACACCAACT

TTGCTGCTGGACAGTCAGTGGTTTCCGTGAAATTAGCGGGCAATTCCTCTCTCTGCCCTGTTAGTGGATGGGCTATATAC

AGTAAAGACAACAGTGTAAGAATCGGTTCCAAGGGGGATGTGTTTGTCATAAGGGAACCATTCATATCATGCTCCCCCTT

GGAATGCAGAACCTTCTTCTTGACTCAAGGGGCCTTGCTAAATGACAAACATTCCAATGGAACCATTAAAGACAGGAGCC

CATATCGAACCCTAATGAGCTGTCCTATTGGTGAAGTTCCCTCTCCATCAACTCAAGATTTGAGTCAGTCGCTTGGTCA

GCAAGTGCTTGTCATGATGGCATCAATTGGCTAACAATTGGAATTTCTGGCCCAGACAATGGGGCAGTGGCTGTGTTAAA

GTACAACGGCATAATAACAGACACTATCAAGAGTTGGAGAAACAATATATTGAGAACACAAGAGTCTGAATGTGCATGTG

TAAATGGTTCTTGCTTTACTGTAATGACCGATGGACCAAGTAATGGACAGGCCTCATACAAGATCTTCAGAATAGAAAAG

GGAAAGATAGTCAAATCAGTCGAAATGAATGCCCCTAATTATCACTATGAGGAATGCTCCTGTTATCCTGATTCTAGTGA

AATCACATGTGTGTGCAGGGATAACTGGCATGGCTCGAATCGACCGTGGGTGTCTTTCAACCAGAATCTGGAATATCAGA

TAGGATACATATGCAGTGGGATTTTCGGAGACAATCCACGCCCTAATGATAAGACAGGCAGTTGTGGTCCAGTATCGTCT

AATGGAGCAAATGGAGTAAAAGGGTTTTCATTCAAATACGGCAATGGTGTTTGGATAGGGAGAACTAAAAGCATTAGTTC

AAGAAACGGTTTTGAGATGATTTGGGATCCGAACGGATGGACTGGGACAGACAATAACTTCTCAATAAAGCAAGATATCG

TAGGAATAAATGAGTGGTCAGGATATAGCGGGAGTTTTGTTCAGCATCCAGAACTAACAGGGCTGGATTGTATAAGACCT

TGCTTCTGGGTTGAACTAATCAGAGGGCGACCCAAAGAGAACACAATCTGGACTAGCGGGAGCAGCATATCCTTTTGTGG

TGTAAACAGTGACACTGTGGGTTGGTCTTGGCCAGACGGTGCTGAGTTGCCATTTACCATTGACAAGTAATTTGTTCAAA

AAACTCCTTGTTTCTACT
```

Figure 37:
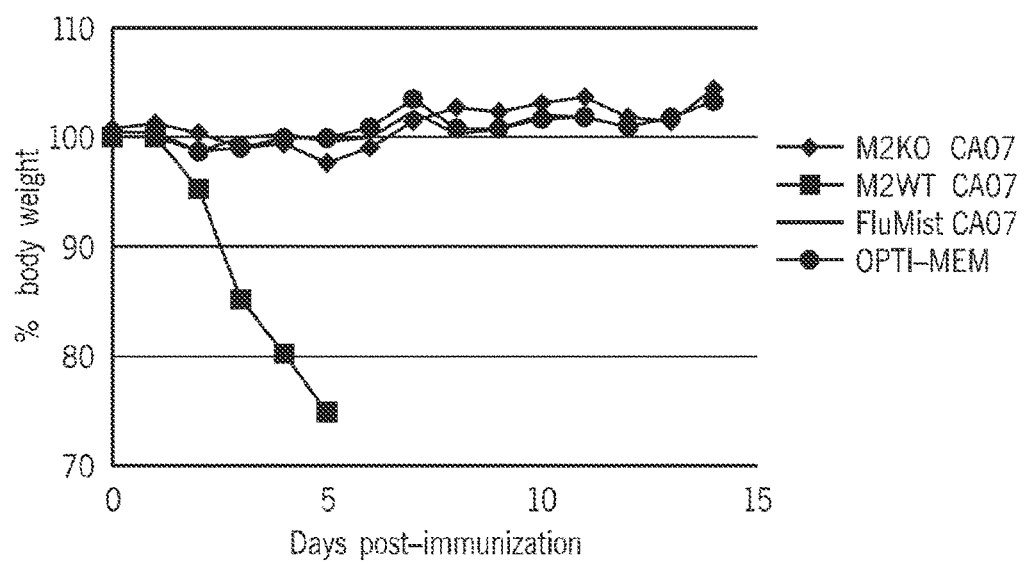
FIG. 37 is a chart showing body weight following administration of M2KO(ΔTM) CA07, WT CA07, and FluMist® CA07 vaccines.

Mice (7-8 weeks old, female BALB/c) were intranasally inoculated with M2KO(ΔTM) CA07 ($10^6$ TCID$_{50}$/mouse), M2WT CA07 ($10^6$ TCID$_{50}$/mouse), FluMist® CA07 ($10^6$ TCID$_{50}$/mouse) or OPTI-MEM™ as naïve control. Body weight and clinical symptoms were observed for 14 days post-inoculation. FIG. 37 shows that M2KO(ΔTM) and FluMist® vaccinated mice did not lose weight whereas the virus that contains the WT M2 loses weight and succumbs to infection. These results demonstrate that deletion of the M2 gene attenuates the virus and that M2KO(ΔTM) is attenuated.

Figure 38:
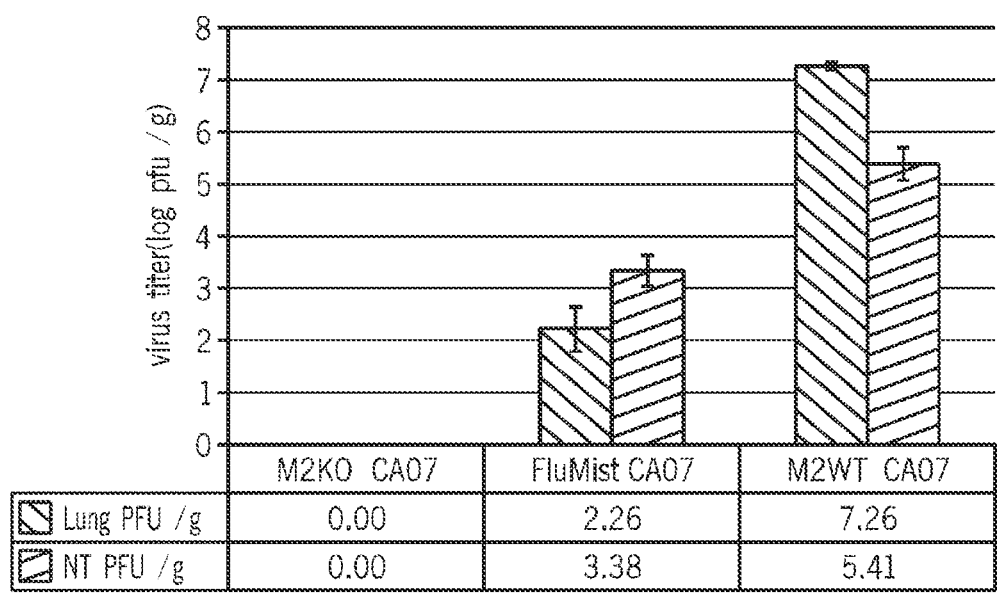
FIG. 38 is a chart showing that M2KO(ΔTM) virus does not replicate in respiratory tract of mice.

FIG. 38 M2KO(ΔTM), FluMist®, and M2 wild-type viral titers lungs and nasal terminates. Lungs and nasal turbinates were harvested on day 3 post-vaccination for titration of virus on cells. No virus was detected in either the lungs or the nasal turbinates in the M2KO(ΔTM) immunized mice. In contrast, FluMist® did have virus replication in both the lung and nasal turbinates although at lower levels than the wild-type virus.

Figure 39:
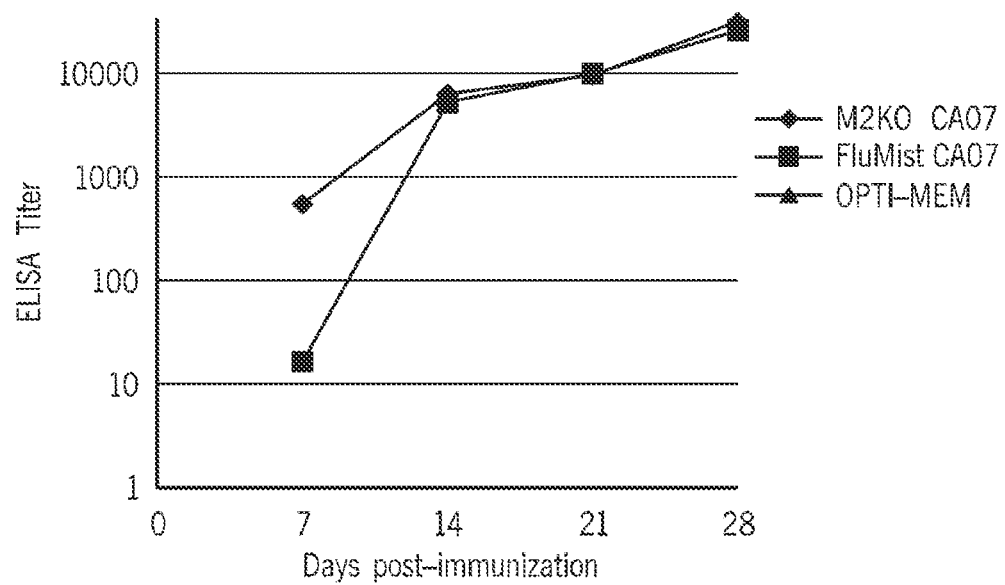
FIG. 39 is a chart showing that M2KO(ΔTM) vaccine displays rapid antibody kinetics.

FIG. 39 M2KO(ΔTM) and FluMist® titers in sera collected 7, 14, and 21 days post-inoculation and anti-HA IgG titers were determined by ELISA. M2KO(ΔTM) induced higher responses that were detected earlier than FluMist® responses. By day 21 peak antibody levels were reached by both viruses.

Figure 40:
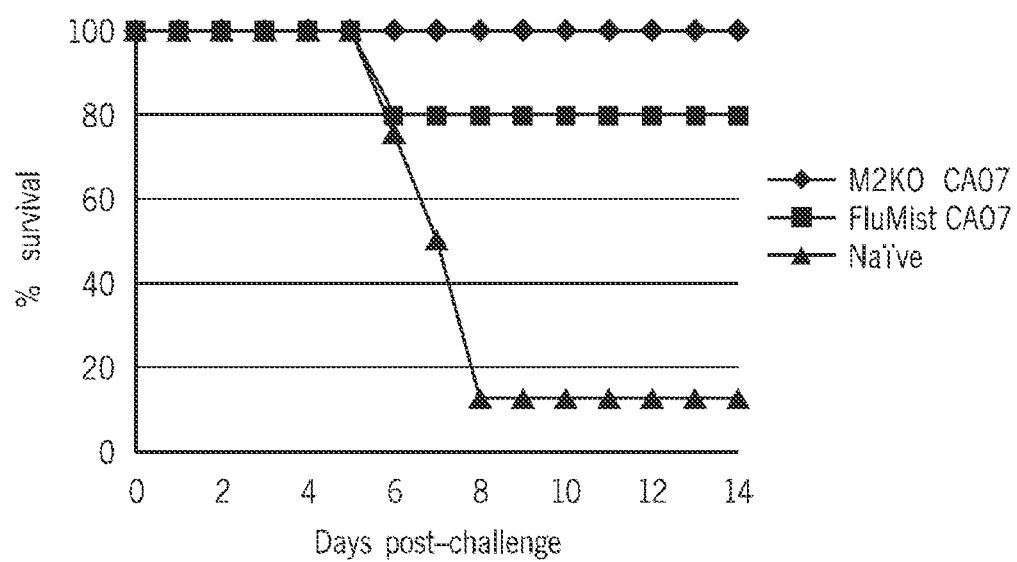
FIG. 40 is a chart showing that M2KO(ΔTM) vaccine protects against heterologous challenge with H3N2 virus, A/Aichi/2/1968.

FIG. 40 shows the percent survival of mice challenged 12 weeks post-immunization with 40 MLD$_{50}$ of heterologous virus, mouse-adapted influenza A/Aichi/2/1968 (H3N2). Body weight change and clinical symptoms were observed for 14 days after challenge. All the M2KO(ΔTM) (H1N1pdm HA,NA) immunized mice were protected against the Aichi (H3N2) challenge whereas only 80% of the FluMist® (H1N1pdm HA,NA) were protected. The surviving FluMist® mice lost close to 20% of their body weight whereas M2KO(ΔTM) mice lost ~10% of their body weight.

Table 26 shows the virus titers in the lungs and nasal turbinates that were collected on day 3 post-challenge. M2KO(ΔTM) and FluMist® controlled challenge virus replication in the lungs and nasal turbinates to similar levels whereas naïve mice displayed virus titers that were a log higher in both the lung and the nasal turbinates.

Figure 41:
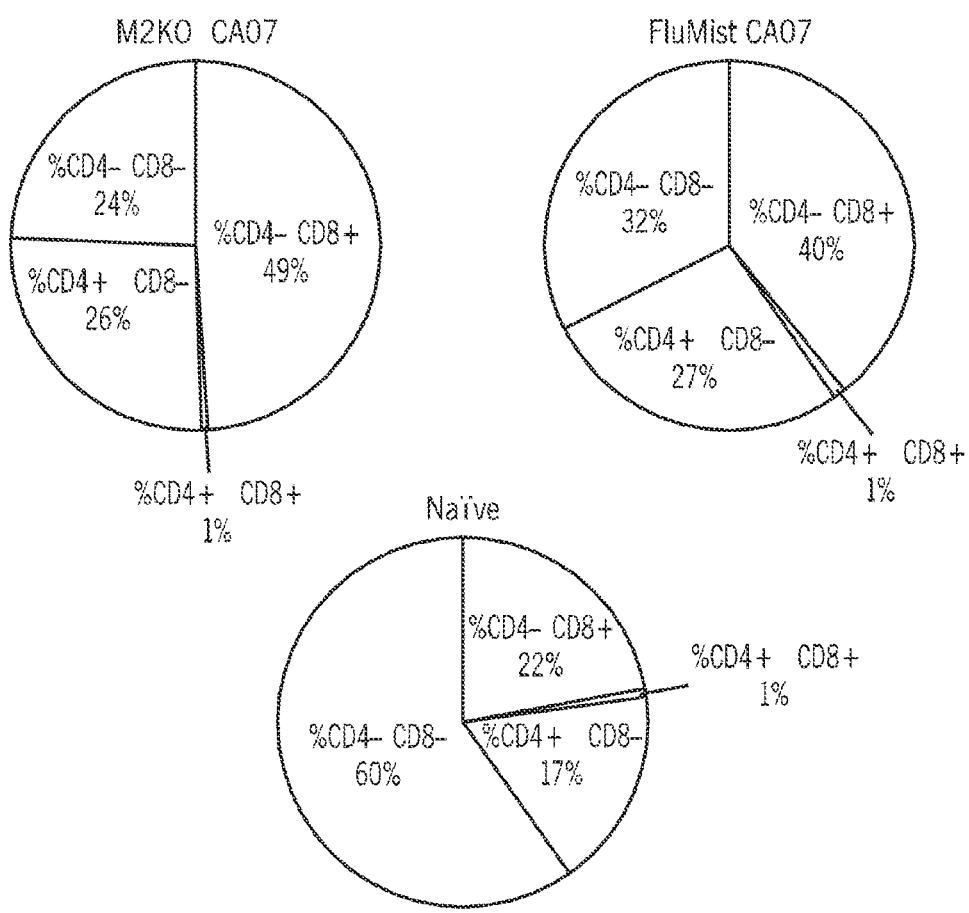
FIG. 41 is a chart showing that M2KO(ΔTM) vaccine primes for cellular responses that are recalled upon challenge.

Intracellular staining of cells in bronchoalveolar lavage (BAL). BAL was collected 3 days post-challenge and stained with surface markers for immunostaining by flow cytometry to detect CD8+CD4+, CD8+CD4−, CD8−CD4+, CD8−CD4− cell populations. Both CD4+ and CD8+ cell populations were greater in the vaccinated mice than the naïve mice indicating that M2KO(ΔTM) primed for a cellular response similar to FluMist®. M2KO(ΔTM) vaccinated mice had greater CD8+CD4− cell population than FluMist® (49% vs 40%) (FIG. 41).

TABLE 26

Virus titers in respiratory tract of mice.

|  | Lung (log pfu/g) | Nasal Turbinate (log pfu/g) |
| --- | --- | --- |
| M2KO CA07 | 5.95 ± 0.59 | 5.61 ± 0.47 |
| FluMist CA07 | 5.94 ± 0.46 | 3.88 ± 0.64 |
| Naive | 6.86 ± 0.06 | 6.52 ± 1.05 |

Example 19

M2KO(ΔTM) mRNA Expression Relative to FluMist® and Wild-Type Virus

In some embodiments, the M2KO(ΔTM) virus is produced in cells that stably provide M2 protein in trans resulting in a virus that has functional M2 protein in the viral membrane but does not encode M2 in its genome. Therefore, we hypothesize that the M2KO(ΔTM) virus behaves similar to wild-type virus in the initial infection and first round of replication in normal cells. We suggest that mRNA levels of viral antigens are similar to wild-type levels early in infection and stimulate a potent immune response sooner than attenuated replicating viral vaccines.

Human lung carcinoma (A549) cells were infected at a multiplicity of infection of 0.5 with M2KO(ΔTM), FluMist® and wild-type viruses. Unadsorbed virus was removed by washing five times with PBS. After addition of virus growth media, the infected cells were placed in the 35° C. $CO_2$ incubator. No trypsin was added to the growth medium to ensure single-cycle replication for all viruses. Cell monolayers were harvested and RNA extracted at 4, 9 and 22 hours post infection.

Total RNA (100 ng) from control and infected A549 cells were used for quantitative RT-PCR analysis. cDNA was synthesized with oligo-dT primers and Superscript II reverse transcriptase (Invitrogen) and quantified by real-time quantitative PCR analysis using gene-specific primers for an early influenza gene, M1, and a late influenza gene, HA and cytokine IP-10 gene. Reactions were performed using SYBR Green reagent (Invitrogen, Carlsbad) according to the manufacturer's instructions. Reaction efficiency was calculated by using serial 10-fold dilutions of the housekeeping gene ¥-actin and sample genes. Reactions were carried out on an ABI 7300 realtime PCR system (Applied Biosystems, Foster City, Calif., USA) and the thermal profile used was Stage 1: 50° C. for 30 min; Stage 2: 95° C. for 15 min; Stage 3: 94° C. for 15 sec, 55° C. for 30 sec; and 72° C. for 30 sec, repeated for 30 cycles. All quantitations (threshold cycle [CT] values) were normalized to that of the housekeeping gene to generate ΔCT, and the difference among the ΔCT value of the sample and that of the reference (wild-type sample) was calculated as −ΔΔCT. The relative level of mRNA expression was expressed as 2−ΔΔCT.

Figure 42:
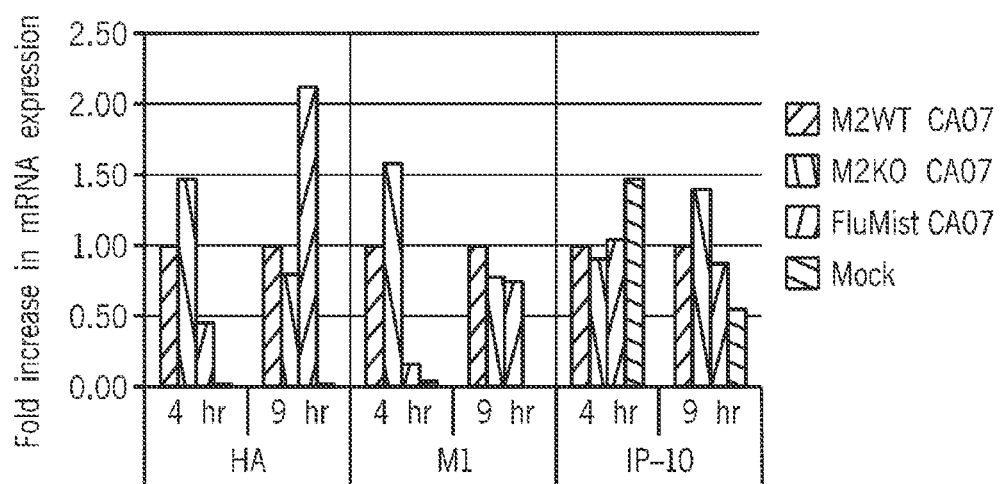
FIG. 42 is a chart showing that M2KO(ΔTM) virus generates mRNA levels similar to virus wild-type for M2.

M2KO(ΔTM) virus HA mRNA expression was similar to wild-type M2 virus for H3 (Table 27), PR8 (Table 28) and H1N1pdm (FIG. 42) at 4 hour post-infection. Cold-adapted FluMist® was less than wild-type and M2KO(ΔTM) in the early timepoints due to slower replication kinetics. When M1, an early timepoint gene, mRNA expression was tested, similar results were observed (Table 27, FIG. 42). These results suggest that M2KO(ΔTM) generates similar levels of mRNA in the early infection cycle to produce de novo viral antigens that create a 'danger signal' similar to wild-type virus and induce a potent immune response.

TABLE 27

Relative mRNA expression of H3 HA genes.

| | $2^{-\Delta\Delta Ct}$ (compare to IVR-147) | | |
| --- | --- | --- | --- |
| | neat | 1:10 dilution | 1:100 dilution |
| 4 hr pi | | | |
| IVR-147 | 1.0 | 1.0 | 1.0 |
| M2KO | 15.4 | 16.1 | 10.8 |
| FluMist | 2.3 | 2.1 | 1.4 |
| Mock | 0.0 | 0.0 | N/A |
| 22 hr pi | | | |
| IVR-147 | 1.0 | 1.0 | 1.0 |
| M2KO | 1.0 | 1.4 | 1.9 |

TABLE 27-continued

Relative mRNA expression of H3 HA genes.

| | 2^-ΔΔCt (compare to IVR-147) | | |
|---|---|---|---|
| | neat | 1:10 dilution | 1:100 dilution |
| FluMist | 1.8 | 3.1 | 1.5 |
| Mock | 0.0 | 0.0 | N/A |

TABLE 28

Relative mRNA expression of the PR8 HA and M1 genes.

| | | HA | | M1 | |
|---|---|---|---|---|---|
| | Sample | neat | 1:10 | neat | 1:10 |
| 4 hr p.i. | PR8 WT | 1.00 | 1.00 | 1.00 | 1.00 |
| | PR8 M2KOTMdel | 3.07 | 1.29 | 3.15 | 2.64 |
| | Mock | 0.02 | 0.30 | 0.15 | 0.32 |
| 9 hr p.i. | PR8 WT | 1.00 | 1.00 | 1.00 | 1.00 |
| | PR8 M2KOTMdel | 2.05 | 3.27 | 4.04 | 5.11 |
| | Mock | 0.00 | 0.00 | 0.00 | 0.00 |

Example 20

Generation of M2 Vero Production Cells

Figure 43:
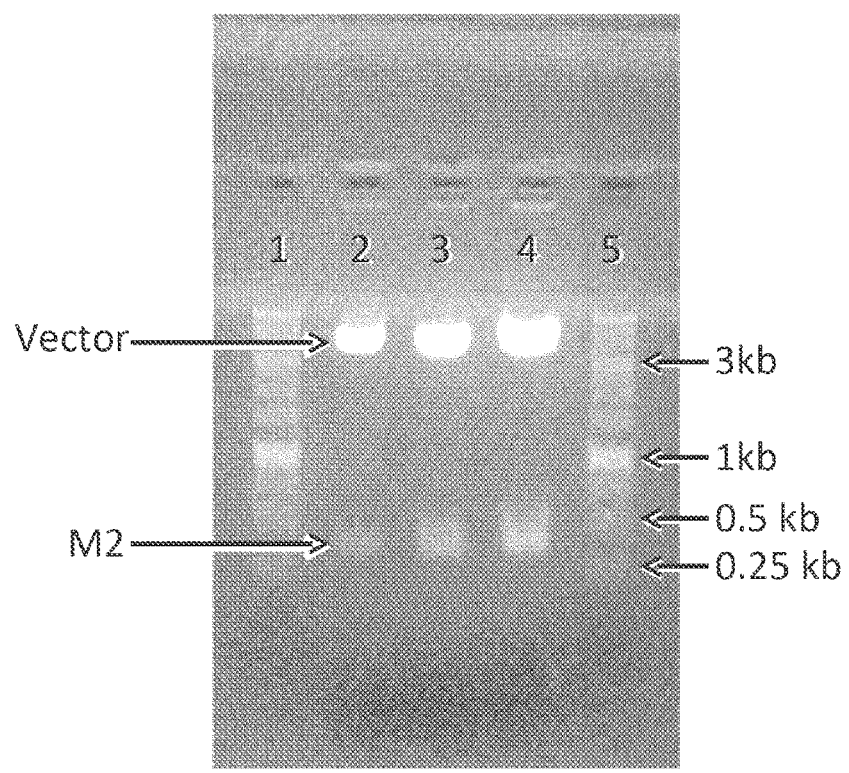
FIG. 43 is an agarose gel showing restriction digests of the pCMV-PR8-M2 expression plasmid. Lanes 1 & 5; 1 Kb DNA Ladder (Promega, Madison, Wis., USA), Lane 2-4; Eco R1 digested pCMLV-PR8-M2: 0.375 μg (Lane 2), 0.75 μg (Lane 3), and 1.5 μg (Lane 4).
Figure 44A:
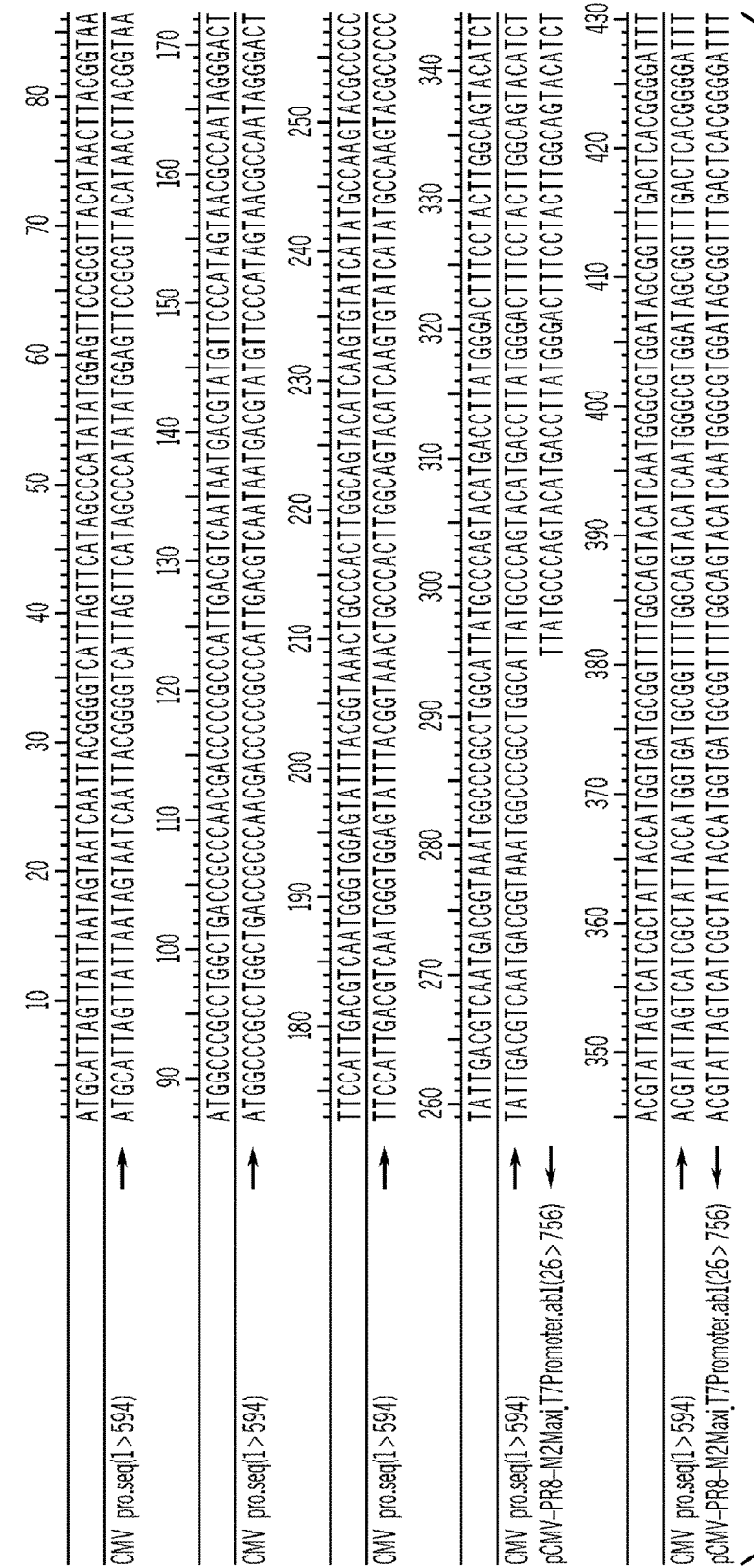

The M2 gene of PR8 virus was cloned into expression vector pCMV-SC (Stratagene, La Jolla, Calif.) by standard molecular techniques to generate pCMV-PR8-M2. The plasmid was digested with EcoR1 to confirm the presence of the 300 bp M2 gene and the 4.5 Kb vector as shown in FIG. 43. The sequence of the plasmid containing the M2 gene insert was confirmed as shown in FIG. 44.

Generation of M2 Vero cells: The pCMV-PR8-M2 plasmid described earlier and containing a neomycin resistant gene, was transfected into Vero cells (ATCC CCL-81) by using the Trans IT-LT1 transfection reagent (Mirus) according to the manufacturer's instructions. Briefly, on the day before transfection, Vero cells were plated at $5 \times 10^5$ cells/100-mm dish. On day 1, 10 µg of plasmid DNA was mixed with 20 µg of Trans IT-LT1 in 0.3 ml of OptiMEM (Invitrogen) and was incubated with these cells at 37° C. in 5% $CO_2$ overnight. On day 2, the transfection mixture was replaced with a complete medium that is modified Eagle's medium (MEM) supplemented with 5% newborn calf serum. The medium also contained 1 mg/ml of geneticin (Invitrogen), a broad spectrum antibiotic that is used to select mammalian cells expressing the neomycin protein. Resistant cells (Vero cells stably expressing M2 gene) began to grow in the selection medium, the medium was replaced with fresh selection medium and geneticin-resistant clones were isolated by limited dilution in TC-96 plates. The surface expression of the M2 protein was demonstrated by immunostaining using a M2 specific monoclonal antibody, 14C2 (Santa Cruz Biotechnology).

Infection of parental and modified M2 Vero cells with M2KO(ΔTM) virus: The ability of M2 Vero cells to serve as production cells for M2KO(ΔTM) virus was tested by infection with M2KO(ΔTM)-PR8 virus. Briefly, monolayers of M2 Vero and parent Vero cells were infected with ten-fold serial dilutions ($10^{-1}$ to $10^{-6}$) of M2KO(ΔTM)-PR8 virus using standard influenza infection procedures. The infected cells were incubated at 35° C. and observed for cytopathic effect (CPE) daily. Only M2 Vero cells displayed CPE indicating virus growth. Supernatant was harvested on day 4 from the $10^{-3}$ well and virus titer was determined by $TCID_{50}$ assay on MDCK cells stably expressing M2 gene (M2CK). M2KO(ΔTM)-PR8 virus titer grown in M2 Vero cells was $10^{6.75} TCID_{50}$/ml indicating that M2 Vero cells can serve as production cells for the manufacture of M2KO (ΔTM) vaccine.

Example 21

Intradermal Delivery of Influenza Vaccines

This example demonstrates the immunogenicity of the seasonal influenza vaccine, FluLaval (2011-2012 formulation), when administered intramuscularly (IM), intradermally (ID), and using a subcutaneous microneedle device such as that described in published U.S. Patent Application 2011/0172609. Hairless guinea pigs were inoculated on day 0 and select groups were boosted on day 30. Sera was collected on days 0, 30 and 60 and analyzed by enzyme-linked immunosorbent assay (ELISA) for hemagglutinin-specific IgG responses.

Figure 51:
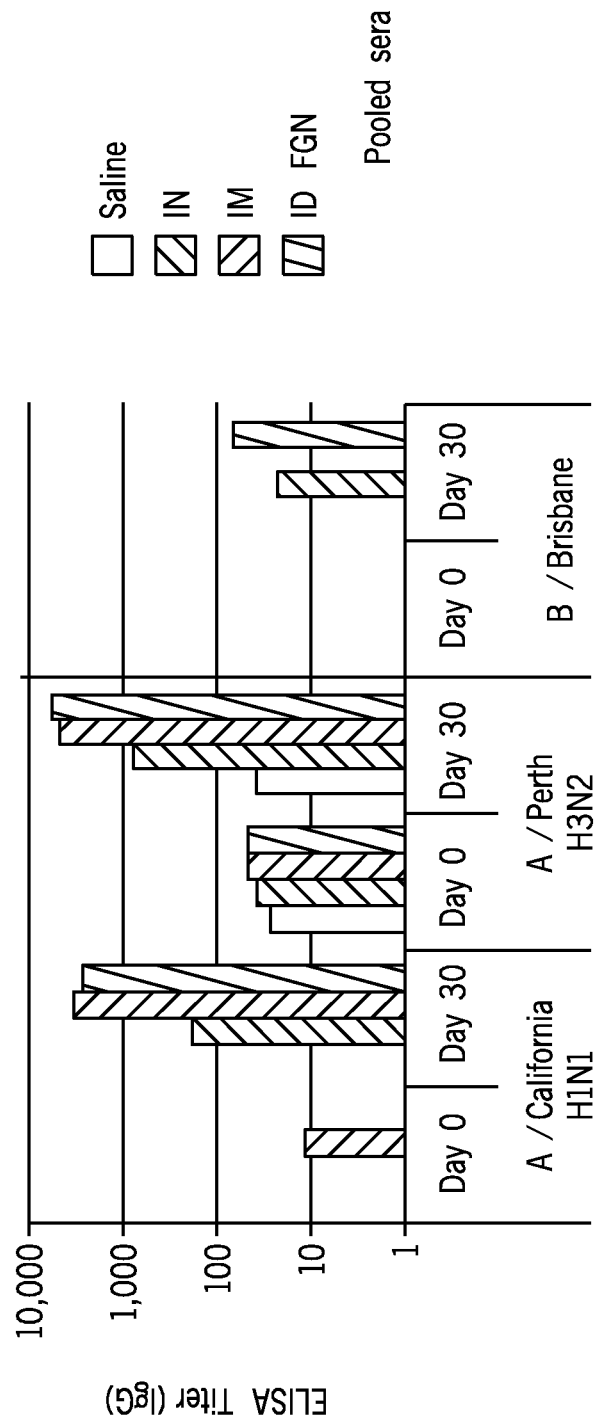
FIG. 51 is a chart showing IgG titers in subjects vaccinated with A/California, A/Perth, and B/Brisbane viruses intranasally (IN), intramuscularly (IM) and intradermally (ID FGN).
Figure 52:
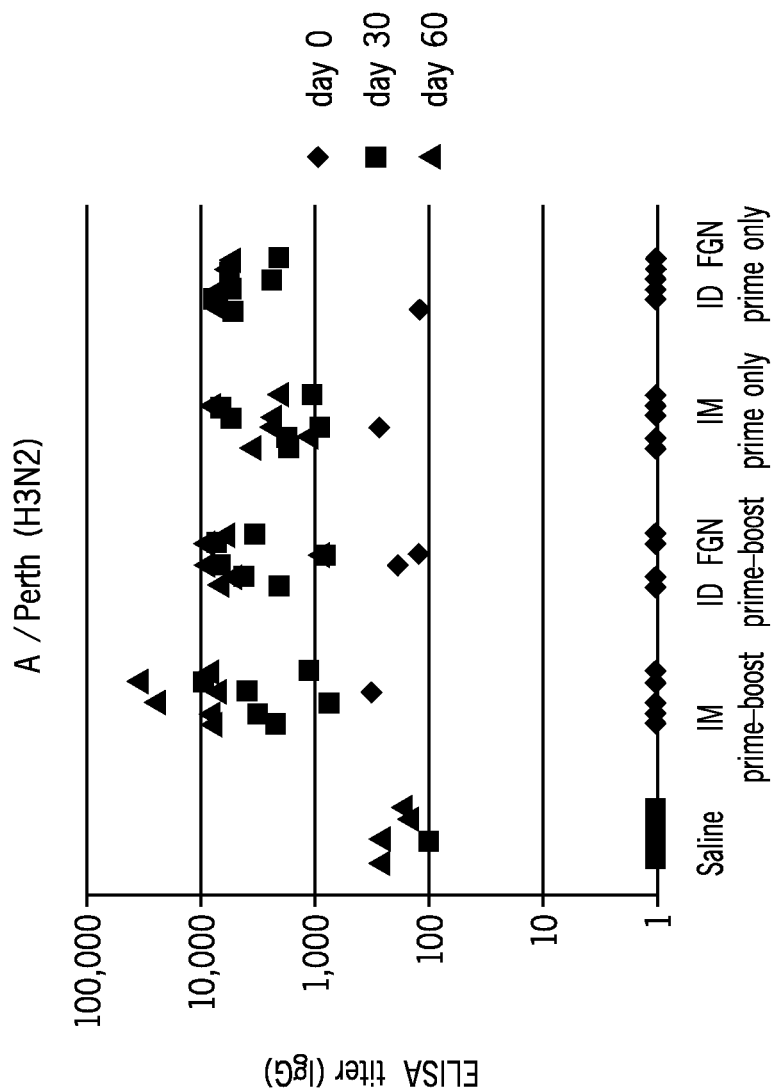
FIG. 52 is a chart showing IgG titers in subjects administered a priming does or a priming and booster dose of A/Perth (H3N2) vaccine intramuscularly (IM) or intradermally (ID FGN).

Results are shown in FIGS. 51-53. The data shows qualitative absorbance of antibody levels to the three strains formulated in the seasonal influenza vaccine FluLaval: A/California/7/2009 NYMC X-181, A/Victoria/210/2009 NYMC X-187 (an A/Perth/16/2009-like virus), and B/Brisbane/60/2008. At day 30, IM and ID delivery produced identical IgG responses to all viral HA. The ID prime only groups displayed higher titers at day 60, suggesting that ID delivery induces long lasting immunity to all viral HA.

Example 22

Preparation of the M2TMDel Influenza Viral Vector

This example demonstrates construction of the M2TMDel influenza viral vector, which is engineered from the M2KO influenza virus comprising SEQ ID NO:1.

The M2KO influenza virus comprising SEQ ID NO:1 was modified by the insertion of a 6×His epitope tag 5' to the two stop codons using site-directed PCR mutagenesis. The M2KO gene in pHH21 was used as a template and amplified using PfuTurbo® DNA Polymerase (Stratagene, La Jolla, Calif., USA) according to manufacturer instructions. Two overlapping oligonucleotide primers encoding the 6×His tag were used to amplify segments of the M gene from the M2KO virus. Separate PCR reactions comprising 1) BM-M-1 with an internal reverse primer, and 2) BM-M-1207 with an internal forward primer were run under according to the Table 29.

TABLE 29

PCR Site-directed mutagenesis of M2KO

Reaction
 24 ng DNA
 0.5 uM each primer
 0.2 mM dNTP
 2.5 units PFU turbo
 50 ul total volume containing 1x reaction buffer.
BM-M-1 Primer
CACACACGTCTCCGGGAGCAAAAGCAGGTAG BM-M-1027 Primer
CACACACGTCTCCTATTAGTAGAAACAAGGTAGTTTTT TABLE 29 -continued PCR Site-directed mutagenesis of M2KO Internal Forward Primer
CACACACGTCTCACATCACCACCACCACCACTAATAGTGCATTTACCGTC
GCTTTAAATACGGACTGAAAGGAGG Internal Reverse Primer
TGTGTGCGTCTCAGATGATGGTGGTGGTGGTGGTGCGCATCACTTGAACC
GTTGCATCTGCACCCCATTCG Amplification
Segment 1: 1 cycle, 95° C. for 2 minutes
Segment 2: 30 cycles, 95° C. for 30 seconds,
primer T$_m$-5° C. for 30 seconds, 72° C. for 1
minute
Segment 3: 1 cycle, 72° C. for 10 minutes The resulting PCR products were gel purified using a QIAquick Gel Extraction Kit, digested using BsmB1 and Dpn1. Dpn1 cleaves methylated DNA, thereby eliminated the template DNA. The BsmB1 digested fragments were ligated to BsmB1-digested pHH21 and transformed into competent DH5-alpha cells using standard procedures. Individual colonies containing the insert were identified using PCR colony screen with insert-specific primers. Plasmid from the positive colonies were purified using QIAGEN DNA purification kits. The recombinant virus containing the 6×His downstream of the M2 ectodomain was generated using standard influenza virus reverse genetics techniques.

Example 23

Rescue of Influenza Virus Using M2TMDel+HIS

This example demonstrates that influenza virus assembly can be rescued by plasmid transfection in 293T cells using M2TMDel+HIS.

Figure 56:
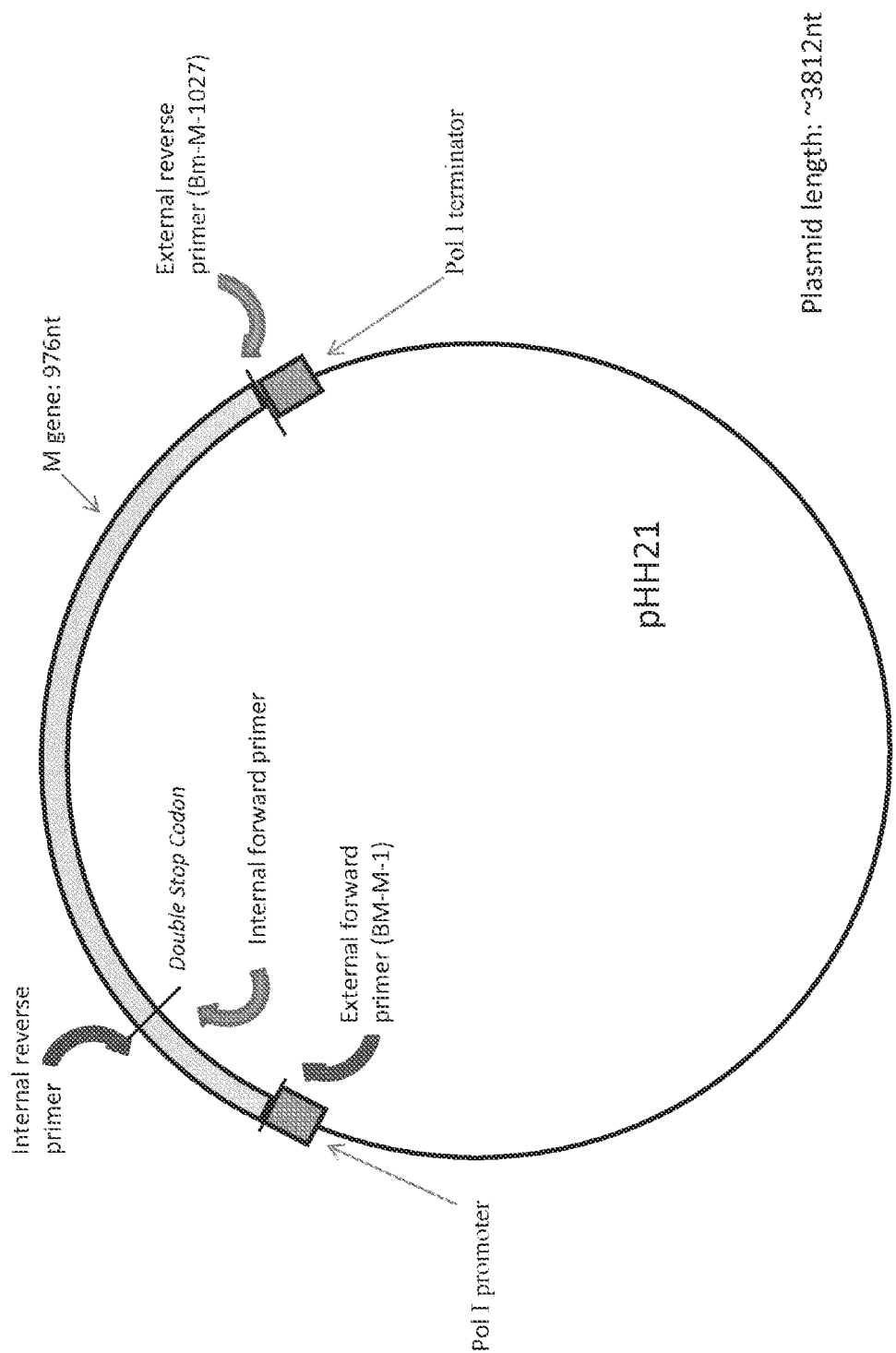
FIG. 56 is a schematic of an exemplary intermediate useful for cloning an antigen of interest into the influenza virus M gene region.
Figure 57:
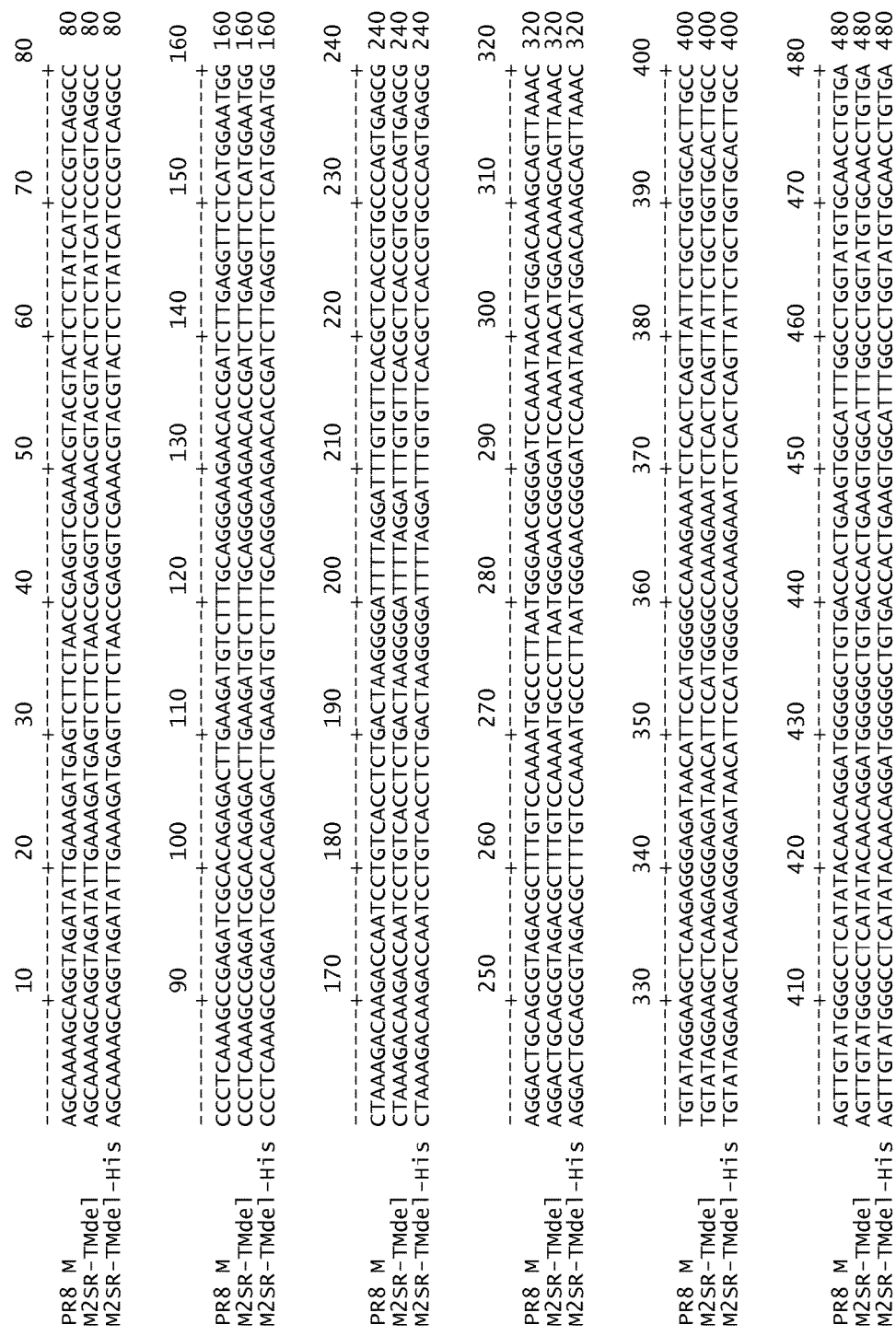
FIG. 57 is a sequence alignment showing a wild-type M gene region, the M2-1 sequence (SEQ ID NO:1), and an exemplary viral vector M gene region including a mutant M2 sequence and exemplary antigen sequence (SEQ ID NO:34).

Rescue of Influenza Virus by Plasmid Transfection of 293T Cells—Influenza virus bearing the M2TMDel+HIS (SEQ ID NO:34) region was generated according to the above example, and cloned into mammalian expression vector pHH21 (FIG. 56). Reagents were prepared according to Table 30:

TABLE 30

Reagents

| | Reagent | Description |
|---|---|---|
| pPolI | PA | PpolI PR8HG PA 0.1 ug/ul |
| | PB1 | PpolI PR8HG PB1 0.1 ug/ul |
| | PB2 | PpolI PR8HG CHO PB2 0.1 ug/ul |
| | NP | PpolI PR8HG CHO NP 0.1 ug/ul |
| | HA | PpolI PR8HG HA 0.1 ug/ul |
| | NA | PpolI PR8HG NA 0.1 ug/ul |
| | NS | PpolI PR8HG NS 0.1 ug/ul |
| pCAGus | PA | 070318 YSK pCAGGS WSN PA 1.0 ug/ul |
| | PB1 | 070319 YSK pCAGGS WSN PB1 1.0 ug/ul |
| | PB2 | 070318 YSK pCAGGS WSN PB2 1.0 ug/ul |
| | NP | pCAGGS WSN NP 1.0 ug/ul |
| pCMV | M2 | pCMV PR8 M2 1.0 ug/ul YH |
| pPolI | M2KOTMdel + HIS K2KOTMdel | Colony 13 midiprep plasmid 2/27/13 pPol m2kotmdel + his 1-02 dilution |
| | WTM2 | 3/28/11 pPolI PR8 HGM midi 11/03/28 0.1 ug/ul |
| TransITLT1 Transfection reagent | | Lot # KLN06393 open 2/28/13 YH exp. 1 year from purchase date. |
| OptiMEM | | |

The M2TMDel+HIS construct was used to produce recombinant virus according to the following:
1. Seed 1,000,000 293T cells per well into a TC6 plate and incubate at 37° C. overnight.
2. After 24 hours or when the cells are ~50-70% confluent begin transfection protocol.
3. Add 200 ul of OptiMEM WITHOUT ANY ANTIBIOTICS into one microcentrifuge tube for every transfection to be made.
4. Mix together with the 200 ul OptiMEM the amounts of each plasmid shown in Table 31. For virus rescue transfections 8 Vrna plasmids (including ONE M pPolI plasmid) must be mixed along with 5 protein expression plasmids. For protein expression transfections ONLY one of the M pPolI vRNA plasmids are added along with FOUR protein expression plasmids NOT INCLUDING M2 protein expression plasmid.
5. Add TransIT LT1 transfection reagent to the DNA/Optimem mix at an amount of 2 ul per ug of plasmid DNA in the mix. Calculation: Total Plasmid DNA (ug)*2 ul TransIT LT1 Reagent. For example add 12.6 ul of LT1 reagent if you have a total of 6.3 ug of DNA in the mix.
6. Incubate OptiMEM/Plasmid DNA/TransIT LT1 mix at RT for 15 minutes.
7. FOR VIRUS RESCUE TRANSFECTION ONLY (for Protein expression transfections skip to step 8):
   a. During the incubation period carefully wash 293T cells 2 times with 1 ul of OptiMEM/well to remove FCS media from the cells. Add media to the walls of the wells to avoid lifting cells off of the monolayer.
   b. Carefully add 1.8 ml of OptiMEM to the side wall of each well. Avoid causing cells to lift off of the well.
8. After 15 minute incubation period carefully add the 200 ul DNA transfection mix to the well drop wise. Carefully avoid causing cells to lift off of wells.
9. Incubate@ 37° C. incubator for 2-3 days

TABLE 31

Plasmid Rescue of Influenza Virus

| Plasmid | Viral Gene | | Amount of plasmid to add for virus rescue transfection |
|---|---|---|---|
| pPolI | PA | | 0.1 ug |
| | PB1 | | 0.1 ug |
| | PB2 | | 0.1 ug |
| | NP | | 0.1 ug |
| | HA | | 0.1 ug |
| | NA | | 0.1 ug |
| | NS | | 0.1 ug |
| | M** | M2TMdel + HIS | 0.5 ug |
| | **(one of these per experiment) | M2TMdel | 0.5 ug |
| | | M2WT | 0.1 ug |
| pCAGus | PA | | 1.0 ug |
| | PB1 | | 1.0 ug |
| | PB2 | | 1.0 ug |
| | NP | | 1.0 ug |
| pCMV | M2** **(only for M2TMdel + HIS and M2TMdel) | | 1.0 ug |
| Total amount of plasmid: | | | 6.3 ug |

Analysis of Transfection Supernatant—Transfection supernatants were analyzed for the presence of influenza virus according to the following:
1. Approximately 72 hours transfection, 293T cell supernatant will contain virus and be ready for infecting confluent M2CK cells. Check TC6 plates and T96 plates to make sure that M2CK cultures are confluent.

2. Harvest viral supernatant and 293T cells together by pipetting supernatant up and down repeatedly in the dish to dislodge cells. Spin cell suspension for 5 minutes at 1000 RPM to separate viral supernatant from cells.
3. Harvest viral supernatant from cell pellets and resuspend each cell pellet in 1 ml of 3% BSA MEM.
4. From M2SR, M2SRHIS, and PR8 WT virus there will about 2 mL of viral supernatant. Three different experiments need to be run using some portion of this 2 ml. Protocols for all three are listed below.

TC6 Well Plate Infections—TC6 well plate infections were used to amplify virus in supernatant according to the following:

1. For the M2SRHIS, M2SR, and WT supernatants make a $10^{-1}$ and $10^{-2}$ serial dilution in a final volume of 800 ul. (Make two tubes with 720 ul of 3% BSA-MEM).
2. Aspirate 10% FCS-MEM media from two TC6 well plates and wash 2× with 1% dPBS.
3. Following plate design shown below For plates #1,2, add 800 ul of neat M2SR viral supernatant into one TC6 well and 800 ul of neat M2SRHIS viral supernatant into another well. Then inoculate 800 ul of $10^{-1}$ and
4. Inoculate 1 ml of WT, M2SR, and M2SRHIS 293T Cell Resuspension Solutions into unused TC6 wells for as a co-cell culture experiment. Add 1 ml of 0.3% BSA-MEM media to the final unused TC6 well as an M2CK cells only control.
5. Incubate plates for 1 hour @37° C. Every 15 minutes rock the plates back and forth.
6. After 1 hour incubation period, add 0.3% BSA-MEM and TPCK-TRYPSIN to each well (No TPCK-Trypsin for cells only control well) so that each well has a total volume of 2 ml and 1.5 ul of 0.75 ug/ul TPCK-Trypsin.
7. Label wells and place overnight in 35° C. incubator Plaque Assay: Plaque assays were performed on approximately 1 mL of viral supernatant on day three according to the following:

1. Take an 880 ul aliquot of neat viral supernatant from each of the three viral samples. From each sample make a $10^{-1}$ dilution by adding 80 ul of viral supernatant to 720 ul of 0.3% BSA-MEM.
2. Follow plate design show below for plate #3. For each viral sample add 800 ul of the neat viral supernatant to one well and 800 ul of the $10^{-1}$ dilution to another well.

3. Incubate plate for 1 hour @37° C. Every 15 minutes rock the plates back and forth.
4. After 1 hour add 1 ml of 1×MEM/0.3% BSA/1% seaplaque agarose with TPCK/trypsin (1 ug/ml).
5. Allow agar to harden on the table top for at least 10 minutes. After agar has hardened place in 35° C. incubator overnight upside down

TABLE 32

| Liquid and Plaque Assays | | | | | |
|---|---|---|---|---|---|
| Plate #1: Liquid | | | Plate #2: Plaque Assay | | |
| M2SR neat | M2SR −1 | M2SR −2 | M2SR neat | M2SRHIS neat | PR8WT neat |
| M2SRHIS neat | M2SRHIS −1 | M2SRHIS −2 | M2SR −1 | M2SRHIS −1 | PR8WT −1 |

Results:—For M2SRTMDEL-HIS, 20 plaques at neat dilution. Control wild-type had 77 plaques at $10^{-1}$ dilution. These results further support that M2SRTMDEL-HIS is a viable virus that can undergo multicycle replication containing the HIS tag.

Viral Titers—M2SRTMDEL-HIS viral titers in transfection supernatants were determined by $TCID_{50}$ assay according to the following:

Mammalian cells (e.g., M2CK cells, MDCK cells that stably express influenza M2 protein) were prepared in 96 well microtitre plates the day before titration seeding with $2\times10^4$ cells/ml. Cells were incubated overnight at 37° C., 5% $CO_2$ (18-22 hrs). Plates were used when cells reached confluence.

Serial dilutions of the transfection supernatants (M2SRTMDEL, M2SRTMdel HIS, PR8WT) were prepared in 0.3% BSA-MEM. Virus dilutions were added to the cell monolayers in 0.3% BSA-MEM media containing trypsin/TPCK at 1 ug/ml. The infected cells were incubated for 4 days in 35° C., 5% $CO_2$. On day 4 the infected cells were scored for cytopathic effect and titer calculated by Reed and Muench method.

Tables 33 and 34 show that M2SRTMDEL-HIS virus was rescued by the plasmid transfection method and that the titer was $1\times10^2$ $TCID_{50}$/ml on the second day of transfection and $1\times10^3$ $TCID_{50}$/ml on the third day of transfection. The control viruses are also shown in Table 33 and 34. The rescue of M2SRTMDEL-HIS indicates that foreign epitopes can be inserted into the M2 gene and viable replication deficient viruses can be obtained without expression of the M2 protein by the virus.

TABLE 33

| Titer ($TCID_{50}$) of rescued virus in Day 2 Supernatant from transfection | | | | | | | | | | | | | |
|---|---|---|---|---|---|---|---|---|---|---|---|---|---|
| Sample | | M2SRTMDEL_HIS | | | | M2SRTMDEL | | | | WTPR8 | | | |
| dilution | | 1 | 2 | 3 | 4 | 5 | 6 | 7 | 8 | 9 | 10 | 11 | 12 |
| Neat | A | + | + | + | + | + | + | + | + | + | + | + | + |
| 10E−01 | B | + | − | + | − | − | − | − | − | + | + | + | + |
| 10E−02 | C | − | − | − | − | − | − | − | − | + | + | + | + |
| 10E−03 | D | − | − | − | − | − | − | − | − | + | + | + | + |
| 10E−04 | E | − | − | − | − | − | − | − | − | − | − | − | − |
| 10E−05 | F | − | − | − | − | − | − | − | − | − | − | − | − |
| | G | | | | | | | | | | | | |
| | H | | | | | | | | | | | | |
| Log $TCID_{50}$/ml | | | $1\times10^2$ | | | | 31.6 | | | | $3.16\times10^4$ | | |

TABLE 34

Titer (TCID$_{50}$) of rescued virus in Day 3 Supernatant from transfection

| Sample | | M2SRTMDEL_HIS | | | | M2SRTMDEL | | | | WTPR8 | | | |
|---|---|---|---|---|---|---|---|---|---|---|---|---|---|
| dilution | | 1 | 2 | 3 | 4 | 5 | 6 | 7 | 8 | 9 | 10 | 11 | 12 |
| Neat | A | + | + | + | + | + | + | + | + | + | + | + | + |
| 10E-01 | B | + | + | + | + | + | + | − | − | + | + | + | + |
| 10E-02 | C | − | + | + | − | − | − | − | − | + | + | + | + |
| 10E-03 | D | − | − | − | − | − | − | − | − | − | − | + | − |
| 10E-04 | E | − | − | − | − | − | − | − | − | − | − | − | − |
| 10E-05 | F | − | − | − | − | − | − | − | − | − | − | − | − |
| | G | | | | | | | | | | | | |
| | H | | | | | | | | | | | | |
| Log TCID$_{50}$/ml | | 1 × 10³ | | | | 1 × 10² | | | | 2.46 × 10³ | | | |

This example shows that M2SRTMDEL may be used to rescue influenza virus by plasmid rescue, and that the construct may be used in methods to express select antigens cloned into the M2 region of the SEQ ID NO:1, as exemplified by M2SRTMDEL-HIS (SEQ ID NO:34). The example shows that methods and compositions described herein are useful for the delivery of select antigens to a host cell or organism to elicit an immune response against the antigen.

Example 24

In Vitro Expression of 6×His from the M2TMDel Influenza Viral Vector

This example will demonstrate that the M2TMDel influenza viral vector can direct robust in vitro expression of foreign epitopes cloned into the M gene locus.

Cultured MDCK cells are infected with the M2TMDel vector or mock infected and maintained in culture for a period of 1-3 days. Cells are lysed and lysates analyzed by SDS-PAGE followed by Western blotting using a monoclonal antibody specific for the 6×HIS tag.

It is expected that the lysates will show robust levels of 6×His protein expressed from the M2TMDel vector.

This Example will demonstrate that the M2TMDel vector is useful for the delivery of antigens to a host cell. As such, the M2TMDel vector described herein is useful in methods and compositions for eliciting an immune response in host.

Example 25

In Vivo Expression of 6×His from the M2TMDel Influenza Viral Vector

This example will demonstrate that the M2TMDel influenza viral vector can direct robust in vivo expression of foreign epitopes cloned into the M gene locus.

Six-week-old female BALB/c mice are anesthetized with isoflurane and infected intranasally with 10⁴ or 10⁵ PFU of wild-type virus or tagged M2TMDel in a 50 µl volume. Mock-infected control mice receive 50 µl PBS. Body weights of the animals are monitored for 14 days after infection. On days 3 and 6 post-infection, three mice from each group are euthanized and their lungs and nasal turbinates collected for viral titer determinations. On day 27 post-infection, three mice per group are euthanized and trachea-lung washes, nasal washes, and sera collected for antibody titer determinations using ELISA and Western blots.

It is expected that the M2TMDel infected animals will show robust expression of the 6×His epitope tag from the M2TMDEL influenza viral vector.

This Example will demonstrate that the M2TMDel vector is useful for the delivery of antigens to a recipient host. As such, the methods and compositions described herein are useful in methods and compositions for eliciting an immune response in host.

Example 26

Preparation of a Vaccine Comprising M2 Mutant Influenza Viral Vector for Delivery of Foreign Antigens There are various different types of vaccines which can be made from the cell-based virus production system disclosed herein and the viral vectors, harboring an antigen sequence of interest, disclosed herein. The present disclosure includes, but is not limited to, the manufacture and production of live attenuated virus vaccines, inactivated virus vaccines, whole virus vaccines, split virus vaccines, virosomal virus vaccines, viral surface antigen vaccines and combinations thereof. Thus, there are numerous vaccines capable of producing a protective immune response specific for different influenza viruses where appropriate formulations of any of these vaccine types are capable of producing an immune response, e.g., a systemic immune response. Live attenuated virus vaccines have the advantage of being also able to stimulate local mucosal immunity in the respiratory tract. As discussed above, the viral vectors also provide advantages for vaccination against an antigen of interest.

A vaccine comprising an M2TMDel vector carrying an antigen if interest, as illustrated by M2SRTMDEL-HIS (SEQ ID NO:34) may be prepared in accordance with examples described herein.

Example 27

Immunization of Mice Against Foreign Eiptopes Delivered Via an M2 Mutant Influenza Viral Vector This example illustrates the immunization of mice against select antigens using the M2TMDEL influenza viral vector, as illustrated by M2SRTMDEL-HIS (SEQ ID NO:34).

Early Immune Response

Groups of five C57BL/6 mice (8-10 weeks old, female 17-20 g in weight) are infected with either M2TMDEL or control PR8 using tribromoethanol anesthesia. BAL are harvested at 2, 6, 12, 24, 48, and 96 hrs post-infection and from the uninfected controls. Cell-free BAL supernatants are collected by centrifugation and frozen in aliquots for later cytokine measurements. Live cell counts are performed on BAL by trypan blue exclusion. Leukocyte subsets in the BAL are analyzed by staining for CD4, CD8, NK1.1, αβTCR, CD19 (B lymphocytes), γδ TCR, 1A8 (neutrophils), F4/80 (macrophages), followed by flow cytometric analysis using a BD FACSCalibur flow cytometer and Cellquest Pro software. BAL from groups of 5 mice are pooled for these assays. A lymphocyte gate is utilized to analyze lymphocyte subsets. The percentage of each subset relative to total BAL cells is used to calculate the total number of cells per mouse. For leukocyte subsets other than lymphocytes, cell counts from cytospins are used. Aliquots of BAL are cytocentrifuged onto microscope slides and stained with a Hema 3 staining kit (Fisher Sciences) to facilitate differential counting of neutrophils monocytes, lymphocytes, basophils, eosinophils and mast cells. Five to ten high power fields are counted per slide (100-500 cells).

T Cell Responses

Groups of three C57BL/6 mice (8-10 weeks old, female 17-20 g in weight) are infected with either M2KO or control PR8. A group of 3 uninfected control mice is also included. BAL and MLN are harvested on day 10 after infection. BAL and MLN cell suspensions are prepared and cell-free BAL supernatants are frozen for later cytokine measurements. Live cell counts for BAL or MLN from individual mice are performed by trypan blue exclusion. Lymphocyte subsets in the BAL are analyzed by staining for CD4, CD8, NK1.1, αβTCR, CD19 (B lymphocytes) and γδ TCR followed by flow cytometric analysis as described above.

The response to the M2TMDEL virus appears is expected to involve components of both the innate and adaptive arms of immune system. The majority of cells in the BAL at early time-points after infection are expected to be macrophages. The M2KO virus will induce a significant T cell response in the BAL at day 10 after infection, a high percentage of which will be CD8+, as expected for influenza infection at that time-point. Similarly, the MLN are expected to be enlarged, reflecting an increase in both T and B lymphocytes.

This Example will demonstrate that the M2TMDel vector is useful for the delivery of antigens to a recipient host, as illustrated by M2SRTMDEL-HIS (SEQ ID NO:34). As such, the methods and compositions described herein are useful in methods and compositions for eliciting an immune response in host.

Example 28

Expression of Foreign Epitopes from within the Influenza M2 Gene Region

This example demonstrates the expression of non-influenza epitopes/antigens (i.e. foreign epitopes/antigens) from nucleic acids cloned into the M2 gene region of the M2KO (ΔTM) virus, (M2SR).

Nucleic acid sequences encoding myc and 12×His epitope tags were cloned into the M2SR (M2KO(ΔTM)) virus using standard techniques, to generate an M2-myc (M2SR-Myc-M2) and M2-12×His (M2SR-12×His) fusions. The epitopes were placed in the M2 transmembrane domain, as shown below. A linker comprising the sequence Gly-Ala-Gly-Ala was incorporated N-terminal to the myc sequence. The mRNA sequence of the M2-myc fusion region is set forth in SEQ ID NO: 38, with the amino acid sequence set forth in SEQ ID NO: 39. The amino acid sequence of the M2-12×His fusion region is set forth in SEQ ID NO: 40. M2 sequences 3' to the foreign epitope cloning site are translated into protein in the myc construct, but are not expressed from the 12×His construct.

M2SR-Myc-M2 (sense)
(SEQ ID NO: 38)
5'AGCAAAAGCAGGTAGATATTGAAAGatgagtcttctaaccgaggtcga aacGTACGTACTCTCTATCATCCCGTCAGGCCCCCTCAAAGCCGAGATCG

CACAGAGACTTGAAGATGTCTTTGCAGGGAAGAACACCGATCTTGAGGTT

CTCATGGAATGGCTAAAGACAAGACCAATCCTGTCACCTCTGACTAAGGG

GATTTTAGGATTTGTGTTCACGCTCACCGTGCCCAGTGAGCGAGGACTGC

AGCGTAGACGCTTTGTCCAAAATGCCCTTAATGGGAACGGGGATCCAAAT

AACATGGACAAAGCAGTTAAACTGTATAGGAAGCTCAAGAGGGAGATAAC

ATTCCATGGGGCCAAAGAAATCTCACTCAGTTATTCTGCTGGTGCACTTG

CCAGTTGTATGGGCCTCATATACAACAGGATGGGGCTGTGACCACTGAA

GTGGCATTTGGCCTGGTATGTGCAACCTGTGAACAGATTGCTGACTCCA

GCATCGGTCTCATAGGCAAATGGTGACAACAACCAATCCACTAATCAGAC

ATGAGAACAGAATGGTTTTAGCCAGCACTACAGCTAAGGCTATGGAGCAA

ATGGCTGGATCGAGTGAGCAAGCAGCAGAGGCCATGGAGGTTGCTAGTCA

GGCTAGACAAATGGTGCAAGCGATGAGAACCATTGGGACTCATCCTAGCT

CCAGTGCTGGTCTGAAAAATGATCTTCTTGAAAATTTGCAGgcctatCag aaacgaatgggggtgcagatgcaacggttcaagtgatcctgcaggtgcag gt<u>GAGCAGAAACTCATCTCTGAAGAGGATCTG</u>gatcgtcttttttcaaa tgcatttaccgtcgctttaaatacggactgaaaggagggccttctacgga aggagtgccaaagtctatgagggaagaatatcgaaaggaacagcagagtg ctgtggatgctgacgatggtcattttgtcagcatagagctggagTAAAAA

ACTACCTTGTTTCTACT3'
bold lower case = Ala-Gly-Ala-Gly linker
Underline = Myc epitope (9e10) inserted; cloning site for foreign epitope sequence
Bold Upper Case = Stop Codons M2SR-Myc-M2 (protein)
(SEQ ID NO: 39)
MSLLTEVETPIRNEWGCRCNGSSDPAGAG<u>EQKLISEEDL</u>DRLFFKCIYRR FKYGLKGGPSTEGVPKSMREEYRKEQQSAVDADDGHFVSIELE
Bold: anti-M2 14C2 epitope
<u>Underline</u>: Myc epitope M2SR-12xHis (protein)
(SEQ ID NO: 40)
MSLLTEVETPIRNEWGCRCNGSSDA<u>HHHHHHHHHHHH</u>
Bold: anti-M2 14C2 epitope
<u>Underline</u>: 12xHis epitope Mutant viruses harboring the M2-myc nucleotide fusion were generated using the virus rescue system of Neumann, et al., Generation of influenza A viruses entirely from clone cDNAs, Proc. Natl. Acad. Sci. USA 96:9345-9350 (1999). Vero cells that stably express the influenza M2 protein ("M2 Vero cells"), were transfected with 12 plasmids: 8 Pol I constructs for 8 RNA segments, one of which harbors the M2 fusion sequences, and 4 protein-expression constructs for 4 structural proteins as follows: NP (pCAGGS-WSNNP0/14); PB1 (pcDNA774); PB2 (pcDNA762); and PA (pcDNA787) of A/Puerto Rico/8/34 (H1N1) virus. The plasmids were mixed with TransIT®-2020 Transfection Reagent (Mirus, Madison, Wis.) per manufacturer instructions, incubated at room temperature for 15-30 minutes, and added to 1×10⁶ M2 Vero cells. Forty-eight hours later, viruses in the supernatant were serially diluted and used to infect M2CK, which are MDCK cells that stably express the influenza M2 protein (J. Virol. 2009 83:5947). Two to four days after inoculation, viruses in the supernatant of the highest dilution showing clear cytopathic effect (CPE) were used to infect fresh M2CK cells for at least two additional passages for the production of stock virus. M2CK cells were infected by washing with PBS followed by adsorbing virus at 35° C. Viral growth media containing trypsin/TPCK was added and the cells were incubated for 2-3 days until CPE was observed. The M segment cDNAs of the generated replication-deficient viruses were fully sequenced to confirm presence of the M2 mutation and the foreign epitopes.

To detect viral expression of the foreign epitopes, MDCK cells (1×10⁶/TC-6 well) grown in MEM containing 10% FCS at 37° C., 5% $CO_2$ for 24 hours to 100% confluency were infected with viral culture supernatants as described above. Twelve hours post-infection, total soluble protein extracts were prepared by direct lysis of the cells in 0.1 mL of lysis buffer (50 mM Tris HCl, pH 7.5; 300 mM NaCl; 1% Triton X-100) containing freshly added protease inhibitor cocktail. Extracts were analyzed by SDS-PAGE and Western blot using a PVDF membrane. Membranes were incubated with an HA-specific polyclonal antibody to detect the viral HA, a murine monoclonal antibody specific for the M2 ectodomain (Thermo Scientific, Rockford, Ill.; clone 14C2), or a murine antibody specific for myc. Proteins were detected using HRP-conjugated secondary antibodies together with 3,3',5,5'-tetramethylbenzidine (TMB) substrate.

The predicted molecular weight of the M2-myc fusion protein is 10.5 kDa. The predicted molecular weight of the M2-12×His fusion is 4.4 kDa. The molecular weights of wild-type M2 and H3 are 11.1 and 60 kDa, respectively.

Figure 58A:
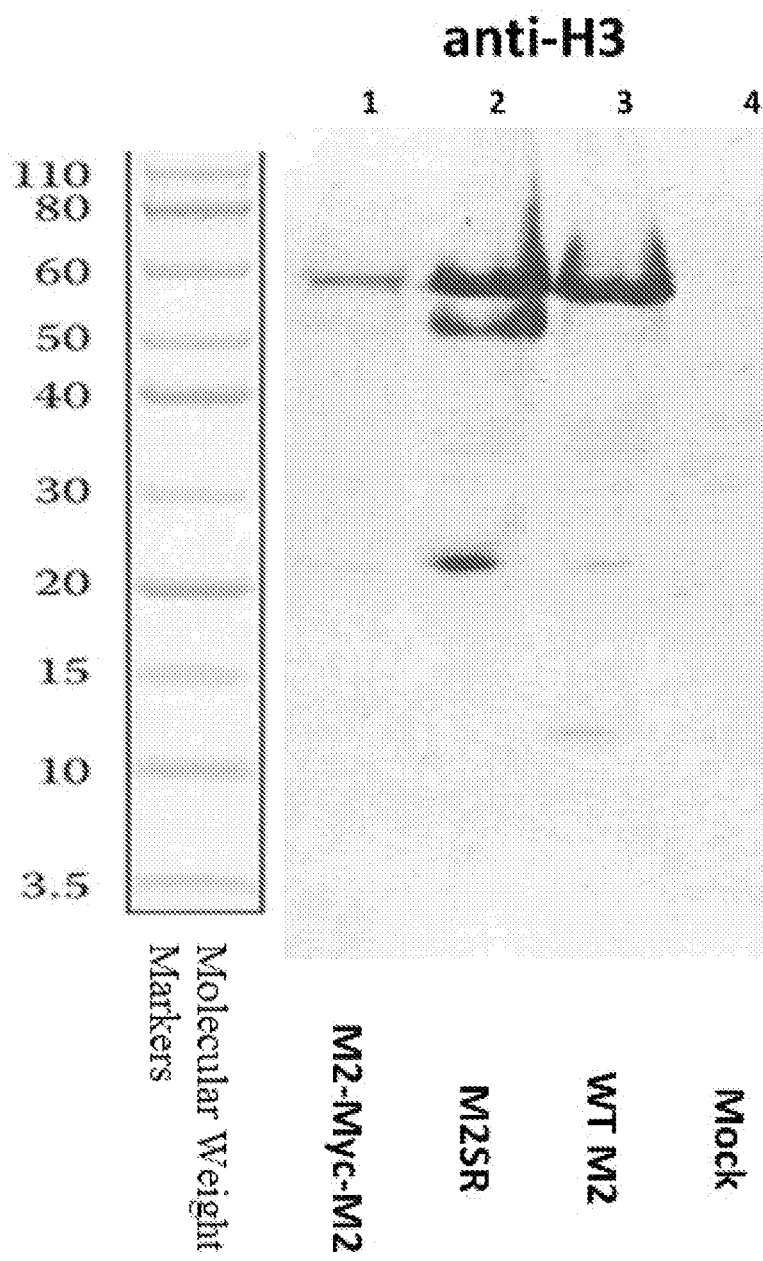
FIG. 58A-C shows Western blotting for HA (A), Myc (B), and the M2 ectodomain (B, C) in lysates from MDCK cells infected with the M2SR-Myc-M2 virus, the M2SR-12×His virus, or a wild-type influenza virus. Abbreviations: M2SR: Internal M2 TM domain deletion and c-terminal truncation; M2SR-Myc: myc-tagged internal M2 TM domain deletion and c-terminal truncation; M2SR-12His: 12×His-tagged internal M2 TM domain deletion; M2-Myc-M2: myc-tagged internal M2 TM domain deletion; WT M2: Influenza Virus Reassortant A/Brisbane/10/2007 (H3N2)×A/PR/8/34 (H1N1), IVR-147; Mock: no virus
Figure 58B:
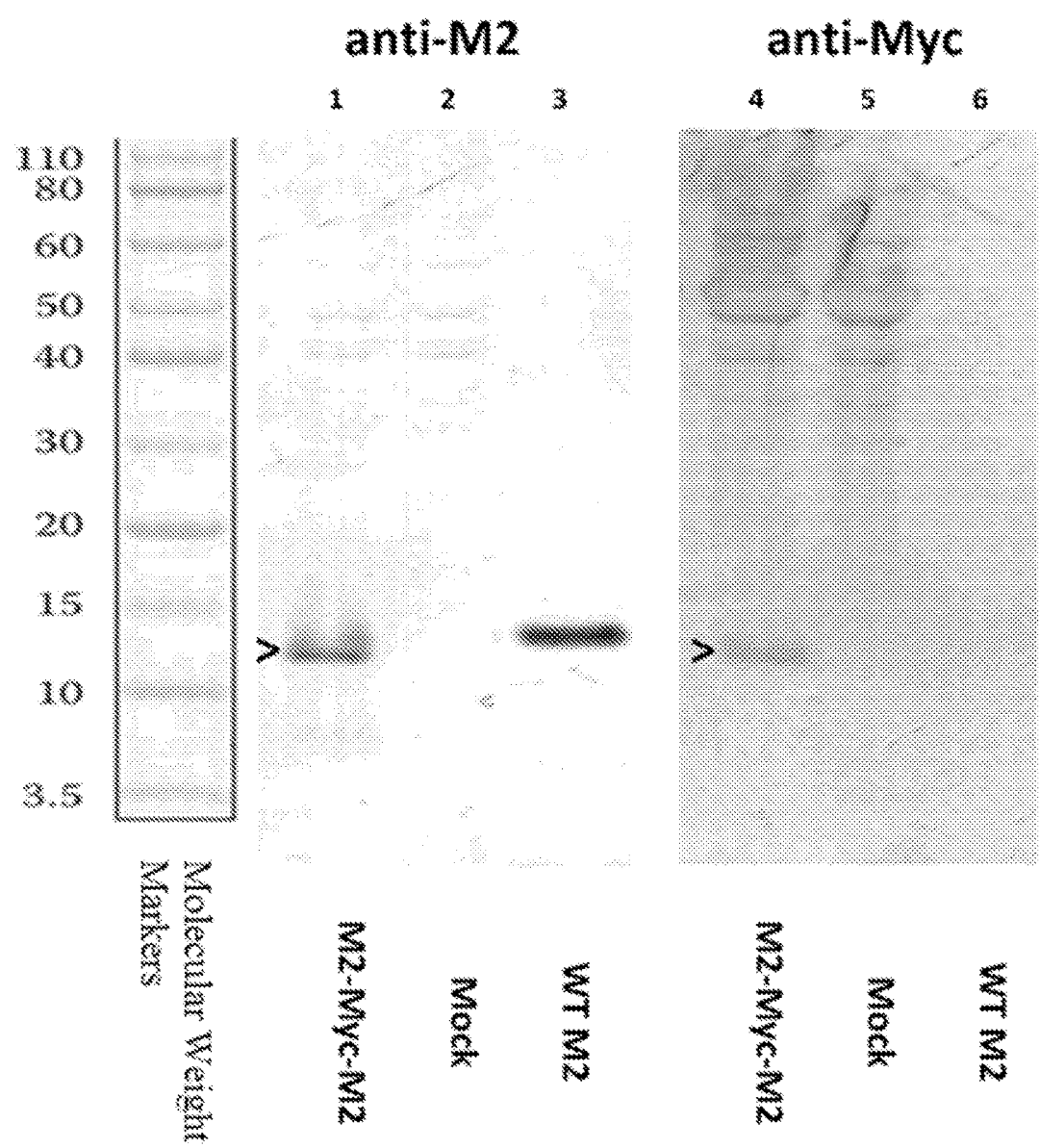
Figure 58C:
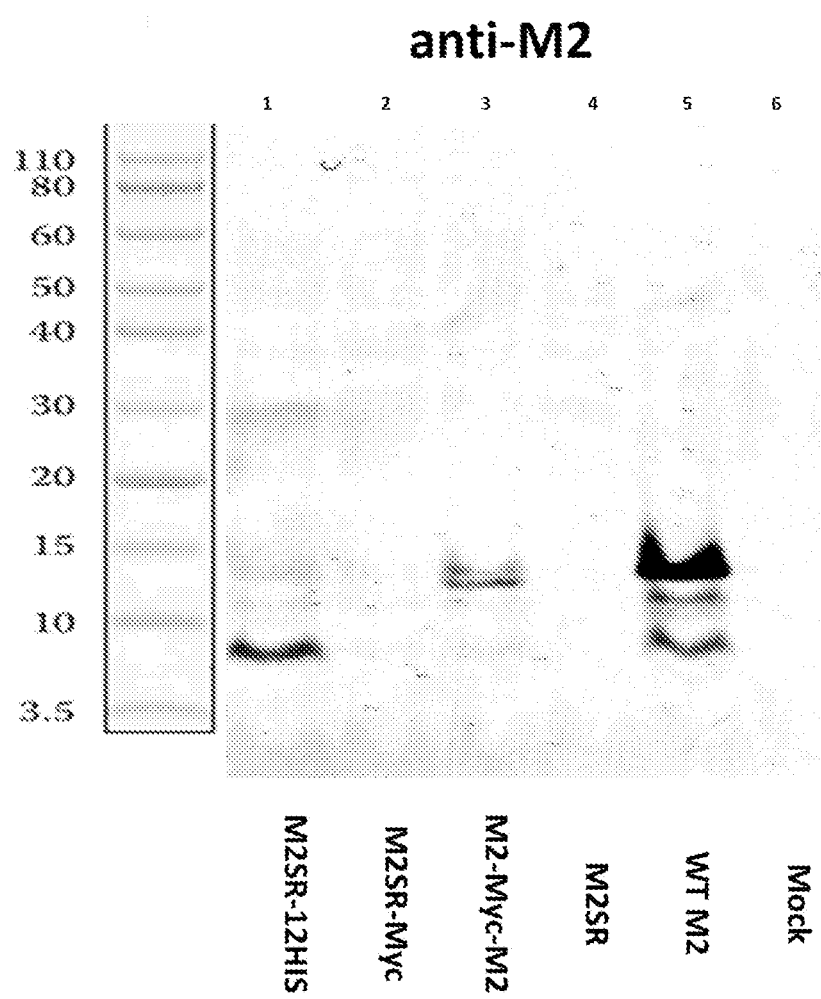

Results are shown in FIG. 58A-B. The M2SR-Myc-M2 virus produces viral H3 protein, demonstrating that the viruses harboring foreign epitopes in the M2 gene region express other viral genes normally (FIG. 58A). A 10.5 kDa protein comprising the M2 ectodomain and myc epitope was detected in lysates of cells infected with the M2SR-Myc-M2 vector (FIG. 58B), and a 4.4 kDa protein comprising the His epitope was detected in lysates of cells infected with the M2SR-12×His vector (FIG. 58C).

These results demonstrate that non-influenza epitopes (i.e. foreign epitopes) may be cloned into and expressed from within the influenza M2 gene region in a host cell. The results further demonstrate that the M2SR vector in particular is useful for the delivery of foreign epitopes to a host cell or a subject. Accordingly, an influenza virus comprising a mutant M2 gene, such as the M2SR vector, and harboring a foreign epitope may be used to express the epitope in vivo in a recipient host, in order to elicit an immune response against the epitope in the host.

Example 29

Expression of a Foreign Epitope from within the Influenza NA Gene Region of the M2SR Virus This example demonstrates the expression of a non-influenza epitope (i.e. a foreign epitope) from nucleic acids cloned into the NA gene of the influenza M2SR virus.

Nucleic acid sequences encoding a pcc epitope tag (KAERADLIAYLKQATAK) were cloned into the NA gene of the M2SR (M2KO(ΔTM)) using standard techniques, to generate an NApcc fusion in the M2SR virus. The sequence of amino acids 1-84 of the NApcc fusion is set forth in SEQ ID NO: 41.

```
NApcc fusion (amino acids 1-84)
                                         SEQ ID NO: 41
MNPNQKIITIGSICMVVGIISLILQIGNIISIWISHSIQTGNKAERADLI AYLKQATAKQNHTGICNQGSITYKVVAGQDSTSV
Underline: pcc epitope
```

Mutant M2SR virus also harboring the NApcc fusion was generated using the viral rescue system of Neumann, et al., Generation of influenza A viruses entirely from clone cDNAs, Proc. Natl. Acad. Sci. USA 96:9345-9350 (1999). 293T cells were transfected with 13 plasmids: 8 Pol I constructs for 8 influenza RNA segments, one of which harbors the replication-deficient M2SR sequence and a second of which comprises the NA sequence with the pcc sequence inserted in-frame within the NA-stalk; and 5 protein-expression constructs for 4 structural proteins and the flu M2 protein as follows: NP (pCAGGS-WSNNP0/14); PB1 (pcDNA774); PB2 (pcDNA762); PA (pcDNA787); and M2 (pCMV-M2) of A/Puerto Rico/8/34 (H1N1) virus. The plasmids were mixed with TransIT®-2020 Transfection Reagent (Mirus, Madison, Wis.) per manufacturer instructions, incubated at room temperature for 15-30 minutes, and added to 1×10⁶ 293 T cells. Forty-eight hours later, viruses in the supernatant were serially diluted and use to infect M2CK cells, which are MDCK cells that stably express the M2 protein (J Virol 2009 83:5947). Two to four days after inoculation, viruses in supernatant that showed clear cytopathic effect (CPE) were used to infect fresh M2CK cells for at least two additional passages for the production of stock virus. M2CK cells were infected by washing with PBS followed by adsorbing virus at 35° C. Virus growth media containing trypsin/TPCK was added and the cells were incubated for 2 days. The M segment and the NA segment cDNAs of the generated replication-deficient viruses were fully sequenced to confirm the mutant M2 gene deletion and the NApcc fusion.

To detect expression of the NApcc fusion, M2CK cells (0.4×10⁶/TC-12 well) were in MEM containing 10% FCS at 37° C., 5% $CO_2$ for 24 hours to 100% confluency were infected with a mutant virus and wild-type control culture supernatants according to standard procedures as described above. At 3, 5, 7, and 9 hours post-infection, total soluble protein extracts were prepared by direct lysis of the cells in 0.05 mL of lysis buffer (50 mM Tris HCl, pH 8.0; 300 mM NaCl; 1% Triton X-100) containing freshly added protease inhibitor cocktail. The infected cell extracts and a recombinant N1 protein standard prepared in baculovirus, were analyzed in duplicate by SDS-PAGE followed by Western analyses after transfer to two PVDF membranes. One membrane was incubated with a mixture of commercially-available murine monoclonal antibodies specific for the influenza nucleoprotein (NP) (Millipore, MAB8257B, MAB8258B). A secondary anti-mouse IgG-HRP antibody conjugate along with TMB substrate were used to detect NP. The second membrane was incubated with a polyclonal goat antisera against influenza virus N1 neuraminidase (NA) (NIH Biodefense and Emerging Infections Research Resources Repository, NIAID, NIH: Polyclonal Anti-Influenza Virus N1 Neuraminidase (NA), A/New Jersey/8/76 (H1N1), (antiserum, Goat), NR-3136) to detect influenza N1 NA protein expression and the recombinant N1 control. A secondary anti-mouse IgG-HRP antibody conjugate along with TMB substrate were used to detect an NA band. The molecular weights of NA and NP are 50 kDa and 56.1 kDa, respectively.

Figure 59:
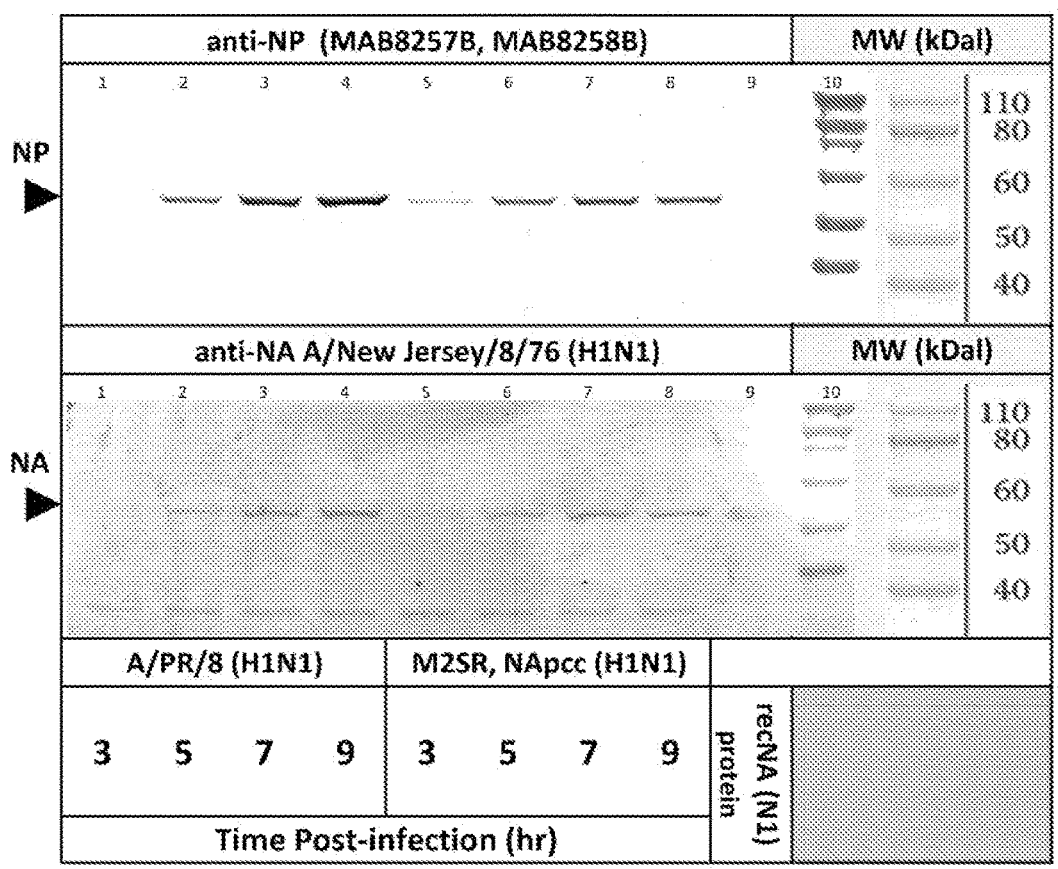
FIG. 59 shows Western blotting for NP (upper panel) and NA (lower panel) in lysates from M2CK cells infected with the M2SR virus encoding the NApcc fusion, or a wild-type virus (A/PR/8 H1N1). Abbreviations: M2SR, NApcc: M2SR virus harboring an NApcc fusion; NP: influenza A nucleoprotein; NA: influenza A neuraminidase; recNA: recombinant N1 protein. Cells were cultured for 3 (lanes 1, 5), 5 (lanes 2, 6), 7 (lanes 3, 7), and 9 (lanes 4, 8) hours post-infection.

The results are shown in FIG. 59. The M2SR-NApcc virus produces viral NP protein, demonstrating that viruses harboring foreign epitopes other viral genes normally (FIG. 59, upper panel). An NP band of the expected size is present in increasing amounts in samples harvested 3, 5, 7, and 9 hours post-infection (upper panel, arrowhead). An NA band of expected size was detected in samples infected with a wild-type control virus (lower panel, arrowhead, lanes 1-4), while viruses harboring the NApcc fusion produced an NA band migrating at a slightly higher molecular weight (lower panel, arrowhead, lanes 5-8).

These results demonstrate that non-influenza epitopes (i.e. foreign epitopes) may be cloned into and expressed from within influenza genes in a host cell. The results further demonstrate that the M2SR vector in particular is useful for the delivery of foreign epitopes to a host cell or a subject. Accordingly, an influenza virus comprising a mutant M2 gene, such as the M2SR vector, and harboring a foreign epitope, may be used to express the epitope in vivo in a recipient host, in order to elicit an immune response against the epitope in the host.

SEQUENCE LISTING

```
<160> NUMBER OF SEQ ID NOS: 144

<210> SEQ ID NO 1
<211> LENGTH: 976
<212> TYPE: DNA
<213> ORGANISM: Influenza A virus

<400> SEQUENCE: 1
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggaacgggg atccaaataa     300
catggacaaa gcagttaaac tgtataggaa gctcaagagg gagataacat tccatggggc     360
caaagaaatc tcactcagtt attctgctgg tgcacttgcc agttgtatgg gcctcatata     420
caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggttttagc cagcactaca gctaaggcta tggagcaaat     600
ggctggatcg agtgagcaag cagcagaggc catggaggtt gctagtcagg ctagacaaat     660
ggtgcaagcg atgagaacca ttgggactca tcctagctcc agtgctggtc tgaaaaatga     720
tcttcttgaa aatttgcagg cctatcagaa acgaatgggg gtgcagatgc aacggttcaa     780
gtgattaata ggatcgtctt tttttcaaat gcatttaccg tcgctttaaa tacggactga     840
aaggagggcc ttctacggaa ggagtgccaa agtctatgag ggaagaatat cgaaaggaac     900
agcagagtgc tgtggatgct gacgatggtc attttgtcag catagagctg gagtaaaaaa     960
ctaccttgtt tctact                                                     976

<210> SEQ ID NO 2
<211> LENGTH: 1027
<212> TYPE: DNA
<213> ORGANISM: Influenza A virus

<400> SEQUENCE: 2
agcaaaagca ggtagatatt gaaagatgag tcttctaacc gaggtcgaaa cctacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggaacgggg atccaaataa     300
```

```
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgattaata gactattgcc gcaaatatca ttgggatctt gcacttgaca ttgtggattc    840
ttgatcgtct tttttcaaa tgcatttacc gtcgctttaa atacggactg aaaggagggc    900
cttctacgga aggagtgcca agtctatga gggaagaata tcgaaggaa cagcagagtg    960 ctgtggatgc tgacgatggt cattttgtca gcatagagct ggagtaaaaa actaccttgt   1020
ttctact                                                             1027

<210> SEQ ID NO 3
<211> LENGTH: 976
<212> TYPE: DNA
<213> ORGANISM: Influenza A virus

<400> SEQUENCE: 3
agcaaaagca ggtagatatt gaaagatgag tcttctaacc gaggtcgaaa cctacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggacgggg atccaaataa    300 catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgattaata ggatcgtctt tttttcaaat gcatttaccg tcgctttaaa tacggactga    840
aaggagggcc ttctacgaa ggagtgccaa agtctatgag ggaagaatat cgaaggaac    900 agcagagtgc tgtggatgct gacgatggtc attttgtcag catagagctg gagtaaaaaa    960
ctaccttgtt tctact                                                    976

<210> SEQ ID NO 4
<211> LENGTH: 24
<212> TYPE: PRT
<213> ORGANISM: Influenza A virus

<400> SEQUENCE: 4

Met Ser Leu Leu Thr Glu Val Glu Thr Pro Ile Arg Asn Glu Trp Gly
1               5                   10                  15
```

Cys Arg Cys Asn Gly Ser Ser Asp
            20

<210> SEQ ID NO 5
<211> LENGTH: 97
<212> TYPE: PRT
<213> ORGANISM: Influenza A virus

<400> SEQUENCE: 5

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 6
<211> LENGTH: 86
<212> TYPE: PRT
<213> ORGANISM: Influenza A virus

<400> SEQUENCE: 6

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Phe Lys Tyr Gly Leu
        35                  40                  45

Lys Gly Gly Pro Ser Thr Glu Gly Val Pro Lys Ser Met Arg Glu Glu
    50                  55                  60

Tyr Arg Lys Glu Gln Gln Ser Ala Val Asp Ala Asp Asp Gly His Phe
65                  70                  75                  80

Val Ser Ile Glu Leu Glu
                85

<210> SEQ ID NO 7
<211> LENGTH: 92
<212> TYPE: PRT
<213> ORGANISM: Influenza A virus

<400> SEQUENCE: 7

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Lys Cys Ile Tyr Arg
        35                  40                  45

Arg Phe Lys Tyr Gly Leu Lys Gly Gly Pro Ser Thr Glu Gly Val Pro
    50                  55                  60

Lys Ser Met Arg Glu Glu Tyr Arg Lys Glu Gln Gln Ser Ala Val Asp

```
                65                  70                  75                  80
Ala Asp Asp Gly His Phe Val Ser Ile Glu Leu Glu
                    85                  90
```

<210> SEQ ID NO 8
<211> LENGTH: 95
<212> TYPE: PRT
<213> ORGANISM: Influenza A virus

<400> SEQUENCE: 8

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
                20                  25                  30

Ile Gly Ile Leu His Leu Thr Leu Trp Ile Leu Leu Phe Phe Lys Cys
            35                  40                  45

Ile Tyr Arg Arg Phe Lys Tyr Gly Leu Lys Gly Gly Pro Ser Thr Glu
        50                  55                  60

Gly Val Pro Lys Ser Met Arg Glu Glu Tyr Arg Lys Glu Gln Gln Ser
65                  70                  75                  80

Ala Val Asp Ala Asp Asp Gly His Phe Val Ser Ile Glu Leu Glu
                85                  90                  95
```

<210> SEQ ID NO 9
<211> LENGTH: 294
<212> TYPE: DNA
<213> ORGANISM: Influenza A virus

<400> SEQUENCE: 9

```
atgagtcttc taaccgaggt cgaaacgcct atcagaaacg aatggggtg cagatgcaac      60 ggttcaagtg atcctctcac tattgccgca aatatcattg ggatcttgca cttgacattg     120
tggattcttg atcgtctttt tttcaaatgc atttaccgtc gctttaaata cggactgaaa     180
ggagggcctt ctacggaagg agtgccaaag tctatgaggg aagaatatcg aaaggaacag     240
cagagtgctg tggatgctga cgatggtcat tttgtcagca tagagctgga gtaa          294
```

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
acacaccgtc tctaggatcg tcttttttc aaatgcattt acc                         43
```

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
cacacacgtc tcctattagt agaaacaagg tagttttt                              38
```

<210> SEQ ID NO 12
<211> LENGTH: 38
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 12
acacaccgtc tcatcctatt aatcacttga accgttgc                              38

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cacacacgtc tccgggagca aaagcaggta g                                     31

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acacaccgtc tccctacgta ctctctatca tcccg                                 35

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacacacgtc tcctattagt agaaacaagg tagttttt                              38

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggagcaaaa gcaggtagat attgaaagat gagtcttcta accgaggtcg aaac            54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtaggtttcg acctcggtta gaagactcat ctttcaatat ctacctgctt ttgc            54

<210> SEQ ID NO 18
<211> LENGTH: 35
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 18
acacaccgtc tccctacgta ctctctatca tcccg                                  35

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacacacgtc tcctattagt agaaacaagg tagttttt                               38

<210> SEQ ID NO 20
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gggagcaaaa gcaggtagat attgaaagat gagtcttcta accgaggtcg aaac            54

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtaggtttcg acctcggtta gaagactcat ctttcaatat ctacctgctt ttgc            54

<210> SEQ ID NO 22
<211> LENGTH: 31
<212> TYPE: DNA
<213> ORGANISM: Influenza A virus

<400> SEQUENCE: 22
caacggttca agtgattaat aaactattgc c                                     31

<210> SEQ ID NO 23
<211> LENGTH: 31
<212> TYPE: DNA
<213> ORGANISM: Influenza A virus

<400> SEQUENCE: 23
caacggttca agtgattggt ggactgttgc c                                     31

<210> SEQ ID NO 24
<211> LENGTH: 1772
<212> TYPE: DNA
<213> ORGANISM: Influenza A virus

<400> SEQUENCE: 24
agcaaaagca ggggaaaata aaacaaccaa aatggagaa aatagtgctt cttttttgcaa      60 tagtcagtct tgttaaaagt gatcagattt gcattggtta ccatgcaaac aactcgacag     120
```

| | |
|---|---:|
| agcaggttga cacaataatg gaaaagaacg ttactgttac acatgcccaa gacatactgg | 180 |
| aaaagaaaca caacgggaag ctctgcgatc tagatggagt gaagcctcta attttgagag | 240 |
| attgtagcgt agctggatgg ctcctcggaa acccaatgtg tgacgaattc atcaatgtgc | 300 |
| cggaatggtc ttacatagtg gagaaggcca atccagtcaa tgacctctgt tacccagggg | 360 |
| atttcaatga ctatgaagaa ttgaaacacc tattgagcag aataaaccat tttgagaaaa | 420 |
| ttcagatcat ccccaaaagt tcttggtcca gtcatgaagc ctcattaggg gtgagctcag | 480 |
| catgtccata ccagggaaag tcctccttt tcagaaatgt ggtatggctt atcaaaaaga | 540 |
| acagtacata cccaacaata aagaggagct acaataatac caaccaagaa gatcttttgg | 600 |
| tactgtgggg gattcaccat cctaatgatg cggcagagca gacaaagctc tatcaaaacc | 660 |
| caaccaccta tatttccgtt gggacatcaa cactaaacca gagattggta ccaagaatag | 720 |
| ctactagatc caaagtaaac gggcaaagtg gaaggatgga gttcttctgg acaattttaa | 780 |
| agccgaatga tgcaatcaac ttcgagagta atggaaattt cattgctcca gaatatgcat | 840 |
| acaaaattgt caagaaaggg gactcaacaa ttatgaaaag tgaattggaa tatggtaact | 900 |
| gcaacaccaa gtgtcaaact ccaatggggg cgataaactc tagcatgcca ttccacaata | 960 |
| tacaccctct caccattggg gaatgcccca aatatgtgaa atcaaacaga ttagtccttg | 1020 |
| cgactgggct cagaaatagc cctcaaagag agactagagg attatttgga gctatagcag | 1080 |
| gttttataga gggaggatgg cagggaatgg tagatggttg gtatgggtac caccatagca | 1140 |
| atgagcaggg gagtgggtac gctgcagaca agaatccac tcaaaaggca atagatggag | 1200 |
| tcaccaataa ggtcaactcg atcattgaca aaatgaacac tcagtttgag gccgttggaa | 1260 |
| gggaatttaa caacttagaa aggagaatag agaatttaaa caagaagatg aagacgggt | 1320 |
| tcctagatgt ctggacttat aatgctgaac ttctggttct catggaaaat gagagaactc | 1380 |
| tagactttca tgactcaaat gtcaagaacc tttacgacaa ggtccgacta cagcttaggg | 1440 |
| ataatgcaaa ggagctgggt aacggttgtt tcgagttcta tcataaatgt gataatgaat | 1500 |
| gtatggaaag tgtaagaaat ggaacgtatg actacccgca gtattcagaa gaagcgagac | 1560 |
| taaaaagaga ggaaataagt ggagtaaaat tggaatcaat aggaatttac caaatactgt | 1620 |
| caatttattc tacagtggcg agttccctag cactggcaat catggtagct ggtctatcct | 1680 |
| tatggatgtg ctccaatggg tcgttacaat gcagaatttg catttaagat tagaatttca | 1740 |
| gagatatgag gaaaaacacc cttgtttcta ct | 1772 |

<210> SEQ ID NO 25
<211> LENGTH: 1398
<212> TYPE: DNA
<213> ORGANISM: Influenza A virus

<400> SEQUENCE: 25

| | |
|---|---:|
| agcaaaagca ggggtttaaa atgaatccaa atcagaagat aataaccatc ggatcaatct | 60 |
| gtatggtaac tggaatagtt agcttaatgt tacaaattgg gaacatgatc tcaatatggg | 120 |
| tcagtcattc aattcacaca gggaatcaac accaatctga accaatcagc aatactaatt | 180 |
| ttcttactga gaaagctgtg gcttcagtaa aattagcggg caattcatct ctttgcccca | 240 |
| ttaacggatg gctgtatac agtaaggaca acagtataag gatcggttcc aagggggatg | 300 |
| tgtttgttat aagagagccg ttcatctcat gctcccactt ggaatgcaga actttctttt | 360 |
| tgactcaggg agccttgctg aatgacaagc actccaatgg gactgtcaaa gacagaagcc | 420 |
| ctcacagaac attaatgagt tgtcctgtgg gtgaggctcc ctccccatat aactcaaggt | 480 |

```
ttgagtctgt tgcttggtca gcaagtgctt gccatgatgg caccagttgg ttgacgattg        540
gaatttctgg cccagacaat ggggctgtgg ctgtattgaa atacaatggc ataataacag        600
acactatcaa gagttggagg aacaacatac tgagaactca agagtctgaa tgtgcatgtg        660
taaatggctc ttgctttact gtaatgactg acggaccaag taatggtcag gcatcacata        720
agatcttcaa aatggaaaaa gggaaagtgg ttaaatcagt cgaattggat gctcctaatt        780
atcactatga ggaatgctcc tgttatccta atgccggaga aatcacatgt gtgtgcaggg        840
ataattggca tggctcaaat cggccatggg tatctttcaa tcaaaatttg gagtatcaaa        900
taggatatat atgcagtgga gttttcggag acaatccacg ccccaatgat ggaacaggta        960
gttgtggtcc ggtgtcctct aacggggcat atggggtaaa agggttttca tttaaatacg       1020
gcaatggtgt ctggatcggg agaaccaaaa gcactaattc caggagcggc tttgaaatga       1080
tttgggatcc aaatgggtgg actgaaacgg acagtagctt ttcagtgaaa caagatatcg       1140
tagcaataac tgattggtca ggatatagcg ggagttttgt ccagcatcca gaactgacag       1200
gactagattg cataagacct tgtttctggg ttgagttgat cagagggcgg cccaaagaga       1260
gcacaatttg gactagtggg agcagcatat ctttttgtgg tgtaaatagt gacactgtgg       1320
gttggtcttg gccagacggt gccgagttgc cattcaccat tgacaagtag tctgttcaaa       1380
aaactccttg tttctact                                                     1398

<210> SEQ ID NO 26
<211> LENGTH: 1779
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
agcaaaagca ggggaaaaca aaagcaacaa aaatgaaggc aatactagta gttctgctat         60
atacatttgc aaccgcaaat gcagacacat tatgtatagg ttatcatgcg aacaattcaa        120
cagacactgt agacacagta ctagaaaaga atgtaacagt aacacactct gttaaccttc        180
tagaagacaa gcataacggg aaactatgca aactaagagg ggtagcccca ttgcatttgg        240
gtaaatgtaa cattgctggc tggatcctgg gaaatccaga gtgtgaatca ctctccacag        300
caagctcatg gtcctacatt gtggaaacac ctagttcaga caatggaacg tgttacccag        360
gagatttcat cgattatgag gagctaagag agcaattgag ctcagtgtca tcatttgaaa        420
ggtttgagat attccccaag acaagttcat ggcccaatca tgactcgaac aaaggtgtaa        480
cggcagcatg tcctcatgct ggagcaaaaa gcttctacaa aaatttaata tggctagtta        540
aaaaaggaaa ttcatacccc aagctcagca atcctacat taatgataaa gggaaagaag        600
tcctcgtgct atggggcatt caccatccat ctactagtgc tgaccaacaa agtctctatc        660
agaatgcaga tgcatatgtt tttgtggggt catcaagata cagcaagamg ttcaagccgg        720
aaatagcaat aagacccaaa gtgagggatc ragaagggag aatgaactat tactggacac        780
tagtagagcc gggagacaaa ataacattcg aagcaactgg aaatctagtg gtaccgagat        840
atgcattcgc aatggaaaga aatgctggat ctggtattat catttcagat acaccagtcc        900
acgattgcaa tacaacttgt caaacaccca agggtgctat aaacaccagc ctcccatttc        960
agaatataca tccgatcaca attggaaaat gtccaaaata tgtaaaaagc acaaaattga       1020
gactggccac aggattgagg aatatcccgt ctattcaatc tagaggccta tttggggcca       1080
```

| | | |
|---|---|---|
| ttgccggttt cattgaaggg gggtggacag ggatggtaga tgatggtac ggttatcacc | 1140 |
| atcaaaatga gcagggtca ggatatgcag ccgacctgaa gagcacacag aatgccattg | 1200 |
| acgagattac taacaaagta aattctgtta ttgaaaagat gaatacacag ttcacagcag | 1260 |
| taggtaaaga gttcaaccac ctggaaaaaa gaatagagaa tttaaataaa aaagttgatg | 1320 |
| atggtttcct ggacatttgg acttacaatg ccgaactgtt ggttctattg gaaaatgaaa | 1380 |
| gaactttgga ctaccacgat tcaaatgtga agaacttata tgaaaaggta agaagccagc | 1440 |
| taaaaaacaa tgccaaggaa attggaaacg gctgctttga attttaccac aaatgcgata | 1500 |
| acacgtgcat ggaaagtgtc aaaaatggga cttatgacta cccaaaatac tcagaggaag | 1560 |
| caaaattaaa cagagaagaa atagatgggg taaagctgga atcaacaagg atttaccaga | 1620 |
| ttttggcgat ctattcaact gtcgccagtt cattggtact ggtagtctcc ctgggggcaa | 1680 |
| tcagtttctg gatgtgctct aatgggtctc tacagtgtag aatatgtatt taacattagg | 1740 |
| atttcagaag catgagaaaa aaacacccctt gtttctact | 1779 |

<210> SEQ ID NO 27
<211> LENGTH: 1458
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

| | | |
|---|---|---|
| agcaaaagca ggagttttaaa atgaatccaa accaaaagat aataaccatt ggttcggtct | 60 |
| gtatgacaat tggaatggct aacttaatat tacaaattgg aaacataatc tcaatatgga | 120 |
| ttagccactc aattcaactt gggaatcaaa atcagattga acatgcaat caaagcgtca | 180 |
| ttacttatga aaacaacact tgggtaaatc agacatatgt taacatcagc aacaccaact | 240 |
| tgctgctgg acagtcagtg gtttccgtga aattagcggg caattcctct ctctgccctg | 300 |
| ttagtggatg ggctatatac agtaaagaca acagtgtaag aatcggttcc aaggggggatg | 360 |
| tgtttgtcat aagggaacca ttcatatcat gctccccctt ggaatgcaga accttcttct | 420 |
| tgactcaagg ggccttgcta aatgacaaac attccaatgg aaccattaaa gacaggagcc | 480 |
| catatcgaac cctaatgagc tgtcctattg gtgaagttcc ctctccatac aactcaagat | 540 |
| ttgagtcagt cgcttggtca gcaagtgctt gtcatgatgg catcaattgg ctaacaattg | 600 |
| gaatttctgg cccagacaat ggggcagtgg ctgtgttaaa gtacaacggc ataataacag | 660 |
| acactatcaa gagttggaga aacaatatat tgagaacaca agagtctgaa tgtgcatgtg | 720 |
| taaatggttc ttgctttact gtaatgaccg atggaccaag taatggacag gcctcataca | 780 |
| agatcttcag aatagaaaag ggaaagatag tcaaatcagt cgaaatgaat gcccctaatt | 840 |
| atcactatga ggaatgctcc tgttatcctg attctagtga atcacatgt gtgtgcaggg | 900 |
| ataactggca tggctcgaat cgaccgtggg tgtctttcaa ccagaatctg gaatatcaga | 960 |
| taggatacat atgcagtggg attttcggag acaatccacg ccctaatgat aagacaggca | 1020 |
| gttgtggtcc agtatcgtct aatggagcaa atggagtaaa agggttttca ttcaaatacg | 1080 |
| gcaatggtgt ttggataggg agaactaaaa gcattagttc aagaaacggt tttgagatga | 1140 |
| tttgggatcc gaacggatgg actgggacag acaataactt ctcaataaag caagatatcg | 1200 |
| taggaataaa tgagtggtca ggatatacg ggagttttgt tcagcatcca gaactaacag | 1260 |
| ggctggattg tataagacct tgcttctggg ttgaactaat cagagggcga cccaaagaga | 1320 |

```
acacaatctg gactagcggg agcagcatat ccttttgtgg tgtaaacagt gacactgtgg    1380
gttggtcttg ccagacggt gctgagttgc catttaccat tgacaagtaa tttgttcaaa    1440
aaactccttg tttctact                                                  1458
```

<210> SEQ ID NO 28
<211> LENGTH: 1027
<212> TYPE: DNA
<213> ORGANISM: Influenza A virus

<400> SEQUENCE: 28

```
agcaaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggacggggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cactattgcc gcaaatatca ttgggatctt gcacttgaca ttgtggattc    840
ttgatcgtct ttttttcaaa tgcatttacc gtcgctttaa atacggactg aaaggagggc    900
cttctacgga aggagtgcca agtctatga gggaagaata tcgaaggaa cagcagagtg    960 ctgtggatgc tgacgatggt catttttgtca gcatagagct ggagtaaaaa actaccttgt   1020
ttctact                                                              1027
```

<210> SEQ ID NO 29
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atgcattagt tattaatagt aatcaattac ggggtcatta gttcatagcc catatatgga     60
gttccgcgtt acataactta cggtaaatgg cccgcctggc tgaccgccca acgaccccg    120 cccattgacg tcaataatga cgtatgttcc catagtaacg ccaatagga ctttccattg    180 acgtcaatgg gtggagtatt tacggtaaac tgcccacttg gcagtacatc aagtgtatca    240
tatgccaagt acgcccccta ttgacgtcaa tgacggtaaa tggcccgcct ggcattatgc    300
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
```

```
gcgtgtacgg tgggaggtct atataagcag agctggttta gtgaaccgtc agatccgcta      600
gcgattacgc caagctcgaa attaaccctc actaaaggga caaaagctg gagctccact        660 gtggaattcg cccttggccg ccatgagtct tctaaccgag gtcgaaacgc ctatcagaaa       720
cgaatggggg tgcagatgca acggttcaag tgatcctctc actattgccg caaatatcat      780
tgggatcttg cacttgacat tgtggattct tgatcgtctt tttttcaaat gcatttaccg      840
tcgctttaaa tacggactga aaggagggcc ttctacggaa ggagtgccaa agtctatcag      900
ggaagaatat cgaaaggaac agcagagtgc tgtggatgct gacgatggtc attttgtcag      960
catagagctg gagtaatagg ccaagggcga attccacatt gggctcgagg ggggccccgg      1020
taccttaatt aattaaggta ccaggtaagt gtacccaatt cgccctatag tgagtcgtat      1080
tacaattcac tcgatcggct cgctgatcag cctcgactgt gccttctagt tgccagccat      1140
ctgttgtttg cccctccccc gtgccttcct tgaccctgga aggtgccact cccactgtcc      1200
tttcctaata aaatgaggaa attgcatcgc attgtctgag taggtgccat tctattctgg      1260
ggggtggggt ggggcaggac agcaagggg aggattggga agacaatagc aggcatgctg       1320
gggaacgcgt aaattgtaag cgttaatatt ttgttaaaat tcgcgttaaa ttttgttaa      1380 atcagctcat ttttaacca ataggccgaa atcggcaaaa tcccttataa atcaaaagaa       1440
tagaccgaga tagggttgag tgttgttcca                                        1470
```

<210> SEQ ID NO 30
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atgcattagt tattaatagt aatcaattac ggggtcatta gttcatagcc catatatgga       60
gttccgcgtt acataactta cggtaaatgg cccgcctggc tgaccgccca acgacccccg      120
cccattgacg tcaataatga cgtatgttcc catagtaacg ccaatagggg ctttccattg      180
acgtcaatgg gtggagtatt tacggtaaac tgcccacttg gcagtacatc aagtgtatca      240
tatgccaagt acgccccta ttgacgtcaa tgacggtaaa tggcccgcct ggcattatgc       300
ccagtacatg accttatggg actttcctac ttggcagtac atctacgtat tagtcatcgc      360
tattaccatg gtgatgcggt tttggcagta catcaatggg cgtggatagc ggtttgactc      420
acggggattt ccaagtctcc accccattga cgtcaatggg agtttgtttt ggcaccaaaa      480
tcaacgggac tttccaaaat gtcgtaacaa ctccgcccca ttgacgcaaa tgggcggtag      540
gcgtgtacgg tgggaggtct atataagcag agctggttta gtgaaccgtc agat           594
```

<210> SEQ ID NO 31
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ttatgcccag tacatgacct tatgggactt tcctacttgg cagtacatct acgtattagt       60
catcgctatt accatggtga tgcggttttg gcagtacatc aatgggcgtg gatagcggtt      120
```

```
tgactcacgg ggatttccaa gtctccaccc cattgacgtc aatgggagtt tgttttggca    180
ccaaaatcaa cgggactttc caaaatgtcg taacaactcc gccccattga cgcaaatggg    240
cggtaggcgt gtacggtggg aggtctatat aagcagagct ggtttagtga accgtcagat    300
ccgctagcga ttacgccaag ctcgaaatta accctcacta agggaacaa aagctggagc    360 tccactgtgg aattcgccct tggccgccat gagtcttcta accgaggtcg aaacgcctat    420
cagaaacgaa tggggtgca gatgcaacgg ttcaagtgat cctctcacta ttgccgcaaa    480
tatcattggg atcttgcact tgacattgtg gattcttgat cgtctttttt tcaaatgcat    540
ttaccgtcgc tttaaatacg gactgaaagg agggccttct acggaaggag tgccaaagtc    600
tatcagggaa gaatatcgaa aggaacagca gagtgctgtg gatgctgacg atggtcattt    660
tgtcagcata gagctggagt aataggccaa gggcgaattc cacattgggc tcgagggggg    720
gcccggtacc t    731
```

\<210\> SEQ ID NO 32
\<211\> LENGTH: 811
\<212\> TYPE: DNA
\<213\> ORGANISM: Artificial Sequence
\<220\> FEATURE:
\<223\> OTHER INFORMATION: Description of Artificial Sequence: Synthetic
      polynucleotide

\<400\> SEQUENCE: 32

```
tgtggaattc gcccttggcc gccatgagtc ttctaaccga ggtcgaaacg cctatcagaa     60
acgaatgggg gtgcagatgc aacggttcaa gtgatcctct cactattgcc gcaaatatca    120
ttgggatctt gcacttgaca ttgtggattc ttgatcgtct tttttcaaa tgcatttacc    180 gtcgctttaa atacgactg aaaggagggc cttctacgga aggagtgcca agtctatca    240 gggaagaata tcgaaaggaa cagcagagtg ctgtggatgc tgacgatggt cattttgtca    300
gcatagagct ggagtaatag gccaagggcg aattccacat tgggctcgag ggggggcccg    360
gtaccttaat taattaaggt accaggtaag tgtacccaat cgccctata gtgagtcgta    420 ttacaattca ctcgatcggc tgctgatca gcctcgactg tgccttctag ttgccagcca    480
tctgttgttt gcccctcccc cgtgccttcc ttgaccctgg aaggtgccac tcccactgtc    540
ctttcctaat aaaatgagga aattgcatcg cattgtctga gtaggtgcca ttctattctg    600
gggggtgggg tggggcagga cagcaagggg gaggattggg aagacaatag caggcatgct    660
ggggaacgcg taaattgtaa gcgttaatat tttgttaaaa ttcgcgttaa attttttgtta    720 aatcagctca ttttttaacc aataggccga atcggcaaa atcccttata aatcaaaga    780 atagaccgag atagggttga gtgttgttcc a    811
```

\<210\> SEQ ID NO 33
\<211\> LENGTH: 294
\<212\> TYPE: DNA
\<213\> ORGANISM: Influenza A virus

\<400\> SEQUENCE: 33

```
atgagtcttc taaccgaggt cgaaacgcct atcagaaacg aatggggtg cagatgcaac     60 ggttcaagtg atcctctcac tattgccgca aatatcattg gatcttgca cttgacattg    120 tggattcttg atcgtctttt tttcaaatgc atttaccgtc gctttaaata cggactgaaa    180
ggagggcctt ctacggaagg agtgccaaag tctatcaggg aagaatatcg aaaggaacag    240
cagagtgctg tggatgctga cgatggtcat tttgtcagca tagagctgga gtaa    294
```

<210> SEQ ID NO 34
<211> LENGTH: 997
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggacggggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcaaga acgaatgggg gtgcagatgc aacggttcaa    780
gtgatgcgca ccaccaccac caccatcatc accaccacca ccactaatag tgcatttacc    840
gtcgctttaa atacggactg aaaggagggc cttctacgga aggagtgcca aagtctatga    900
gggaagaata tcgaaaggaa cagcagagtg ctgtggatgc tgacgatggt cattttgtca    960
gcatagagct ggagtaaaaa actaccttgt ttctact                             997
```

<210> SEQ ID NO 35
<211> LENGTH: 759
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggacggggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
```

```
tcttcttgaa aatttgcaga aaactacctt gtttctact                              759
```

<210> SEQ ID NO 36
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gcctatcaga acgaatggg ggtgcagatg caacggttca agtgattaat aggatcgtct      60
tttttcaaa tgcatttacc gtcgctttaa atacggactg aaaggagggc cttctacgga     120
aggagtgcca aagtctatga gggaagaata tcgaaaggaa cagcagagtg ctgtggatgc     180
tgacgatggt cattttgtca gcatagagct ggagtaa                             217
```

<210> SEQ ID NO 37
<211> LENGTH: 211
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gcctatcaga acgaatggg ggtgcagatg caacggttca agtgatgatc gtctttttt       60
caaatgcatt taccgtcgct ttaaatacgg actgaaagga gggccttcta cggaaggagt    120
gccaaagtct atgagggaag aatatcgaaa ggaacagcag agtgctgtgg atgctgacga    180
tggtcatttt gtcagcatag agctggagta a                                   211
```

<210> SEQ ID NO 38
<211> LENGTH: 1015
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatgggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcgaa acgaatgggg gtgcagatgc aacggttcaa    780
gtgatcctgc aggtgcaggt gagcagaaac tcatctctga agaggatctg gatcgtcttt    840
```

```
ttttcaaatg catttaccgt cgctttaaat acggactgaa aggagggcct tctacggaag    900
gagtgccaaa gtctatgagg gaagaatatc gaaaggaaca gcagagtgct gtggatgctg    960
acgatggtca ttttgtcagc atagagctgg agtaaaaaac taccttgttt ctact        1015
```

<210> SEQ ID NO 39
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Met Ser Leu Leu Thr Glu Val Glu Thr Pro Ile Arg Asn Glu Trp Gly
1               5                   10                  15

Cys Arg Cys Asn Gly Ser Ser Asp Pro Ala Gly Ala Gly Glu Gln Lys
            20                  25                  30

Leu Ile Ser Glu Glu Asp Leu Asp Arg Leu Phe Phe Lys Cys Ile Tyr
        35                  40                  45

Arg Arg Phe Lys Tyr Gly Leu Lys Gly Gly Pro Ser Thr Glu Gly Val
    50                  55                  60

Pro Lys Ser Met Arg Glu Glu Tyr Arg Lys Glu Gln Gln Ser Ala Val
65                  70                  75                  80

Asp Ala Asp Asp Gly His Phe Val Ser Ile Glu Leu Glu
                85                  90
```

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Ser Leu Leu Thr Glu Val Glu Thr Pro Ile Arg Asn Glu Trp Gly
1               5                   10                  15

Cys Arg Cys Asn Gly Ser Ser Asp Ala His His His His His His
            20                  25                  30

His His His His His
        35
```

<210> SEQ ID NO 41
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Lys Ala Glu Arg Ala Asp
        35                  40                  45

Leu Ile Ala Tyr Leu Lys Gln Ala Thr Ala Lys Gln Asn His Thr Gly
    50                  55                  60
```

Ile Cys Asn Gln Gly Ser Ile Thr Tyr Lys Val Val Ala Gly Gln Asp
 65                  70                  75                  80

Ser Thr Ser Val

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      12xHis tag

<400> SEQUENCE: 42

His His His His His His His His His His His His
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 43

His His His His His His
1               5

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 44

Xaa Cys Cys Xaa Pro Ala Cys Gly Xaa Xaa Xaa Xaa Cys Xaa
1               5                   10

<210> SEQ ID NO 45
<211> LENGTH: 18
<212> TYPE: PRT
<213> ORGANISM: Bordetella pertussis

<400> SEQUENCE: 45

Lys Pro Asp Gln Gly Glu Val Val Ala Val Gly Pro Gly Lys Lys Thr
1               5                   10                  15

Glu Asp

<210> SEQ ID NO 46
<211> LENGTH: 9

<212> TYPE: PRT
<213> ORGANISM: Bordetella pertussis

<400> SEQUENCE: 46

Gly Val Ala Pro Thr Ala Gln Gln Leu
1               5

<210> SEQ ID NO 47
<211> LENGTH: 17
<212> TYPE: PRT
<213> ORGANISM: Bordetella pertussis

<400> SEQUENCE: 47

Gly Val Ala Thr Lys Gly Leu Gly Val His Ala Lys Ser Ser Asp Trp
1               5                   10                  15

Gly

<210> SEQ ID NO 48
<211> LENGTH: 17
<212> TYPE: PRT
<213> ORGANISM: Bordetella pertussis

<400> SEQUENCE: 48

Gln Val Asp Leu His Asp Leu Ser Ala Ala Arg Gly Ala Asp Ile Ser
1               5                   10                  15

Gly

<210> SEQ ID NO 49
<211> LENGTH: 9
<212> TYPE: PRT
<213> ORGANISM: Bordetella pertussis

<400> SEQUENCE: 49

Leu Ala Ala Ile Ala Ser Ala Ala His
1               5

<210> SEQ ID NO 50
<211> LENGTH: 14
<212> TYPE: PRT
<213> ORGANISM: Bordetella pertussis

<400> SEQUENCE: 50

Leu Ser Ala Pro His Gly Asn Val Ile Glu Thr Gly Gly Ala
1               5                   10

<210> SEQ ID NO 51
<211> LENGTH: 23
<212> TYPE: PRT
<213> ORGANISM: Bordetella pertussis

<400> SEQUENCE: 51

Ser Thr Pro Gly Ile Val Ile Pro Pro Gln Glu Gln Ile Thr Gln His
1               5                   10                  15

Gly Ser Pro Tyr Gly Arg Cys
            20

<210> SEQ ID NO 52
<211> LENGTH: 15
<212> TYPE: PRT
<213> ORGANISM: Human herpesvirus 5

<400> SEQUENCE: 52

Ala Leu Ser Thr Pro Phe Leu Met Glu His Thr Met Pro Val Thr

<210> SEQ ID NO 53
<211> LENGTH: 15
<212> TYPE: PRT
<213> ORGANISM: Human herpesvirus 5

<400> SEQUENCE: 53

Lys Lys Asp Glu Leu Arg Arg Lys Met Met Tyr Met Cys Tyr Arg
1               5                   10                  15

<210> SEQ ID NO 54
<211> LENGTH: 15
<212> TYPE: PRT
<213> ORGANISM: Human herpesvirus 5

<400> SEQUENCE: 54

Met Ser Ile Tyr Val Tyr Ala Leu Pro Leu Lys Met Leu Asn Ile
1               5                   10                  15

<210> SEQ ID NO 55
<211> LENGTH: 9
<212> TYPE: PRT
<213> ORGANISM: Human herpesvirus 5

<400> SEQUENCE: 55

Ile Met Arg Glu Phe Asn Ser Tyr Lys
1               5

<210> SEQ ID NO 56
<211> LENGTH: 8
<212> TYPE: PRT
<213> ORGANISM: Human herpesvirus 5

<400> SEQUENCE: 56

Pro Ser Ala Met Leu Ser Ala Ile
1               5

<210> SEQ ID NO 57
<211> LENGTH: 9
<212> TYPE: PRT
<213> ORGANISM: Ebola virus

<400> SEQUENCE: 57

Lys Gln Ile Pro Ile Trp Leu Pro Leu
1               5

<210> SEQ ID NO 58
<211> LENGTH: 8
<212> TYPE: PRT
<213> ORGANISM: Ebola virus

<400> SEQUENCE: 58

Thr Glu Leu Arg Thr Phe Ser Ile
1               5

<210> SEQ ID NO 59
<211> LENGTH: 9
<212> TYPE: PRT
<213> ORGANISM: Ebola virus

<400> SEQUENCE: 59

Tyr Gln Val Asn Asn Leu Glu Glu Ile
1               5

```
<210> SEQ ID NO 60
<211> LENGTH: 11
<212> TYPE: PRT
<213> ORGANISM: Ebola virus

<400> SEQUENCE: 60

Val Tyr Gln Val Asn Asn Leu Glu Glu Ile Cys
1               5                   10

<210> SEQ ID NO 61
<211> LENGTH: 9
<212> TYPE: PRT
<213> ORGANISM: Ebola virus

<400> SEQUENCE: 61

Gly Arg Ile Pro Val Ser Asp Ile Phe
1               5

<210> SEQ ID NO 62
<211> LENGTH: 17
<212> TYPE: PRT
<213> ORGANISM: Enterovirus

<400> SEQUENCE: 62

Glu Ala Ile Pro Ala Leu Thr Ala Val Glu Thr Gly His Thr Ser Gln
1               5                   10                  15

Val

<210> SEQ ID NO 63
<211> LENGTH: 12
<212> TYPE: PRT
<213> ORGANISM: Enterovirus

<400> SEQUENCE: 63

Ala Thr Cys Arg Phe Tyr Thr Leu Asp Ser Ile Lys
1               5                   10

<210> SEQ ID NO 64
<211> LENGTH: 12
<212> TYPE: PRT
<213> ORGANISM: Enterovirus

<400> SEQUENCE: 64

Gly Asp Val Glu Glu Ala Ile Glu Arg Ala Val Val
1               5                   10

<210> SEQ ID NO 65
<211> LENGTH: 9
<212> TYPE: PRT
<213> ORGANISM: Enterovirus

<400> SEQUENCE: 65

Glu Ile Pro Ala Leu Thr Ala Val Glu
1               5

<210> SEQ ID NO 66
<211> LENGTH: 20
<212> TYPE: PRT
<213> ORGANISM: Enterovirus

<400> SEQUENCE: 66

Ala His Glu Thr Ser Leu Asn Ala Ala Gly Asn Ser Val Ile His Tyr
1               5                   10                  15
```

Thr Asn Ile Asn
        20

<210> SEQ ID NO 67
<211> LENGTH: 37
<212> TYPE: PRT
<213> ORGANISM: Hepatitis C virus

<400> SEQUENCE: 67

Asp Ser Thr Val Thr Glu Asn Asp Ile Arg Val Glu Glu Ser Ile Tyr
1               5                   10                  15

Gln Cys Cys Asp Leu Ala Pro Glu Ala Arg Gln Ala Ile Lys Ser Leu
            20                  25                  30

Thr Glu Arg Leu Tyr
        35

<210> SEQ ID NO 68
<211> LENGTH: 15
<212> TYPE: PRT
<213> ORGANISM: Hepatitis C virus

<400> SEQUENCE: 68

Met Ala Pro Ile Thr Ala Tyr Ser Gln Gln Thr Arg Gly Leu Leu
1               5                   10                  15

<210> SEQ ID NO 69
<211> LENGTH: 12
<212> TYPE: PRT
<213> ORGANISM: Hepatitis C virus

<400> SEQUENCE: 69

Gln Leu Ile Asn Thr Asn Gly Ser Trp His Val Asn
1               5                   10

<210> SEQ ID NO 70
<211> LENGTH: 14
<212> TYPE: PRT
<213> ORGANISM: Hepatitis C virus

<400> SEQUENCE: 70

Met Ser Thr Asn Pro Lys Pro Gln Arg Lys Thr Lys Arg Asn
1               5                   10

<210> SEQ ID NO 71
<211> LENGTH: 27
<212> TYPE: PRT
<213> ORGANISM: Hepatitis C virus

<400> SEQUENCE: 71

Asn Thr Tyr Ala Ser Gly Gly Ala Val Gly His Gln Thr Ala Ser Phe
1               5                   10                  15

Val Arg Leu Leu Ala Pro Gly Pro Gln Gln Asn
            20                  25

<210> SEQ ID NO 72
<211> LENGTH: 8
<212> TYPE: PRT
<213> ORGANISM: Human immunodeficiency virus

<400> SEQUENCE: 72

Glu Ile Tyr Lys Arg Trp Ile Ile
1               5

```
<210> SEQ ID NO 73
<211> LENGTH: 6
<212> TYPE: PRT
<213> ORGANISM: Human immunodeficiency virus

<400> SEQUENCE: 73

Glu Leu Asp Lys Trp Ala
1               5

<210> SEQ ID NO 74
<211> LENGTH: 10
<212> TYPE: PRT
<213> ORGANISM: Human immunodeficiency virus

<400> SEQUENCE: 74

Gly Pro Gly His Lys Ala Arg Val Leu Ala
1               5                   10

<210> SEQ ID NO 75
<211> LENGTH: 9
<212> TYPE: PRT
<213> ORGANISM: Human immunodeficiency virus

<400> SEQUENCE: 75

Ile Val Leu Pro Glu Lys Asp Ser Trp
1               5

<210> SEQ ID NO 76
<211> LENGTH: 12
<212> TYPE: PRT
<213> ORGANISM: Human immunodeficiency virus

<400> SEQUENCE: 76

Leu Glu Leu Asp Lys Trp Ala Gly Leu Trp Ser Trp
1               5                   10

<210> SEQ ID NO 77
<211> LENGTH: 20
<212> TYPE: PRT
<213> ORGANISM: Human parvovirus B19

<400> SEQUENCE: 77

Gly Ile Met Thr Val Thr Met Thr Phe Lys Leu Gly Pro Arg Lys Ala
1               5                   10                  15

Thr Gly Arg Trp
            20

<210> SEQ ID NO 78
<211> LENGTH: 9
<212> TYPE: PRT
<213> ORGANISM: Human parvovirus B19

<400> SEQUENCE: 78

Gly Leu Phe Asn Asn Val Leu Tyr His
1               5

<210> SEQ ID NO 79
<211> LENGTH: 20
<212> TYPE: PRT
<213> ORGANISM: Human parvovirus B19

<400> SEQUENCE: 79

His His Arg His Gly Tyr Glu Lys Pro Glu Glu Leu Trp Thr Ala Lys
1               5                   10                  15
```

-continued

Ser Arg Val His
            20

<210> SEQ ID NO 80
<211> LENGTH: 20
<212> TYPE: PRT
<213> ORGANISM: Human parvovirus B19

<400> SEQUENCE: 80

Leu Ala Ser Glu Glu Ser Ala Phe Tyr Val Leu Glu His Ser Ser Phe
1               5                   10                  15

Gln Leu Leu Gly
            20

<210> SEQ ID NO 81
<211> LENGTH: 19
<212> TYPE: PRT
<213> ORGANISM: Human parvovirus B19

<400> SEQUENCE: 81

His Gly Tyr Glu Lys Pro Glu Glu Leu Trp Thr Ala Lys Ser Arg Val
1               5                   10                  15

His Pro Leu

<210> SEQ ID NO 82
<211> LENGTH: 10
<212> TYPE: PRT
<213> ORGANISM: Measles virus

<400> SEQUENCE: 82

Ser Leu Trp Gly Ser Gly Leu Leu Met Leu
1               5                   10

<210> SEQ ID NO 83
<211> LENGTH: 15
<212> TYPE: PRT
<213> ORGANISM: Measles virus

<400> SEQUENCE: 83

Met Thr Arg Ser Ser His Gln Ser Leu Val Ile Lys Leu Met Pro
1               5                   10                  15

<210> SEQ ID NO 84
<211> LENGTH: 15
<212> TYPE: PRT
<213> ORGANISM: Measles virus

<400> SEQUENCE: 84

Met Gly Leu Lys Val Asn Val Ser Ala Ile Phe Met Ala Val Leu
1               5                   10                  15

<210> SEQ ID NO 85
<211> LENGTH: 10
<212> TYPE: PRT
<213> ORGANISM: Measles virus

<400> SEQUENCE: 85

Ile Leu Leu Glu Arg Leu Asp Val Gly Thr
1               5                   10

<210> SEQ ID NO 86
<211> LENGTH: 15
<212> TYPE: PRT
<213> ORGANISM: Measles virus

<400> SEQUENCE: 86

Lys Phe Leu Asn Pro Asp Arg Glu Tyr Asp Phe Arg Asp Leu Thr
1               5                   10                  15

<210> SEQ ID NO 87
<211> LENGTH: 12
<212> TYPE: PRT
<213> ORGANISM: Mumps virus

<400> SEQUENCE: 87

Gly Glu Gln Ala Arg Tyr Leu Ala Leu Leu Glu Ala
1               5                   10

<210> SEQ ID NO 88
<211> LENGTH: 12
<212> TYPE: PRT
<213> ORGANISM: Mumps virus

<400> SEQUENCE: 88

Asn Ser Thr Leu Gly Val Lys Ser Ala Arg Glu Phe
1 5 10

<210> SEQ ID NO 89
<211> LENGTH: 8
<212> TYPE: PRT
<213> ORGANISM: Mumps virus

<400> SEQUENCE: 89

Asp Ile Phe Ile Val Ser Pro Arg
1 5

<210> SEQ ID NO 90
<211> LENGTH: 20
<212> TYPE: PRT
<213> ORGANISM: Mycobacterium tuberculosis

<400> SEQUENCE: 90

Ala Ala Ala Gly Phe Ala Ser Lys Thr Pro Ala Asn Gln Ala Ile Ser
1 5 10 15

Met Ile Asp Gly
20

<210> SEQ ID NO 91
<211> LENGTH: 8
<212> TYPE: PRT
<213> ORGANISM: Mycobacterium tuberculosis

<400> SEQUENCE: 91

Ala Ala Ala Ser Ala Ile Gln Gly
1 5

<210> SEQ ID NO 92
<211> LENGTH: 8
<212> TYPE: PRT
<213> ORGANISM: Mycobacterium tuberculosis

<400> SEQUENCE: 92

Glu Gly Gly Thr Trp Arg Ile Gly
1 5

<210> SEQ ID NO 93
<211> LENGTH: 9
<212> TYPE: PRT

```
<213> ORGANISM: Mycobacterium tuberculosis

<400> SEQUENCE: 93

Glu Gly Lys Gln Ser Leu Thr Lys Leu
1               5

<210> SEQ ID NO 94
<211> LENGTH: 16
<212> TYPE: PRT
<213> ORGANISM: Mycobacterium tuberculosis

<400> SEQUENCE: 94

Phe Ala Tyr Gly Ser Phe Val Arg Thr Val Ser Leu Pro Val Gly Ala
1               5                   10                  15

<210> SEQ ID NO 95
<211> LENGTH: 9
<212> TYPE: PRT
<213> ORGANISM: Norovirus

<400> SEQUENCE: 95

Ser Trp Val Pro Arg Leu Tyr Gln Leu
1               5

<210> SEQ ID NO 96
<211> LENGTH: 15
<212> TYPE: PRT
<213> ORGANISM: Norovirus

<400> SEQUENCE: 96

Asp Val Ala Leu Leu Arg Phe Val Asn Pro Asp Thr Gly Arg Val
1               5                   10                  15

<210> SEQ ID NO 97
<211> LENGTH: 15
<212> TYPE: PRT
<213> ORGANISM: Norovirus

<400> SEQUENCE: 97

Pro Phe Leu Leu His Leu Ser Gln Met Tyr Asn Gly Trp Val Gly
1               5                   10                  15

<210> SEQ ID NO 98
<211> LENGTH: 30
<212> TYPE: PRT
<213> ORGANISM: Norovirus

<400> SEQUENCE: 98

Ala Lys Leu His Lys Leu Gly Phe Ile Thr Ile Ala Lys Asn Gly Asp
1               5                   10                  15

Ser Pro Ile Thr Val Pro Pro Asn Gly Tyr Phe Arg Phe Glu
            20                  25                  30

<210> SEQ ID NO 99
<211> LENGTH: 13
<212> TYPE: PRT
<213> ORGANISM: Norovirus

<400> SEQUENCE: 99

Cys Lys Leu Thr Ala Asn Pro Ser Leu Ala Ala Val Val
1               5                   10

<210> SEQ ID NO 100
<211> LENGTH: 9
```

```
<212> TYPE: PRT
<213> ORGANISM: Parainfluenza virus

<400> SEQUENCE: 100

Ile Pro Lys Ser Ala Lys Leu Phe Phe
1               5

<210> SEQ ID NO 101
<211> LENGTH: 9
<212> TYPE: PRT
<213> ORGANISM: Parainfluenza virus

<400> SEQUENCE: 101

Ile Pro Asn Pro Leu Leu Gly Leu Asp
1               5

<210> SEQ ID NO 102
<211> LENGTH: 14
<212> TYPE: PRT
<213> ORGANISM: Parainfluenza virus

<400> SEQUENCE: 102

Gly Lys Pro Ile Pro Asn Pro Leu Leu Gly Leu Asp Ser Thr
1               5                   10

<210> SEQ ID NO 103
<211> LENGTH: 8
<212> TYPE: PRT
<213> ORGANISM: Plasmodium falciparum

<400> SEQUENCE: 103

Ala Asp Glu Leu Ile Lys Tyr Leu
1               5

<210> SEQ ID NO 104
<211> LENGTH: 8
<212> TYPE: PRT
<213> ORGANISM: Plasmodium falciparum

<400> SEQUENCE: 104

Ala Asp Ile Lys Lys Leu Thr Glu
1               5

<210> SEQ ID NO 105
<211> LENGTH: 8
<212> TYPE: PRT
<213> ORGANISM: Plasmodium falciparum

<400> SEQUENCE: 105

Gly Pro Ala Val Val Glu Glu Ser
1               5

<210> SEQ ID NO 106
<211> LENGTH: 9
<212> TYPE: PRT
<213> ORGANISM: Plasmodium falciparum

<400> SEQUENCE: 106

Gly Pro Phe Met Lys Ala Val Cys Val
1               5

<210> SEQ ID NO 107
<211> LENGTH: 20
<212> TYPE: PRT
<213> ORGANISM: Plasmodium falciparum
```

```
<400> SEQUENCE: 107

Gly Pro Leu Asp Asn Thr Ser Glu Glu Thr Thr Glu Arg Ile Ser Asn
1               5                   10                  15

Asn Glu Tyr Lys
            20

<210> SEQ ID NO 108
<211> LENGTH: 14
<212> TYPE: PRT
<213> ORGANISM: Respiratory syncytial virus

<400> SEQUENCE: 108

Ala Lys Thr Leu Glu Arg Thr Trp Asp Thr Leu Asn His Leu
1               5                   10

<210> SEQ ID NO 109
<211> LENGTH: 20
<212> TYPE: PRT
<213> ORGANISM: Respiratory syncytial virus

<400> SEQUENCE: 109

Ala Val Ile Arg Arg Ala Asn Asn Val Leu Lys Asn Glu Met Lys Arg
1               5                   10                  15

Tyr Lys Gly Leu
            20

<210> SEQ ID NO 110
<211> LENGTH: 16
<212> TYPE: PRT
<213> ORGANISM: Respiratory syncytial virus

<400> SEQUENCE: 110

Cys Glu Tyr Asn Val Phe His Asn Lys Thr Phe Glu Leu Pro Arg Ala
1               5                   10                  15

<210> SEQ ID NO 111
<211> LENGTH: 15
<212> TYPE: PRT
<213> ORGANISM: Respiratory syncytial virus

<400> SEQUENCE: 111

Cys Ser Ile Cys Ser Asn Asn Pro Thr Cys Trp Ala Ile Cys Lys
1               5                   10                  15

<210> SEQ ID NO 112
<211> LENGTH: 11
<212> TYPE: PRT
<213> ORGANISM: Respiratory syncytial virus

<400> SEQUENCE: 112

Cys Ser Ile Ser Asn Ile Glu Thr Val Ile Glu
1               5                   10

<210> SEQ ID NO 113
<211> LENGTH: 10
<212> TYPE: PRT
<213> ORGANISM: Human rhinovirus

<400> SEQUENCE: 113

Ala Glu Thr Arg Leu Asn Pro Asp Leu Gln
1               5                   10
```

<210> SEQ ID NO 114
<211> LENGTH: 20
<212> TYPE: PRT
<213> ORGANISM: Human rhinovirus

<400> SEQUENCE: 114

```
Phe Cys Leu Arg Met Ala Arg Asp Thr Asn Leu His Leu Gln Ser Gly
1               5                   10                  15

Ala Ile Ala Gln
            20
```

<210> SEQ ID NO 115
<211> LENGTH: 16
<212> TYPE: PRT
<213> ORGANISM: Human rhinovirus

<400> SEQUENCE: 115

```
Lys Leu Ile Leu Ala Tyr Thr Pro Pro Gly Ala Arg Gly Pro Gln Asp
1               5                   10                  15
```

<210> SEQ ID NO 116
<211> LENGTH: 6
<212> TYPE: PRT
<213> ORGANISM: Human rhinovirus

<400> SEQUENCE: 116

```
Leu Asn Pro Asp Leu Gln
1               5
```

<210> SEQ ID NO 117
<211> LENGTH: 24
<212> TYPE: PRT
<213> ORGANISM: Human rhinovirus

<400> SEQUENCE: 117

```
Gly Ala Gln Val Ser Arg Gln Asn Val Gly Thr His Ser Thr Gln Asn
1               5                   10                  15

Met Val Ser Asn Gly Ser Ser Leu
            20
```

<210> SEQ ID NO 118
<211> LENGTH: 9
<212> TYPE: PRT
<213> ORGANISM: SARS coronavirus

<400> SEQUENCE: 118

```
Ala Ala Asn Thr Val Ile Trp Asp Tyr
1               5
```

<210> SEQ ID NO 119
<211> LENGTH: 17
<212> TYPE: PRT
<213> ORGANISM: SARS coronavirus

<400> SEQUENCE: 119

```
Ala Ala Thr Lys Met Ser Glu Cys Val Leu Gly Gln Ser Lys Arg Val
1               5                   10                  15

Asp
```

<210> SEQ ID NO 120
<211> LENGTH: 15
<212> TYPE: PRT
<213> ORGANISM: SARS coronavirus

```
<400> SEQUENCE: 120

Ala Ala Thr Val Leu Gln Leu Pro Gln Gly Thr Thr Leu Pro Lys
1               5                   10                  15

<210> SEQ ID NO 121
<211> LENGTH: 9
<212> TYPE: PRT
<213> ORGANISM: SARS coronavirus

<400> SEQUENCE: 121

Val Leu Asn Asp Ile Leu Ser Arg Leu
1               5

<210> SEQ ID NO 122
<211> LENGTH: 15
<212> TYPE: PRT
<213> ORGANISM: SARS coronavirus

<400> SEQUENCE: 122

Val Leu Pro Phe His Arg Trp His Thr Met Val Gln Thr Cys Thr
1               5                   10                  15

<210> SEQ ID NO 123
<211> LENGTH: 5
<212> TYPE: PRT
<213> ORGANISM: Streptococcus pneumoniae

<400> SEQUENCE: 123

Pro Lys Pro Glu Gln
1               5

<210> SEQ ID NO 124
<211> LENGTH: 18
<212> TYPE: PRT
<213> ORGANISM: Streptococcus pneumoniae

<400> SEQUENCE: 124

Val Arg Gly Ala Val Asn Asp Leu Leu Ala Lys Trp His Gln Asp Tyr
1               5                   10                  15

Gly Gln

<210> SEQ ID NO 125
<211> LENGTH: 5
<212> TYPE: PRT
<213> ORGANISM: Streptococcus pneumoniae

<400> SEQUENCE: 125

Trp Glu Trp Trp Arg
1               5

<210> SEQ ID NO 126
<211> LENGTH: 15
<212> TYPE: PRT
<213> ORGANISM: Streptococcus pneumoniae

<400> SEQUENCE: 126

Tyr Phe Ser Lys Ala Tyr Gly Val Pro Ser Ala Tyr Ile Trp Glu
1               5                   10                  15

<210> SEQ ID NO 127
<211> LENGTH: 9
<212> TYPE: PRT
<213> ORGANISM: Streptococcus pneumoniae
```

-continued

<400> SEQUENCE: 127

Gln Ile Ser Asn Tyr Val Gly Arg Lys
1               5

<210> SEQ ID NO 128
<211> LENGTH: 12
<212> TYPE: PRT
<213> ORGANISM: Lymphocytic choriomeningitis virus

<400> SEQUENCE: 128

Ser Glu Arg Pro Gln Ala Ser Gly Val Tyr Met Gly
1               5                   10

<210> SEQ ID NO 129
<211> LENGTH: 9
<212> TYPE: PRT
<213> ORGANISM: Respiratory syncytial virus

<400> SEQUENCE: 129

Arg Ala Arg Arg Glu Leu Pro Arg Phe
1               5

<210> SEQ ID NO 130
<211> LENGTH: 9
<212> TYPE: PRT
<213> ORGANISM: Respiratory syncytial virus

<400> SEQUENCE: 130

Ile Ala Val Gly Leu Leu Leu Tyr Cys
1               5

<210> SEQ ID NO 131
<211> LENGTH: 9
<212> TYPE: PRT
<213> ORGANISM: Respiratory syncytial virus

<400> SEQUENCE: 131

Val Ile Thr Ile Glu Leu Ser Asn Ile
1               5

<210> SEQ ID NO 132
<211> LENGTH: 10
<212> TYPE: PRT
<213> ORGANISM: Parainfluenza virus 3

<400> SEQUENCE: 132

Gly Glu Pro Gln Ser Ser Ile Ile Gln Tyr
1               5                   10

<210> SEQ ID NO 133
<211> LENGTH: 40
<212> TYPE: PRT
<213> ORGANISM: Parainfluenza virus 3

<400> SEQUENCE: 133

Glu Met Ala Ile Asp Glu Glu Pro Glu Gln Phe Glu His Arg Ala Asp
1               5                   10                  15

Gln Glu Gln Asp Gly Glu Pro Gln Ser Ser Ile Ile Gln Tyr Ala Trp
            20                  25                  30

Ala Glu Gly Asn Arg Ser Asp Asp
        35                  40

<210> SEQ ID NO 134

```
<211> LENGTH: 13
<212> TYPE: PRT
<213> ORGANISM: Bordetella pertussis

<400> SEQUENCE: 134

Gly Asn Asn Asp Asn Val Leu Asp His Leu Thr Gly Arg
1               5                   10

<210> SEQ ID NO 135
<211> LENGTH: 18
<212> TYPE: PRT
<213> ORGANISM: Bordetella pertussis

<400> SEQUENCE: 135

Gln Gln Thr Arg Ala Asn Pro Asn Pro Tyr Thr Ser Arg Arg Ser Val
1               5                   10                  15

Ala Ser

<210> SEQ ID NO 136
<211> LENGTH: 17
<212> TYPE: PRT
<213> ORGANISM: Bordetella pertussis

<400> SEQUENCE: 136

Asp Asp Pro Pro Ala Thr Val Tyr Arg Tyr Asp Ser Arg Pro Pro Glu
1               5                   10                  15

Asp

<210> SEQ ID NO 137
<211> LENGTH: 9
<212> TYPE: PRT
<213> ORGANISM: SARS coronavirus

<400> SEQUENCE: 137

Phe Ile Ala Gly Leu Ile Ala Ile Val
1               5

<210> SEQ ID NO 138
<211> LENGTH: 43
<212> TYPE: PRT
<213> ORGANISM: Norwalk virus

<400> SEQUENCE: 138

Met Met Met Ala Ser Lys Asp Ala Thr Ser Ser Val Asp Gly Ala Ser
1               5                   10                  15

Gly Ala Gly Gln Leu Val Pro Glu Val Asn Thr Ser Asp Pro Leu Ala
            20                  25                  30

Met Asp Pro Val Ala Gly Ser Ser Thr Ala Val
        35                  40

<210> SEQ ID NO 139
<211> LENGTH: 8
<212> TYPE: PRT
<213> ORGANISM: Norwalk virus

<400> SEQUENCE: 139

Gln Ala Ser Gly Val Tyr Met Gly
1               5

<210> SEQ ID NO 140
<211> LENGTH: 75
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 140
cacacacgtc tcacatcacc accaccacca ctaatagtgc atttaccgtc gctttaaata      60
cggactgaaa ggagg                                                      75

<210> SEQ ID NO 141
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tgtgtgcgtc tcagatgatg gtggtggtgg tggtgcgcat cacttgaacc gttgcatctg      60 caccccatt cg                                                           72

<210> SEQ ID NO 142
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Ala Gly Ala
1

<210> SEQ ID NO 143
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Gly Ala Gly
1

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Ala Glu Arg Ala Asp Leu Ile Ala Tyr Leu Lys Gln Ala Thr Ala
1               5                  10                  15

Lys
```

What is claimed is:

1. A nucleic acid sequence comprising SEQ ID NO:35, wherein SEQ ID NO:35 further comprises a nucleic acid sequence encoding one or more foreign antigens.

2. The nucleic acid sequence of claim 1, wherein:
   (a) the nucleic acid sequence further comprises part or all of SEQ ID NO:36; or
   (b) the one or more foreign antigens comprises an amino acid sequence derived from a pathogen or a tumor.

3. The nucleic acid sequence of claim 2, wherein the pathogen comprises a virus, bacteria, fungus, protozoan, multi-cellular parasite, or prion.

4. A composition comprising the nucleic acid sequence of claim 1, operably linked to (i) a promoter, and (ii) a transcription termination sequence.

5. The composition of claim 4, wherein:
(a) the nucleic acid further comprises part or all of SEQ ID NO:36; or
(b) the one or more foreign antigens comprises an amino acid sequence derived from a pathogen or a tumor.

6. The composition of claim 5, wherein the pathogen comprises a virus, bacteria, fungus, protozoan, multi-cellular parasite, or prion.

7. A recombinant influenza virus, comprising the nucleic acid sequence of claim 1.

8. A method for immunizing a subject, comprising: administering a composition comprising a recombinant influenza virus comprising the nucleic acid sequence of claim 1.

9. The method of claim 8, wherein:
(a) the nucleic acid sequence further comprises part or all of SEQ ID NO:36; or
(b) the one or more foreign antigens comprises an amino acid sequence derived from a pathogen or a tumor.

10. The method of claim 9, wherein the pathogen comprises a virus, bacteria, fungus, protozoan, multi-cellular parasite, or prion.

11. A method for reducing the likelihood or severity of infection by a pathogen in a subject comprising: administering a composition comprising the nucleic acid sequence of claim 1, wherein the one ore more foreign antigens comprises an antigen derived from a pathogen.

12. The method of claim 11, wherein:
(a) the nucleic acid sequence further comprises part or all of SEQ ID NO:36; or
(b) the pathogen comprises a virus, bacteria, fungus, protozoan, multi-cellular parasite, or prion.

13. The method of claim 11, wherein the composition is administered intranasally, intramuscularly, or intracutaneously.

14. A method for eliciting an immune response in a subject, comprising administering to the subject an influenza viral vector, wherein the influenza viral vector comprises nucleic acid encoding one or more foreign antigens, wherein the virus comprises SEQ ID NO: 1, SEQ ID NO: 34 or SEQ ID NO: 35.

15. The method of claim 14, wherein the influenza viral vector nucleic acid bears a mutation in the M2 gene.

16. The method of claim 15, wherein the mutation causes the loss of M2 expression or expression of a truncated M2 protein.

17. The method of claim 11, wherein the composition comprises a recombinant influenza virus comprising the nucleic acid of SEQ ID NO: 1.

18. The method of claim 14, wherein the one or more foreign antigens are expressed from within a viral gene selected from the group consisting of the M2 gene, the M1 gene, the NA gene, the HA gene, the NS gene, the NP gene, the PA gene, the PB1 gene, and the PB2 gene.

19. The method of claim 18, wherein part or all of the viral gene is deleted and replaced with the one or more foreign antigens.

* * * * *